US 11,673,894 B2

(12) United States Patent
Wang et al.

(10) Patent No.: US 11,673,894 B2
(45) Date of Patent: Jun. 13, 2023

(54) IMIDAZOPYRIMIDINES AND TRIAZOLOPYRIMIDINES AS A2A / A2B INHIBITORS

(71) Applicant: Incyte Corporation, Wilmington, DE (US)

(72) Inventors: Xiaozhao Wang, Mt. Laurel, NJ (US); Pei Gan, Claymont, DE (US); Taisheng Huang, Wilmington, DE (US); Chao Qi, Newark, DE (US); Ding-Quan Qian, Newark, DE (US); Liangxing Wu, Wilmington, DE (US); Wenqing Yao, Chadds Ford, PA (US); Zhiyong Yu, Wilmington, DE (US); Fenglei Zhang, Berwyn, PA (US); Le Zhao, Wilmington, DE (US); Chunhong He, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/077,713

(22) Filed: Oct. 22, 2020

(65) Prior Publication Data
US 2021/0139485 A1      May 13, 2021

Related U.S. Application Data

(63) Continuation of application No. 16/285,787, filed on Feb. 26, 2019, now abandoned.

(60) Provisional application No. 62/793,015, filed on Jan. 16, 2019, provisional application No. 62/721,312, filed on Aug. 22, 2018, provisional application No. 62/718,216, filed on Aug. 13, 2018, provisional application No. 62/635,926, filed on Feb. 27, 2018.

(51) Int. Cl.

| | |
|---|---|
| *C07D 497/04* | (2006.01) |
| *C07D 487/04* | (2006.01) |
| *C07D 491/056* | (2006.01) |
| *C07D 519/00* | (2006.01) |
| *A61P 35/00* | (2006.01) |
| *A61P 25/00* | (2006.01) |
| *A61P 9/00* | (2006.01) |
| *A61P 29/00* | (2006.01) |

(52) U.S. Cl.
CPC ............. *C07D 487/04* (2013.01); *A61P 9/00* (2018.01); *A61P 25/00* (2018.01); *A61P 29/00* (2018.01); *A61P 35/00* (2018.01); *C07D 491/056* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 4,399,216 | A | 8/1983 | Axel et al. |
| 4,634,665 | A | 1/1987 | Axel et al. |
| 5,057,313 | A | 10/1991 | Shih et al. |
| 5,156,840 | A | 10/1992 | Goers et al. |
| 5,179,017 | A | 1/1993 | Axel et al. |
| 5,530,101 | A | 6/1996 | Queen et al. |
| 5,585,089 | A | 12/1996 | Queen et al. |
| 5,624,821 | A | 4/1997 | Winter et al. |
| 5,648,260 | A | 7/1997 | Winter et al. |
| 5,693,761 | A | 12/1997 | Queen et al. |
| 5,693,762 | A | 12/1997 | Queen et al. |
| 5,714,350 | A | 2/1998 | Co et al. |
| 5,731,168 | A | 3/1998 | Carter et al. |
| 5,849,992 | A | 12/1998 | Meade et al. |
| 5,859,205 | A | 1/1999 | Adair et al. |
| 5,869,046 | A | 2/1999 | Presta et al. |
| 6,222,035 | B1 | 4/2001 | Tsumuki et al. |
| 6,300,064 | B1 | 10/2001 | Knippik et al. |
| 6,350,861 | B1 | 2/2002 | Co et al. |

(Continued)

FOREIGN PATENT DOCUMENTS

| | | |
|---|---|---|
| AU | 2005260031 | 1/2006 |
| CL | 201802358 | 11/2018 |

(Continued)

OTHER PUBLICATIONS

Agata et al., "Expression of the PD-1 antigen on the surface of stimulated mouse T and B lymphocytes," (1996) Int. Immunol. 8(5):765-772.
Angal et al., "A single amino acid substitution abolishes the heterogeneity of chimeric mouse/human (IgG4) antibody," Mol. Immunol., 1993, 30:105-108.
Barber et al., "Restoring function in exhausted CD8 T cells during chronic viral infection," Nature, 2006, 439:682-687.

(Continued)

*Primary Examiner* — Clinton A Brooks
(74) *Attorney, Agent, or Firm* — Fish & Richardson P.C.

(57) ABSTRACT

This application relates to compounds of Formula (I):

(I)

or pharmaceutically acceptable salts or stereoisomers thereof, which modulate the activity of adenosine receptors, such as subtypes A2A and A2B receptors, and are useful in the treatment of diseases related to the activity of adenosine receptors including, for example, cancer, inflammatory diseases, cardiovascular diseases, and neurodegenerative diseases.

25 Claims, No Drawings

(56) References Cited

U.S. PATENT DOCUMENTS

| | | |
|---|---|---|
| 6,407,213 B1 | 6/2002 | Carter et al. |
| 6,545,000 B1 | 4/2003 | Shimada et al. |
| 6,803,192 B1 | 10/2004 | Chen |
| 6,808,710 B1 | 10/2004 | Wood et al. |
| 6,921,762 B2 | 7/2005 | Cai et al. |
| 7,041,666 B2 | 5/2006 | Matasi et al. |
| 7,101,550 B2 | 9/2006 | Wood et al. |
| 7,306,631 B2 | 12/2007 | Glenn, Jr. et al. |
| 7,452,892 B2 | 11/2008 | Wu et al. |
| 7,488,802 B2 | 2/2009 | Collins et al. |
| 7,501,411 B2 | 3/2009 | Andrews et al. |
| 7,511,050 B2 | 3/2009 | Zheng et al. |
| 7,563,788 B2 | 7/2009 | Sciotti et al. |
| 7,635,757 B2 | 12/2009 | Freeman et al. |
| 7,674,791 B2 | 3/2010 | Dowling et al. |
| 7,700,594 B2 | 4/2010 | Chen et al. |
| 7,709,468 B2 | 5/2010 | Calderwood et al. |
| 7,722,868 B2 | 5/2010 | Freeman et al. |
| 7,794,710 B2 | 9/2010 | Chen et al. |
| 7,834,014 B2 | 11/2010 | Peng et al. |
| 7,943,743 B2 | 5/2011 | Korman et al. |
| 8,008,449 B2 | 8/2011 | Korman et al. |
| 8,053,574 B2 | 11/2011 | Bruce et al. |
| 8,133,895 B2 | 3/2012 | Andrews et al. |
| 8,168,757 B2 | 5/2012 | Finnefrock et al. |
| 8,202,869 B2 | 6/2012 | Kase et al. |
| 8,217,149 B2 | 7/2012 | Irving et al. |
| 8,273,752 B2 | 9/2012 | Siegel et al. |
| 8,288,536 B2 | 10/2012 | Dong et al. |
| 8,349,850 B2 | 1/2013 | Tworowski et al. |
| 8,431,596 B2 | 4/2013 | Pave et al. |
| 8,569,300 B2 | 10/2013 | Borchardt et al. |
| 8,575,183 B2 | 11/2013 | Cushing et al. |
| 8,580,812 B2 | 11/2013 | Ihle et al. |
| 8,637,542 B2 | 1/2014 | Liu et al. |
| 8,865,731 B2 | 10/2014 | Ouchi et al. |
| 8,865,734 B2 | 10/2014 | No et al. |
| 9,029,389 B2 | 5/2015 | No et al. |
| 9,029,393 B2 | 5/2015 | Schann et al. |
| 9,034,872 B2 | 5/2015 | Tworowski et al. |
| 9,085,560 B2 | 7/2015 | Ren et al. |
| 9,090,697 B2 | 7/2015 | Sim |
| 9,127,000 B2 | 9/2015 | Ren et al. |
| 9,249,162 B2 | 2/2016 | Campbell et al. |
| 9,254,283 B2 | 2/2016 | Ikeda et al. |
| 9,328,121 B1 | 5/2016 | Takahashi et al. |
| 9,388,249 B2 | 7/2016 | Sugioka et al. |
| 9,394,301 B2 | 7/2016 | Pave et al. |
| 9,394,311 B2 | 7/2016 | Flohr et al. |
| 9,573,948 B2 | 2/2017 | Cole et al. |
| 9,605,080 B2 | 3/2017 | Lonberg et al. |
| 9,695,167 B2 | 7/2017 | Wu et al. |
| 9,938,356 B2 | 4/2018 | Hay et al. |
| 9,944,647 B2 | 4/2018 | He et al. |
| 10,100,129 B2 | 10/2018 | Lonberg et al. |
| 10,287,362 B2 | 5/2019 | Hay et al. |
| 10,577,422 B2 | 3/2020 | Shah et al. |
| 11,161,850 B2 | 11/2021 | Wang et al. |
| 11,168,089 B2 | 11/2021 | Want et al. |
| 11,390,624 B2 | 7/2022 | Huang et al. |
| 2002/0193376 A1 | 12/2002 | Gall |
| 2003/0027820 A1 | 2/2003 | Gall |
| 2003/0143199 A1 | 7/2003 | Carson et al. |
| 2004/0142342 A1 | 7/2004 | Barden et al. |
| 2004/0186148 A1 | 9/2004 | Shankar et al. |
| 2005/0008625 A1 | 1/2005 | Balint et al. |
| 2005/0037000 A1 | 2/2005 | Stavenhagen et al. |
| 2005/0059051 A1 | 3/2005 | Chen |
| 2005/0079574 A1 | 4/2005 | Bond |
| 2005/0272765 A1 | 12/2005 | Feng et al. |
| 2005/0288502 A1 | 12/2005 | Anderson et al. |
| 2006/0040944 A1 | 2/2006 | Gosselin et al. |
| 2006/0058320 A1 | 3/2006 | Iida et al. |
| 2006/0154930 A1 | 7/2006 | Brown et al. |
| 2006/0178399 A1 | 8/2006 | Nishizawa et al. |
| 2006/0211739 A1 | 9/2006 | Perez-Medrano et al. |
| 2007/0009518 A1 | 1/2007 | Novabrantseva et al. |
| 2007/0010522 A1 | 1/2007 | Vu et al. |
| 2007/0117804 A1 | 5/2007 | Zhao et al. |
| 2007/0202100 A1 | 8/2007 | Wood et al. |
| 2007/0213332 A1 | 9/2007 | Burkamp et al. |
| 2007/0281942 A1 | 12/2007 | Cao et al. |
| 2008/0021026 A1 | 1/2008 | Kahraman |
| 2008/0021217 A1 | 1/2008 | Borchardt et al. |
| 2008/0096892 A1 | 4/2008 | Cheng et al. |
| 2008/0132501 A1 | 6/2008 | Sun et al. |
| 2008/0293739 A1 | 11/2008 | Trede |
| 2008/0311117 A1 | 12/2008 | Collins et al. |
| 2009/0055944 A1 | 2/2009 | Korman et al. |
| 2009/0105277 A1 | 4/2009 | Kadowaki et al. |
| 2009/0110667 A1 | 4/2009 | Mozaffarian et al. |
| 2009/0118301 A1 | 5/2009 | Lu et al. |
| 2009/0163489 A1 | 6/2009 | Booker et al. |
| 2009/0176778 A1 | 7/2009 | Schmitz et al. |
| 2009/0258877 A1 | 10/2009 | Siegel et al. |
| 2009/0274666 A1 | 11/2009 | Chen |
| 2009/0313687 A1 | 12/2009 | Popp et al. |
| 2010/0105733 A1 | 4/2010 | Lyttle et al. |
| 2010/0160355 A1 | 6/2010 | DeGoey et al. |
| 2010/0168138 A1 | 7/2010 | DeGoey et al. |
| 2010/0261679 A1 | 10/2010 | Sutton et al. |
| 2010/0292232 A1 | 11/2010 | Elleder et al. |
| 2011/0105457 A1 | 5/2011 | Taniyama et al. |
| 2011/0190269 A1 | 8/2011 | Baumann et al. |
| 2011/0201649 A1 | 8/2011 | Matsuzaki et al. |
| 2011/0206607 A1 | 8/2011 | Olsson et al. |
| 2011/0288074 A1 | 11/2011 | Schann et al. |
| 2011/0300136 A1 | 12/2011 | Benyunes |
| 2012/0021519 A1 | 1/2012 | Ichida et al. |
| 2012/0083498 A1 | 4/2012 | Kashanchi |
| 2012/0121540 A1 | 5/2012 | Schmitz et al. |
| 2012/0232089 A1 | 9/2012 | Kase et al. |
| 2013/0225568 A1 | 8/2013 | Burgdorf et al. |
| 2015/0197503 A1 | 7/2015 | Russo et al. |
| 2016/0009711 A1 | 1/2016 | Wu et al. |
| 2016/0046648 A1 | 2/2016 | Petrukhin et al. |
| 2016/0096835 A1 | 4/2016 | Cole et al. |
| 2016/0129108 A1 | 5/2016 | Sachsenmeier et al. |
| 2016/0168154 A1 | 6/2016 | Marineau et al. |
| 2016/0354375 A1 | 12/2016 | Sheridan et al. |
| 2017/0107216 A1 | 4/2017 | Wu et al. |
| 2017/0114077 A1 | 4/2017 | Frideman et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0009816 A1 | 1/2018 | Buesking et al. |
| 2018/0009899 A1 | 1/2018 | Griffin et al. |
| 2018/0016260 A1 | 1/2018 | Yu et al. |
| 2018/0030144 A1 | 2/2018 | Chanteux et al. |
| 2018/0057486 A1 | 3/2018 | Wu et al. |
| 2018/0177784 A1 | 6/2018 | Wu et al. |
| 2018/0177870 A1 | 6/2018 | Lu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0237536 A1 | 8/2018 | Perrot et al. |
| 2018/0258043 A1 | 9/2018 | Gunzner-Toste et al. |
| 2018/0264107 A1 | 9/2018 | Curd et al. |
| 2018/0273519 A1 | 9/2018 | Wu et al. |
| 2019/0031766 A1 | 1/2019 | Prinz et al. |
| 2019/0055250 A1 | 2/2019 | He et al. |
| 2019/0062345 A1 | 2/2019 | Xiao et al. |
| 2019/0076433 A1 | 3/2019 | Willingham et al. |
| 2019/0077873 A1 | 3/2019 | Griffin et al. |
| 2019/0092784 A1 | 3/2019 | Wu et al. |
| 2019/0144439 A1 | 5/2019 | Wu et al. |
| 2019/0202824 A1 | 7/2019 | Wu et al. |
| 2019/0225601 A1 | 7/2019 | Wu et al. |
| 2019/0225703 A1 | 7/2019 | Caux et al. |
| 2019/0256598 A1 | 8/2019 | Wang et al. |

(56) References Cited

U.S. PATENT DOCUMENTS

| | | |
|---|---|---|
| 2019/0292188 A1 | 9/2019 | Wang et al. |
| 2019/0300524 A1 | 10/2019 | Wu et al. |
| 2019/0337957 A1 | 11/2019 | Wang et al. |
| 2019/0345170 A1 | 11/2019 | Wu et al. |
| 2019/0375752 A1 | 12/2019 | Wang et al. |
| 2020/0031835 A1 | 1/2020 | Wang et al. |
| 2020/0095322 A1 | 3/2020 | Cornfeld et al. |
| 2020/0102315 A1 | 4/2020 | Buesking et al. |
| 2020/0172533 A1 | 6/2020 | Wu et al. |
| 2020/0172541 A1 | 6/2020 | Li et al. |
| 2020/0181126 A1 | 6/2020 | Lu et al. |
| 2020/0255424 A1 | 8/2020 | Wu et al. |
| 2020/0270244 A1 | 8/2020 | Huang et al. |
| 2020/0277309 A1 | 9/2020 | Wu et al. |
| 2020/0283423 A1 | 9/2020 | Yu et al. |
| 2020/0325115 A1 | 10/2020 | Wu et al. |
| 2020/0397893 A1 | 12/2020 | Liu et al. |
| 2020/0407357 A1 | 12/2020 | Lajkiewicz et al. |
| 2021/0002276 A1 | 1/2021 | Wu et al. |
| 2021/0017164 A1 | 1/2021 | Lu et al. |
| 2021/0017175 A1 | 1/2021 | Li et al. |
| 2021/0040090 A1 | 2/2021 | Jia et al. |
| 2021/0061809 A1 | 3/2021 | Han et al. |
| 2021/0094976 A1 | 4/2021 | Li et al. |
| 2021/0107900 A1 | 4/2021 | Wu et al. |
| 2021/0115025 A1 | 4/2021 | Yu et al. |
| 2021/0115068 A1 | 4/2021 | Wu et al. |
| 2021/0139511 A1 | 5/2021 | Jia et al. |
| 2021/0205311 A1 | 7/2021 | Wang et al. |
| 2021/0221819 A1 | 7/2021 | Li et al. |
| 2021/0261555 A1 | 8/2021 | Wang et al. |
| 2022/0135570 A1 | 5/2022 | Wang et al. |
| 2022/0144830 A1 | 5/2022 | Zhou et al. |
| 2022/0144831 A1 | 5/2022 | Wang et al. |
| 2022/0144832 A1 | 5/2022 | Jia et al. |
| 2022/0233529 A1 | 7/2022 | Wang et al. |

FOREIGN PATENT DOCUMENTS

| | | | | |
|---|---|---|---|---|
| CL | 201900486 | 6/2019 | | |
| CL | 202101116 | 11/2021 | | |
| CN | WO2018184590 | * 4/2018 | ........... | C07D 487/04 |
| CN | 109535161 | 3/2019 | | |
| DE | 102006041292 | 3/2008 | | |
| EP | 404097 | 12/1990 | | |
| EP | 0976753 | 2/2000 | | |
| EP | 1448564 | 8/2004 | | |
| EP | 1453835 | 9/2004 | | |
| EP | 1544200 | 6/2005 | | |
| EP | 1902716 | 3/2008 | | |
| EP | 1905418 | 4/2008 | | |
| EP | 2155747 | 2/2010 | | |
| JP | 2007039633 | 2/2007 | | |
| WO | WO 90/07861 | 7/1990 | | |
| WO | WO 93/11161 | 6/1993 | | |
| WO | WO 98/03511 | 1/1998 | | |
| WO | WO 98/42711 | 10/1998 | | |
| WO | WO 01/14557 | 3/2001 | | |
| WO | WO 2001/017999 | 3/2001 | | |
| WO | WO 01/39722 | 6/2001 | | |
| WO | WO 2001/080884 | 11/2001 | | |
| WO | WO 2001/092264 | 12/2001 | | |
| WO | WO 2002/000196 | 1/2002 | | |
| WO | WO 02/086083 | 10/2002 | | |
| WO | WO 03/042402 | 5/2003 | | |
| WO | WO 2003/044021 | 5/2003 | | |
| WO | WO 2003/048164 | 6/2003 | | |
| WO | WO 2003/062236 | 7/2003 | | |
| WO | WO 2004/079013 | 9/2004 | | |
| WO | WO 2004/092173 | 10/2004 | | |
| WO | WO 2004/092177 | 10/2004 | | |
| WO | WO 2005/003175 | 1/2005 | | |
| WO | WO 2005/016892 | 2/2005 | | |
| WO | WO 2005/018572 | 3/2005 | | |
| WO | WO 2003/068776 | 6/2005 | | |
| WO | WO 2006/129626 | 12/2006 | | |
| WO | WO 2007/011759 | 1/2007 | | |
| WO | WO 2007/028051 | 3/2007 | | |
| WO | WO 2007/058942 | 5/2007 | | |
| WO | WO 2007/150025 | 12/2007 | | |
| WO | WO 2008/011560 | 1/2008 | | |
| WO | WO 2008/037607 | 4/2008 | | |
| WO | WO 2008/056176 | 5/2008 | | |
| WO | WO 2008/113469 | 9/2008 | | |
| WO | WO 2008/149168 | 12/2008 | | |
| WO | WO 2008/156712 | 12/2008 | | |
| WO | WO 2009/019505 | 2/2009 | | |
| WO | WO 2009/023179 | 2/2009 | | |
| WO | WO 2009/047514 | 4/2009 | | |
| WO | WO 2009/085185 | 7/2009 | | |
| WO | WO 2009/114870 | 9/2009 | | |
| WO | WO 2009/117421 | 9/2009 | | |
| WO | WO 2009/117734 | 9/2009 | | |
| WO | WO 2010/036959 | 4/2010 | | |
| WO | WO 2010/075074 | 7/2010 | | |
| WO | WO 2010/089411 | 8/2010 | | |
| WO | WO 2010/104306 | 9/2010 | | |
| WO | WO 2011/019780 | 2/2011 | | |
| WO | WO 2011/022439 | 2/2011 | | |
| WO | WO 2011/060207 | 5/2011 | | |
| WO | WO 2011/066342 | 6/2011 | | |
| WO | WO 2011/078143 | 6/2011 | | |
| WO | WO 2011/082400 | 7/2011 | | |
| WO | WO 2011/089004 | 7/2011 | | |
| WO | WO 2011/101409 | 8/2011 | | |
| WO | WO 2011/112766 | 9/2011 | | |
| WO | WO 2011/135303 | 11/2011 | | |
| WO | WO 2011/153588 | 12/2011 | | |
| WO | WO 2011/159877 | 12/2011 | | |
| WO | WO 2011/161699 | 12/2011 | | |
| WO | WO 2012/061156 | 5/2012 | | |
| WO | WO 2012/116237 | 8/2012 | | |
| WO | WO 2012/129344 | 9/2012 | | |
| WO | WO 2012/147890 | 11/2012 | | |
| WO | WO 2013/026516 | 2/2013 | | |
| WO | WO 2013/087943 | 6/2013 | | |
| WO | WO 2013/106254 | 7/2013 | | |
| WO | WO 2014/078479 | 5/2014 | | |
| WO | WO 2014/126580 | 8/2014 | | |
| WO | WO 2014/153424 | 9/2014 | | |
| WO | WO 2016/007235 | 1/2016 | | |
| WO | WO 2016/007722 | 1/2016 | | |
| WO | WO 2016/057522 | 4/2016 | | |
| WO | WO 2016/075099 | 5/2016 | | |
| WO | WO 2016/144703 | 9/2016 | | |
| WO | WO 2016/161282 | 10/2016 | | |
| WO | WO 2017/019846 | 2/2017 | | |
| WO | WO 2017/070089 | 4/2017 | | |
| WO | WO 2017/087777 | 5/2017 | | |
| WO | WO 2017/100670 | 6/2017 | | |
| WO | WO 2017/106634 | 6/2017 | | |
| WO | WO 2017/112730 | 6/2017 | | |
| WO | WO 2016/129684 | 11/2017 | | |
| WO | WO 2017/192961 | 11/2017 | | |
| WO | WO 2017/205464 | 11/2017 | | |
| WO | WO 2017/222976 | 12/2017 | | |
| WO | WO 2018/004478 | 1/2018 | | |
| WO | WO 2018/013789 | 1/2018 | | |
| WO | WO 2018/110555 | 6/2018 | | |
| WO | WO 2018/119221 | 6/2018 | | |
| WO | WO 2018/119224 | 6/2018 | | |
| WO | WO 2018/119236 | 6/2018 | | |
| WO | WO 2018/119263 | 6/2018 | | |
| WO | WO 2018/119266 | 6/2018 | | |
| WO | WO 2018/119286 | 6/2018 | | |
| WO | WO 2018/136265 | 7/2018 | | |
| WO | WO 2018/137598 | 8/2018 | | |
| WO | WO 2018/166493 | 9/2018 | | |
| WO | WO 2018/184590 | 10/2018 | | |
| WO | WO 2018/187512 | 10/2018 | | |
| WO | WO 2018/215535 | 11/2018 | | |
| WO | WO 2018/226976 | 12/2018 | | |
| WO | WO 2018/237173 | 12/2018 | | |
| WO | WO 2019/002606 | 1/2019 | | |

(56) References Cited

FOREIGN PATENT DOCUMENTS

| WO | WO 2019/081353 | 5/2019 |
|---|---|---|
| WO | WO 2019/099838 | 5/2019 |
| WO | WO 2019/152678 | 8/2019 |
| WO | WO 2019/152687 | 8/2019 |
| WO | WO 2019/159120 | 8/2019 |
| WO | WO 2019/168847 | 9/2019 |
| WO | WO 2019/170131 | 9/2019 |
| WO | WO 2019/173291 | 9/2019 |
| WO | WO 2019/173692 | 9/2019 |
| WO | WO 2019/191707 | 10/2019 |
| WO | WO 2019/200256 | 10/2019 |
| WO | WO 2019/217821 | 11/2019 |
| WO | WO 2019/222677 | 11/2019 |
| WO | WO 2019/246110 | 12/2019 |
| WO | WO 2020/010197 | 1/2020 |
| WO | WO 2020/035424 | 2/2020 |
| WO | WO 2020/035425 | 2/2020 |
| WO | WO 2020/038983 | 2/2020 |
| WO | WO 2020/039051 | 2/2020 |
| WO | WO 2020/052631 | 3/2020 |
| WO | WO 2020/069027 | 4/2020 |
| WO | WO 2020/073945 | 4/2020 |
| WO | WO 2020/106560 | 5/2020 |
| WO | WO 2020/108613 | 6/2020 |
| WO | WO 2020/159905 | 8/2020 |
| WO | WO 2021/041360 | 3/2021 |
| WO | WO 2021/138467 | 7/2022 |

OTHER PUBLICATIONS

Better et al., "*Escherichia coli* secretion of an active chimeric antibody fragment," Science, 1988, 240:1041-1043.

Better et al., "Expression of engineered antibodies and antibody fragments in microorganisms," Methods in Enzymology, 1989, 178:476-496.

Bird et al., "Single chain antibody variable regions," TIBTECH, 1991, 9:132-137.

Blank et al, "PD-L1/B7H-1 inhibits the effector phase of tumor rejection by T cell receptor (TCR) transgenic CD8+ T cells," Cancer Res., 2004, 64(3):1140-1145.

Blank et al., "Contribution of the PD-L1/PD-1 pathway to T-cell exhaustion: an update on implications for chronic infections and tumor evasion," Immunol Immunother., 2006, 56(5):739-745.

Boyd et al., "Some Practical Considerations and Applications of the National Cancer Institute In Vitro Anticancer Drug Discovery Screen," Drug Development Research, 1995, 34(2):91-109.

Braganhol et al., "Ecto-5'-nucleotidase/CD73 inhibition by quercetin in the human U138MG glioma cell line," Biochim. Biophys. Acta., 2007, 1770(9):1352-1359.

Carter et al., "High level *Escherichia coli* expression and production of a bivalent humanized antibody fragment," Bio/Technology, 1992, 10:163-167.

Carter et al., "Humanization of an anti-p185HER2 antibody for human cancer therapy," PNAS, 1992, 89(10):4285-4289.

Carter et al., "PD-1:PD-L inhibitory pathway affects both CD4(+) and CD8(+) T cells and is overcome by IL-2," Eur J Immunol., 2002, 32(3):634-643.

CAS Reg. No. 1374853-91-4, "Pembrolizumab," retrieved on Aug. 12, 2021, retrieved from URL <https://chem.nlm.nih.gov/chemidplus/rn/1374853-91-4>, 1 page.

CAS Reg. No. 1380723-44-3, "Atezolizumab," retrieved on Aug. 12, 2021, retrieved from URL <https://chem.nlm.nih.gov/chemidplus/rn/1380723-44-3>, 1 page.

Chothia et al., "Structural repertoire of the human VH segments," J Mol Bio., 1992, 227:799-817.

Co et al., "A humanized antibody specific for the platelet integrin gpIIb/IIIa," J Immunol., 1994, 152:2968-2976.

Cook et al., "The human immunoglobulin VH repertoire," Immunol Today., 1995, 16(5):237-242.

Davies et al., "Single antibody domains as small recognition units: design and in vitro antigen selection of camelized, human VH domains with improved protein stability," Protein Eng., 1996, 9(6):531-537.

DiRenzo et al., "AB928 a Dual Antagonist of the A2aR and A2bR Adenosine Receptors, Relieves Adenosine-Mediated Immuno Suppression," Arcus Biosciences Poster, 2018, 1 page.

Dorai et al., "Aglycosylated Chimeric Mouse/Human IgG1 Antibody Retains Some Effector Function," Hybridoma, 1991, 10(2):211-217.

Eisenhauer et al., "New response evaluation criteria in solid tumours: revised RECIST guideline (version 1.1)," Eur J Cancer., 2009, 45(2):228-247.

Eurasian Office Action in Eurasian Application No. 202190204, dated Mar. 11, 2022, 9 pages (with English translation).

Flies et al., "The new B7s: playing a pivotal role in tumor immunity," J Immunother., 2007, 30(3):251-260.

Freeman et al., "Engagement of the PD-1 immunoinhibitory receptor by a novel B7 family member leads to negative regulation of lymphocyte activation," J Exp Med., 2000, 192(7):1027-1034.

Friend et al., "Phase I study of an engineered aglycosylated humanized CD3 antibody in renal transplant rejection," Transplantation, 1999, 68:1632-1637.

GenBank Accession No. NP_000667, "adenosine receptor A2b [*Homo sapiens*]," dated Apr. 22, 2022, 4 pages.

GenBank Accession No. NP_001265428, "adenosine receptor A2a [*Homo sapiens*]," dated May 3, 2022, 4 pages.

GenBank Accession No. NP_002517, "5'-nucleotidase isoform 1 preproprotein [*Homo sapiens*]," dated Apr. 17, 2022, 3 pages.

Genbank Accession No. NP_005009, "programmed cell death protein 1 precursor [*Homo sapiens*]," dated Aug. 2, 2021, 4 pages.

GenBank Accession No. NP_035981, "5'-nucleotidase preproprotein [Mus musculus]" dated May 3, 2022, 4 pages.

Georgian Office Action in Georgian Application No. AP2019 15551, dated Dec. 2, 2021, 4 pages.

Georgian Office Action in Georgian Application No. AP 2019 15761, dated Jan. 11, 2022, 4 pages.

Graddis et al., "Designing proteins that work using recombinant technologies," Curr Pharm Biotechnol., 2002, 3:285-297.

Greene and Wuts, "Protective Groups in Organic Synthesis," Wiley & Sons, Inc., New York, 1999, 3rd Ed., 799 pages.

Hand et al., "Comparative biological properties of a recombinant chimeric anti-carcinoma mAb and a recombinant aglycosylated variant," Cancer Immunol Immunother., 1992, 35:165-174.

Harmsen et al., "Properties, production, and applications of camelid single-domain antibody fragments," Appl Microbiol Biotechnol., 2007, 77(1):13-22.

Hobbs et al., "Interaction of aglycosyl immunoglobulins with the IgG Fc transport receptor from neonatal rat gut: comparison of deglycosylation by tunicamycin treatment and genetic engineering," Mol Immunol., 1992, 29(7-8):949-956.

Holliger et al., ""Diabodies": small bivalent and bispecific antibody fragments," Proc Natl Acad Sci USA., 1993, 90:6444-6448.

Huang et al., "The prognostic significance of PD-L1 in bladder cancer," Oncol Rep., 2015, 33(6):3075-84.

Hudson et al., "High avidity scFv multimers; diabodies and triabodies," J Immunol Methods., 1999, 231:177-189.

Huston et al., "Protein engineering of antibody binding sites: recovery of specific activity in an anti-digoxin single-chain Fv analogue produced in *Escherichia coli*," Proc Natl Acad Sci USA., 1988, 85:5879-5883.

Indian Office Action in Indian Patent Application No. 202017041726, dated Feb. 25, 2022, 7 pages.

International Preliminary Report on Patentability in International Application No. PCT/US2020/047714, dated Mar. 10, 2022, 8 pages.

International Search Report and Written Opinion in International Application No. PCT/US2020/067593, dated May 6, 2021, 20 pages.

Isaacs et al., "Therapy with monoclonal antibodies. An in vivo model for the assessment of therapeutic potential," J Immunol., 1992, 148:3062-3071.

Ishida et al., "Induced expression of PD-1, a novel member of the immunoglobulin gene superfamily, upon programmed cell death," EMBO J., 1992, 11(11):3887-3895.

(56) References Cited

OTHER PUBLICATIONS

Iwai et al., "Involvement of PD-L1 on tumor cells in the escape from host immune system and tumor immunotherapy by PD-L1 blockade," PNAS., 2002, 99(19):12293-12297.
Ji et al., "Modified toxicity probability interval design: a safer and more reliable method than the 3+ 3 design for practical phase I trials," J Clin Oncol., 2013, 31:1785-1791.
Ji et al., "A modified toxicity probability interval method for dose-finding trials," Clin Trials., 2010, 7:653-663.
Kaufman and Sharp "Amplification and expression of sequences cotransfected with a modular dihydrofolate reductase complementary dna gene," Mol Biol., 1982, 159:601-621.
Knapp et al., "Crystal structure of the human ecto-5'-nucleotidase (CD73): insights into the regulation of purinergic signaling," Structure, 2012, 20(12):2161-2173.
Komiyama et al., "IL-17 plays an important role in the development of experimental autoimmune encephalomyelitis," J Immunol., 2006, 177:566-73.
Lamoyi, "Preparation of F(ab')2 fragments from mouse IgG of various subclasses," Methods in Enzymology, 1989, 121:652-663.
Latchman et al., "PD-L2 is a second ligand for PD-1 and inhibits T cell activation," Nat Immunol., 2001, 2(3):261-268.
Leatherbarrow et al., "The effect of aglycosylation on the binding of mouse IgG to staphylococcal protein A," FEBS Lett., Dec. 12, 1983, 164(2):227-230.
Leatherbarrow et al., "Effector functions of a monoclonal aglycosylated mouse IgG2a: Binding and activation of complement component C1 and interaction with human monocyte Fc receptor," Mol Immunol., 1985, 22(4):407-415.
Lei et al., "Characterization of the Erwinia carotovora peIB gene and its product pectate lyase," J Bacteriol., 1987, 169:4379-4383.
Leone et al., "Inhibition of the adenosine A2a receptor modulates expression of T cell coinhibitory receptors and improves effector function for enhanced checkpoint blockade and ACT in murine cancer models," Cancer Immunol Immuother., Aug. 2018, 67(8):1271-1284.
Marshak et al., "Strategies for Protein Purification and Characterization: A Laboratory Course Manual," Ed Daniel R. Cold Spring Harbor Laboratory Press, 1996, 3(2/3):4 pages (Abstract and Table of Contents Only).
Martin-Orozco et al., "Inhibitory costimulation and anti-tumor immunity," Semin Cancer Biol., 2007, 17(4):288-298.
Millstein et al., "Hybrid hybridomas and their use in immunohistochemistry," Nature, 1983, 305(5934):537-539.
Mizushima et al., "pEF-BOS, a powerful mammalian expression vector," Nucleic Acids Res., 1990, 18:5322.
Moller et al., "Intracellular activation of interferon regulatory factor-1 by nanobodies to the multifunctional (Mf1) domain," J Biol Chem., 2010, 285(49):38348-38361.
Morrison, "Transfectomas provide novel chimeric antibodies," Science, 1985, 229:1202-1207.
Mosely et al., "Rational Selection of Syngeneic Preclinical Tumor Models for Immunotherapeutic Drug Discovery," Cancer Immunol Res., Jan. 2017, 5(1):29-41.
Mulligan et al., "Synthesis of rabbit beta-globin in cultured monkey kidney cells following infection with a SV40 beta-globin recombinant genome," Nature, 1979, 277:108-114.
Niemeläet al., "IFN-alpha induced adenosine production on the endothelium: a mechanism mediated by CD73 (ecto-5'-nucleotidase) up-regulation," J Immunol., 2004, 172:1646-1653.
Nishimura et al., "Development of lupus-like autoimmune diseases by disruption of the PD-1 gene encoding an ITIM motif-carrying immunoreceptor," Immunity, 1999, 11:141-151.
Nishimura et al., "Autoimmune dilated cardiomyopathy in PD-1 receptor-deficient mice," Science, 2001, 291(5502):319-322.
Nishimura et al., "Facilitation of beta selection and modification of positive selection in the thymus of PD-1-deficient mice," J Exp Med., 2000, 191:891-898.

Nose and Wigzell, "Biological significance of carbohydrate chains on monoclonal antibodies," Proc Natl Acad Sci USA., Nov. 1983, 80(21):6632-6636.
Parry et al., "CTLA-4 and PD-1 Receptors Inhibit T-Cell Activation by Distinct Mechanisms," Mol Cell Biol., 2005, 9543-9553.
Pluckthun, "Antibodies from *Escherichia coli*," The Pharmacology of Monoclonal Antibodies, 1994, 113:269-315 (Abstract Only).
Pluckthun and Skerra, "Expression of Functional Antibody Fv and Fab Fragments in *Escherichia coli*," Methods in Enzymology, 1989, 178:496-515.
Postow et al., "Immune Checkpoint Blockade in Cancer Therapy," J Clinical Oncology., Jun. 10, 2015, 33(17):1974-1982.
Powers et al., "Expression of single-chain Fv-Fc fusions in Pichia pastoris," J Immunol Methods., 2001, 251:123-135.
Raju "Glycosylation Variations with Expression Systems and Their Impact on Biological Activity of Therapeutic Immunoglobulins," BioProcess International, Apr. 2003, pp. 44-53.
Rousseaux et al., "Optimal conditions for the preparation of proteolytic fragments from monoclonal IgG of different rat IgG subclasses," Methods in Enzymology, 1989, 121:663-669.
Sabatier et al., "Prognostic and predictive value of PDL1 expression in breast cancer," Oncotarget, 2015, 6(7):5449-5464.
Sadej et al., "Ecto-5'-nucleotidase (eN, CD73) is coexpressed with metastasis promoting antigens in human melanoma cells," Nucleosides Nucleotides Nucleic Acids, 2006, 25(9-11):1119-1123.
Salmi and Jalkanen, "Host CD73 impairs anti-tumor immunity," Oncoimmunology, Mar. 1, 2012, 1(2):247-248.
Sharpe et al, "The function of programmed cell death 1 and its ligands in regulating autoimmunity and infection," Nat Immunol., 2007, 8:239-245.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem., Mar. 2, 2001, 276(9):6591-6604.
Shields et al., "Lack of fucose on human IgG1 N-linked oligosaccharide improves binding to human Fcgamma RIII and antibody-dependent cellular toxicity," J Biol Chem., 2002; 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., 2003, 278(5):3466-3473.
Stagg and Smyth, "Extracellular adenosine triphosphate and adenosine in cancer," Oncogene, 2010, 29(39):5346-5358.
Stagg, "The double-edge sword effect of anti-CD73 cancer therapy," OncoImmunology, 2012, 1:217-218.
Tao, "Studies of aglycosylated chimeric mouse-human IgG. Role of carbohydrate in the structure and effector functions mediated by the human IgG constant region," J Immunol., Oct. 15, 1989., 143(8):2595-2601 (Abstract Only).
Tempest et al., "Reshaping a human monoclonal antibody to inhibit human respiratory syncytial virus infection in vivo," Biotechnology, 1991, 9:266-271.
Tomlinson et al., "The repertoire of human germline VH sequences reveals about fifty groups of VH segments with different hypervariable loops," J Mol Biol., 1992, 227:776-798.
Tomlinson et al., "The structural repertoire of the human V kappa domain," EMBO J., 1995, 14:4628-4638.
Umana et al., "Engineered glycoforms of an antineuroblastoma IgG1 with optimized antibody-dependent cellular cytotoxic activity," Nat Biotechnol., Feb. 1999, 17(2):176-180.
Urlaub and Chasin "Isolation of Chinese hamster cell mutants deficient in dihydrofolate reductase activity," Proc Natl Acad Sci USA., 1980, 77:4216-4220.
Vigano et al., "Targeting Adenosine in Cancer Immunotherapy to Enhance T-Cell Function," Front Immunol., Jun. 6, 2019, 2019, 10:925.
Walker et al., "Aglycosylation of human IgG1 and IgG3 monoclonal antibodies can eliminate recognition by human cells expressing FcγRI and/or FcγRII receptors," Biochem J., 1989, 259:347-353.

(56) References Cited

OTHER PUBLICATIONS

Wang et al., "The prognostic value of PD-L1 expression for non-small cell lung cancer patients: a meta-analysis," Eur J Surg Oncol., 2015, 41(4):450-456.
Ward and Ghetie, "The effector functions of immunoglobulins: implications for therapy," Therapeutic Immunology, 1995, 2:77-94.
Ward et al., "Binding activities of a repertoire of single immunoglobulin variable domains secreted from *Escherichia coli*," Nature, 1989, 341:544-546.
Willingham et al., "A2AR Antagonism with CPI-444 Induces Antitumor Responses and Augments Efficacy to Anti-PD-(L)1 and Anti-CTLA-4 in Preclinical Models," Cancer Immunol Res., Oct. 2018, 6(10):1136-1149.
Wright & Morrison, "Effect of glycosylation on antibody function: implications for genetic engineering," Trends in Biotechnology, Jan. 1997, 15(1):26-32.
Yamazaki et al., "Expression of programmed death 1 ligands by murine T cells and APC," J Immunol., 2002, 169:5538-5545.
Zhang, "CD73 promotes tumor growth and metastasis," OncoImmunology, 2012, 1(1):67-70.
Zhang, "CD73: a novel target for cancer immunotherapy," Cancer Res., 2010, 70:6407-6411.
Hackam, et al., "Translation of Research Evidence From Animals to Humans," JAMA, Oct. 2006, 296(14):1731-1732.
Jordan, "Tamoxifen: a most unlikely pioneering medicine," Nature Reviews: Drug Discovery, 2003, 2:205-213.
International Preliminary Report on Patentability in International Application No. PCT/US2019/032948, dated Nov. 24, 2020, 9 pages.
Allard et al., "Immunosuppressive activities of adenosine in cancer," Curr Opin in Pharma., 2016, 29:7-16.
Antonioli et al., "Immunity, Inflammation and Cancer: a leading role for adenosine," Nature Reviews Cancer, Nov. 14, 2013, 13:842-857.
Baraldi et al., "Adenosine receptor antagonists: translating medicinal chemistry and pharmacology into clinical utility," Chem. Rev., Jan. 2008, 108(1):238-263.
Beavis et al., "Blockade of A2A receptors potently suppresses the metastasis of CD73+ tumors," Proc Natl Acad Sci. USA, Sep. 3, 2013, 110(36):14711-14716.
Beavis et al., "Targeting the adenosine 2A receptor enhances chimeric antigen receptor T cell efficacy," Journ. of Clin Invest., Mar. 2017, 127(3):929-941.
Berge et al., "Pharmaceutical Salts," Journal of Pharmaceutical Science, 1977, vol. 66, 21 pages.
Borrmann et al., "1-alkyl-8-(piperazine-1-sulfonyl)phenylxanthines: development and characterization of adenosine A2B receptor antagonists and a new radioligand with subnanomolar affinity and subtype specificity," J. Med. Chem., 2009, 52(13):3994-4006.
Carlsson et al., "Structure-based discovery of A2A adenosine receptor ligands," J. Med. Chem., 2010, 53(9):3748-3755.
Cekic et al., "Adenosine A2B receptor blockade slows growth of bladder and breast tumors," J Immunol, Jan. 1, 2012, 188(1):198-205.
Collins et al., "The novel adenosine A2A antagonist Lu AA47070 reverses the motor and motivational effects produced by dopamine D2 receptor blockade," Pharmacol. Biochem. Behav., Jan. 2012, 100(3)498-505.
Dowling et al., "Synthesis of [1,2,4]triazolo[1,5-a]pyrazines as adenosine A2A receptor antagonists," Bioorganic & Medicinal Chemistry Letters., Nov. 1, 2005, 15(21):4809-4813.
Eisenstein et al., "The Many Faces of the A2b Adenosine Receptor in Cardiovascular and Metabolic Diseases," J Cell Physiol., Dec. 2015, 230(12):2891-2897.
Figler et al. "Links Between Insulin Resistance, Adenosine A2B Receptors, and Inflammatory Markers in Mice and Humans," Diabetes, Feb. 2011, 60(2):669-679.
Globenewswire.com [website], "Corvus Pharmaceuticals Announces Interim Results from Ongoing Phase 1/lb Study Demonstrating Safety and Clinical Activity of Lead Checkpoint Inhibitor CPI-444 in Patients with Advanced Cancers," Apr. 4, 2017, [retrieved on Apr. 4, 2019] retrieved from URL <https://globenewswire.com/news-release/2017/04/04/954192/0/en/Corvus-Pharmaceuticals-Announces-Interim-Results-from-Ongoing-Phase-1-1b-Study-Demonstrating-Safety-and-Clinical-Activity-of-Lead-Checkpoint-Inhibitor-CPI-444-in-Patients-with-Adva.html>, 7 pages.
Hasko et al., "Shaping of monocyte and macrophage function by adenosine receptors," Pharmacol. Ther., Feb. 2007, 113(2):264-275.
Iannone et al., "Adenosine limits the therapeutic effectiveness of anti-CTLA4 mAb in a mouse melanoma model," Am. J. Cancer Res. 2014, 4(2):172-181.
Iannone et al., "Blockade of A2b Adenosine Receptor Reduces Tumor Growth and Immune Suppression Mediated by Myeloid-Derived Suppressor Cells in a Mouse Model of Melanoma," Neoplasia, 2013, 15:1400-1410.
International Search Report and Written Opinion in International Application No. PCT/US2019/019582, dated Jul. 18, 2019, 19 pages.
International Search Report and Written Opinion in International Application No. PCT/US2019/032948, dated Aug. 8, 2019, 15 pages.
International Search Report and Written Opinion in International Application No. PCT/US2019/040496, dated Sep. 17, 2019, 17 pages.
International Search Report and Written Opinion in International Application No. PCT/US2020/015294, dated May 6, 2020, 12 pages.
International Preliminary Report on Patentability in International Application No. PCT/US2019/019582, dated Sep. 3, 2020, 11 pages.
Invitation to Pay Additional Fees in International Application No. PCT/US2019/019582, dated May 20, 2019, 9 pages.
Kerekes et. al., "Aurora kinase inhibitors based on the imidazo[1,2-a]pyrazine core: fluorine and deuterium incorporation improve oral absorption and exposure," J. Med. Chem., Jan. 13, 2011, 54(1):201-210.
Leone et al., "A2aR antagonists: Next generation checkpoint blockade for cancer immunotherapy," Computational and Structural Biotechnology Journal, 2015, 13:365-272.
Livingston et al., "Adenosine, inflammation and asthma—a review," Inflamm. Res., May 2004, 53(5):471-178.
Matsumoto et al., "Alterations in vasoconstrictor responses to the endothelium-derived contracting factor uridine adenosine tetraphosphate are region specific in DOCA-salt hypertensive rats," Pharmacol. Res., Jan. 2012, 65(1):81-90.
Remington's Pharmaceutical Sciences, 17th ed., Mack Publishing Company, Easton, Pa., 1985, p. 1418.
Ryzhov et al., "Host A(2B) adenosine receptors promote carcinoma growth," Neoplasia, 2008, 10(9):987-995.
Sachdeva et al., "Adenosine and its receptors as therapeutic targets: An overview," Saudi Pharma Journ., Jun. 23, 2012, 21(3):245-253.
Sattin et al., "The effect of adenosine and adenine nucleotides on the cyclic adenosine 3', 5'-phosphate content of guinea pig cerebral cortex slices," Mol. Pharmacol., Jan. 1970, 6(1):13-23.
STN Search Report, 2017-078, dated Jul. 19, 2017, 73 pages.
STN Search Report, 2017-133, dated Nov. 22, 2017, 140 pages.
Tamura et al., "A general synthesis of s-triazolo[1,5-x] diazines," J Hetero Chem., Feb. 1975, 12(1):107-110.
Tautenhahn et al. "Purinergic modulation of the excitatory synaptic input onto rat striatal neurons," Neuropharmacology, Mar. 2012, 62(4)4756-1766.
Yao et al., "Synthesis of alkyne derivatives of a novel triazolopyrazine as A2A adenosine receptor antagonists," Bioorganic & Medicinal Chemistry Letters, 2005, 15:511-515.
Chilean Office Action in Chilean Application No. 2198-2020, dated Oct. 13, 2021, 24 pages.
Eurasian Office Action in Eurasian Application No. 202092016, dated Oct. 18, 2021, 7 pages.
International Preliminary Report on Patentability in International Application No. PCT/US2020/015294, dated Jul. 27, 2021, 7 pages.
Ecuador Opposition in Ecuador Application No. SENADI-2020-60827, dated Apr. 27, 2021, 20 pages.

(56) References Cited

OTHER PUBLICATIONS

International Search Report and Written Opinion in International Application No. PCT/US2020/047714, dated Oct. 29, 2020, 15 pages.
International Preliminary Report on Patentability in International Application No. PCT/US2019/040496, dated Jan. 5, 2021, 9 pages.
Matasi et al., "2-(2-Furanyl)-7-phenyl[1,2,4]triazolo[1,5-c]pyrimidin-5-amine analogs: Highly potent, orally active, adenosine A2A antagonists. Part 1," Bioorganic & Medicinal Chemistry Letters, Aug. 15, 2005, 15(16):3670-3674.
Vietnamese Office Action in Vietnamese Application No. 1-2020-05531, dated Jan. 11, 2021, 2 pages.
Allard et al., "Targeting CD73 Enhances the Antitumor Activity of Anti-PD-1 and Anti-CTLA-4 mAbs," Clin Canc Res., 2013, 19(20):5626-5635.
Chilean Office Action in Chilean Application No. 202100004, dated May 31, 2022, 14 pages.
Ecuador Opposition in Ecuador Application No. SENADI-2020-60827, dated Jun. 2022, 19 pages.
International Preliminary Report on Patentability in International Application No. PCT/US2020/067593, dated Jul. 5, 2022, pages.
International Search Report and Written Opinion in International Application No. PCT/US2021/065472, dated Jun. 15, 2022, 18 pages.
Lawrence et al., "Safety and clinical activity of adenosine A2a receptor (A2aR) antagonist, CPI-444, in anti-PD1/PDL1 treatment-refractory renal cell (RCC) and non-small cell lung cancer (NSCLC) patients," ASCO Annual meetings, 2017, retrieved from URL <https://www.corvuspharma.com/file.cfm/23/docs/FongASC017_3004.FINAL_6.05.2017.pdf>, 17 pages.

\* cited by examiner

IMIDAZOPYRIMIDINES AND TRIAZOLOPYRIMIDINES AS A2A / A2B INHIBITORS

TECHNICAL FIELD

The present invention provides imidazopyrimidine and triazolopyrimidine compounds that modulate the activity of adenosine receptors, such as subtypes A2A and A2B, and are useful in the treatment of diseases related to the activity of adenosine receptors including, for example, cancer, inflammatory diseases, cardiovascular diseases, and neurodegenerative diseases.

BACKGROUND

Adenosine is an extracellular signaling molecule that can modulate immune responses through many immune cell types. Adenosine was first recognized as a physiologic regulator of coronary vascular tone by Drury and Szent-Györgyu (Sachdeva, S. and Gupta, M. *Saudi Pharmaceutical Journal*, 2013, 21, 245-253), however it was not until 1970 that Sattin and Rall showed that adenosine regulates cell function via occupancy of specific receptors on the cell surface (Sattin, A., and Rall, T. W., 1970. *Mol. Pharmacol.* 6, 13-23; Haskó, G., at al., 2007, *Pharmacol. Ther.* 113, 264-275).

Adenosine plays a vital role in various other physiological functions. It is involved in the synthesis of nucleic acids, when linked to three phosphate groups; it forms ATP, the integral component of the cellular energy system. Adenosine can be generated by the enzymatic breakdown of extracellular ATP, or can be also released from injured neurons and glial cells by passing the damaged plasma membrane (Tautenhahn, M. et al. *Neuropharmacology*, 2012, 62, 1756-1766). Adenosine produces various pharmacological effects, both in periphery and in the central nervous system, through an action on specific receptors localized on cell membranes (Matsumoto, T. et al. *Pharmacol. Res.*, 2012, 65, 81-90). Alternative pathways for extracellular adenosine generation have been described. These pathways include the production of adenosine from nicotinamide dinucleotide (NAD) instead of ATP by the concerted action of CD38, CD203a and CD73. CD73-independent production of adenosine can also occur by other phosphates such as alkaline phosphatase or prostate-specific phosphatase.

There are four known subtypes of adenosine receptor in humans including A1, A2A, A2B, and A3 receptors. A1 and A2A are high affinity receptors, whereas A2B and A3 are low affinity receptors. Adenosine and its agonists can act via one or more of these receptors and can modulate the activity of adenylate cyclase, the enzyme responsible for increasing cyclic AMP (cAMP). The different receptors have differential stimulatory and inhibitory effects on this enzyme. Increased intracellular concentrations of cAMP can suppress the activity of immune and inflammatory cells (Livingston, M. et al., *Inflamm. Res.*, 2004, 53, 171-178).

The A2A adenosine receptor can signal in the periphery and the CNS, with agonists explored as anti-inflammatory drugs and antagonists explored for neurodegenerative diseases (Carlsson, J. et al., *J. Med Chem.*, 2010, 53, 3748-3755). In most cell types the A2A subtype inhibits intracellular calcium levels whereas the A2B potentiates diem. The A2A receptor generally appears to inhibit inflammatory response from immune cells (Borrmann, T. et al., *J. Med Chem.*, 2009, 52(13), 3994-4006).

A2B receptors are highly expressed in the gastrointestinal tract, bladder, lung and on mast cells (Antonioli, L. et al., *Nature Reviews Cancer*, 2013, 13, 842-857). The A2B receptor, although structurally closely related to the A2A receptor and able to activate adenylate cyclase is functionally different. It has been postulated that this subtype may utilize signal transduction systems other than adenylate cyclase (Livingston, M. et al., *Inflamm. Res.*, 2004, 53, 171-178). Among all the adenosine receptors, the A2B adenosine receptor is a low affinity receptor that is thought to remain silent under physiological conditions and to be activated in consequence of increased extracellular adenosine levels (Ryzhov, S. et al. *Neoplasia*, 2008, 10, 987-995). Activation of A2B adenosine receptor can stimulate adenylate cyclase and phospholipase C through activation of Gs and Gq proteins, respectively. Coupling to mitogen activated protein kinases has also been described (Borrmann, T. et al., *J. Med. Chem.*, 2009, 52(13), 3994-4006).

In the immune system, engagement of adenosine signaling can be a critical regulatory mechanism that protects tissues against excessive immune reactions. Adenosine can negatively modulate immune responses through many immune cell types, including T-cells, natural-killer cells, macrophages, dendritic cells, mast cells and myeloid-derived suppressor cells (Allard, B. et al. *Current Opinion in Pharmacology*, 2016, 29, 7-16).

In tumors, this pathway is hijacked by tumor microenvironments and sabotages the antitumor capacity of immune system, promoting cancer progression. In the tumor micro-environment, adenosine was mainly generated from extracellular ATP by CD39 and CD73. Multiple cell types can generate adenosine by expressing CD39 and CD73. This is the case for tumor cells, T-effector cells, T-regulatory cells, tumor associated macrophages, myeloid derived suppressive cells (MDSCs), endothelial cells, cancer-associated fibroblast (CAFs) and mesenchymal stromal/stem cells (MSCs). Hypoxia, inflammation and other immune-suppressive signaling in tumor micro-environment can induce expression of CD39, CD73 and subsequent adenosine production. As a result, adenosine level in solid tumors is unusually high compared to normal physiological conditions.

A2A are mostly expressed on lymphoid-derived cells, including T-effector cells, T regulatory cells and nature killing cells. Blocking A2A receptor can prevent downstream immunosuppressive signals that temporarily inactivate T cells. A2B receptors are mainly expressed on monocyte-derived cells including dendritic cells, tumor-associated macrophages, myeloid derived suppressive cells (MDSCs), and mesenchymal stromal/stem cells (MSCs). Blocking A2B receptor in preclinical models can suppress tumor growth, block metastasis, and increase the presentation of tumor antigens.

In terms of safety profile of ADORA2A/ADORA2B (A2A/A2B) blockage, the A2A and A2B receptor knockout mice are all viable, showing no growth abnormalities and are fertile (Allard, B. et al. *Current Opinion in Pharmacology*, 2016, 29, 7-16). A2A KO mice displayed increased levels of pro-inflammatory cytokines only upon challenge with LPS and no evidence of inflammation at baseline (Antonioli, L. et al., *Nature Reviews Cancer*, 2013, 13, 842-857). A2B KO mice exhibited normal platelet, red blood, and white cell counts but increased inflammation at baseline (TNF-alpha, IL-6) in naive A2B KO mice (Antonioli, L. et al., *Nature Reviews Cancer*, 2013, 13, 842-857). Exaggerated production of TNF-alpha and IL-6 was detected following LPS treatment. A2B KO mice also exhibited increased vascular adhesion molecules that mediate inflammation as well leukocyte adhesion/rolling; enhanced mast-cell activation; increased sensitivity to IgE-mediated anaphylaxis and increased vascular leakage and neutrophil influx under hypoxia (Antonioli, L. et al., *Nature Reviews Cancer*, 2013, 13, 842-857).

In summary, there is a need to develop new adenosine receptor selective ligands, such as for subtypes A2A and A2B, for the treatment of diseases such as cancer, inflammatory diseases, cardiovascular diseases and neurodegenerative diseases. This application is directed to this need and others.

SUMMARY

The present invention relates to, inter alia, compounds of Formula (I):

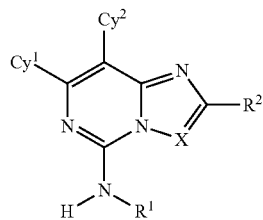

or pharmaceutically acceptable salts thereof, wherein constituent members are defined herein.

The present invention further provides pharmaceutical compositions comprising a compound of Formula (I), or a pharmaceutically acceptable salt thereof, and a pharmaceutically acceptable carrier.

The present invention further provides methods of inhibiting an activity of an adenosine receptor, comprising contacting the receptor with a compound of Formula (I), or a pharmaceutically acceptable salt thereof.

The present invention further provides methods of treating a disease or a disorder associated with abnormal expression of adenosine receptors, comprising administering to said patient a therapeutically effective amount of a compound of Formula (I), or a pharmaceutically acceptable salt thereof.

The present invention further provides a compound of Formula (I), or a pharmaceutically acceptable salt thereof, for use in any of the methods described herein.

The present invention further provides use of a compound of Formula (I), or a pharmaceutically acceptable salt thereof, for the preparation of a medicament for use in any of the methods described herein.

DETAILED DESCRIPTION

Compounds

The present invention relates to, infer alia, compounds of Formula (I):

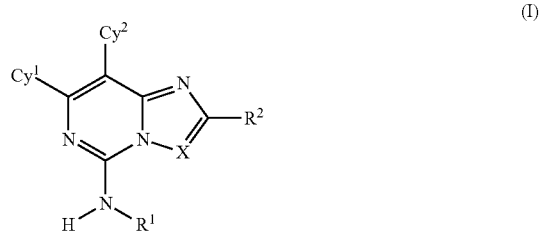

or pharmaceutically acceptable salts thereof; wherein:

X is N or $CR^3$;

$R^1$ is selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, $OR^{a1}$, $C(O)R^{b1}$, $C(O)NR^{c1}R^{d1}$, $C(O)OR^{a1}$, $C(=NR^{c1})R^{b1}$, $C(=NR^{c1})NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^1$ are each optionally substituted with 1, 2, 3, 4, 5, 6, 7, or 8 independently selected $R^B$ substituents;

$R^2$ is selected from H, D, halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^2$ are each optionally substituted with 1, 2, 3, 4, 5, 6, 7, or 8 independently selected $R^C$ substituents;

$R^3$ is selected from H, D, halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a3}$, $SR^{a3}$, $NHOR^{a3}$, $C(O)R^{b3}$, $C(O)NR^{c3}R^{d3}$, $C(O)NR^{c3}(OR^{a3})$, $C(O)OR^{a3}$, $OC(O)R^{b3}$, $OC(O)NR^{c3}R^{d3}$, $NR^{c3}R^{d3}$, $NR^{c3}NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})$ NR$^{c3}$R$^{d3}$, NR$^{c3}$C(=NR$^{e3}$)R$^{b3}$, NR$^{c3}$S(O)NR$^{c3}$R$^{d3}$, NR$^{c3}$S(O)R$^{b3}$, NR$^{c3}$S(O)$_2$R$^{b3}$, NR$^{c3}$S(O)(=NR$^{e3}$)R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, S(O)$_2$NR$^{c3}$R$^{d3}$, OS(O)(=NR$^{e3}$)R$^{b3}$, OS(O)$_2$R$^{b3}$, SF$_5$, P(O)R$^{f3}$R$^{g3}$, OP(O)(OR$^{h3}$)(OR$^{i3}$), P(O)(OR$^{h3}$)(OR$^{i3}$), and BR$^{j3}$R$^{k3}$, wherein the C$_{1-6}$ alkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl- of R$^3$ are each optionally substituted with 1, 2, 3, 4, 5, 6, 7, or 8 independently selected R$^D$ substituents;

Cy$^1$ is C$_{6-14}$ aryl, C$_{3-14}$ cycloalkyl, 5-14 membered heteroaryl, or 4-14 membered heterocycloalkyl, wherein the C$_{6-14}$ aryl, C$_{3-14}$ cycloalkyl, 5-14 membered heteroaryl, or 4-14 membered heterocycloalkyl is optionally substituted with 1, 2, 3, 4, 5, 6, 7, or 8 independently selected R$^E$ substituents;

provided that when X is N and Cy$^1$ is 4-14 membered heterocycloalkyl, then the 4-14 membered heterocycloalkyl of Cy$^1$ is other than unsubstituted morpholinyl;

provided that Cy$^1$ is not pyridin-4-yl optionally substituted with 1, 2, 3, or 4 independently selected R$^E$ substituents;

provided that Cy$^1$ is not pyrimidin-4-yl optionally substituted with 1, 2, or 3, independently selected R$^E$ substituents;

provided that Cy$^1$ is not quinolin-4-yl optionally substituted with 1, 2, 3, 4, 5, or 6 independently selected R$^E$ substituents;

Cy$^2$ is C$_{6-14}$ aryl, C$_{3-14}$ cycloalkyl, 5-14 membered heteroaryl, or 4-14 membered heterocycloalkyl, wherein the C$_{6-14}$ aryl, C$_{3-14}$ cycloalkyl, 5-14 membered heteroaryl, or 4-14 membered heterocycloalkyl is optionally substituted with 1, 2, 3, 4, 5, 6, 7, or 8 independently selected R$^F$ substituents;

each R$^{a1}$, R$^{c1}$, R$^{d1}$, R$^{a2}$, R$^{c2}$, R$^{d2}$, R$^{a3}$, R$^{c3}$, and R$^{d3}$ is independently selected from H, C$_{1-6}$ alkyl, C$_{1-6}$ haloalkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl-, wherein the C$_{1-6}$ alkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$alkyl-, C$_{3-14}$ cycloalkyl-C$_{1-6}$alkyl-, (5-14 membered heteroaryl)-C$_{1-6}$ alkyl-, and (4-14 membered heterocycloalkyl)-C$_{1-6}$ alkyl- of R$^{a1}$, R$^{c1}$, R$^{d1}$, R$^{a2}$, R$^{c2}$, R$^{d2}$, R$^{a3}$, R$^{c3}$, and R$^{d3}$ are each optionally substituted with 1, 2, 3, 4, 5, 6, 7, or 8 independently selected R$^G$ substituents;

or, any R$^{c1}$ and R$^{d1}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected R$^G$ substituents;

or any R$^{c2}$ and R$^{d2}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected R$^G$ substituents;

or any R$^{c3}$ and R$^{d3}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected R$^G$ substituents;

each R$^{b1}$, R$^{b2}$, and R$^{b3}$ is independently selected from H, C$_{1-6}$ alkyl, C$_{1-6}$ haloalkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl-, wherein the C$_{1-6}$ alkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl- of R$^{b1}$, R$^{b2}$, and R$^{b3}$ are each optionally substituted with 1, 2, 3, 4, 5, 6, 7, or 8 independently selected R$^G$ substituents;

each R$^{e1}$, R$^{e2}$, and R$^{e3}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl-;

each R$^{f2}$, R$^{g2}$, R$^{f3}$, and R$^{g3}$ is independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl-;

each R$^{h2}$, R$^{i2}$, R$^{h2}$, and R$^{i3}$ is independently selected from H, C$_{1-6}$ alkyl, C$_{1-6}$ haloalkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl-;

each R$^{j2}$, R$^{k2}$, R$^{j3}$, and R$^{k3}$ is independently selected from OH, C$_{1-6}$alkoxy, and C$_{1-6}$ haloalkoxy;

or any R$^{j2}$ and R$^{k2}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$haloalkyl;

or any R$^{j3}$ and R$^{k3}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$haloalkyl;

each R$^B$, R$^C$, R$^D$, R$^E$, R$^F$, and R$^G$ is independently selected from D, halo, oxo, C$_{1-6}$ alkyl, C$_{1-6}$ haloalkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, (4-14 membered heterocycloalkyl)-C$_{1-6}$ alkyl-, CN, NO$_2$, OR$^{a4}$, SR$^{a4}$, NHOR$^{a4}$, C(O)R$^{b4}$, C(O)NR$^{c4}$R$^{d4}$, C(O)NR$^{c4}$(OR$^{a4}$), C(O)OR$^{a4}$, OC(O)R$^{b4}$, OC(O)NR$^{c4}$R$^{d4}$, NR$^{c4}$R$^{d4}$, NR$^{c4}$NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$C(=NR$^{e4}$)R$^{b4}$, NR$^{c4}$S(O)R$^{b4}$, NR$^{c4}$S(O)NR$^{c4}$R$^{d4}$, NR$^{c4}$S(O)$_2$R$^{b4}$, NR$^{c4}$S(O)(=NR$^{e4}$)R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, S(O)$_2$NR$^{c4}$R$^{d4}$, OS(O)(=NR$^{e4}$)R$^{b4}$, OS(O)$_2$R$^{b4}$, SF$_5$, P(O)R$^{f4}$R$^{g4}$, OP(O)(OR$^{h4}$)(OR$^{i4}$), P(O)(OR$^{h4}$)(OR$^{i4}$), and BR$^{j4}$R$^{k4}$, wherein the C$_{1-6}$ alkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl- of $R^B$, $R^C$, $R^D$, $R^E$, $R^F$, and $R^G$ are each optionally substituted with 1, 2, 3, 4, 5, 6, 7, or 8 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a4}$, $R^{c4}$, and $R^{d4}$ are each optionally substituted with 1, 2, 3, 4, 5, 6, 7, or 8 independently selected $R^H$ substituents;

or, any $R^{c4}$ and $R^{d4}$ attached to the same N atom, together with the N atom to which they are attached, optionally form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^H$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b4}$ are each optionally substituted with 1, 2, 3, 4, 5, 6, 7, or 8 independently selected $R^H$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f4}$ and $R^{g4}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or, any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^H$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b3}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^H$ are each optionally substituted with 1, 2, 3, or 4 independently selected $R^I$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a5}$, $R^{c5}$, and $R^{d5}$ are each optionally substituted with 1, 2, 3, or 4 independently selected $R^I$ substituents;

or any $R^{c5}$ and $R^{d5}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^I$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b5}$ are each optionally substituted with 1, 2, 3, or 4 independently selected $R^I$ substituents;

each $R^{e5}$ is independently selected from H, OH, CN, $C_{1-6}$ alkyl, $C_{1-6}$alkoxy, $C_{1-6}$haloalkyl, $C_{1-6}$haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, and (4-14 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$haloalkyl, $C_{1-6}$haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h5}$ and $R^{g5}$ is independently selected from H, $C_{1-6}$ alkyl, $C_{1-6}$haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or, any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c5}R^{d6}$, $C(=NR^{e6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)NR^{c6}R^{d6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^I$ are each optionally substituted with 1, 2, 3, or 4 independently selected $R^J$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a6}$, $R^{c6}$, and $R^{d6}$ are each optionally substituted with 1, 2, 3, or 4 independently selected $R^J$ substituents;

or any $R^{c6}$ and $R^{d6}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^J$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b6}$ are each optionally substituted with 1, 2, 3, or 4 independently selected $R^J$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or, any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^{c7}C(=NR^{e7})NR^{c7}R^{d7}$, $NR^{c7}C(=NR^{e7})R^{b7}$, $NR^{c7}S(O)R^{b7}$, $NR^{c7}S(O)NR^{c7}R^{d7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, $OS(O)_2R^{b7}$, $SF_5$, $P(O)R^{f7}R^{g7}$, $OP(O)(OR^{h7})(OR^{i7})$, $P(O)(OR^{h7})(OR^{i7})$, and $BR^{j7}R^{k7}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^J$ are each optionally substituted with 1, 2, 3, or 4 independently selected $R^K$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, and (4-14 membered heterocycloalkyl)-$C_{1-6}$alkyl- wherein the $C_{1-6}$ alkyl, $C_{2-6}$alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a7}$, $R^{c7}$, and $R^{d7}$ are each optionally substituted with 1, 2, 3, or 4 independently selected $R^K$ substituents;

or any $R^{c7}$ and $R^{d7}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^K$ substituents;

each $R^{b7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b7}$ are each optionally substituted with 1, 2, 3, or 4 independently selected $R^K$ substituents;

each $R^{e7}$ is independently selected from H, OH, CN, $C_{1-6}$ alkyl, $C_{2-6}$ alkenyl, $C_{1-6}$ alkoxy, $C_{1-6}$ haloalkyl, $C_{1-6}$ haloalkoxy, $C_{2-6}$ alkynyl, $C_{6-14}$ aryl, $C_{3-14}$ cycloalkyl, 5-14 membered heteroaryl, and 4-14 membered heterocycloalkyl;

each $R^{f7}$ and $R^{g7}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j7}$ and $R^{k7}$ is independently selected from OH, $C_{1-6}$ alkoxy, and $C_{1-6}$ haloalkoxy;

or, any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^K$ is independently selected from H, D, OH, halo, oxo, CN, C(O)OH, NH$_2$, NO$_2$, SF$_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-; and wherein any heteroaryl group of any of the above-recited substituents optionally comprises an N-oxide on any ring-forming nitrogen.

In some embodiments,

X is N or CR$^3$;

R$^1$ is selected from H, $C_{1-6}$ alkyl, $C_{2-6}$ alkenyl, $C_{2-6}$ alkynyl, and $C_{1-6}$ haloalkyl;

R$^2$ is selected from H, D, halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, NO$_2$, OR$^{a2}$, SR$^{a2}$, NHOR$^{a2}$, C(O)R$^{b2}$, C(O)NR$^{c2}$R$^{d2}$, C(O)NR$^{c2}$(OR$^{a2}$), C(O)OR$^{a2}$, OC(O)R$^{b2}$, OC(O)NR$^{c2}$R$^{d2}$, NR$^{c2}$R$^{d2}$, NR$^{c2}$NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$) NR$^{c2}$R$^{d2}$, NR$^{c2}$C(=NR$^{e2}$)R$^{b2}$, NR$^{c2}$S(O)NR$^{c2}$R$^{d2}$, NR$^{c2}$S (O)R$^{b2}$, NR$^{c2}$S(O)$_2$R$^{b2}$, NR$^{c2}$S(O)(=NR$^{e2}$)R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, S(O)$_2$NR$^{c2}$R$^{d2}$, OS(O)(=NR$^{e2}$)R$^{b2}$, OS(O)$_2$R$^{b2}$, SF$_5$, P(O) R$^{f2}$R$^{g2}$, OP(O)(OR$^{h2}$)(OR$^{i2}$), P(O)(OR$^{h2}$)(OR$^{i2}$), and BR$^{j2}$R$^{k2}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, and (4-14 membered heterocycloalkyl)-$C_{1-6}$ alkyl- of R$^2$ are each optionally substituted with 1, 2, 3, 4, 5, 6, 7, or 8 independently selected R$^C$ substituents;

R$^3$ is selected from H, D, halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, NO$_2$, OR$^{a3}$, SR$^{a3}$, NHOR$^{a3}$, C(O)R$^{b3}$, C(O)NR$^{c3}$R$^{d3}$, C(O)NR$^{c3}$(OR$^{a3}$), C(O)OR$^{a3}$, OC(O)R$^{b3}$, OC(O)NR$^{c3}$R$^{d3}$, NR$^{c3}$R$^{d3}$, NR$^{c3}$NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$) NR$^{c3}$R$^{d3}$, NR$^{c3}$C(=NR$^{e3}$)R$^{b3}$, NR$^{c3}$S(O)NR$^{c3}$R$^{d3}$, NR$^{c3}$S (O)R$^{b3}$, NR$^{c3}$S(O)$_2$R$^{b3}$, NR$^{c3}$S(O)(=NR$^{e3}$)R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, S(O)$_2$NR$^{c3}$R$^{d3}$, OS(O)(=NR$^{e3}$)R$^{b3}$, OS(O)$_2$R$^{b3}$, SF$_5$, P(O) R$^{f3}$R$^{g3}$, OP(O)(OR$^{h3}$)(OR$^{i3}$), P(O)(OR$^{h3}$)(OR$^{i3}$), and BR$^{j3}$R$^{k3}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of R$^3$ are each optionally substituted with 1, 2, 3, 4, 5, 6, 7, or 8 independently selected R$^D$ substituents;

Cy$^1$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected R$^E$ substituents;

provided that when X is N and Cy$^1$ is 4-14 membered heterocycloalkyl, then the 4-14 membered heterocycloalkyl of Cy$^1$ is other than unsubstituted morpholinyl;

Cy$^2$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected R$^F$ substituents;

each R$^{a2}$, R$^{c2}$, R$^{d2}$, R$^{a3}$, R$^{c3}$, and R$^{d3}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of R$^{a2}$, R$^{c2}$, R$^{d2}$, R$^{a3}$, R$^{c3}$, and R$^{d3}$ are each optionally substituted with 1, 2, 3, 4, 5, 6, 7, or 8 independently selected R$^G$ substituents;

or any R$^{c2}$ and R$^{d2}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected R$^G$ substituents;

or any R$^{c3}$ and R$^{d3}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

each $R^{b2}$, and $R^{b3}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b2}$ and $R^{b3}$ are each optionally substituted with 1, 2, 3, 4, 5, 6, 7, or 8 independently selected $R^G$ substituents;

each $R^{e2}$ and $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f2}$, $R^{g2}$, $R^{f3}$, and $R^{g3}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h2}$, $R^{i2}$, $R^{h3}$, and $R^{i3}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j2}$, $R^{k2}$, $R^{j3}$, and $R^{k3}$ is independently selected from OH, $C_{1-6}$alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

or any $R^{j3}$ and $R^{k3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^C$, $R^D$, $R^E$, $R^F$, and $R^G$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$ $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$ $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^C$, $R^D$, $R^E$, $R^F$, and $R^G$ are each optionally substituted with 1, 2, 3, 4, 5, 6, 7, or 8 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a4}$, $R^{c4}$, and $R^{d4}$ are each optionally substituted with 1, 2, 3, 4, 5, 6, 7, or 8 independently selected $R^H$ substituents;

or, any $R^{c4}$ and $R^{d4}$ attached to the same N atom, together with the N atom to which they are attached, optionally form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^H$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b4}$ are each optionally substituted with 1, 2, 3, 4, 5, 6, 7, or 8 independently selected $R^H$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f4}$ and $R^{g4}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or, any $R^{a4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^H$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^H$ are each optionally substituted with 1, 2, 3, or 4 independently selected $R^I$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a5}$, $R^{c5}$, and $R^{d5}$ are each optionally substituted with 1, 2, 3, or 4 independently selected $R^I$ substituents;

or any $R^{c5}$ and $R^{d5}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^I$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b5}$ are each optionally substituted with 1, 2, 3, or 4 independently selected $R^I$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, and (4-14 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$haloalkyl, $C_{1-6}$haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h5}$ and $R^{i5}$ is independently selected from H, $C_{1-6}$ alkyl, $C_{1-6}$haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or, any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a5}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)NR^{c6}R^{d6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^I$ are each optionally substituted with 1, 2, 3, or 4 independently selected $R^J$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a6}$, $R^{c6}$, and $R^{d6}$ are each optionally substituted with 1, 2, 3, or 4 independently selected $R^J$ substituents;

or any $R^{c6}$ and $R^{d6}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^J$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b6}$ are each optionally substituted with 1, 2, 3, or 4 independently selected $R^J$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or, any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^{c7}C(=NR^{e7})NR^{c7}R^{d7}$, $NR^{c7}C(=NR^{e7})R^{b7}$, $NR^{c7}S(O)R^{b7}$, $NR^{c7}S(O)NR^{c7}R^{d7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, $OS(O)_2R^{b7}$, $SF_5$, $P(O)R^{f7}R^{g7}$, $OP(O)(OR^{h7})(OR^{i7})$, $P(O)(OR^{h7})(OR^{i7})$, and $BR^{j7}R^{k7}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^J$ are each optionally substituted with 1, 2, 3, or 4 independently selected $R^K$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, and (4-14 membered heterocycloalkyl)-$C_{1-6}$alkyl- wherein the $C_{1-6}$ alkyl, $C_{2-6}$alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a7}$, $R^{c7}$, and $R^{d7}$ are each optionally substituted with 1, 2, 3, or 4 independently selected $R^K$ substituents;

or any $R^{c7}$ and $R^{d7}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^K$ substituents;

each $R^{b7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b7}$ are each optionally substituted with 1, 2, 3, or 4 independently selected $R^K$ substituents;

each $R^{e7}$ is independently selected from H, OH, CN, $C_{1-6}$ alkyl, $C_{2-6}$ alkenyl, $C_{1-6}$ alkoxy, $C_{1-6}$haloalkyl, $C_{1-6}$ haloalkoxy, $C_{2-6}$ alkynyl, $C_{6-14}$ aryl, $C_{3-14}$ cycloalkyl, 5-14 membered heteroaryl, and 4-14 membered heterocycloalkyl;

each $R^{f7}$ and $R^{g7}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j7}$ and $R^{k7}$ is independently selected from OH, $C_{1-6}$ alkoxy, and $C_{1-6}$ haloalkoxy;

or, any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^K$ is independently selected from H, D, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-; and wherein any heteroaryl group of any of the above-recited substituents optionally comprises an N-oxide on any ring-forming nitrogen.

In some embodiments,

X is $CR^3$;

$R^1$ is selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, $OR^{a1}$, $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^1$ are each optionally substituted with 1, 2, 3, 4, 5, 6, 7, or 8 independently selected $R^B$ substituents;

$R^2$ is selected from H, D, halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c3}R^{d3}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{j2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^2$ are each optionally substituted with 1, 2, 3, 4, 5, 6, 7, or 8 independently selected $R^C$ substituents;

$R^3$ is selected from H, D, halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a3}$, $SR^{a3}$, $NHOR^{a3}$, $C(O)R^{b3}$, $C(O)NR^{c3}R^{d3}$, $C(O)NR^{c3}(OR^{a3})$, $C(OX)R^{a3}$, $OC(O)R^{b3}$, $OC(O)NR^{c3}R^{d3}$, $NR^{c3}R^{d3}$, $NR^{c3}NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}C(=NR^{e3})R^{b3}$, $NR^{c3}S(O)NR^{c3}R^{d3}$, $NR^{c3}S(O)R^{b3}$, $NR^{c3}S(O)_2R^{b3}$, $NR^{c3}S(O)(=NR^{e3})R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, $OS(O)(=NR^{e3})R^{b3}$, $OS(O)_2R^{b3}$, $SF_5$, $P(O)R^{j3}R^{g3}$, $OP(O)(OR^{h3})(OR^{i3})$, $P(O)(OR^{h3})(OR^{i3})$, and $BR^{j3}R^{k3}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^3$ are each optionally substituted with 1, 2, 3, 4, 5, 6, 7, or 8 independently selected $R^D$ substituents;

$Cy^1$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^E$ substituents;

provided that $Cy^1$ is not pyridin-4-yl optionally substituted with 1, 2, 3, or 4 independently selected $R^E$ substituents;

provided that $Cy^1$ is not pyrimidin-4-yl optionally substituted with 1, 2, or 3, independently selected $R^E$ substituents;

provided that $Cy^1$ is not quinoline-4-yl optionally substituted with 1, 2, 3, 4, 5, or 6 independently selected $R^E$ substituents;

$Cy^2$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^F$ substituents;

each $R^{a1}$, $R^{c1}$, $R^{d1}$, $R^{a2}$, $R^{c2}$, $R^{a2}$, $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a1}$, $R^{c1}$, $R^{d1}$, $R^{a2}$, $R^{c2}$, $R^{d2}$, $R^{a3}$, $R^{c3}$, and $R^{d3}$ are each optionally substituted with 1, 2, 3, 4, 5, 6, 7, or 8 independently selected $R^G$ substituents;

or, any $R^{c1}$ and $R^{d1}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

or any $R^{c2}$ and $R^{d2}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

or any $R^{c3}$ and $R^{d3}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

each $R^{b1}$, $R^{b2}$, and $R^{b3}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b1}$, $R^{b2}$, and $R^{b3}$ are each optionally substituted with 1, 2, 3, 4, 5, 6, 7, or 8 independently selected $R^G$ substituents;

each $R^{e1}$, $R^{e2}$, and $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f2}$, $R^{g2}$, $R^{f3}$, and $R^{g3}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h2}$, $R^{i2}$, $R^{h3}$, and $R^{i3}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j2}$, $R^{k2}$, $R^{j3}$, and $R^{k3}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

or any $R^{j3}$ and $R^{k3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^B$, $R^C$, $R^D$, $R^E$, $R^F$, and $R^G$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, (4-14 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$ $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^B$, $R^C$, $R^D$, $R^E$, $R^F$, and $R^G$ are each optionally substituted with 1, 2, 3, 4, 5, 6, 7, or 8 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, and (4-14 membered heterocycloalkyl)-$C_{1-6}$alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a4}$, $R^{c4}$, and $R^{d4}$ are each optionally substituted with 1, 2, 3, 4, 5, 6, 7, or 8 independently selected $R^H$ substituents;

or, any $R^{c4}$ and $R^{d4}$ attached to the same N atom, together with the N atom to which they are attached, optionally form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^H$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b4}$ are each optionally substituted with 1, 2, 3, 4, 5, 6, 7, or 8 independently selected $R^H$ substituents;

each $R^{e4}$ is independently selected from H, OH, CN, $C_{1-6}$ alkyl, $C_{1-6}$alkoxy, $C_{1-6}$haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, and (4-14 membered heterocycloalkyl)-$C_{1-6}$ alkyl-;

each $R^{f4}$ and $R^{g4}$ is independently selected from H, $C_{1-6}$ alkyl, $C_{1-6}$ alkoxy, $C_{1-6}$haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h4}$ and $R^{i4}$ is independently selected from H, $C_{1-6}$ alkyl, $C_{1-6}$haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or, any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^H$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{1-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^H$ are each optionally substituted with 1, 2, 3, or 4 independently selected $R^I$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a5}$, $R^{c5}$, and $R^{d5}$ are each optionally substituted with 1, 2, 3, or 4 independently selected $R^I$ substituents;

or any $R^{c5}$ and $R^{d5}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^I$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b5}$ are each optionally substituted with 1, 2, 3, or 4 independently selected $R^J$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or, any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, NO$_2$, OR$^{a6}$, SR$^{a6}$, NHOR$^{a6}$, C(O)R$^{b6}$, C(O)NR$^{c6}$R$^{d6}$, C(O)NR$^{c6}$(OR$^{a6}$), C(O)OR$^{a6}$, OC(O)R$^{b6}$, OC(O)NR$^{c6}$R$^{d6}$, NR$^{c6}$R$^{d6}$, NR$^{c6}$NR$^{c6}$R$^{d6}$, NR$^{c6}$C(O)R$^{b6}$, NR$^{c6}$C(O)OR$^{a6}$, NR$^{c6}$C(O)NR$^{c5}$R$^{d6}$, C(=NR$^{e6}$)R$^{b6}$, C(=NR$^{e6}$)NR$^{c6}$R$^{d6}$, NR$^{c6}$C(=NR$^{e6}$)NR$^{c6}$R$^{d6}$, NR$^{c6}$C(=NR$^{e6}$)R$^{b6}$, NR$^{c6}$S(O)R$^{b6}$, NR$^{c6}$S(O)NR$^{c6}$R$^{d6}$, NR$^{c6}$S(O)$_2$R$^{b6}$, NR$^{c6}$S(O)(=NR$^{e6}$)R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, S(O)$_2$NR$^{c6}$R$^{d6}$, OS(O)(=NR$^{e6}$)R$^{b6}$, OS(O)$_2$R$^{b6}$, SF$_5$, P(O)R$^{f6}$R$^{g6}$, OP(O)(OR$^{h6}$)(OR$^{i6}$), P(O)(OR$^{h6}$)(OR$^{i6}$), and BR$^{j6}$R$^{k6}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^I$ are each optionally substituted with 1, 2, 3, or 4 independently selected $R^J$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a6}$, $R^{c6}$, and $R^{d6}$ are each optionally substituted with 1, 2, 3, or 4 independently selected $R^J$ substituents;

or any $R^{c6}$ and $R^{d6}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^J$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b6}$ are each optionally substituted with 1, 2, 3, or 4 independently selected $R^J$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or, any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, NO$_2$, OR$^{a7}$, SR$^{a7}$, NHOR$^{a7}$, C(O)R$^{b7}$, C(O)NR$^{c7}$R$^{d7}$, C(O)NR$^{c7}$(OR$^{a7}$), C(O)OR$^{a7}$, OC(O)R$^{b7}$, OC(O)NR$^{c7}$R$^{d7}$, NR$^{c7}$R$^{d7}$, NR$^{c7}$NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$, C(=NR$^{e7}$)R$^{b7}$, C(=NR$^{e7}$)NR$^{c7}$R$^{d7}$, NR$^{c7}$C(=NR$^{e7}$)NR$^{c7}$R$^{d7}$, NR$^{c7}$C(=NR$^{e7}$)R$^{b7}$, NR$^{c7}$S(O)R$^{b7}$, NR$^{c7}$S(O)NR$^{c7}$R$^{d7}$, NR$^{c7}$S(O)$_2$R$^{b7}$, NR$^{c7}$S(O)(=NR$^{e7}$)R$^{b7}$, NR$^{c7}$S(O)$_2$NR$^{c7}$R$^{d7}$, S(O)R$^{b7}$, S(O)NR$^{c7}$R$^{d7}$, S(O)$_2$R$^{b7}$, S(O)$_2$NR$^{c7}$R$^{d7}$, OS(O)(=NR$^{e7}$)R$^{b7}$, OS(O)$_2$R$^{b7}$, SF$_5$, P(O)R$^{f7}$R$^{g7}$, OP(O)(OR$^{h7}$)(OR$^{i7}$), P(O)(OR$^{h7}$)(OR$^{i7}$), and BR$^{j7}$R$^{k7}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{3-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$alkyl- of $R^J$ are each optionally substituted with 1, 2, 3, or 4 independently selected $R^K$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- wherein the $C_{1-6}$ alkyl, $C_{2-6}$alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a7}$, $R^{c7}$, and $R^{d7}$ are each optionally substituted with 1, 2, 3, or 4 independently selected $R^K$ substituents;

or any $R^{c7}$ and $R^{d7}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^K$ substituents;

each $R^{b7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b7}$ are each optionally substituted with 1, 2, 3, or 4 independently selected $R^K$ substituents;

each $R^{e7}$ is independently selected from H, OH, CN, $C_{1-6}$ alkyl, $C_{2-6}$ alkenyl, $C_{1-6}$ alkoxy, $C_{1-6}$ haloalkyl, $C_{1-6}$ haloalkoxy, $C_{2-6}$ alkynyl, $C_{6-14}$ aryl, $C_{3-14}$ cycloalkyl, 5-14 membered heteroaryl, and 4-14 membered heterocycloalkyl;

each $R^{f7}$ and $R^{g7}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j7}$ and $R^{k7}$ is independently selected from OH, $C_{1-6}$ alkoxy, and $C_{1-6}$ haloalkoxy;

or, any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^K$ is independently selected from H, D, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-; and wherein any heteroaryl group of any of the above-recited substituents optionally comprises an N-oxide on any ring-forming nitrogen.

In some embodiments,

X is $CR^3$;

$R^1$ is selected from H, $C_{1-6}$ alkyl, $C_{2-6}$ alkenyl, $C_{2-6}$ alkynyl, and $C_{1-6}$ haloalkyl;

$R^2$ is selected from H, D, halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^2$ are each optionally substituted with 1, 2, 3, 4, 5, 6, 7, or 8 independently selected $R^C$ substituents;

$R^3$ is selected from H, D, halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a3}$, $SR^{a3}$, $NHOR^{a3}$, $C(O)R^{b3}$, $C(O)NR^{c3}R^{d3}$, $C(O)NR^{c3}(OR^{a3})$, $C(O)OR^{a3}$, $OC(O)R^{b3}$, $OC(O)NR^{c3}R^{d3}$, $NR^{c3}R^{d3}$, $NR^{c3}NR^{c3}R^{d3}$, $NR^{c3}C(O)R^{b3}$, $NR^{c3}C(=NR^{a3})R^{b3}$, $NR^{c3}S(O)NR^{c3}R^{d3}$, $NR^{c3}S(O)R^{b3}$, $NR^{c3}S(O)_2R^{b3}$, $NR^{c3}S(O)(=NR^{e3})R^{b3}$, $NR^{c3}S(O)_2NR^{c3}R^{d3}$, $S(O)R^{b3}$, $S(O)_2R^{b3}$, $S(O)_2R^{b3}$, $S(O)_2NR^{c3}R^{d3}$, $OS(O)(=NR^{e3})R^{b3}$, $OS(O)_2R^{b3}$, $SF_5$, $P(O)R^{f3}R^{g3}$, $OP(O)(OR^{h3})(OR^{i3})$, $P(O)(OR^{h3})(OR^{i3})$, and $BR^{j3}R^{k3}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, and (4-14 membered heterocycloalkyl)-$C_{1-6}$ alkyl- of $R^3$ are each optionally substituted with 1, 2, 3, 4, 5, 6, 7, or 8 independently selected $R^D$ substituents;

$Cy^1$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^E$ or $R^M$ substituents;

$Cy^2$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^F$ substituents;

each $R^{a2}$, $R^{c2}$, $R^{a2}$, $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-

$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a2}$, $R^{c2}$, $R^{a3}$, $R^{c3}$, and $R^{d3}$ are each optionally substituted with 1, 2, 3, 4, 5, 6, 7, or 8 independently selected $R^G$ substituents;

or any $R^{c2}$ and $R^{d2}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

or any $R^{c3}$ and $R^{d3}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

each $R^{b2}$ and $R^{b3}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b2}$ and $R^{b3}$ are each optionally substituted with 1, 2, 3, 4, 5, 6, 7, or 8 independently selected $R^G$ substituents;

each $R^{e2}$ and $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f2}$, $R^{g2}$, $R^{f3}$, and $R^{g3}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h2}$, $R^{i2}$, $R^{h3}$, and $R^{i3}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j2}$, $R^{k2}$, $R^{j3}$, and $R^{k3}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

or any $R^{j3}$ and $R^{k3}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^C$, $R^D$, $R^E$, $R^M$, $R^F$, and $R^G$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, (4-14 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$, $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^C$, $R^D$, $R^E$, $R^M$, $R^F$, and $R^G$ are each optionally substituted with 1, 2, 3, 4, 5, 6, 7, or 8 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a4}$, $R^{c4}$, and $R^{d4}$ are each optionally substituted with 1, 2, 3, 4, 5, 6, 7, or 8 independently selected $R^H$ substituents;

or, any $R^{c4}$ and $R^{d4}$ attached to the same N atom, together with the N atom to which they are attached, optionally form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^H$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b4}$ are each optionally substituted with 1, 2, 3, 4, 5, 6, 7, or 8 independently selected $R^H$ substituents;

each $R^{e4}$ is independently selected from H, OH, CN, $C_{1-6}$ alkyl, $C_{1-6}$alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, and (4-14 membered heterocycloalkyl)-$C_{1-6}$ alkyl-;

each $R^{f4}$ and $R^{g4}$ is independently selected from H, $C_{1-6}$ alkyl, $C_{1-6}$ alkoxy, $C_{1-6}$haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or, any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^H$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, (4-14 membered heterocycloalkyl)-$C_{1-6}$alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{a5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $SF_5$, $P(O)R^{j5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{1-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^H$ are each optionally substituted with 1, 2, 3, or 4 independently selected $R^I$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{3-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a5}$, $R^{c5}$, and $R^{d5}$ are each optionally substituted with 1, 2, 3, or 4 independently selected $R^I$ substituents;

or any $R^{c5}$ and $R^{d5}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^I$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b5}$ are each optionally substituted with 1, 2, 3, or 4 independently selected $R^I$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or, any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a5}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c5}R^{d6}$, $C(=NR^{e6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)NR^{c6}R^{d6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^I$ are each optionally substituted with 1, 2, 3, or 4 independently selected $R^J$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, and (4-14 membered heterocycloalkyl)-$C_{1-6}$alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a6}$, $R^{c6}$, and $R^{d6}$ are each optionally substituted with 1, 2, 3, or 4 independently selected $R^J$ substituents;

or any $R^{c6}$ and $R^{d6}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^J$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b6}$ are each optionally substituted with 1, 2, 3, or 4 independently selected $R^J$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{1-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or, any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{d7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^{c7}C(=NR^{e7})NR^{c7}R^{d7}$, $NR^{c7}C(=NR^{e7})R^{b7}$, $NR^{c7}S(O)R^{b7}$, $NR^{c7}S(O)NR^{c7}R^{d7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, $OS(O)_2R^{b7}$, $SF_5$, $P(O)R^{f7}R^{g7}$, $OP(O)(OR^{h7})(OR^{i7})$, $P(O)(OR^{h7})(OR^{i7})$, and $BR^{j7}R^{k7}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{1-14}$ cycloalkyl-$C_{1-6}$ alkyl-, (5-14 membered heteroaryl)-$C_{1-6}$ alkyl-, and (4-14 membered heterocycloalkyl)-$C_{1-6}$alkyl- of $R^J$ are each optionally substituted with 1, 2, 3, or 4 independently selected $R^K$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$-aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a7}$, $R^{c7}$, and $R^{d7}$ are each optionally substituted with 1, 2, 3, or 4 independently selected $R^K$ substituents;

or any $R^{c7}$ and $R^{d7}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^K$ substituents;

each $R^{b7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b7}$ are each optionally substituted with 1, 2, 3, or 4 independently selected $R^K$ substituents;

each $R^{e7}$ is independently selected from H, OH, CN, $C_{1-6}$ alkyl, $C_{2-6}$ alkenyl, $C_{1-6}$ alkoxy, $C_{1-6}$ haloalkyl, $C_{1-6}$ haloalkoxy, $C_{2-6}$ alkynyl, $C_{6-14}$ aryl, $C_{3-14}$ cycloalkyl, 5-14 membered heteroaryl, and 4-14 membered heterocycloalkyl;

each $R^{f7}$ and $R^{g7}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j7}$ and $R^{k7}$ is independently selected from OH, $C_{1-6}$ alkoxy, and $C_{1-6}$ haloalkoxy;

or, any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^K$ is independently selected from H, D, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-; and wherein any heteroaryl group of any of the above-recited substituents optionally comprises an N-oxide on any ring-forming nitrogen.

In some embodiments:

X is N;

$R^1$ is selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, $OR^{a1}$, $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^1$ are each optionally substituted with 1, 2, 3, 4, 5, 6, 7, or 8 independently selected $R^B$ substituents;

$R^2$ is selected from H, D, halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, and (4-14 membered heterocycloalkyl)-$C_{1-6}$ alkyl- of $R^2$ are each optionally substituted with 1, 2, 3, 4, 5, 6, 7, or 8 independently selected $R^G$ substituents;

$Cy^1$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^E$ substituents;

provided that when $Cy^1$ is 4-14 membered heterocycloalkyl, then the 4-14 membered heterocycloalkyl of $Cy^1$ is other than unsubstituted morpholinyl;

$Cy^2$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^F$ substituents;

each $R^{a1}$, $R^{c1}$, $R^{d1}$, $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a1}$, $R^{c1}$, $R^{d1}$, $R^{a2}$, $R^{c2}$, and $R^{d2}$ are each optionally substituted with 1, 2, 3, 4, 5, 6, 7, or 8 independently selected $R^G$ substituents;

or, any $R^{c1}$ and $R^{d1}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

or any $R^{c2}$ and $R^{d2}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

each $R^{b1}$ and $R^{b2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b1}$, $R^{b2}$, and $R^{b3}$ are each optionally substituted with 1, 2, 3, 4, 5, 6, 7, or 8 independently selected $R^G$ substituents;

each $R^{e1}$ and $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f2}$ and $R^{g2}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^B$, $R^C$, $R^E$, $R^F$, and $R^G$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S$ $O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$, $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^B$, $R^C$, $R^E$, $R^F$, and $R^G$ are each optionally substituted with 1, 2, 3, 4, 5, 6, 7, or 8 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, and (4-14 membered heterocycloalkyl)-$C_{1-6}$alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a4}$, $R^{c4}$, and $R^{d4}$ are each optionally substituted with 1, 2, 3, 4, 5, 6, 7, or 8 independently selected $R^H$ substituents;

or, any $R^{c4}$ and $R^{d4}$ attached to the same N atom, together with the N atom to which they are attached, optionally form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^H$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b4}$ are each optionally substituted with 1, 2, 3, 4, 5, 6, 7, or 8 independently selected $R^H$ substituents;

each $R^{e4}$ is independently selected from H, OH, CN, $C_{1-6}$ alkyl, $C_{1-6}$ alkoxy, $C_{1-6}$ haloalkyl, $C_{1-6}$haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f4}$ and $R^{g4}$ is independently selected from H, $C_{1-6}$ alkyl, $C_{1-6}$ alkoxy, $C_{1-6}$ haloalkyl, $C_{1-6}$haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, and (4-14 membered heterocycloalkyl)-$C_{1-6}$ alkyl-;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or, any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^H$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^H$ are each optionally substituted with 1, 2, 3, or 4 independently selected $R^I$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a5}$, $R^{c5}$, and $R^{d5}$ are each optionally substituted with 1, 2, 3, or 4 independently selected $R^I$ substituents;

or any $R^{c5}$ and $R^{d5}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^I$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b3}$ are each optionally substituted with 1, 2, 3, or 4 independently selected $R^I$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or, any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c5}R^{d6}$, $C(=NR^{e6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)NR^{c6}R^{d6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^I$ are each optionally substituted with 1, 2, 3, or 4 independently selected $R^J$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a6}$, $R^{c6}$, and $R^{d6}$ are each optionally substituted with 1, 2, 3, or 4 independently selected $R^J$ substituents;

or any $R^{c6}$ and $R^{d6}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^J$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b6}$ are each optionally substituted with 1, 2, 3, or 4 independently selected $R^J$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or, any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^{c7}C(=NR^{e7})NR^{c7}R^{d7}$, $NR^{c7}C(=NR^{e7})R^{b7}$, $NR^{c7}S(O)R^{b7}$, $NR^{c7}S(O)NR^{c7}R^{d7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, $OS(O)_2R^{b7}$, $SF_5$, $P(O)R^{f7}R^{g7}$, $OP(O)(OR^{h7})(OR^{i7})$, $P(O)(OR^{h7})(OR^{i7})$, and $BR^{j7}R^{k7}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^J$ are each optionally substituted with 1, 2, 3, or 4 independently selected $R^K$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a7}$, $R^{c7}$, and $R^{d7}$ are each optionally substituted with 1, 2, 3, or 4 independently selected $R^K$ substituents;

or any $R^{c7}$ and $R^{d7}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^K$ substituents;

each $R^{b7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b7}$ are each optionally substituted with 1, 2, 3, or 4 independently selected $R^K$ substituents;

each $R^{e7}$ is independently selected from H, OH, CN, $C_{1-6}$ alkyl, $C_{2-6}$ alkenyl, $C_{1-6}$ alkoxy, $C_{1-6}$ haloalkyl, $C_{1-6}$ haloalkoxy, $C_{2-6}$ alkynyl, $C_{6-14}$ aryl, $C_{3-14}$ cycloalkyl, 5-14 membered heteroaryl, and 4-14 membered heterocycloalkyl;

each $R^{f7}$ and $R^{g7}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j7}$ and $R^{k7}$ is independently selected from OH, $C_{1-6}$ alkoxy, and $C_{1-6}$ haloalkoxy;

or, any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^K$ is independently selected from H, D, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-; and wherein any heteroaryl group of any of the above-recited substituents optionally comprises an N-oxide on any ring-forming nitrogen.

In some embodiments:

X is N;

$R^1$ is selected from H, $C_{1-6}$ alkyl, $C_{2-6}$ alkenyl, $C_{2-6}$ alkynyl, and $C_{1-6}$ haloalkyl;

$R^2$ is selected from H, D, halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^2$ are each optionally substituted with 1, 2, 3, 4, 5, 6, 7, or 8 independently selected $R^G$ substituents;

$Cy^1$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^E$ or $R^M$ substituents;

$Cy^2$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^F$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a2}$, $R^{c2}$, and $R^{d2}$ are each optionally substituted with 1, 2, 3, 4, 5, 6, 7, or 8 independently selected $R^G$ substituents;

or any $R^{c2}$ and $R^{d2}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b2}$ are each optionally substituted with 1, 2, 3, 4, 5, 6, 7, or 8 independently selected $R^G$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f2}$ and $R^{g2}$ is independently selected from H, $C_{1-6}$ alkyl, $C_{1-6}$ haloalkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^C$, $R^E$, $R^M$, $R^F$, and $R^G$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, (4-14 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$ $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$ $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^C$, $R^E$, $R^M$, $R^F$, and $R^G$ are each optionally substituted with 1, 2, 3, 4, 5, 6, 7, or 8 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a4}$, $R^{c4}$, and $R^{d4}$ are each optionally substituted with 1, 2, 3, 4, 5, 6, 7, or 8 independently selected $R^H$ substituents;

or, any $R^{c4}$ and $R^{d4}$ attached to the same N atom, together with the N atom to which they are attached, optionally form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^H$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b4}$ are each optionally substituted with 1, 2, 3, 4, 5, 6, 7, or 8 independently selected $R^H$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f4}$ and $R^{g4}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h4}$ and $R^{i4}$ is independently selected from H, $C_{1-6}$ alkyl, $C_{1-6}$haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or, any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^H$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, (4-14 membered heterocycloalkyl)-$C_{1-6}$alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{3-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$alkyl- of $R^H$ are each optionally substituted with 1, 2, 3, or 4 independently selected $R^I$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a5}$, $R^{c5}$, and $R^5$ are each optionally substituted with 1, 2, 3, or 4 independently selected $R^I$ substituents;

or any $R^{c5}$ and $R^{d5}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^I$ substituents;

each $R^{b5}$ is independently selected from H, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b3}$ are each optionally substituted with 1, 2, 3, or 4 independently selected $R^I$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h5}$ and $R^{i3}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or, any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{b6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c5}R^{d6}$, $C(=NR^{e6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)NR^{c6}R^{d6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, $OS(O)_2R^{b6}$, $SF_5$, $P(O)R^{c6}R^{d6}$, $OP(O)(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^I$ are each optionally substituted with 1, 2, 3, or 4 independently selected $R^J$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a6}$, $R^{c6}$, and $R^{d6}$ are each optionally substituted with 1, 2, 3, or 4 independently selected $R^J$ substituents;

or any $R^{c6}$ and $R^{d6}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^J$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b6}$ are each optionally substituted with 1, 2, 3, or 4 independently selected $R^J$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or, any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, NO$_2$, OR$^{a7}$, SR$^{a7}$, NHOR$^{a7}$, C(O)R$^{b7}$, C(O)NR$^{c7}$R$^{d7}$, C(O)NR$^{c7}$(OR$^{a7}$), C(O)OR$^{a7}$, OC(O)R$^{b7}$, OC(O)NR$^{c7}$R$^{d7}$, NR$^{c7}$R$^{d7}$, NR$^{c7}$NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$, C(=NR$^{e7}$)R$^{b7}$, C(=NR$^{e7}$)NR$^{c7}$R$^{d7}$, NR$^{c7}$C(=NR$^{e7}$)NR$^{c7}$R$^{d7}$, NR$^{c7}$C(=NR$^{e7}$)R$^{b7}$, NR$^{c7}$S(O)R$^{b7}$, NR$^{c7}$S(O)NR$^{c7}$R$^{d7}$, NR$^{c7}$S(O)$_2$R$^{b7}$, NR$^{c7}$S(O)(=NR$^{e7}$)R$^{b7}$, NR$^{c7}$S(O)$_2$NR$^{c7}$R$^{d7}$, S(O)R$^{b7}$, S(O)NR$^{c7}$R$^{d7}$, S(O)$_2$R$^{b7}$, S(O)$_2$NR$^{c7}$R$^{d7}$, OS(O)(=NR$^{e7}$)R$^{b7}$, OS(O)$_2$R$^{b7}$, SF$_5$, P(O)R$^{f7}$R$^{g7}$, OP(O)(OR$^{h7}$)(OR$^{i7}$), P(O)(OR$^{h7}$)(OR$^{i7}$), and BR$^{j7}$R$^{k7}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of R$^J$ are each optionally substituted with 1, 2, 3, or 4 independently selected R$^K$ substituents;

each R$^{a7}$, R$^{c7}$, and R$^{d7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- wherein the $C_{1-6}$ alkyl, $C_{2-6}$alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of R$^{a7}$, R$^{c7}$, and R$^{d7}$ are each optionally substituted with 1, 2, 3, or 4 independently selected R$^K$ substituents;

or any R$^{c7}$ and R$^{d7}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected R$^K$ substituents;

each R$^{b7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of R$^{b7}$ are each optionally substituted with 1, 2, 3, or 4 independently selected R$^K$ substituents;

each R$^{e7}$ is independently selected from H, OH, CN, $C_{1-6}$ alkyl, $C_{2-6}$ alkenyl, $C_{1-6}$ alkoxy, $C_{1-6}$ haloalkyl, $C_{1-6}$ haloalkoxy, $C_{2-6}$ alkynyl, $C_{6-14}$ aryl, $C_{3-14}$ cycloalkyl, 5-14 membered heteroaryl, and 4-14 membered heterocycloalkyl;

each R$^{f7}$ and R$^{g7}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each R$^{h7}$ and R$^{i7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each R$^{j7}$ and R$^{k7}$ is independently selected from OH, $C_{1-6}$ alkoxy, and $C_{1-6}$ haloalkoxy;

or, any R$^{j7}$ and R$^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each R$^K$ is independently selected from H, D, OH, halo, oxo, CN, C(O)OH, NH$_2$, NO$_2$, SF$_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-; and wherein any heteroaryl group of any of the above-recited substituents optionally comprises an N-oxide on any ring-forming nitrogen.

In some embodiments, each R$^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, and (4-14 membered heterocycloalkyl)-$C_{1-6}$alkyl-, CN, NO$_2$, OR$^{a7}$, SR$^{a7}$, NHOR$^{a7}$, C(O)R$^{b7}$, C(O)NR$^{c7}$R$^{d7}$, C(O)NR$^{c7}$(OR$^{a7}$), C(O)OR$^{a7}$, OC(O)R$^{b7}$, OC(O)NR$^{c7}$R$^{d7}$, NR$^{c7}$R$^{d7}$, NR$^{c7}$NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$, C(=NR$^{e7}$)R$^{b7}$, C(=NR$^{e7}$)NR$^{c7}$R$^{d7}$, NR$^{c7}$C(=NR$^{e7}$)NR$^{c7}$R$^{d7}$, NR$^{c7}$C(=NR$^{e7}$)R$^{b7}$, NR$^{c7}$S(O)R$^{b7}$, NR$^{c7}$S(O)NR$^{c7}$R$^{d7}$, NR$^{c7}$S(O)$_2$R$^{b7}$, NR$^{c7}$S(O)(=NR$^{e7}$)R$^{b7}$, NR$^{c7}$S(O)$_2$NR$^{c7}$R$^{d7}$, S(O)R$^{b7}$, S(O)NR$^{c7}$R$^{d7}$, S(O)$_2$R$^{b7}$, S(O)$_2$NR$^{c7}$R$^{d7}$, OS(O)(=NR$^{e7}$)R$^{b7}$, OS(O)$_2$R$^{b7}$, SF$_5$, P(O)R$^{f7}$R$^{g7}$, OP(O)(OR$^{h7}$)(OR$^{i7}$), P(O)(OR$^{h7}$)(OR$^{i7}$), and BR$^{j7}$R$^{k7}$;

each R$^{a7}$, R$^{c7}$, and R$^{d7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

or any R$^{c7}$ and R$^{d7}$ attached to the same N atom, together with the N atom to which they are attached, form a 5- or 6-membered heteroaryl or a 4-14-membered heterocycloalkyl group; and each R$^{b7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-.

In some embodiments, each R$^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, NO$_2$, OR$^{a6}$, SR$^{a6}$, NHOR$^{a6}$, C(O)R$^{b6}$, C(O)NR$^{c6}$R$^{d6}$, C(O)NR$^{c6}$(OR$^{a6}$), C(O)OR$^{a5}$, OC(O)R$^{b6}$, OC(O)NR$^{c6}$R$^{d6}$, NR$^{c6}$R$^{d6}$, NR$^{c6}$NR$^{c6}$R$^{d6}$, NR$^{c6}$C(O)R$^{b6}$, NR$^{c6}$C(O)OR$^{a6}$, NR$^{c6}$C(O)NR$^{c5}$R$^{d6}$, C(=NR$^{e6}$)R$^{b6}$, C(=NR$^{e6}$)NR$^{c6}$R$^{d6}$, NR$^{c6}$C(=NR$^{e6}$)NR$^{c6}$R$^{d6}$, NR$^{c6}$C(=NR$^{e6}$)R$^{b6}$, NR$^{c6}$S(O)R$^{b6}$, NR$^{c6}$S(O)NR$^{c6}$R$^{d6}$, NR$^{c6}$S(O)$_2$R$^{b6}$, NR$^{c6}$S(O)(=NR$^{e6}$)R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, S(O)$_2$NR$^{c6}$R$^{d6}$, OS(O)(=NR$^{e6}$)R$^{b6}$, OS(O)$_2$R$^{b6}$, SF$_5$, P(O)R$^{f6}$R$^{g6}$, OP(O)(OR$^{h6}$)(OR$^{i6}$), P(O)(OR$^{h6}$)(OR$^{i6}$), and BR$^{j6}$R$^{k6}$;

each R$^{a6}$, R$^{c6}$, and R$^{d6}$ is independently selected from H, C$_{1-6}$ alkyl, C$_{1-6}$ haloalkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl-;

or any R$^{c6}$ and R$^{d6}$ attached to the same N atom, together with the N atom to which they are attached, form a 5- or 6-membered heteroaryl or a 4-14-membered heterocycloalkyl group; and each R$^{b6}$ is independently selected from H, C$_{1-6}$ alkyl, C$_{1-6}$ haloalkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl-.

In some embodiments, each R$^H$ is independently selected from D, halo, oxo, C$_{1-6}$ alkyl, C$_{1-6}$ haloalkyl, C$_{2-6}$ alkenyl, C$_{2-6}$ alkynyl, CN, C$_{1-6}$ alkoxy, C$_{1-6}$ haloalkoxy, amino, C$_{1-6}$ alkylamino, di-C$_{1-6}$ alkylamino, C$_{1-6}$ alkylsulfonyl, aminosulfonyl, C$_{1-6}$ alkylaminosulfonyl, di-C$_{1-6}$ alkylaminosulfonyl, and C$_{1-6}$ alkylsulfonylamino; wherein said C$_{1-6}$ alkyl is optionally substituted by 1, 2, 3, 4, 5, 6, 7, or 8 independently selected halogens.

In some embodiments, each R$^{a5}$, R$^{c5}$, and R$^{d5}$ is independently selected from H, C$_{1-6}$ alkyl, C$_{1-6}$ haloalkyl, C$_{2-6}$ alkenyl, C$_{2-6}$ alkynyl, phenyl, cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{a5}$, R$^{c5}$, and R$^{d5}$ are each optionally substituted with 1, 2, 3, or 4 independently selected R$^I$ substituents;

each R$^{b5}$ is independently selected from H, C$_{1-6}$ alkyl, C$_{1-6}$ haloalkyl, C$_{2-6}$ alkenyl, C$_{2-6}$ alkynyl, phenyl, cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$alkyl-, (5-6 membered heteroaryl)-C$_{1-6}$alkyl-, and (4-7 membered heterocycloalkyl)-C$_{1-6}$ alkyl- of R$^{b5}$ are each optionally substituted with 1, 2, 3, or 4 independently selected R$^I$ substituents;

each R$^{e5}$ is independently selected from H, OH, CN, C$_{1-6}$ alkyl, C$_{1-6}$alkoxy, C$_{1-6}$ haloalkyl, and C$_{1-6}$ haloalkoxy;

each R$^{f5}$ and R$^{g5}$ is independently selected from H, C$_{1-6}$ alkyl, C$_{1-6}$ haloalkyl, C$_{2-6}$ alkenyl, C$_{2-6}$ alkynyl, phenyl, cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-;

each R$^{h5}$ and R$^{i5}$ is independently selected from H, C$_{1-6}$ haloalkyl, C$_{1-6}$ alkyl, C$_{2-6}$ alkenyl, C$_{2-6}$ alkynyl, phenyl, cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-;

each R$^{j5}$ and R$^{k5}$ is independently selected from OH, C$_{1-6}$ alkoxy, and C$_{1-6}$ haloalkoxy; and each R$^I$ is D, halo, oxo, C$_{1-6}$ alkyl, C$_{1-6}$ haloalkyl, C$_{2-6}$ alkenyl, C$_{2-6}$ alkynyl, CN, C$_{1-6}$ alkoxy, C$_{1-6}$ haloalkoxy, amino, C$_{1-6}$ alkylamino, di-C$_{1-6}$ alkylamino, C$_{1-6}$ alkylsulfonyl, aminosulfonyl, C$_{1-6}$ alkylaminosulfonyl, di-C$_{1-6}$ alkylaminosulfonyl, and C$_{1-6}$ alkylsulfonylamino.

In some embodiments, each R$^I$ and R$^J$ is independently selected from D, halo, oxo, C$_{1-6}$ alkyl, C$_{1-6}$ haloalkyl, C$_{2-6}$ alkenyl, C$_{2-6}$ alkynyl, CN, C$_{1-6}$ alkoxy, C$_{1-6}$ haloalkoxy, amino, C$_{1-6}$ alkylamino, di-C$_{1-6}$ alkylamino, C$_{1-6}$ alkylsulfonyl, aminosulfonyl, C$_{1-6}$ alkylaminosulfonyl, di-C$_{1-6}$ alkylaminosulfonyl, and C$_{1-6}$ alkylsulfonylamino; and each R$^K$ is independently selected from H, D, OH, halo, oxo, CN, C(O)OH, NH$_2$, NO$_2$, SF$_5$, C$_{1-6}$ alkyl, C$_{1-6}$ alkoxy, C$_{1-6}$ haloalkoxy, C$_{1-6}$ haloalkyl, C$_{2-6}$ alkenyl, and C$_{2-6}$ alkynyl.

In some embodiments:

X is N;

R$^1$ is selected from H, C$_{1-6}$ alkyl, C$_{1-6}$ haloalkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$alkyl-, C$_{3-14}$ cycloalkyl-C$_{1-6}$ alkyl-, (5-14 membered heteroaryl)-C$_{1-6}$ alkyl-, (4-14 membered heterocycloalkyl)-C$_{1-6}$ alkyl-, OR$^{a1}$, C(O)R$^{b1}$, C(O)NR$^{c1}$R$^{d1}$, C(O)OR$^{a1}$, C(=NR$^{e1}$)R$^{b1}$, C(=NR$^{e1}$)NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, wherein the C$_{1-6}$ alkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl- of R$^I$ are each optionally substituted with 1, 2, 3, 4, 5, 6, 7, or 8 independently selected R$^B$ substituents;

R$^2$ is selected from H, D, halo, C$_{1-6}$ alkyl, C$_{1-6}$ haloalkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, (4-14 membered heterocycloalkyl)-C$_{1-6}$ alkyl-, CN, NO$_2$, OR$^{a2}$, SR$^{a2}$, NHOR$^{a2}$, C(O)R$^{b2}$, C(O)NR$^{c2}$R$^{d2}$, C(O)NR$^{c2}$(OR$^{a2}$), C(O)OR$^{a2}$, OC(O)R$^{b2}$, OC(O)NR$^{c2}$R$^{d2}$, NR$^{c3}$R$^{d3}$, NR$^{c2}$NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$C(=NR$^{e2}$)R$^{b2}$, NR$^{c2}$S(O)NR$^{c2}$R$^{d2}$, NR$^{c2}$S(O)R$^{b2}$, NR$^{c2}$S(O)$_2$R$^{b2}$, NR$^{c2}$S(O)(=NR$^{e2}$)R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, S(O)$_2$NR$^{b2}$, OS(O)(=NR$^{e2}$)R$^{b2}$, OS(O)$_2$R$^{b2}$, SF$_5$, P(O)R$^{f2}$R$^{g2}$, OP(O)(OR$^{h2}$)(OR$^{i2}$), P(O)(OR$^{h2}$)(OR$^{i2}$), and BR$^{j2}$R$^{k2}$, wherein the C$_{1-6}$ alkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl- of R$^2$ are each optionally substituted with 1, 2, 3, 4, 5, 6, 7, or 8 independently selected R$^C$ substituents;

Cy$^1$ is C$_{6-14}$ aryl, C$_{3-14}$ cycloalkyl, 5-14 membered heteroaryl, or 4-14 membered heterocycloalkyl, wherein the C$_{6-14}$ aryl, C$_{3-14}$ cycloalkyl, 5-14 membered heteroaryl, or 4-14 membered heterocycloalkyl is optionally substituted with 1, 2, 3, 4, 5, 6, 7, or 8 independently selected R$^E$ substituents;

provided that when Cy$^1$ is 4-14 membered heterocycloalkyl, then the 4-14 membered heterocycloalkyl of Cy$^1$ is other than unsubstituted morpholinyl;

provided that $Cy^1$ is not pyridin-4-yl optionally substituted with 1, 2, 3, or 4 independently selected $R^E$ substituents;

provided that $Cy^1$ is not pyrimidin-4-yl optionally substituted with 1, 2, or 3, independently selected $R^E$ substituents;

provided that $Cy^1$ is not quinolin-4-yl optionally substituted with 1, 2, 3, 4, 5, or 6 independently selected $R^E$ substituents;

$Cy^2$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^F$ substituents;

each $R^{a1}$, $R^{c1}$, $R^{d1}$, $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a1}$, $R^{c1}$, $R^{d1}$, $R^{a2}$, $R^{c2}$, and $R^{d2}$ are each optionally substituted with 1, 2, 3, 4, 5, 6, 7, or 8 independently selected $R^G$ substituents;

or, any $R^{c1}$ and $R^{d1}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

or any $R^{c2}$ and $R^{d2}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

each $R^{b1}$ and $R^{b2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, and (4-14 membered heterocycloalkyl)-$C_{1-6}$alkyl- of $R^{b1}$, $R^{b2}$, and $R^{b3}$ are each optionally substituted with 1, 2, 3, 4, 5, 6, 7, or 8 independently selected $R^G$ substituents;

each $R^{e1}$ and $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f2}$ and $R^{g2}$ is independently selected from H, $C_{1-6}$ alkyl, $C_{1-6}$ alkoxy, $C_{1-6}$haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^B$, $R^C$, $R^E$, $R^F$, and $R^G$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$, $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^B$, $R^C$, $R^E$, $R^F$, and $R^G$ are each optionally substituted with 1, 2, 3, 4, 5, 6, 7, or 8 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a4}$, $R^{c4}$, and $R^{d4}$ are each optionally substituted with 1, 2, 3, 4, 5, 6, 7, or 8 independently selected $R^H$ substituents;

or, any $R^{c4}$ and $R^{d4}$ attached to the same N atom, together with the N atom to which they are attached, optionally form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^H$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b4}$ are each optionally substituted with 1, 2, 3, 4, 5, 6, 7, or 8 independently selected $R^H$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f4}$ and $R^{g4}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or, any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^H$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^H$ are each optionally substituted with 1, 2, 3, or 4 independently selected $R^I$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a5}$, $R^{c5}$, and $R^{d5}$ are each optionally substituted with 1, 2, 3, or 4 independently selected $R^I$ substituents;

or any $R^{c5}$ and $R^{d5}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^I$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b5}$ are each optionally substituted with 1, 2, 3, or 4 independently selected $R^I$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j5}$ and $R^{g5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or, any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, and (4-14 membered heterocycloalkyl)-$C_{1-6}$alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c5}R^{d6}$, $C(=NR^{e6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)NR^{c6}R^{d6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^I$ are each optionally substituted with 1, 2, 3, or 4 independently selected $R^J$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a6}$, $R^{c6}$, and $R^{d6}$ are each optionally substituted with 1, 2, 3, or 4 independently selected $R^J$ substituents;

or any $R^{c6}$ and $R^{d6}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^J$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b6}$ are each optionally substituted with 1, 2, 3, or 4 independently selected $R^J$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, and (4-14 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or, any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$, $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^{c7}C(=NR^{e7})NR^{c7}R^{d7}$, $NR^{c7}C(=NR^{e7})R^{b7}$, $NR^{c7}S(O)R^{b7}$, $NR^{c7}S(O)NR^{c7}R^{d7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, $OS(O)_2R^{b7}$, $SF_5$, $P(O)R^{f7}R^{g7}$, $OP(O)(OR^{h7})(OR^{i7})$, $P(O)(OR^{h7})(OR^{i7})$, and $BR^{j7}R^{k7}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^J$ are each optionally substituted with 1, 2, 3, or 4 independently selected $R^K$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- wherein the $C_{1-6}$ alkyl, $C_{2-6}$alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a7}$, $R^{c7}$, and $R^{d7}$ are each optionally substituted with 1, 2, 3, or 4 independently selected $R^K$ substituents;

or any $R^{c7}$ and $R^{d7}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^K$ substituents;

each $R^{b7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b7}$ are each optionally substituted with 1, 2, 3, or 4 independently selected $R^K$ substituents;

each $R^{e7}$ is independently selected from H, OH, CN, $C_{1-6}$ alkyl, $C_{2-6}$ alkenyl, $C_{1-6}$ alkoxy, $C_{1-6}$ haloalkyl, $C_{1-6}$ haloalkoxy, $C_{2-6}$ alkynyl, $C_{6-14}$ aryl, $C_{3-14}$ cycloalkyl, 5-14 membered heteroaryl, and 4-14 membered heterocycloalkyl;

each $R^{f7}$ and $R^{g7}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j7}$ and $R^{k7}$ is independently selected from OH, $C_{1-6}$ alkoxy, and $C_{1-6}$ haloalkoxy;

or, any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^K$ is independently selected from H, D, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-; and wherein any heteroaryl group of any of the above-recited substituents optionally comprises an N-oxide on any ring-forming nitrogen.

In some embodiments:

X is N;

$R^1$ is selected from H, $C_{1-6}$ alkyl, $C_{2-6}$ alkenyl, $C_{2-6}$ alkynyl, and $C_{1-6}$ haloalkyl;

$R^2$ is selected from H, D, halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^2$ are each optionally substituted with 1, 2, 3, 4, 5, 6, 7, or 8 independently selected $R^C$ substituents;

$Cy^1$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^E$ or $R^M$ substituents;

provided that when $Cy^1$ is 4-14 membered heterocycloalkyl, then the 4-14 membered heterocycloalkyl of $Cy^1$ is other than unsubstituted morpholinyl;

$Cy^2$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^F$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, and (4-14 membered heterocycloalkyl)-$C_{1-6}$alkyl- of $R^{a2}$, $R^{c2}$, and $R^{d2}$ are each optionally substituted with 1, 2, 3, 4, 5, 6, 7, or 8 independently selected $R^G$ substituents;

or any $R^{c2}$ and $R^{d2}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b2}$ are each optionally substituted with 1, 2, 3, 4, 5, 6, 7, or 8 independently selected $R^G$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f2}$ and $R^{g2}$ is independently selected from H, $C_{1-6}$ alkyl, $C_{1-6}$ haloalkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^C$, $R^E$, $R^M$, $R^F$, and $R^G$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, (4-14 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$ $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$ $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^C$, $R^E$, $R^M$, $R^F$, and $R^G$ are each optionally substituted with 1, 2, 3, 4, 5, 6, 7, or 8 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a4}$, $R^{c4}$, and $R^{d4}$ are each optionally substituted with 1, 2, 3, 4, 5, 6, 7, or 8 independently selected $R^H$ substituents;

or, any $R^{c4}$ and $R^{d4}$ attached to the same N atom, together with the N atom to which they are attached, optionally form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^H$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b4}$ are each optionally substituted with 1, 2, 3, 4, 5, 6, 7, or 8 independently selected $R^H$ substituents;

each $R^{e4}$ is independently selected from H, OH, CN, $C_{1-6}$ alkyl, $C_{1-6}$alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f4}$ and $R^{g4}$ is independently selected from H, $C_{1-6}$ alkyl, $C_{1-6}$ alkoxy, $C_{1-6}$haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f4}$ and $R^{g4}$ is independently selected from H, $C_{1-6}$ alkyl, $C_{1-6}$haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or, any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^H$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, (4-14 membered heterocycloalkyl)-$C_{1-6}$alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $SF_5$, $P(O)R^{j5}R^{k5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{3-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$alkyl- of $R^H$ are each optionally substituted with 1, 2, 3, or 4 independently selected $R^I$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a5}$, $R^{c5}$, and $R^{d5}$ are each optionally substituted with 1, 2, 3, or 4 independently selected $R^I$ substituents;

or any $R^{c5}$ and $R^{d5}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^I$ substituents;

each $R^{b5}$ is independently selected from H, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b3}$ are each optionally substituted with 1, 2, 3, or 4 independently selected $R^I$ substituents;

each $R^{e5}$ is independently selected from H, OH, CN, $C_{1-6}$ alkyl, $C_{1-6}$alkoxy, $C_{1-6}$haloalkyl, $C_{1-6}$haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f5}$ and $R^{g5}$ is independently selected from H, $C_{1-6}$ alkyl, $C_{1-6}$alkoxy, $C_{1-6}$ haloalkyl, $C_{1-6}$haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h5}$ and $R^{i5}$ is independently selected from H, $C_{1-6}$ alkyl, $C_{1-6}$haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or, any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, and (4-14 membered heterocycloalkyl)-$C_{1-6}$alkyl-, CN, NO$_2$, OR$^{a6}$, SR$^{a6}$, NHOR$^{a6}$, C(O)R$^{b6}$, C(O)NR$^{c6}$R$^{d6}$, C(O)NR$^{c6}$(OR$^{a6}$), C(O)OR$^{a6}$, OC(O)R$^{b6}$, OC(O)NR$^{c6}$R$^{d6}$, NR$^{c6}$R$^{d6}$, NR$^{c6}$NR$^{c6}$R$^{d6}$, NR$^{c6}$C(O)R$^{b6}$, NR$^{c6}$C(O)OR$^{a6}$, NR$^{c6}$C(O)NR$^{c5}$R$^{d6}$, C(=NR$^{e6}$)R$^{b6}$, C(=NR$^{e6}$)NR$^{c6}$R$^{d6}$, NR$^{c6}$C(=NR$^{e6}$)NR$^{c6}$R$^{d6}$, NR$^{c6}$C(=NR$^{e6}$)R$^{b6}$, NR$^{c6}$S(O)R$^{b6}$, NR$^{c6}$S(O)NR$^{c6}$R$^{d6}$, NR$^{c6}$S(O)$_2$R$^{b6}$, NR$^{c6}$S(O)(=NR$^{e6}$)R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, S(O)$_2$NR$^{c6}$R$^{d6}$, OS(O)(=NR$^{e6}$)R$^{b6}$, OS(O)$_2$R$^{b6}$, SF$_5$, P(O)R$^{f6}$R$^{g6}$, OP(O)(OR$^{h6}$)(OR$^{i6}$), P(O)(OR$^{h6}$)(OR$^{i6}$), and BR$^{j6}$R$^{k6}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^I$ are each optionally substituted with 1, 2, 3, or 4 independently selected $R^J$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a6}$, $R^{c6}$, and $R^{d6}$ are each optionally substituted with 1, 2, 3, or 4 independently selected $R^J$ substituents;

or any $R^{c6}$ and $R^{d6}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^J$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b6}$ are each optionally substituted with 1, 2, 3, or 4 independently selected $R^J$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or, any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, NO$_2$, OR$^{a7}$, SR$^{a7}$, NHOR$^{a7}$, C(O)R$^{b7}$, C(O)NR$^{c7}$R$^{d7}$, C(O)NR$^{c7}$(OR$^{a7}$), C(O)OR$^{a7}$, OC(O)R$^{b7}$, OC(O)NR$^{c7}$R$^{d7}$, NR$^{c7}$R$^{d7}$, NR$^{c7}$NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$, C(=NR$^{e7}$)R$^{b7}$, C(=NR$^{e7}$)NR$^{c7}$R$^{d7}$, NR$^{c7}$C(=NR$^{e7}$)NR$^{c7}$R$^{d7}$, NR$^{c7}$C(=NR$^{e7}$)R$^{b7}$, NR$^{c7}$S(O)R$^{b7}$, NR$^{c7}$S(O)NR$^{c7}$R$^{d7}$, NR$^{c7}$S(O)$_2$R$^{b7}$, NR$^{c7}$S(O)(=NR$^{e7}$)R$^{b7}$, NR$^{c7}$S(O)$_2$NR$^{c7}$R$^{d7}$, S(O)R$^{b7}$, S(O)NR$^{c7}$R$^{d7}$, S(O)$_2$R$^{b7}$, S(O)$_2$NR$^{c7}$R$^{d7}$, OS(O)(=NR$^{e7}$)R$^{b7}$, OS(O)$_2$R$^{b7}$, SF$_5$, P(O)R$^{f7}$R$^{g7}$, OP(O)(OR$^{h7}$)(OR$^{i7}$), P(O)(OR$^{h7}$)(OR$^{i7}$), and BR$^{j7}$R$^{k7}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^J$ are each optionally substituted with 1, 2, 3, or 4 independently selected $R^K$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- wherein the $C_{1-6}$ alkyl, $C_{2-6}$alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a7}$, $R^{c7}$, and $R^{d7}$ are each optionally substituted with 1, 2, 3, or 4 independently selected $R^K$ substituents;

or any $R^{c7}$ and $R^{d7}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^K$ substituents;

each $R^{b7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b7}$ are each optionally substituted with 1, 2, 3, or 4 independently selected $R^K$ substituents;

each $R^{e7}$ is independently selected from H, OH, CN, $C_{1-6}$ alkyl, $C_{2-6}$ alkenyl, $C_{1-6}$ alkoxy, $C_{1-6}$ haloalkyl, $C_{1-6}$ haloalkoxy, $C_{2-6}$ alkynyl, $C_{6-14}$ aryl, $C_{3-14}$ cycloalkyl, 5-14 membered heteroaryl, and 4-14 membered heterocycloalkyl;

each $R^{f7}$ and $R^{g7}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j7}$ and $R^{k7}$ is independently selected from OH, $C_{1-6}$ alkoxy, and $C_{1-6}$ haloalkoxy;

or, any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^K$ is independently selected from H, D, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-; and wherein any heteroaryl group of any of the above-recited substituents optionally comprises an N-oxide on any ring-forming nitrogen.

In some embodiments:

X is N;

$R^1$ is selected from H, $C_{1-6}$ alkyl, $C_{2-6}$ alkenyl, $C_{2-6}$ alkynyl, and $C_{1-6}$ haloalkyl;

$R^2$ is selected from H, D, halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^2$ are each optionally substituted with 1, 2, 3, 4, 5, 6, 7, or 8 independently selected $R^C$ substituents;

$Cy^1$ is $C_{6-14}$ aryl, $C_{3-14}$ cycloalkyl, or 5-14 membered heteroaryl, wherein the $C_{6-14}$ aryl, $C_{3-14}$ cycloalkyl, or 5-14 membered heteroaryl is optionally substituted with 1, 2, 3, 4, 5, 6, 7, or 8 independently selected $R^E$ or $R^M$ substituents;

$Cy^2$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^F$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a2}$, $R^{c2}$, and $R^{d2}$ are each optionally substituted with 1, 2, 3, 4, 5, 6, 7, or 8 independently selected $R^G$ substituents;

or any $R^{c2}$ and $R^{d2}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b2}$ are each optionally substituted with 1, 2, 3, 4, 5, 6, 7, or 8 independently selected $R^G$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f2}$ and $R^{g2}$ is independently selected from H, $C_{1-6}$ alkyl, $C_{1-6}$ haloalkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^C$, $R^E$, $R^M$, $R^F$, and $R^G$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, NO$_2$, OR$^{a4}$, SR$^{a4}$, NHOR$^{a4}$, C(O)R$^{b4}$, C(O)NR$^{c4}$R$^{d4}$, C(O)NR$^{c4}$(OR$^{a4}$), C(O)OR$^{a4}$, OC(O)R$^{b4}$, OC(O)NR$^{c4}$R$^{d4}$, NR$^{c4}$R$^{d4}$, NR$^{c4}$NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$C(=NR$^{e4}$)R$^{b4}$, NR$^{c4}$S(O)R$^{b4}$, NR$^{c4}$S(O)NR$^{c4}$R$^{d4}$, NR$^{c4}$S(O)$_2$R$^{b4}$, NR$^{c4}$S(O)(=NR$^{e4}$)R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, S(O)$_2$NR$^{c4}$R$^{d4}$, OS(O)(=NR$^{e4}$)R$^{b4}$, OS(O)$_2$R$^{b4}$, SF$_5$, P(O)R$^{j4}$R$^{g4}$ OP(O)(OR$^{h4}$)(OR$^{i4}$), P(O)(OR$^{h4}$)(OR$^{i4}$), and BR$^{j4}$R$^{k4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^C$, $R^E$, $R^M$, $R^F$, and $R^G$ are each optionally substituted with 1, 2, 3, 4, 5, 6, 7, or 8 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a4}$, $R^{c4}$, and $R^{d4}$ are each optionally substituted with 1, 2, 3, 4, 5, 6, 7, or 8 independently selected $R^H$ substituents;

or, any $R^{c4}$ and $R^{d4}$ attached to the same N atom, together with the N atom to which they are attached, optionally form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^H$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b4}$ are each optionally substituted with 1, 2, 3, 4, 5, 6, 7, or 8 independently selected $R^H$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f4}$ and $R^{g4}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or, any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^H$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, NO$_2$, OR$^{a5}$, SR$^{a5}$, NHOR$^{a5}$, C(O)R$^{b5}$, C(O)NR$^{c5}$R$^{d5}$, C(O)NR$^{c5}$(OR$^{a5}$), C(O)OR$^{a5}$, OC(O)R$^{b4}$, OC(O)NR$^{c5}$R$^{d5}$, NR$^{c5}$R$^{d5}$, NR$^{c5}$NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$C(=NR$^{e5}$)R$^{b5}$, NR$^{c5}$S(O)R$^{b5}$, NR$^{c5}$S(O)NR$^{c5}$R$^{d5}$, NR$^{c5}$S(O)$_2$R$^{b5}$, NR$^{c5}$S(O)(=NR$^{e5}$)R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, S(O)$_2$NR$^{c5}$R$^{d5}$, OS(O)(=NR$^{e5}$)R$^{b5}$, OS(O)$_2$R$^{b5}$, SF$_5$, P(O)R$^{c5}$R$^{d5}$, OP(O)(OR$^{h5}$)(OR$^{i5}$), P(O)(OR$^{h5}$)(OR$^{i5}$), and BR$^{j5}$R$^{k5}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^H$ are each optionally substituted with 1, 2, 3, or 4 independently selected $R^I$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, and (4-14 membered heterocycloalkyl)-$C_{1-6}$alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a5}$, $R^{c5}$, and $R^{d5}$ are each optionally substituted with 1, 2, 3, or 4 independently selected $R^I$ substituents;

or any $R^{c5}$ and $R^{d5}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^I$ substituents;

each $R^{b5}$ is independently selected from H, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b3}$ are each optionally substituted with 1, 2, 3, or 4 independently selected $R^I$ substituents;

each $R^{e5}$ is independently selected from H, OH, CN, $C_{1-6}$ alkyl, $C_{1-6}$alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$alkyl-, (5-14 membered heteroaryl)-$C_{1-6}$ alkyl-, and (4-14 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h5}$ and $R^{i3}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or, any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, and (4-14 membered heterocycloalkyl)-$C_{1-6}$alkyl-, CN, NO$_2$, OR$^{a6}$, SR$^{a6}$, NHOR$^{a6}$, C(O)R$^{b6}$, C(O)NR$^{c6}$R$^{d6}$, C(O)NR$^{c6}$(OR$^{a6}$), C(O)OR$^{a5}$, OC(O)R$^{b6}$, OC(O)NR$^{c6}$R$^{d6}$, NR$^{c6}$R$^{d6}$, NR$^{c6}$NR$^{c6}$R$^{d6}$, NR$^{c6}$C(O)R$^{b6}$, NR$^{c6}$C(O)OR$^{a6}$, NR$^{c6}$C(O)NR$^{c5}$R$^{d6}$, C(=NR$^{e6}$)R$^{b6}$, C(=NR$^{e6}$)NR$^{c6}$R$^{d6}$, NR$^{c6}$C(=NR$^{e6}$)NR$^{c6}$R$^{d6}$, NR$^{c6}$C(=NR$^{e6}$)R$^{b6}$, NR$^{c6}$S(O)R$^{b6}$, NR$^{c6}$S(O)NR$^{c6}$R$^{d6}$, NR$^{c6}$S(O)$_2$R$^{b6}$, NR$^{c6}$S(O)(=NR$^{e6}$)R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$, S(O)$_2$NR$^{c6}$R$^{d6}$, OS(O)(=NR$^{e6}$)R$^{b6}$, OS(O)$_2$R$^{b6}$, SF$_5$, P(O)R$^{f6}$R$^{g6}$, OP(O)(OR$^{h6}$)(OR$^{i6}$), P(O)(OR$^{h6}$)(OR$^{i6}$), and BR$^{j6}$R$^{k6}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^I$ are each optionally substituted with 1, 2, 3, or 4 independently selected $R^J$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a6}$, $R^{c6}$, and $R^{d6}$ are each optionally substituted with 1, 2, 3, or 4 independently selected $R^J$ substituents;

or any $R^{c6}$ and $R^{d6}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^J$ substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b6}$ are each optionally substituted with 1, 2, 3, or 4 independently selected $R^J$ substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or, any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$haloalkyl;

each $R^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, NO$_2$, OR$^{a7}$, SR$^{a7}$, NHOR$^{a7}$, C(O)R$^{b7}$, C(O)NR$^{c7}$R$^{d7}$, C(O)NR$^{c7}$(OR$^{a7}$), C(O)OR$^{a7}$, OC(O)R$^{b7}$, OC(O)NR$^{c7}$R$^{d7}$, NR$^{c7}$R$^{d7}$, NR$^{c7}$NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$, C(=NR$^{e7}$)R$^{b7}$, C(=NR$^{e7}$)NR$^{c7}$R$^{d7}$, NR$^{c7}$C(=NR$^{e7}$)NR$^{c7}$R$^{d7}$, NR$^{c7}$C(=NR$^{e7}$)R$^{b7}$, NR$^{c7}$S(O)R$^{b7}$, NR$^{c7}$S(O)NR$^{c7}$R$^{d7}$, NR$^{c7}$S(O)$_2$R$^{b7}$, NR$^{c7}$S(O)(=NR$^{e7}$)R$^{b7}$, NR$^{c7}$S(O)$_2$NR$^{c7}$R$^{d7}$, S(O)R$^{b7}$, S(O)NR$^{c7}$R$^{d7}$, S(O)$_2$R$^{b7}$, S(O)$_2$NR$^{c7}$R$^{d7}$, OS(O)(=NR$^{e7}$)R$^{b7}$, OS(O)$_2$R$^{b7}$, SF$_5$, P(O)R$^{f7}$R$^{g7}$, OP(O)(OR$^{h7}$)(OR$^{i7}$), P(O)(OR$^{h7}$)(OR$^{i7}$), and BR$^{j7}$R$^{k7}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl- of R$^J$ are each optionally substituted with 1, 2, 3, or 4 independently selected R$^K$ substituents;

each R$^{a7}$, R$^{c7}$, and R$^{d7}$ is independently selected from H, C$_{1-6}$ alkyl, C$_{1-6}$ haloalkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$alkyl-, and (4-14 membered heterocycloalkyl)-C$_{1-6}$alkyl- wherein the C$_{1-6}$ alkyl, C$_{2-6}$alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl- of R$^{a7}$, R$^{c7}$, and R$^{d7}$ are each optionally substituted with 1, 2, 3, or 4 independently selected R$^K$ substituents;

or any R$^{c7}$ and R$^{d7}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected R$^K$ substituents;

each R$^{b7}$ is independently selected from H, C$_{1-6}$ alkyl, C$_{1-6}$ haloalkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl-, wherein the C$_{1-6}$ alkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl- of R$^{b7}$ are each optionally substituted with 1, 2, 3, or 4 independently selected R$^K$ substituents;

each R$^{e7}$ is independently selected from H, OH, CN, C$_{1-6}$ alkyl, C$_{2-6}$ alkenyl, C$_{1-6}$ alkoxy, C$_{1-6}$haloalkyl, C$_{1-6}$ haloalkoxy, C$_{2-6}$ alkynyl, C$_{6-14}$ aryl, C$_{3-14}$ cycloalkyl, 5-14 membered heteroaryl, and 4-14 membered heterocycloalkyl;

each R$^{f7}$ and R$^{g7}$ is independently selected from H, C$_{1-6}$ alkyl, C$_{1-6}$alkoxy, C$_{1-6}$haloalkyl, C$_{1-6}$ haloalkoxy, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl-;

each R$^{h7}$ and R$^{i7}$ is independently selected from H, C$_{1-6}$ alkyl, C$_{1-6}$haloalkyl, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{6-14}$ aryl-C$_{1-6}$ alkyl-, C$_{3-14}$ cycloalkyl-C$_{1-6}$ alkyl-, (5-14 membered heteroaryl)-C$_{1-6}$alkyl-, and (4-14 membered heterocycloalkyl)-C$_{1-6}$alkyl-;

each R$^{j7}$ and R$^{k7}$ is independently selected from OH, C$_{1-6}$ alkoxy, and C$_{1-6}$ haloalkoxy;

or, any R$^{j7}$ and R$^{k7}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$haloalkyl;

each R$^K$ is independently selected from H, D, OH, halo, oxo, CN, C(O)OH, NH$_2$, NO$_2$, SF$_5$, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-14}$ aryl, C$_{3-14}$ cycloalkyl, 5-14 membered heteroaryl, 4-14 membered heterocycloalkyl, C$_{3-14}$ aryl-C$_{1-6}$ alkyl-, C$_{3-14}$ cycloalkyl-C$_{1-6}$ alkyl-, (5-14 membered heteroaryl)-C$_{1-6}$ alkyl-, and (4-14 membered heterocycloalkyl)-C$_{1-6}$ alkyl-; and wherein any heteroaryl group of any of the above-recited substituents optionally comprises an N-oxide on any ring-forming nitrogen.

In some embodiments, the compound of Formula (I) is a compound of Formula (II):

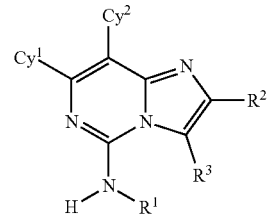

(II)

or a pharmaceutically acceptable salt thereof.

In some embodiments, the compound of Formula (I) is a compound of Formula (III):

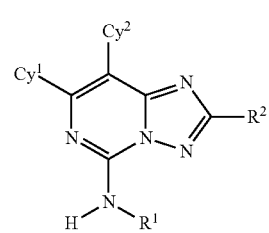

(III)

or a pharmaceutically acceptable salt thereof.

In some embodiments, Cy$^1$ is C$_{6-14}$ aryl, wherein the C$_{6-14}$ aryl is optionally substituted with 1, 2, 3, or 4 independently selected R$^E$ substituents.

In some embodiments, Cy$^1$ is C$_{3-14}$ cycloalkyl, wherein the C$_{3-14}$ cycloalkyl is optionally substituted with 1, 2, 3, or 4 independently selected R$^E$ substituents.

In some embodiments, Cy$^1$ is 5-14 membered heteroaryl, wherein the 5-14 membered heteroaryl is optionally substituted with 1, 2, 3, or 4 independently selected R$^E$ substituents.

In some embodiments, Cy$^1$ is 4-14 membered heterocycloalkyl, wherein the 4-14 membered heterocycloalkyl is optionally substituted with 1, 2, 3, or 4 independently selected R$^E$ substituents.

In some embodiments, Cy$^1$ is C$_{6-10}$ aryl, wherein the C$_{6-10}$ aryl is optionally substituted with 1, 2, 3, or 4 independently selected R$^E$ substituents.

In some embodiments, Cy$^1$ is cycloalkyl, wherein the C$_{3-7}$ cycloalkyl is optionally substituted with 1, 2, 3, or 4 independently selected R$^E$ substituents.

In some embodiments, Cy$^1$ is 5-10 membered heteroaryl, wherein the 5-10 membered heteroaryl is optionally substituted with 1, 2, 3, or 4 independently selected R$^E$ substituents.

In some embodiments, Cy$^1$ is 4-10 membered heterocycloalkyl, wherein the 4-10 membered heterocycloalkyl is optionally substituted with 1, 2, 3, or 4 independently selected R$^E$ substituents.

In some embodiments, Cy$^1$ is phenyl or 5-10 membered heteroaryl, wherein the phenyl or 5-10 membered heteroaryl is optionally substituted with 1, 2, 3, or 4 independently selected R$^E$ substituents.

In some embodiments, $Cy^1$ is phenyl, optionally substituted with 1, 2, 3, or 4 independently selected $R^M$ substituents, or $C_{7-14}$ aryl or 5-14 membered heteroaryl wherein the $C_{7-14}$ aryl and 5-14 membered heteroaryl are optionally substituted with 1, 2, 3, or 4 independently selected $R^E$ substituents, and wherein each $R^M$ is independently selected from D, halo, oxo, $C_{1-6}$ alkyl, $C_{1-6}$ haloalkyl, $C_{1-6}$ alkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, 2-CN, 3-CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)R^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, and $NR^{c4}S(O)_2NR^{c4}R^{d4}$, wherein the $C_{1-6}$ alkyl, $C_{1-6}$ alkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl of $R^M$ are each optionally substituted with 1, 2, 3, or 4 independently selected $R^H$ substituents.

In some embodiments, $Cy^1$ is selected from phenyl, pyridinyl, furanyl, benzofuranyl, and pyrazolyl, each of which is optionally substituted with 1, 2, or 3 substituents selected from $C_{1-3}$ alkyl, halo, CN, and $C_{1-3}$ alkoxy.

In some embodiments, the optionally substituted $Cy^1$ is selected from cyanophenyl, cyanofluorophenyl, 2,3-dihydro-1H-pyrrolo[2,3,-b]pyridine, phenyl, methoxyphenyl, fluorophenyl, pyridinyl, methylfuranyl, benzofuranyl, and methyl-1H-pyrazolyl.

In some embodiments, the optionally substituted $Cy^1$ is selected from cyanophenyl, 2,3-dihydro-1H-pyrrolo[2,3,-b]pyridine, phenyl, methoxyphenyl, fluorophenyl, pyridinyl, methylfuranyl, benzofuranyl, and methyl-1H-pyrazolyl.

In some embodiments, $Cy^1$ is selected from 2-cyanophenyl, 3-cyanophenyl, 3-cyano-2-fluorophenyl, 2,3-dihydro-1H-pyrrolo[2,3,-b]pyridine, phenyl, 3-methoxyphenyl, 2-fluorophenyl, pyridine-4-yl, 2-methylfuran-3-yl, benzofuran-2-yl, and 1-methyl-1H-pyrazol-4-yl.

In some embodiments, the optionally substituted $Cy^1$ is selected from 2-cyanophenyl, 3-cyanophenyl, 2,3-dihydro-1H-pyrrolo[2,3,-b]pyridine, phenyl, 3-methoxyphenyl, 2-fluorophenyl, pyridine-4-yl, 2-methylfuran-3-yl, benzofuran-2-yl, and 1-methyl-1H-pyrazol-4-yl.

In some embodiments, the optionally substituted $Cy^1$ is selected from 3-cyanophenyl and phenyl.

In some embodiments, $Cy^1$ is 3-cyanophenyl.

In some embodiments, $Cy^2$ is $C_{6-14}$ aryl, $C_{4-14}$ cycloalkyl, 5-14 membered heteroaryl or 4-14 membered heterocycloalkyl wherein the $C_{6-14}$ aryl, $C_{4-14}$ cycloalkyl, 5-14 membered heteroaryl and 4-14 membered heterocycloalkyl are optionally substituted with 1, 2, 3, 4, 5, 6, 7, or 8 independently selected $R^F$ substituents.

In some embodiments, $Cy^2$ is $C_{6-14}$ aryl, wherein the $C_{6-14}$ aryl is optionally substituted with 1, 2, 3, or 4 independently selected $R^F$ substituents.

In some embodiments, $Cy^2$ is $C_{3-14}$ cycloalkyl, wherein the $C_{3-14}$ cycloalkyl is optionally substituted with 1, 2, 3, or 4 independently selected $R^F$ substituents.

In some embodiments, $Cy^2$ is 5-14 membered heteroaryl, wherein the 5-14 membered heteroaryl is optionally substituted with 1, 2, 3, or 4 independently selected $R^F$ substituents.

In some embodiments, $Cy^2$ is 4-14 membered heterocycloalkyl, wherein the 4-14 membered heterocycloalkyl is optionally substituted with 1, 2, 3, or 4 independently selected $R^F$ substituents.

In some embodiments, $Cy^2$ is $C_{6-10}$ aryl, wherein the $C_{6-10}$ aryl is optionally substituted with 1, 2, 3, or 4 independently selected $R^F$ substituents.

In some embodiments, $Cy^2$ is cycloalkyl, wherein the $C_{3-7}$ cycloalkyl is optionally substituted with 1, 2, 3, or 4 independently selected $R^F$ substituents.

In some embodiments, $Cy^2$ is 5-10 membered heteroaryl, wherein the 5-10 membered heteroaryl is optionally substituted with 1, 2, 3, or 4 independently selected $R^F$ substituents.

In some embodiments, $Cy^2$ is 4-10 membered heterocycloalkyl, wherein the 4-10 membered heterocycloalkyl is optionally substituted with 1, 2, 3, or 4 independently selected $R^F$ substituents.

In some embodiments, $Cy^2$ is selected from $C_{3-6}$ cycloalkyl, phenyl, 5-10 membered heteroaryl, and 5-10 membered heterocycloalkyl;

wherein the 5-10 membered heteroaryl and 5-10 membered heterocycloalkyl each comprise one, two, or three nitrogen atoms as ring-forming heteroatoms, wherein one of the one or two nitrogen atoms is optionally an N-oxide, and wherein a ring-forming carbon atom is optionally substituted by oxo; and wherein the $C_{3-6}$ cycloalkyl, phenyl, 5-10 membered heteroaryl, and 5-10 membered heterocycloalkyl are each optionally substituted with 1, 2, or 3 substituents selected from $C_{1-3}$ alkyl, $C_{1-3}$ alkyl-OH, halo, CN, $C_{1-3}$ alkoxy, and $C(O)NH_2$ In some embodiments, $Cy^2$ is selected from $C_{3-6}$ cycloalkyl, phenyl, 5-10 membered heteroaryl, and 5-10 membered heterocycloalkyl;

wherein the 5-10 membered heteroaryl and 5-10 membered heterocycloalkyl each comprise one or two nitrogen atoms as ring-forming heteroatoms, wherein one of the one or two nitrogen atoms is optionally an N-oxide, and wherein a ring-forming carbon atom is optionally substituted by oxo; and wherein the $C_{3-6}$ cycloalkyl, $C_6$-aryl, 5-10 membered heteroaryl, and 5-10 membered heterocycloalkyl are each optionally substituted with 1, 2, or 3 substituents selected from $C_{1-3}$ alkyl, halo, CN, $C_{1-3}$ alkoxy, and $C(O)NH_2$.

In some embodiments, $Cy^2$ is selected from pyridinyl, tetrahydropyridinyl, piperidinyl, pyridine-N-oxide, oxo-dihydropyridinyl, phenyl, pyrazolo[1,5-a]pyridin-3-yl, pyrazolo[1,5-b]pyridazinyl, pyrazolyl, pyrimidinyl, quinolinyl, oxazolyl, 2,3-dihydro-[1,4]dioxino[2,3-b]pyridin-8-yl, and triazolyl each of which is optionally substituted with 1, 2, or 3 substituents selected from $C_{1-3}$ alkyl, $C_{1-3}$ alkyl-OH, halo, CN, $C_{1-3}$ alkoxy, and $C(O)NH_2$ In some embodiments, $Cy^2$ is selected from pyridinyl, tetrahydropyridinyl, piperidinyl, pyridine-N-oxide, oxo-dihydropyridinyl, phenyl, pyrazolo[1,5-a]pyridin-3-yl, pyrazolo[1,5-b]pyridazinyl, pyrazolyl, pyrimidinyl, quinolinyl, oxazolyl, and 2,3-dihydro-[1,4]dioxino[2,3-b]pyridin-8-yl, each of which is optionally substituted with 1, 2, or 3 substituents selected from $C_{1-3}$ alkyl, halo, CN, $C_{1-3}$ alkoxy, and $C(O)NH_2$.

In some embodiments, $Cy^2$ is selected from pyridinyl, tetrahydropyridinyl, piperidinyl, pyridine-N-oxide, oxo-dihydropyridinyl, phenyl, pyrazolo[1,5-a]pyridin-3-yl, pyrazolyl, pyrimidinyl, and 2,3-dihydro-[1,4]dioxino[2,3-b]pyridin-8-yl, each of which is optionally substituted with 1, 2, or 3 substituents selected from $C_{1-3}$ alkyl, halo, CN, $C_{1-3}$ alkoxy, and $C(O)NH_2$.

In some embodiments, $Cy^2$ is cyclopropyl optionally substituted with 1, 2, or 3 substituents selected from $C_{1-3}$ alkyl, halo, CN, $C_{1-3}$ alkoxy, and $C(O)NH_2$.

In some embodiments, the optionally substituted $Cy^2$ is selected from 2,6-dimethylpyridin-4-yl, pyridin-4-yl, 2-methylpyridin-4-yl, 1-carbamoyl-1,2,3,6-tetrahydropyridin-4-yl, 1-carbamoylpiperidin-4-yl, 2-methoxypyridin-4-yl, 2-methoxy-6-methylpyridin-4-yl, 2,6-dimethylpyridin-4-yl-1-oxide, 1-ethyl-6-oxo-1,6-dihydropyridin-3-yl, 3-methylpyridin-4-yl, 3-fluoropyridin-4-yl, 3-chloropyridin-4-yl, 3-methoxypyridin-4-yl, 3-cyanopyridin-4-yl, 4-carbamoylphenyl, pyrazolo[1,5-a]pyridin-3-yl, pyrazolo[1,5-b]pyridazin-3-yl, 5-methyl-1H-pyrazol-4-yl, 1-ethyl-1H-pyrazol-5-yl, 1-isopropyl-1H-pyrazol-5-yl, 1-propyl-1H-pyrazol-5-yl, pyrimidin-4-yl, 2,3-dihydro-[1,4]dioxino[2,3-b]pyridin-8-yl, quinolin-5-yl, 5-fluoropyrimidin-4-yl, oxazol-5-yl, 4-methyloxazol-5-yl, 4-ethyloxazol-5-yl, 4-(hydroxymethyl)-2-methyloxazol-5-yl, 4-(methoxymethyl)-2-methyloxazol-5-yl, 4-(hydroxymethyl)-2-methyloxazol-5-yl, 1-ethyl-1H-1,2,3-triazol-5-yl, and cyclopropyl In some embodiments, the optionally substituted $Cy^2$ is selected from 2,6-dimethylpyridin-4-yl, pyridin-4-yl, 2-methylpyridin-4-yl, 1-carbamoyl-1,2,3,6-tetrahydropyridin-4-yl, 1-carbamoylpiperidin-4-yl, 2-methoxypyridin-4-yl, 2-methoxy-6-methylpyridin-4-yl, 2,6-dimethylpyridin-4-yl-1-oxide, 1-ethyl-6-oxo-1,6-dihydropyridin-3-yl, 3-methylpyridin-4-yl, 3-fluoropyridin-4-yl, 3-chloropyridin-4-yl, 3-methoxypyridin-4-yl, 3-cyanopyridin-4-yl, 4-carbamoylphenyl, pyrazolo[1,5-a]pyridin-3-yl, pyrazolo[1,5-b]pyridazin-3-yl, 5-methyl-1H-pyrazol-4-yl, 1-ethyl-1H-pyrazol-5-yl, 1-isopropyl-1H-pyrazol-5-yl, 1-propyl-1H-pyrazol-5-yl, pyrimidin-4-yl, 2,3-dihydro-[1,4]dioxino[2,3-b]pyridin-8-yl, quinolin-5-yl, 5-fluoropyrimidin-4-yl, 4-methyloxazol-5-yl, 4-(hydroxymethyl)-2-methyloxazol-5-yl, 4-(methoxymethyl)-2-methyloxazol-5-yl, and cyclopropyl.

In some embodiments, the optionally substituted $Cy^2$ is selected from 2,6-dimethylpyridin-4-yl, pyridin-4-yl, 2-methylpyridin-4-yl, 1-carbamoyl-1,2,3,6-tetrahydropyridin-4-yl, 1-carbamoylpiperidin-4-yl, 2-methoxypyridin-4-yl, 2,6-dimethylpyridin-4-yl-1-oxide, 1-ethyl-6-oxo-1,6-dihydropyridin-3-yl, 3-methylpyridin-4-yl, 3-fluoropyridin-4-yl, 3-chloropyridin-4-yl, 3-methoxypyridin-4-yl, 3-cyanopyridin-4-yl, 4-carbamoylphenyl, pyrazolo[1,5-a]pyridin-3-yl, 5-methyl-1H-pyrazol-4-yl, 1-ethyl-1H-pyrazol-5-yl, 1-isopropyl-1H-pyrazol-5-yl, 1-propyl-1H-pyrazol-5-yl, pyrimidin-4-yl, 2,3-dihydro-[1,4]dioxino[2,3-b]pyridin-8-yl, and cyclopropyl.

In some embodiments, $R^1$ is selected from H, D, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$alkyl-, (4-14 membered heterocycloalkyl)-$C_{1-6}$alkyl-, $OR^{a1}$, $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, $S(O)R^{b1}$, $S(O)NR^{c1}R^{d1}$, $S(O)_2R^{b1}$ and $S(O)_2NR^{c1}R^{d1}$, wherein the $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^1$ are each optionally substituted with 1, 2, 3, 4, 5, 6, 7, or 8 independently selected $R^B$ substituents.

In some embodiments, $R^1$ is selected from H, D, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-8 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-8 membered heteroaryl)-$C_{1-6}$ alkyl-, (4-14 membered heterocycloalkyl)-$C_{1-6}$ alkyl-, $OR^{a1}$, $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, $S(O)R^{b1}$, $S(O)NR^{c1}R^{d1}$, $S(O)_2R^{b1}$ and $S(O)_2NR^{c1}R^{d1}$, wherein the $C_{2-6}$ alkenyl, $C_{2-6}$ alkynyl, $C_{6-14}$ aryl, $C_{3-14}$ cycloalkyl, 5-8 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-8 membered heteroaryl)-$C_{1-6}$ alkyl-, and (4-14 membered heterocycloalkyl)-$C_{1-6}$ alkyl- of $R^1$ are each optionally substituted with 1, 2, 3, 4, 5, 6, 7, or 8 independently selected $R^B$ substituents.

In some embodiments, $R^1$ is selected from H, $C_{1-6}$ alkyl, and 5-8 membered heteroaryl, wherein the 5-8 membered heteroaryl is optionally substituted by 1 or 2 independently selected $R^B$ substituents.

In some embodiments, $R^1$ is H, $C_{1-6}$ alkyl, or a 5-8 membered heteroaryl

In some embodiments, $R^1$ is H or $C_{1-6}$ alkyl.

In some embodiments, $R^1$ is H or $C_{1-3}$ alkyl.

In some embodiments, $R^1$ is H, ethyl, or nicotinonitrile.

In some embodiments, $R^1$ is H or ethyl.

In some embodiments, $R^1$ is H.

In some embodiments, $R^1$ is 5-8 membered heteroaryl which is optionally substituted by 1 or 2 independently selected $R^B$ substituents.

In some embodiments, $R^1$ is 5-8 membered heteroaryl.

In some embodiments, $R^1$ is pyridyl which is optionally substituted by 1 or 2 $R^B$ substituents.

In some embodiments, $R^1$ is pyridyl which is optionally substituted by cyano.

In some embodiments, $R^1$ is nicotinonitrile.

In some embodiments, $R^1$ is 3-cyanopyridyl.

In some embodiments, $R^2$ is selected from halo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- are each optionally substituted with 1, 2, 3, 4, 5, 6, 7, or 8 independently selected $R^C$ substituents; and wherein the $C_{1-6}$ alkyl is substituted with 1, 2, 3, 4, 5, 6, 7, or 8 independently selected $R^C$ substituents.

In some embodiments, $R^2$ is selected from $C_{1-6}$ alkyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, $C(O)R^{b2}$, $C(O)NR^{c2}R^{d2}$, $C(O)OR^{a2}$, and $NR^{c2}R^{d2}$, wherein the $C_{3-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- are each optionally substituted with 1, 2, 3, 4, or 5 independently selected $R^C$ substituents; and wherein the $C_{1-6}$ alkyl is substituted with 1, 2, 3, 4, or 5 independently selected $R^C$ substituents.

In some embodiments, $R^2$ is selected from $C_{6\text{-}14}$ aryl, $C_{3\text{-}14}$ cycloalkyl, 5-14 membered heteroaryl, 4-14 membered heterocycloalkyl, $C_{6\text{-}14}$ aryl-$C_{1\text{-}6}$ alkyl-, $C_{3\text{-}14}$ cycloalkyl-$C_{1\text{-}6}$ alkyl-, (5-14 membered heteroaryl)-$C_{1\text{-}6}$ alkyl-, (4-14 membered heterocycloalkyl)-$C_{1\text{-}6}$ alkyl-, $C(O)R^{b2}$, $C(O)NR^{c2}R^{d2}$, $C(O)OR^{a2}$, and $NR^{c2}R^{d2}$, wherein the $C_{6\text{-}14}$ aryl, $C_{3\text{-}14}$ cycloalkyl, 5-14 membered heteroaryl, 4-14 membered heterocycloalkyl, $C_{6\text{-}14}$ aryl-$C_{1\text{-}6}$ alkyl-, $C_{3\text{-}14}$ cycloalkyl-$C_{1\text{-}6}$ alkyl-, (5-14 membered heteroaryl)-$C_{1\text{-}6}$ alkyl-, and (4-14 membered heterocycloalkyl)-$C_{1\text{-}6}$ alkyl- are each optionally substituted with 1, 2, 3, 4, or 5 independently selected $R^G$ substituents.

In some embodiments, $R^2$ is selected from $C_{6\text{-}14}$ aryl, $C_{3\text{-}14}$ cycloalkyl, 5-14 membered heteroaryl, 4-14 membered heterocycloalkyl, $C_{6\text{-}14}$ aryl-$C_{1\text{-}6}$ alkyl-, $C_{3\text{-}14}$ cycloalkyl-$C_{1\text{-}6}$ alkyl-, (5-14 membered heteroaryl)-$C_{1\text{-}6}$ alkyl-, and (4-14 membered heterocycloalkyl)-$C_{1\text{-}6}$ alkyl-, wherein the $C_{6\text{-}14}$ aryl, $C_{3\text{-}14}$ cycloalkyl, 5-14 membered heteroaryl, 4-14 membered heterocycloalkyl, $C_{6\text{-}14}$ aryl-$C_{1\text{-}6}$ alkyl-, $C_{3\text{-}14}$ cycloalkyl-$C_{1\text{-}6}$ alkyl-, (5-14 membered heteroaryl)-$C_{1\text{-}6}$ alkyl-, and (4-14 membered heterocycloalkyl)-$C_{1\text{-}6}$ alkyl- are each optionally substituted with 1, 2, 3, 4, or 5 independently selected $R^C$ substituents.

In some embodiments, $R^2$ is selected from H, $C_{1\text{-}6}$ alkyl, $C_{3\text{-}14}$ cycloalkyl, $C_{6\text{-}14}$ aryl, 5-14 membered heteroaryl, 4-14 membered heterocycloalkyl, $C_{6\text{-}14}$ aryl-$C_{1\text{-}6}$ alkyl-, $C_{3\text{-}14}$ cycloalkyl-$C_{1\text{-}6}$ alkyl-, (5-14 membered heteroaryl)-$C_{1\text{-}6}$ alkyl-, (4-14 membered heterocycloalkyl)-$C_{1\text{-}6}$ alkyl-, $NR^{c2}R^{d2}$, $C(O)R^{b2}$, $C(O)NR^{c2}R^{d2}$, and $C(O)OR^{a2}$, wherein the $C_{1\text{-}6}$ alkyl, $C_{3\text{-}14}$ cycloalkyl, $C_{6\text{-}14}$ aryl, 5-14 membered heteroaryl, 4-14 membered heterocycloalkyl, $C_{6\text{-}14}$ aryl-$C_{1\text{-}6}$alkyl-, $C_{3\text{-}14}$ cycloalkyl-$C_{1\text{-}6}$ alkyl-, (5-14 membered heteroaryl)-$C_{1\text{-}6}$ alkyl-, and (4-14 membered heterocycloalkyl)-$C_{1\text{-}6}$ alkyl- are each optionally substituted with 1, 2, or 3 independently selected $R^C$ substituents.

In some embodiments, $R^2$ is selected from H, $C_{1\text{-}6}$ alkyl, $C_{6\text{-}14}$ aryl, $C_{3\text{-}14}$ cycloalkyl, 5-14 membered heteroaryl, 4-14 membered heterocycloalkyl, $C_{6\text{-}14}$ aryl-$C_{1\text{-}6}$ alkyl-, $C_{3\text{-}14}$ cycloalkyl-$C_{1\text{-}6}$ alkyl-, (5-14 membered heteroaryl)-$C_{1\text{-}6}$ alkyl-, (4-14 membered heterocycloalkyl)-$C_{1\text{-}6}$ alkyl-, $OR^{a2}$, $NR^{c2}R^{d2}$, $C(O)R^{b2}$, $C(O)NR^{c2}R^{d2}$, and $C(O)OR^{a2}$, wherein the $C_{1\text{-}6}$ alkyl, $C_{6\text{-}14}$ aryl, $C_{3\text{-}14}$ cycloalkyl, 5-14 membered heteroaryl, 4-14 membered heterocycloalkyl, $C_{6\text{-}14}$ aryl-$C_{1\text{-}6}$ alkyl-, $C_{3\text{-}14}$ cycloalkyl-$C_{1\text{-}6}$ alkyl-, (5-14 membered heteroaryl)-$C_{1\text{-}6}$ alkyl-, and (4-14 membered heterocycloalkyl)-$C_{1\text{-}6}$ alkyl-, are each optionally substituted with 1, 2, or 3 independently selected $R^C$ substituents.

In some embodiments, $R^2$ is selected from H, $C_{1\text{-}6}$ alkyl, $C_{6\text{-}14}$ aryl, 5-14 membered heteroaryl, 4-14 membered heterocycloalkyl, $C_{6\text{-}14}$ aryl-$C_{1\text{-}6}$ alkyl-, (5-14 membered heteroaryl)-$C_{1\text{-}6}$ alkyl-, (4-14 membered heterocycloalkyl)-$C_{1\text{-}6}$ alkyl-, $NR^{c2}R^{d2}$, $C(O)R^{b2}$, $C(O)NR^{c2}R^{d2}$, and $C(O)OR^{a2}$, wherein the $C_{1\text{-}6}$ alkyl, $C_{6\text{-}14}$ aryl, 5-14 membered heteroaryl, 4-14 membered heterocycloalkyl, $C_{6\text{-}14}$ aryl-$C_{1\text{-}6}$ alkyl-, (5-14 membered heteroaryl)-$C_{1\text{-}6}$ alkyl-, and (4-14 membered heterocycloalkyl)-$C_{1\text{-}6}$ alkyl- are each optionally substituted with 1, 2, or 3 independently selected $R^C$ substituents.

In some embodiments, $R^2$ is selected from H, $C_{1\text{-}6}$ alkyl, $C_{6\text{-}14}$ aryl, $C_{3\text{-}14}$ cycloalkyl, 5-14 membered heteroaryl, 4-14 membered heterocycloalkyl, $C_{6\text{-}14}$ aryl-$C_{1\text{-}6}$ alkyl-, $C_{3\text{-}14}$ cycloalkyl-$C_{1\text{-}6}$ alkyl-, (5-14 membered heteroaryl)-$C_{1\text{-}6}$ alkyl-, and (4-14 membered heterocycloalkyl)-$C_{1\text{-}6}$ alkyl-, are each substituted with 1, 2, or 3 independently selected $R^C$ substituents In some embodiments, $R^2$ is selected from H, $C_{1\text{-}6}$ alkyl, $C_{6\text{-}14}$ aryl, $C_{3\text{-}14}$ cycloalkyl, 5-14 membered heteroaryl, 4-14 membered heterocycloalkyl, $C_{6\text{-}14}$ aryl-$C_{1\text{-}6}$ alkyl-, $C_{3\text{-}14}$ cycloalkyl-$C_{1\text{-}6}$ alkyl-, (5-14 membered heteroaryl)-$C_{1\text{-}6}$ alkyl-, (4-14 membered heterocycloalkyl)-$C_{1\text{-}6}$ alkyl-, $NR^{c2}R^{d2}$, $C(O)R^{b2}$, $C(O)NR^{c2}R^{d2}$, and $C(O)OR^{a2}$, wherein the $C_{1\text{-}6}$ alkyl, $C_{6\text{-}14}$ aryl, $C_{3\text{-}14}$ cycloalkyl, 5-14 membered heteroaryl, 4-14 membered heterocycloalkyl, $C_{6\text{-}14}$ aryl-$C_{1\text{-}6}$alkyl-, $C_{3\text{-}14}$ cycloalkyl-$C_{1\text{-}6}$ alkyl-, (5-14 membered heteroaryl)-$C_{1\text{-}6}$ alkyl-, and (4-14 membered heterocycloalkyl)-$C_{1\text{-}6}$ alkyl- are each substituted with 1, 2, or 3 independently selected $R^C$ substituents.

In some embodiments, $R^2$ is selected from H, $C_{6\text{-}14}$ aryl, 5-14 membered heteroaryl, $C(O)R^{b2}$, $C(O)NR^{c2}R^{d2}$, and $C(O)OR^{a2}$, wherein the $C_{6\text{-}14}$ aryl and 5-14 membered heteroaryl are each optionally substituted with 1, 2, or 3 independently selected $R^C$ substituents.

In some embodiments, $R^2$ is selected from H, $C_{1\text{-}6}$ alkyl, phenyl, 5-6 membered heteroaryl, 4-10 membered heterocycloalkyl, $C_{6\text{-}10}$ aryl-$C_{1\text{-}6}$ alkyl-, (5-10 membered heteroaryl)-$C_{1\text{-}6}$alkyl-, (4-10 membered heterocycloalkyl)-$C_{1\text{-}6}$alkyl-, $NR^{c2}R^{d2}$, $C(O)R^{b2}$, $C(O)NR^{c2}R^{d2}$, and $C(O)OR^{a2}$, wherein the $C_{1\text{-}6}$ alkyl, phenyl, 5-6 membered heteroaryl, 4-10 membered heterocycloalkyl, $C_{6\text{-}10}$ aryl-$C_{1\text{-}6}$ alkyl-, (5-10 membered heteroaryl)-$C_{1\text{-}6}$ alkyl-, and (4-10 membered heterocycloalkyl)-$C_{1\text{-}6}$ alkyl- are each optionally substituted with 1 or 2 independently selected $R^C$ substituents. In some embodiments, $R^2$ is selected from H, phenyl, 5-6 membered heteroaryl, $C(O)R^{b2}$, $C(O)NR^{c2}R^{d2}$, and $C(O)OR^{a2}$, wherein the phenyl and 5-6 membered heteroaryl are each optionally substituted with 1 or 2 independently selected $R^C$ substituents.

In some embodiments, $R^2$ is selected from H, $C(O)OEt$, $CONH_2$, and $C(O)NHEt$.

In some embodiments, $R^2$ selected from phenyl and 5-6 membered heteroaryl, each of which is optionally substituted with $C(O)OMe$.

In some embodiments, the optionally substituted $R^2$ is selected from pyridinylmethyl, hydroxy(phenyl)methyl, hydroxyethylamino(phenyl)ethyl, cyclohexylmethyl, fluorobenzyl, hydroxy(fluorophenyl)methyl, (methylpyridinyl)methyl, (fluoropyridinyl)methyl, (trifluoromethylpyridinyl)methyl, ((hydroxymethyl)pyridinyl)methyl, (methoxypyridinyl)methyl, (methylpyrazolyl)benzyl, (methylpyrazolyl)methyl, benzoisoxazolylmethyl, (methylindazolyl)methyl, (hydroxyazetidinyl)methyl, benzoyl, phenylcyclopropyl, (cyano(phenyl)methyl)amino, tetrahydrofuranyl, phenyl(pyridinyloxy)methyl, fluoro((fluorohydroxypyrrolidinyl)methyl)benzyl, ((carboxypiperidinyl)methyl)fluorobenzyl, fluoro((N-methylmethylsulfonamido)methyl)benzyl, ((dioxoimidazolidinyl)methyl)fluorobenzyl, (difluorophenyl)(hydroxy)methyl, (pyridinyl-1H-tetrazolyl)methyl, (pyrazolyl-1H-tetrazolyl)methyl, (thiazolyl-1H-tetrazolyl)methyl, (methyltrifluoromethylpyrazolyl)methyl, ((1,1-dioxidoisothiazolidinyl)methyl)fluorobenzyl, ((methyl-2,5-dioxoimidazolidinyl)methyl)benzyl, and (cyanophenoxy)methyl.

In some embodiments, the optionally substituted $R^2$ is selected from pyridinylmethyl, hydroxy(phenyl)methyl, hydroxyethylamino(phenyl)ethyl, cyclohexylmethyl, fluorobenzyl, hydroxy(fluorophenyl)methyl, (methylpyridinyl)methyl, (fluoropyridinyl)methyl, (methoxypyridinyl)methyl, (methylpyrazolyl)benzyl, benzoisoxazolylmethyl, (methylindazolyl)methyl, (hydroxyazetidinyl)methyl, benzoyl, phenylcyclopropyl, (cyano(phenyl)methyl)amino, tetrahydrofuranyl, phenyl(pyridinyloxy)methyl, fluoro ((fluorohydroxypyrrolidinyl)methyl)benzyl, ((carboxypiperidinyl)methyl)fluorobenzyl, fluoro((N-methylmethylsulfonamido)methyl)benzyl, ((dioxoimidazolidinyl)methyl)fluorobenzyl, and (difluorophenyl)(hydroxy)methyl.

In some embodiments, R² is selected from pyridinylmethyl, hydroxy(phenyl)methyl, hydroxyethylamino(phenyl)ethyl, cyclohexylmethyl, fluorobenzyl, hydroxy(fluorophenyl)methyl, (methylpyridinyl)methyl, (fluoropyridinyl)methyl, (methoxypyridinyl)methyl, (methylpyiazolyl)benzyl, benzoisoxazolylmethyl, (methylindazolyl)methyl, (hydroxyazetidinyl)methyl, benzoyl, phenylcyclopropyl, (cyano(phenyl)methyl)amino, tetrahydrofuranyl, and phenyl(pyridinyloxy)methyl.

In some embodiments, R² is

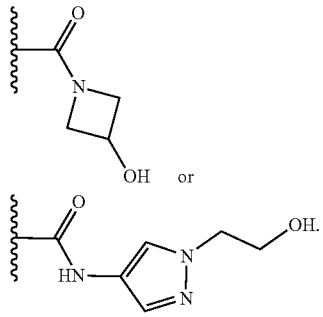

In some embodiments, R² is selected from pyridin-2-ylmethyl, hydroxy(phenyl)methyl, (2-hydroxyethylamino)(phenyl)methyl, cyclohexylmethyl, 2-fluorobenzyl, (2-fluorophenyl)(hydroxy)methyl, (6-methylpyridin-2-yl)methyl, (3-fluoropyridin-2-yl)methyl, (3-methoxypyridin-2-yl)methyl, 2-(1-methyl-1H-pyrazol-4-yl)benzyl, benzo[d]isoxazol-3-ylmethyl, (1-methyl-1H-indazol-3-yl)methyl, (3-hydroxyazetidin-1-yl)methyl, benzoyl, 1-phenylcyclopropyl, (cyano(phenyl)methyl)amino, tetrahydrofuran-3-yl, phenyl(pyridin-2-yloxy)methyl, 2-fluoro-6-(((3R,4R)-3-fluoro-4-hydroxypyrrolidin-1-yl)methyl)benzyl, 2-((4-carboxypiperidin-1-yl)methyl)-6-fluorobenzyl, 2-fluoro-6-((N-methylmethylsulfonamido)methyl)benzyl, 2-((2,5-dioxoimidazolidin-1-yl)methyl)-6-fluorobenzyl, (2,6-difluorophenyl)(hydroxy)methyl, (5-(pyridin-2-yl)-1H-tetrazol-1-yl)methyl, (5-(1H-pyrazol-1-yl)-1H-tetrazol-1-yl)methyl, (5-(thiazol-4-yl)-1H-tetrazol-1-yl)methyl, (5-methyl-3-(trifluoromethyl)-1H-pyrazol-1-yl)methyl, (3-methylpyridin-2-yl)methyl, 2-((1,1-dioxidoisothiazolidin-2-yl)methyl)-6-fluorobenzyl, 2-fluoro-6-((3-methyl-2,5-dioxoimidazolidin-1-yl)methyl)benzyl, (6-(trifluoromethyl)pyridin-2-yl)methyl, (3-(hydroxymethyl)pyridin-2-yl)methyl, (1-methyl-1H-pyrazol-3-yl)methyl, and (2-cyanophenoxy)methyl,(3-methylpyridin-2-yl)methoxy, (6-methylpyridin-2-yl)methoxy, and ((3-methylpyridin-2-yl)methyl)amino.

In some embodiments, R² is selected from pyridin-2-ylmethyl, hydroxy(phenyl)methyl, (2-hydroxyethylamino)(phenyl)methyl, cyclohexylmethyl, 2-fluorobenzyl, (2-fluorophenyl)(hydroxy)methyl, (6-methylpyridin-2-yl)methyl, (3-fluoropyridin-2-yl)methyl, (3-methoxypyridin-2-yl)methyl, 2-(1-methyl-1H-pyrazol-4-yl)benzyl, benzo[d]isoxazol-3-ylmethyl, (1-methyl-1H-indazol-3-yl)methyl, (3-hydroxyazetidin-1-yl)methyl, benzoyl, 1-phenylcyclopropyl, (cyano(phenyl)methyl)amino, tetrahydrofuran-3-yl, phenyl(pyridin-2-yloxy)methyl, 2-fluoro-6-(((3R,4R)-3-fluoro-4-hydroxypyrrolidin-1-yl)methyl)benzyl, 2-((4-carboxypiperidin-1-yl)methyl)-6-fluorobenzyl, 2-fluoro-6-((N-methylmethylsulfonamido)methyl)benzyl, 2-((2,5-dioxoimidazolidin-1-yl)methyl)-6-fluorobenzyl, and (2,6-difluorophenyl)(hydroxy)methyl.

In some embodiments, R² is selected from pyridin-2-ylmethyl, hydroxy(phenyl)methyl, 2-hydroxyethylamino)(phenyl)methyl, cyclohexylmethyl, 2-fluorobenzyl, 2-fluorophenyl)(hydroxy)methyl, 6-methylpyridin-2-yl)methyl, 3-fluoropyridin-2-yl)methyl, 3-methoxypyridin-2-yl)methyl, 2-(1-methyl-1H-pyrazol-4-yl)benzyl, benzo[d]isoxazol-3-ylmethyl, 1-methyl-1H-indazol-3-yl)methyl, 3-hydroxyazetidin-1-yl)methyl, benzoyl, 1-phenylcyclopropyl, (cyano(phenyl)methyl)amino, tetrahydrofuran-3-yl, and phenyl(pyridin-2-yloxy)methyl.

In some embodiments, $R^{a2}$ is selected from H and $C_{1-6}$ alkyl, wherein the $C_{1-6}$ alkyl is optionally substituted 1, 2, or 3 independently selected $R^H$ substituents.

In some embodiments, $R^{b2}$ is selected from H, $C_{1-6}$ alkyl, $C_{6-14}$ aryl, and 4-14 membered heterocycloalkyl, wherein the $C_{1-6}$ alkyl, $C_{6-14}$ aryl, and 4-14 membered heterocycloalkyl are each optionally substituted with 1, 2, or 3 independently selected $R^G$ substituents.

In some embodiments, $R^{c2}$ and $R^{d2}$ are each independently selected from H, $C_{1-6}$ alkyl, 5-14 membered heteroaryl, and $C_{6-14}$ aryl-$C_{1-6}$alkyl-, wherein the $C_{1-6}$ alkyl, 5-14 membered heteroaryl, and $C_{6-14}$ aryl-$C_{1-6}$ alkyl- are each optionally substituted with 1, 2, or 3 independently selected $R^G$ substituents.

In some embodiments, each $R^G$ is independently selected from CN, $OR^{a4}$, and $C_{1-6}$ alkyl, wherein the $C_{1-6}$ alkyl is optionally substituted 1, 2, or 3 independently selected $R^H$ substituents.

In some embodiments, each $R^C$ is independently selected from halo, $C_{1-6}$ alkyl, $C_{6-14}$ aryl, 5-14 membered heteroaryl, (4-14 membered heterocycloalkyl)-$C_{1-6}$ alkyl-, $OR^{a4}$, C(O)$OR^{a4}$, and $NR^{c4}R^{d4}$, wherein the $C_{1-6}$ alkyl, 5-14 membered heteroaryl, and (4-14 membered heterocycloalkyl)-$C_{1-6}$ alkyl- are optionally substituted with 1, 2, or 3 independently selected $R^H$ substituents.

In some embodiments, each $R^C$ is independently selected from halo, $C_{1-6}$ alkyl, $C_{6-14}$ aryl, 5-14 membered heteroaryl, (4-14 membered heterocycloalkyl)-$C_{1-6}$ alkyl-, $OR^{a4}$, C(O)$OR^{a4}$, and $NR^{c4}R^{d4}$, wherein the $C_{1-6}$ alkyl, 5-14 membered heteroaryl, and (4-14 membered heterocycloalkyl)-$C_{1-6}$ alkyl- are substituted with 1, 2, or 3 independently selected $R^H$ substituents.

In some embodiments, $R^{a4}$ is selected from H, $C_{1-6}$ alkyl, $C_{6-14}$ aryl, and 5-14 membered heteroaryl.

In some embodiments, each $R^{c4}$ and $R^{d4}$ are independently selected from H and $C_{1-6}$ alkyl, wherein the $C_{1-6}$ alkyl is optionally substituted by 1, 2, or 3 independently selected $R^H$ substituents.

In some embodiments, each $R^H$ is independently selected from halo, oxo, $C_{1-6}$ alkyl, $C_{1-6}$ haloalkyl, $OR^{a5}$, C(O)$OR^{a5}$, and $NR^{c5}S(O)_2R^{b5}$.

In some embodiments, each $R^{a5}$, and $R^{c5}$ is selected from H and $C_{1-6}$ alkyl.

In some embodiments, $R^{b5}$ is selected from H and $C_{1-6}$ alkyl.

In some embodiments, $R^3$ is selected from H, D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a3}$, $SR^{a3}$, $NHOR^{a3}$, $C(O)R^{b3}$, $C(O)NR^{c3}R^{d3}$, $C(O)NR^{c3}(OR^{a3})$, $C(O)OR^{a3}$, $OC(O)R^{b3}$, $OC(O)NR^{c3}R^{d3}$, $NR^{c3}NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}C(=NR^{e3})R^{b3}$, $NR^{c3}S(O)NR^{c3}R^{d3}$, $NR^{c3}S(O)R^{b3}$, $NR^{c3}S(O)_2R^{b3}$, $NR^{c3}S(O)(=NR^{e3})R^{b3}$, $NR^{c3}S(O)_2NR^{c3}R^{d3}$, $S(O)R^{b3}$, $S(O)NR^{c3}R^{d3}$, $S(O)_2R^{b3}$, $OS(O)(=NR^{e3})R^{b3}$, $OS(O)_2R^{b3}$, $SF_5$, $P(O)R^{f3}R^{g3}$, $OP(O)(OR^{f3})(OR^{g3})$, $P(O)(OR^{f3})(OR^{g3})$, $B(OR^{h3})_2$ and $S(O)_2NR^{c3}R^{d3}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^3$ are each optionally substituted with 1, 2, 3, 4, 5, 6, 7, or 8 independently selected $R^D$ substituents.

In some embodiments, $R^3$ is selected from H, halo, $C_{1-6}$ alkyl, $C_{1-6}$ haloalkyl, $C_{6-14}$ aryl, 5-14 membered heteroaryl, CN, and $OR^{a3}$, wherein the $C_{1-6}$ alkyl, $C_{6-14}$ aryl, and 5-14 membered heteroaryl are each optionally substituted with 1, 2, or 3 independently selected $R^D$ substituents.

In some embodiments, $R^3$ is selected from H, $C_{1-3}$ alkyl, halo, CN, morpholinomethyl, 4-ethoxyphenyl, 2-hydroxyethoxy, and pyridinyl.

In some embodiments, $R^3$ is selected from H, methyl, bromo, CN, morpholinomethyl, 4-ethoxyphenyl, 2-hydroxyethoxy, and pyridinyl.

In some embodiments, X is $CR^3$; and $R^1$ is H or $C_{1-6}$ alkyl.

In some embodiments, X is $CR^3$; and $R^1$ is H or $C_{1-3}$ alkyl.

In some embodiments,

X is $CR^3$;

$R^1$ is selected from H and $C_{1-6}$ alkyl;

$R^2$ is selected from H, D, $C_{6-14}$ aryl, 5-14 membered heteroaryl, $C(O)R^{b2}$, $C(O)NR^{c2}R^{d2}$, and $C(O)OR^{a2}$, wherein the $C_{6-14}$ aryl and 5-14 membered heteroaryl of $R^2$ are each optionally substituted with 1, 2, 3, or 4 independently selected $R^C$ substituents;

$R^3$ is selected from H, D, halo, $C_{1-6}$ alkyl, $C_{1-6}$ haloalkyl, $C_{6-14}$ aryl, 5-14 membered heteroaryl, CN, and $OR^{a3}$, wherein the $C_{1-6}$ alkyl, $C_{6-14}$ aryl, and 5-14 membered heteroaryl of $R^3$ are each optionally substituted with 1, 2, 3, or 4 independently selected $R^D$ substituents;

$Cy^1$ is phenyl optionally substituted with 1, 2, 3, or 4 independently selected $R^M$ substituents, or $C_{10-14}$ aryl or 5-14 membered heteroaryl, wherein the $C_{10-14}$ aryl and 5-14 membered heteroaryl of $Cy^1$ is optionally substituted with 1, 2, 3, or 4 independently selected $R^E$ substituents;

$Cy^2$ is $C_{6-14}$ aryl, $C_{3-14}$ cycloalkyl, 5-14 membered heteroaryl or 4-14 membered heterocycloalkyl, wherein the $C_{6-14}$ aryl, $C_{3-14}$ cycloalkyl, 5-14 membered heteroaryl and 4-14 membered heterocycloalkyl of $Cy^2$ are each optionally substituted with 1, 2, 3, or 4 independently selected $R^F$ substituents;

each $R^{a2}$, $R^{c2}$, $R^{d2}$, and $R^{a3}$ is independently selected from H, $C_{1-6}$ alkyl, $C_{1-6}$ haloalkyl, $C_2$. 6 alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^{a2}$, $R^{c2}$, $R^{d2}$, and $R^{a3}$ are each optionally substituted with 1, 2, 3, or 4 independently selected $R^G$ substituents;

each $R^{b2}$ is independently selected from $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl are each optionally substituted with 1, 2, 3, or 4 independently selected $R^G$ substituents;

each $R^C$, $R^D$, $R^E$, $R^F$, and $R^G$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{b4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, and $NR^{c4}S(O)_2NR^{c4}R^{d4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^C$, $R^D$, $R^E$, $R^F$, and $R^G$ are each optionally substituted with 1, 2, 3, or 4 independently selected $R^H$ substituents;

each $R^M$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, 2-CN, 3-CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{d4}$ $NR^{c4}S(O)_2R^{b4}$, and $NR^{c4}S(O)_2NR^{c4}R^{d4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^M$ are each optionally substituted with 1, 2, 3, or 4 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^{a4}$, $R^{c4}$, and $R^{d4}$ are each optionally substituted with 1, 2, 3, or 4 independently selected $R^H$ substituents;

each $R^{b4}$ is independently selected from $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl are each optionally substituted with 1, 2, 3, or 4 independently selected $R^H$ substituents;

each $R^{e4}$ is independently selected from H, OH, CN, $C_{1-6}$ alkyl, $C_{1-6}$alkoxy, $C_{1-6}$ haloalkyl, and $C_{1-6}$ haloalkoxy;

each $R^H$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, CN, $NO_2$, $OR^{a5}$, $SR^{a5}$, $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, and $NR^{c5}S(O)_2NR^{c5}R^{d5}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, of $R^H$ are each optionally substituted with 1, 2, 3, or 4 independently selected $R^I$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^{a4}$, $R^{c4}$, and $R^{d4}$ are each optionally substituted with 1, 2, 3, or 4 independently selected $R^I$ substituents;

each $R^{b5}$ is independently selected from $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl are each optionally substituted with 1, 2, 3, or 4 independently selected $R^I$ substituents;

each $R^{e5}$ is independently selected from H, OH, CN, $C_{1-6}$ alkyl, $C_{1-6}$alkoxy, $C_{1-6}$ haloalkyl, and $C_{1-6}$haloalkoxy;

each $R^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, CN, $NO_2$, $OR^{a6}$, $SR^{a6}$, $NHOR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $C(=NR^{e6})R^{b6}$, $C(=NR^{e6})NR^{c6}R^{d6}$, $NR^{c6}C(=NR^{e6})NR^{c6}R^{d5}$, $NR^{c6}S(O)R^{b6}$, $NR^{c6}S(O)_2R^{b6}$, and $NR^{c6}S(O)_2NR^{c6}R^{d6}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, of $R^H$ are each optionally substituted with 1, 2, 3, or 4 independently selected $R^J$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^{a6}$, $R^{c6}$, and $R^{d6}$ are each optionally substituted with 1, 2, 3, or 4 independently selected $R^J$ substituents;

each $R^{b6}$ is independently selected from $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl are each optionally substituted with 1, 2, 3, or 4 independently selected $R^J$ substituents;

each $R^{e6}$ is independently selected from H, OH, CN, $C_{1-6}$ alkyl, $C_{1-6}$alkoxy, $C_{1-6}$ haloalkyl, and $C_{1-6}$haloalkoxy;

each $R^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, CN, $NO_2$, $OR^{a7}$, $SR^{a7}$, $NHOR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c6}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^{c7}C(=NR^{e7})NR^{c7}R^{d7}$, $NR^{c7}S(O)R^{b7}$, $NR^{c7}S(O)_2R^{b7}$, and $NR^{c7}S(O)_2NR^{c7}R^{d7}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, of $R^H$ are each optionally substituted with 1, 2, 3, or 4 independently selected $R^K$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^{a7}$, $R^{c7}$, and $R^{d7}$ are each optionally substituted with 1, 2, 3, or 4 independently selected $R^K$ substituents;

each $R^{b7}$ is independently selected from $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl are each optionally substituted with 1, 2, 3, or 4 independently selected $R^K$ substituents;

each $R^{e7}$ is independently selected from H, OH, CN, $C_{1-6}$ alkyl, $C_{1-6}$alkoxy, $C_{1-6}$ haloalkyl, and $C_{1-6}$haloalkoxy;

each $R^K$ is independently selected from H, D, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl; and wherein any heteroaryl group of any of the above-recited substituents optionally comprises an N-oxide on any ring-forming nitrogen.

In some embodiments,

X is $CR^3$;

$R^1$ is selected from H and $C_{1-6}$ alkyl;

$R^2$ is selected from H, D, $C_{6-14}$ aryl, 5-14 membered heteroaryl, $C(O)R^{b2}$, $C(O)NR^{c2}R^{d2}$, and $C(O)OR^{a2}$, wherein the $C_{6-14}$ aryl and 5-14 membered heteroaryl of $R^2$ are each optionally substituted with 1, 2, 3, or 4 independently selected $R^G$ substituents;

$R^3$ is selected from H, D, halo, $C_{1-6}$ alkyl, $C_{6-14}$ aryl, 5-14 membered heteroaryl, CN, and $OR^{a3}$, wherein the $C_{1-6}$ alkyl, $C_{6-14}$ aryl, and 5-14 membered heteroaryl of $R^3$ are each optionally substituted with 1, 2, 3, or 4 independently selected $R^D$ substituents;

$Cy^1$ is phenyl, optionally substituted with 1, 2, 3, or 4 independently selected $R^M$ substituents; or $Cy^1$ is $C_{10-14}$ aryl or 5-14 membered heteroaryl, wherein the $C_{10-14}$ aryl and 5-14 membered heteroaryl of $Cy^1$ are each optionally substituted with 1, 2, 3, or 4 independently selected $R^E$ substituents;

$Cy^2$ is $C_{6-14}$ aryl, $C_{3-14}$ cycloalkyl, 5-14 membered heteroaryl or 4-14 membered heterocycloalkyl, wherein the $C_{6-14}$ aryl, $C_{3-14}$ cycloalkyl, 5-14 membered heteroaryl and 4-14 membered heterocycloalkyl of $Cy^2$ are each optionally substituted with 1, 2, 3, or 4 independently selected $R^F$ substituents;

each $R^{a2}$, $R^{c2}$, $R^{d2}$, and $R^{a3}$ is independently selected from H, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{6-14}$ cycloalkyl, 5-14 membered heteroaryl, and 4-14 membered heterocycloalkyl of $R^{a2}$, $R^{c2}$, $R^{d2}$, and $R^{a3}$ are each optionally substituted with 1, 2, 3, or 4 independently selected $R^G$ substituents;

each $R^{b2}$ is independently selected from $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl are each optionally substituted with 1, 2, 3, or 4 independently selected $R^G$ substituents;

each $R^C$, $R^D$, $R^E$, $R^F$, and $R^G$ is independently selected from D, halo, oxo, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, and $NR^{c4}S(O)_2NR^{c4}R^{d4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^C$, $R^D$, $R^E$, $R^F$, and $R^G$ are each optionally substituted with 1, 2, 3, or 4 independently selected $R^H$ substituents;

each $R^M$ is independently selected from D, halo, oxo, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, 2-CN, 3-CN, $NO_2$, $OR^{a4}$, $SR^{a4}$, $NHOR^{a4}$, $C(O)R^{b4}$, $C(O)NR^{c4}R^{d4}$, $C(O)OR^{a4}$ $OC(O)R^{b4}$, $OC(O)NR^{c4}R^{d4}$, $NR^{c4}R^{d4}$, $NR^{c4}C(O)R^{b4}$, $NR(O)R^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, and $NR^{c4}S(O)_2NR^{c4}R^{d4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^M$ are each optionally substituted with 1, 2, 3, or 4 independently selected $R^H$ substituents;

each $R^{a4}$, $R^{c4}$, and $R^{d4}$ is independently selected from H, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^{a4}$, $R^{c4}$, and $R^{d4}$ are each optionally substituted with 1, 2, 3, or 4 independently selected $R^H$ substituents;

each $R^{b4}$ is independently selected from $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl are each optionally substituted with 1, 2, 3, or 4 independently selected $R^H$ substituents;

each $R^{e4}$ is independently selected from H, OH, CN, $C_{1-6}$ alkyl, $C_{1-6}$ alkoxy, $C_{1-6}$ haloalkyl, and $C_{1-6}$ haloalkoxy;

each $R^H$ is independently selected from D, halo, oxo, $C_{1-6}$ alkyl, CN, $NO_2$, $OR^{a5}$, $SR^{a5}$, $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, and $NR^{c5}S(O)_2NR^{c5}R^{d5}$; and each $R^{a5}$, $R^{c5}$, and $R^{d5}$ is independently selected from H, and $C_{1-6}$ alkyl;

each $R^{b5}$ is independently selected from $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl; and each $R^{e5}$ is independently selected from H and $C_{1-6}$ alkyl.

In some embodiments,

X is $CR^3$;

$R^1$ is selected from H and $C_{1-6}$ alkyl;

$R^2$ is selected from H, D, $C_{6-10}$ aryl, 5-10 membered heteroaryl, $C(O)R^{b2}$, $C(O)NR^{c2}R^{d2}$, and $C(O)OR^{a2}$, wherein the $C_{6-10}$ aryl and 5-10 membered heteroaryl of $R^2$ are each optionally substituted with 1, 2, 3, or 4 independently selected $R^C$ substituents;

$R^3$ is selected from H, D, halo, $C_{1-6}$ alkyl, $C_{6-10}$ aryl, 5-10 membered heteroaryl, CN, and $OR^{a3}$, wherein the $C_{1-6}$ alkyl, $C_{6-10}$ aryl, and 5-10 membered heteroaryl of $R^3$ are each optionally substituted with 1, 2, 3, or 4 independently selected $R^D$ substituents;

$Cy^1$ is phenyl, optionally substituted with 1, 2, 3, or 4 independently selected $R^M$ substituents; or $Cy^1$ is $C_{10}$ aryl, 4-10 membered heterocycloalkyl, or 5-10 membered heteroaryl, wherein the $C_{10}$ aryl, 4-10 membered heterocycloalkyl, and 5-10 membered heteroaryl of $Cy^1$ are each optionally substituted with 1, 2, 3, or 4 independently selected $R^E$ substituents;

$Cy^2$ is $C_{6-10}$ aryl, $C_{3-14}$ cycloalkyl, 5-10 membered heteroaryl or 4-10 membered heterocycloalkyl, wherein the $C_{6-10}$ aryl, $C_{3-7}$ cycloalkyl, 5-10 membered heteroaryl and 4-10 membered heterocycloalkyl of $Cy^2$ are each optionally substituted with 1, 2, 3, or 4 independently selected $R^F$ substituents;

each $R^{a2}$, $R^{c2}$, $R^{d2}$, and $R^{a3}$ is independently selected from H, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, and 4-10 membered heterocycloalkyl of $R^{a2}$, $R^{c2}$, $R^{d2}$, and $R^{a3}$ are each optionally substituted with 1, 2, 3, or 4 independently selected $R^G$ substituents;

each $R^{b2}$ is independently selected from $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, and 4-10 membered heterocycloalkyl are each optionally substituted with 1, 2, 3, or 4 independently selected $R^G$ substituents;

each $R^C$, $R^D$, $R^E$, $R^F$, and $R^G$ is independently selected from D, halo, oxo, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, CN, $NO_2$, $OR^{a4}$, $SR^{a4}$, $NHOR^{a4}$, $C(O)R^{b4}$, $C(O)NR^{c4}R^{d4}$, $C(O)OR^{a4}$ $OC(O)R^{b4}$, $OC(O)NR^{c4}R^{d4}$, $NR^{c4}R^{d4}$ $NR^{c4}C(O)R^{b4}$, $NR(O)R^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, and $NR^{c4}S(O)_2NR^{c4}R^{d4}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, and 4-10 membered heterocycloalkyl of $R^C$, $R^D$, $R^E$, $R^F$, and $R^G$ are each optionally substituted with 1, 2, 3, or 4 independently selected $R^H$ substituents;

each $R^M$ is independently selected from D, halo, oxo, $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, 2-CN, 3-CN, $NO_2$, $OR^{a4}$, $SR^{a4}$, $NHOR^{a4}$, $C(O)R^{b4}$, $C(O)NR^{c4}R^{d4}$, $C(O)OR^{a4}$ $OC(O)R^{b4}$, $OC(O)NR^{c4}R^{d4}$, $NR^{c4}R^{d4}$, $NR^{c4}C(O)R^{b4}$, $NR(O)R^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, and $NR^{c4}S(O)_2NR^{c4}R^{d4}$, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, and 4-10 membered heterocycloalkyl of $R^M$ are each optionally substituted with 1, 2, 3, or 4 independently selected $R^H$ substituents;

each $R^{a4}$, $R^{c4}$, and $R^{d4}$ is independently selected from H, $C_{1-6}$ alkyl, $C_{2-6}$ alkenyl, $C_{2-6}$ alkynyl, $C_{6-10}$-aryl, $C_{3-7}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, and 4-10 membered heterocycloalkyl of $R^{a4}$, $R^{c4}$, and $R^{d4}$ are each optionally substituted with 1, 2, 3, or 4 independently selected $R^H$ substituents;

each $R^{b4}$ is independently selected from $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, and 4-10 membered heterocycloalkyl are each optionally substituted with 1, 2, 3, or 4 independently selected $R^H$ substituents;

each $R^{e4}$ is independently selected from H, OH, CN, $C_{1-6}$ alkyl, $C_{1-6}$ alkoxy, $C_{1-6}$ haloalkyl, and $C_{1-6}$ haloalkoxy;

each $R^H$ is independently selected from D, halo, oxo, $C_{1-6}$ alkyl, CN, $NO_2$, $OR^{a5}$, $SR^{a5}$, $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR(O)R^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, and $NR^{c5}S(O)_2NR^{c5}R^{d5}$; and each $R^{a5}$, $R^{c5}$, and $R^{d5}$ is independently selected from H, and $C_{1-6}$ alkyl;

each $R^{b5}$ is independently selected from $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl; and each $R^{e5}$ is independently selected from H and $C_{1-6}$ alkyl.

In some embodiments,

X is N;

$R^1$ is selected from H, $C_{1-6}$ alkyl, and a 5-14 membered heteroaryl, wherein the $C_{1-6}$ alkyl and a 5-14 membered heteroaryl are each optionally substituted with 1, 2, or 3 independently selected $R^B$ substituents;

$R^2$ is selected from H, D, $C_{1-6}$ alkyl, $C_{6-14}$ aryl, 5-14 membered heteroaryl, 4-14 membered heterocycloalkyl, $C_{6-14}$ aryl-$C_{1-6}$alkyl-, (5-14 membered heteroaryl)-$C_{1-6}$alkyl-, (4-14 membered heterocycloalkyl)-$C_{1-6}$ alkyl-, $NR^{c2}R^{d2}$, $C(O)R^{b2}$, $C(O)NR^{c2}R^{d2}$, and $C(O)OR^{a2}$, wherein the $C_{1-6}$ alkyl, $C_{6-14}$ aryl, 5-14 membered heteroaryl, 4-14 membered heterocycloalkyl, $C_{6-14}$ aryl-$C_{1-6}$ alkyl-, (5-14 membered heteroaryl)-$C_{1-6}$ alkyl-, (4-14 membered heterocycloalkyl)-$C_{1-6}$ alkyl- of $R^2$ are each optionally substituted with 1, 2, 3, or 4 independently selected $R^C$ substituents;

$Cy^1$ is phenyl, optionally substituted with 1, 2, 3, or 4 independently selected $R^M$ substituents, or $C_{10-14}$ aryl or 5-14 membered heteroaryl, wherein the $C_{10-14}$ aryl and 5-14 membered heteroaryl of $Cy^1$ is optionally substituted with 1, 2, 3, or 4 independently selected $R^E$ substituents;

$Cy^2$ is $C_{6-14}$ aryl, $C_{3-14}$ cycloalkyl, 5-14 membered heteroaryl or 4-14 membered heterocycloalkyl, wherein the $C_{6-14}$ aryl, $C_{3-14}$ cycloalkyl, 5-14 membered heteroaryl and 4-14 membered heterocycloalkyl of $Cy^2$ are each optionally substituted with 1, 2, 3, or 4 independently selected $R^F$ substituents;

each $R^{a2}$, $R^{c2}$, and $R^{d2}$ is independently selected from H, $C_{1-6}$ alkyl, $C_{2-6}$ alkenyl, $C_{2-6}$ alkynyl, $C_{6-14}$ aryl, $C_{6-14}$ aryl-$C_{1-6}$ alkyl-, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{6-14}$ aryl-$C_{1-6}$ alkyl-, $C_{3-14}$ cycloalkyl, 5-14 membered heteroaryl, and 4-14 membered heterocycloalkyl of $R^{a2}$, $R^{c2}$, and $R^{d2}$ are each optionally substituted with 1, 2, 3, or 4 independently selected $R^G$ substituents;

each $R^{b2}$ is independently selected from $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl are each optionally substituted with 1, 2, 3, or 4 independently selected $R^G$ substituents;

each $R^B$, $R^C$, $R^E$, $R^F$, and $R^G$ is independently selected from D, halo, oxo, $C_{1-6}$ alkyl, $C_{2-6}$ alkenyl, $C_{2-6}$ alkynyl, $C_{6-14}$ aryl, $C_{3-14}$ cycloalkyl, 5-14 membered heterocycloalkyl, CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, and $NR^{c4}S(O)_2NR^{c4}R^{d4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^B$, $R^C$, $R^E$, $R^F$, and $R^G$ are each optionally substituted with 1, 2, 3, or 4 independently selected $R^H$ substituents;

each $R^M$ is independently selected from D, halo, oxo, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, 2-CN, 3-CN, $NO_2$, $OR^{a4}$, $SR^{a4}$, $NHOR^{a4}$, $C(O)R^{b4}$, $C(O)NR^{c4}R^{d4}$, $C(O)OR^{a4}$ $OC(O)R^{b4}$, $OC(O)NR^{c4}R^{d4}$, $NR^{c4}R^{d4}$, $NR^{c4}C(O)R^{b4}$, $NR(O)R^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, and $NR^{c4}S(O)_2NR^{c4}R^{d4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^M$ are each optionally substituted with 1, 2, 3, or 4 independently selected $R^H$ substituents;

each $R^{a4}$, $R^{c4}$, and $R^{d4}$ is independently selected from H, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^{a4}$, $R^{c4}$, and $R^{d4}$ are each optionally substituted with 1, 2, 3, or 4 independently selected $R^H$ substituents;

each $R^{b4}$ is independently selected from $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl are each optionally substituted with 1, 2, 3, or 4 independently selected $R^H$ substituents;

each $R^{e4}$ is independently selected from H, OH, CN, $C_{1-6}$ alkyl, $C_{1-6}$ alkoxy, $C_{1-6}$ haloalkyl, and $C_{1-6}$ haloalkoxy;

each $R^H$ is independently selected from D, halo, oxo, $C_{1-6}$ alkyl, CN, $NO_2$, $OR^{a5}$, $SR^{a5}$, $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, and $NR^{c5}S(O)_2NR^{c5}R^{d5}$; and each $R^{a5}$, $R^{c5}$, and $R^{d5}$ is independently selected from H, and $C_{1-6}$ alkyl;

each $R^{b5}$ is independently selected from $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl; and each $R^{e5}$ is independently selected from H and $C_{1-6}$ alkyl.

In some embodiments,

X is N;

$R^1$ is H or a 5-14 membered heteroaryl optionally substituted with 1, 2, or 3 independently selected $R^B$ substituents;

$R^2$ is selected $C_{1-6}$ alkyl, 4-14 membered heterocycloalkyl, $C_{6-14}$ aryl-$C_{1-6}$alkyl-, (5-14 membered heteroaryl)-$C_{1-6}$ alkyl-, (4-14 membered heterocycloalkyl)-$C_{1-6}$ alkyl-, and $NR^{c2}R^{d2}$, wherein the $C_{1-6}$ alkyl, 4-14 membered heterocycloalkyl, $C_{6-14}$ aryl-$C_{1-6}$ alkyl-, (5-14 membered heteroaryl)-$C_{1-6}$ alkyl-, and (4-14 membered heterocycloalkyl)-$C_{1-6}$ alkyl- of $R^2$ are each optionally substituted with 1, 2, or 3 independently selected $R^C$ substituents;

$Cy^1$ is phenyl optionally substituted with 1, 2, or 3 independently selected $R^E$ substituents; and $Cy^2$ is 5-14 membered heteroaryl optionally substituted with 1, 2, or 3 independently selected $R^F$ substituents.

In some embodiments,

X is N;

$R^1$ is H or a 5-14 membered heteroaryl optionally substituted with 1, 2, or 3 independently selected $R^B$ substituents;

each $R^B$ is independently selected from D, halo, oxo, $C_{1-6}$ alkyl, $C_{1-6}$ haloalkyl, $C_{2-6}$ alkenyl, CN, $NO_2$ and OH;

$R^2$ is selected $C_{1-6}$ alkyl, 4-14 membered heterocycloalkyl, $C_{6-14}$ aryl-$C_{1-6}$ alkyl-, (5-14 membered heteroaryl)-$C_{1-6}$ alkyl-, (4-14 membered heterocycloalkyl)-$C_{1-6}$ alkyl-, and $NR^{c2}R^{d2}$, wherein the $C_{1-6}$ alkyl, 4-14 membered heterocycloalkyl, $C_{6-14}$ aryl-$C_{1-6}$ alkyl-, (5-14 membered heteroaryl)-$C_{1-6}$ alkyl-, and (4-14 membered heterocycloalkyl)-$C_{1-6}$ alkyl- of $R^2$ are each optionally substituted with 1, 2, or 3 independently selected $R^C$ substituents;

each $R^{c2}$ and $R^{d2}$ are independently selected from H, $C_{1-6}$ alkyl, $C_{6-14}$ aryl-$C_{1-6}$ alkyl-, wherein the $C_{1-6}$ alkyl and $C_{6-14}$ aryl-$C_{1-6}$ alkyl- of $R^{c2}$ and $R^{d2}$ are each optionally substituted with 1, 2, or 3 independently selected $R^G$ substituents;

each $R^C$ is independently selected from D, halo, oxo, $C_{1-6}$ alkyl, $C_{6-14}$ aryl, $C_{3-14}$ cycloalkyl, 5-14 membered heteroaryl, 4-14 membered heterocycloalkyl, $OR^{a4}$, $C(O)NR^{c4}R^{d4}$ and $NR^{c4}R^{d4}$, wherein the $C_{1-6}$ alkyl, $C_{6-14}$ aryl, $C_{3-14}$ cycloalkyl, 5-14 membered heteroaryl, and 4-14 membered heterocycloalkyl, of $R^C$ is optionally substituted with 1, 2, or 3 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, and 5-14 membered heteroaryl, wherein the $C_{1-6}$ alkyl, $C_{2-6}$ alkenyl, and 5-14 membered heteroaryl, of $R^{a4}$, $R^{c4}$, and $R^{d4}$ are each optionally substituted with 1, 2, or 3 independently selected $R^H$ substituents;

each $R^G$ is independently selected from D, halo, oxo, $C_{1-6}$ alkyl, CN, $NO_2$, and OH;

$Cy^1$ is phenyl optionally substituted with 1, 2, or 3 independently selected $R^E$ substituents;

each $R^E$ is independently selected from D, halo, oxo, $C_{1-6}$ alkyl, CN, $NO_2$ and OH;

$Cy^2$ is 5-14 membered heteroaryl optionally substituted with 1, 2, or 3 independently selected $R^F$ substituents;

each $R^F$ is independently selected from D, halo, oxo, $C_{1-6}$ alkyl, $C_{2-6}$ alkenyl, CN, $NO_2$, and $OR^{a4}$, wherein the $C_{1-6}$ alkyl and $C_{2-6}$ alkenyl of $R^F$ are each optionally substituted with 1, 2, or 3 independently selected $R^H$ substituents;

each $R^{a4}$ is independently selected from H, $C_{1-6}$ alkyl and $C_{1-6}$ alkoxy; and each $R^H$ is independently selected from D, halo, oxo, $C_{1-6}$ alkyl, CN, $NO_2$ and OH.

In some embodiments,

X is N;

$R^1$ is H or a 5-10 membered heteroaryl optionally substituted with 1, 2, or 3 independently selected $R^B$ substituents;

each $R^B$ is independently selected from D, halo, oxo, $C_{1-6}$ alkyl, $C_{1-6}$ haloalkyl, $C_{2-6}$ alkenyl, CN, $NO_2$ and OH;

$R^2$ is selected $C_{1-6}$ alkyl, 4-10 membered heterocycloalkyl, $C_{6-10}$ aryl-$C_{1-6}$ alkyl-, (5-10 membered heteroaryl)-$C_{1-6}$ alkyl-, (4-10 membered heterocycloalkyl)-$C_{1-6}$ alkyl-, and $NR^{c2}R^{d2}$, wherein the $C_{1-6}$ alkyl, 4-10 membered heterocycloalkyl, $C_{6-10}$ aryl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, or 3 independently selected $R^C$ substituents;

each $R^{c2}$ and $R^{d2}$ are independently selected from H, $C_{1-6}$ alkyl, $C_{6-10}$ aryl-$C_{1-6}$ alkyl-, wherein the $C_{1-6}$ alkyl and $C_{6-10}$ aryl-$C_{1-6}$ alkyl- of $R^{c2}$ and $R^{d2}$ are each optionally substituted with 1, 2, or 3 independently selected $R^G$ substituents;

each $R^C$ is independently selected from D, halo, oxo, $C_{1-6}$ alkyl, $C_{6-10}$ aryl, Cy-7 cycloalkyl, 5-10 membered heteroaryl, 4-10 membered heterocycloalkyl, $OR^{a4}$, $C(O)NR^{c4}R^{d4}$ and $NR^{c4}R^{d4}$, wherein the $C_{1-6}$ alkyl, $C_{6-10}$ aryl, $C_{3-7}$ cycloalkyl, 5-10 membered heteroaryl, and 4-10 membered heterocycloalkyl, of $R^C$ is optionally substituted with 1, 2, or 3 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, and 5-10 membered heteroaryl, wherein the $C_{1-6}$ alkyl, $C_{2-6}$ alkenyl, and 5-10 membered heteroaryl, of $R^{a4}$, $R^{c4}$, and $R^{d4}$ are each optionally substituted with 1, 2, or 3 independently selected $R^H$ substituents;

each $R^G$ is independently selected from D, halo, oxo, $C_{1-6}$ alkyl, CN, $NO_2$, and OH;

$Cy^1$ is phenyl optionally substituted with 1, 2, or 3 independently selected $R^E$ substituents;

each $R^E$ is independently selected from D, halo, oxo, $C_{1-6}$ alkyl, CN, $NO_2$ and OH;

$Cy^2$ is 5-10 membered heteroaryl optionally substituted with 1, 2, or 3 independently selected $R^F$ substituents;

each $R^F$ is independently selected from D, halo, oxo, $C_{1-6}$ alkyl, $C_{2-6}$ alkenyl, CN, $NO_2$, and $OR^{a4}$, wherein the $C_{1-6}$ alkyl and $C_{2-6}$ alkenyl of $R^F$ are each optionally substituted with 1, 2, or 3 independently selected $R^H$ substituents;

each $R^{a4}$ is independently selected from H, $C_{1-6}$ alkyl and $C_{1-6}$ alkoxy; and each $R^H$ is independently selected from D, halo, oxo, $C_{1-6}$ alkyl, CN, $NO_2$ and OH.

In some embodiments,

X is N;

$R^1$ is H or nicotinonitrile;

$R^2$ is pyridinylmethyl, hydroxy(phenyl)methyl, hydroxyethylamino(phenyl)ethyl, cyclohexylmethyl, fluorobenzyl, hydroxy(fluorophenyl)methyl, methylpyridinylmethyl, fluoropyridinylmethyl, methoxypyridinylmethyl, methylpyrazolylbenzyl-benzoisoxazolylmethyl, methylindazolylmethyl, hydroxyazetidinylmethyl, benzoyl, phenylcyclopropyl, cyano(phenyl)methylamino, tetrahydrofuranyl, or phenyl(pyridin-2-yloxy)methyl;

$Cy^1$ is cyanophenyl; and $Cy^2$ is pyrimidinyl, ethylpyrazolyl propylpyrazolyl, quinolinyl, fluoropyrimidinyl, pyridinyl, methylpyridinyl, methoxy-methylpyridinyl, pyrazolopyridazinyl, methyloxazolyl, hydroxymethyl-methyloxazolyl, or methoxymethyl-methyloxazolyl.

In some embodiments,

X is N;

$R^1$ is H;

$R^2$ is selected from pyridin-2-ylmethyl, hydroxy(phenyl)methyl, (2-hydroxyethylamino)(phenyl)methyl, cyclohexylmethyl, 2-fluorobenzyl, (2-fluorophenyl)(hydroxy)methyl, (6-methylpyridin-2-yl)methyl, (3-fluoropyridin-2-yl)methyl, (3-methoxypyridin-2-yl)methyl, 2-(1-methyl-1H-pyrazol-4-yl)benzyl, benzo[d]isoxazol-3-ylmethyl, (1-methyl-1H-indazol-3-yl)methyl, (3-hydroxyazetidin-1-yl)methyl, benzoyl, 1-phenylcyclopropyl, (cyano(phenyl)methyl)amino, tetrahydrofuran-3-yl, phenyl(pyridin-2-yloxy)methyl, 2-fluoro-6-(((3R,4R)-3-fluoro-4-hydroxypyrrolidin-1-yl)methyl)benzyl, 2-((4-carboxypiperidin-1-yl)methyl)-6-fluorobenzyl, 2-fluoro-6-((N-methylmethylsulfonamido)methyl)benzyl, 2-((2,5-dioxoimidazolidin-1-yl)methyl)-6-fluorobenzyl, (2,6-difluorophenyl)(hydroxy)methyl, (5-(pyridin-2-yl)-1H-tetrazol-1-yl)methyl, (5-(1H-pyrazol-1-yl)-1H-tetrazol-1-yl)methyl, (5-(thiazol-4-yl)-1H-tetrazol-1-yl)methyl, (5-methyl-3-(trifluoromethyl)-1H-pyrazol-1-yl)methyl, (3-methylpyridin-2-yl)methyl, 2-((1,1-dioxidoisothiazolidin-1-yl)methyl)-6-fluorobenzyl, 2-fluoro-6-((3-methyl-2,5-dioxoimidazolidin-1-yl)methyl)benzyl, (6-(trifluoromethyl)pyridin-2-yl)methyl, (3-(hydroxymethyl)pyridin-2-yl)methyl, (1-methyl-1H-pyrazol-3-yl)methyl, and (2-cyanophenoxy)methyl,(3-methylpyridin-2-yl)methoxy, (6-methylpyridin-2-yl)methoxy, and ((3-methylpyridin-2-yl)methyl)amino;

$Cy^1$ is cyanophenyl; and $Cy^2$ is selected from 2,6-dimethylpyridin-4-yl, pyridin-4-yl, 2-methylpyridin-4-yl, 1-carbamoyl-1,2,3,6-tetrahydropyridin-4-yl, 1-carbamoylpiperidin-4-yl, 2-methoxypyridin-4-yl, 2-methoxy-6-methylpyridin-4-yl, 2,6-dimethylpyridin-4-yl-1-oxide, 1-ethyl-6-oxo-1,6-dihydropyridin-3-yl, 3-methylpyridin-4-yl, 3-fluoropyridin-4-yl, 3-chloropyridin-4-yl, 3-methoxypyridin-4-yl, 3-cyanopyridin-4-yl, 4-carbamoylphenyl, pyrazolo[1,5-a]pyridin-3-yl, pyrazolo[1,5-b]pyridazin-3-yl, 5-methyl-1H-pyrazol-4-yl, 1-ethyl-1H-pyrazol-5-yl, 1-isopropyl-1H-pyrazol-5-yl, 1-propyl-1H-pyrazol-5-yl, pyrimidin-4-yl, 2,3-dihydro-[1,4]dioxino[2,3-b]pyridin-8-yl, quinolin-5-yl, 5-fluoropyrimidin-4-yl, oxazol-5-yl, 4-methyloxazol-5-yl, 4-ethyloxazol-5-yl, 4-(hydroxymethyl)-2-methyloxazol-5-yl, 4-(methoxymethyl)-2-methyloxazol-5-yl, 4-(hydroxymethyl)-2-methyloxazol-5-yl, 1-ethyl-1H-1,2,3-triazol-5-yl, and cyclopropyl.

In some embodiments, the compound is the (S)-enantiomer of one of the preceding compounds, or a pharmaceutically acceptable salt thereof. In some embodiments, the compound is the (R)-enantiomer of one of the preceding compounds, or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, rec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula-O-alkyl, wherein the alkyl group has n to m carbons. Example alkoxy groups include, but are not limited to, methoxy, ethoxy, propoxy (e g., n-propoxy and isopropoxy), butoxy (e g., n-butoxy and tert-butoxy), and the like. In some embodiments, the alkyl group has 1 to 6, 1 to 4, or 1 to 3 carbon atoms.

As used herein, the term "amino" refers to a group of formula —$NH_2$.

As used herein, the term "aryl", employed alone or in combination with other terms, refers to an aromatic hydrocarbon group, which may be monocyclic or polycyclic (e.g., having 2, 3, or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 5 to 14 carbon atoms. In some embodiments, the aryl group has from 5 to 10 carbon atoms. In some embodiments, the aryl group is phenyl or naphthyl. In some embodiments, the aryl group is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "$C_{n-m}$ haloalkoxy" refers to a group of formula —O-haloalkyl having n to m carbon atoms. Example haloalkoxy groups include $OCF_3$ and $OCF_2$. An example haloalkoxy group is $OCHF_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2 s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include $CF_3$, $C_2F_5$, $CHF_2$, $CCl_3$, $CHCl_2$, $C_2Cl_5$ and the like.

As used herein, the term "thio" refers to a group of formula-SH.

As used herein, the term "carbamyl" to a group of formula —$C(O)NH_2$.

As used herein, the term "carbonyl", employed alone or in combination with other terms, refers to a —C(O)— group.

As used herein, "cycloalkyl" refers to non-aromatic cyclic hydrocarbons including cyclized alkyl and alkenyl groups. Cycloalkyl groups can include mono- or polycyclic (e.g., having 2, 3, or 4 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, 12, 13, or 14 ring-forming carbons (i.e., $C_{3-14}$). In some embodiments, the cycloalkyl is a $C_{3-14}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2, 3, or 4 fused rings) aromatic heterocycle having at least one heteroatom ring member selected from N, O, S, and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-6 monocyclic heteroaryl having 1, 2, or 3 heteroatom ring members independently selected from N, O, S, and B. In some embodiments, the heteroaryl is a five-membered or six-membereted heteroaryl ring. A five-membered heteroaryl ring is a heteroaryl with a ring having five ring atoms wherein one or more (e.g., 1, 2, or 3) ring atoms are independently selected from N, O, S, and B. In some embodiments, the heteroaryl group contains 3 to 14, 4 to 14, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1,2-b]thiazole, purine, triazine, thieno[3,2-b]pyridine, imidazo[1,2-a]pyridine, 1,5-naphthyridine, 1H-pyrazolo[4,3-b]pyridine, and the like.

A five-membered heteroaryl is a heteroaryl group having five ring-forming atoms wherein one or more (e.g., 1, 2, or 3) of the ring-forming atoms are independently selected from N, O, B, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine.

A six-membered heteroaryl ring is a heteroaryl with a ring having six ring-forming atoms wherein one or more (e.g., 1, 2, or 3) ring atoms are independently selected from N, O, S, and B. Exemplary six-membered ring heteroaryls are pyridyl, pyrazinyl, pyrimidinyl, triazinyl and pyridazinyl.

As used herein, "heterocycloalkyl" refers to monocyclic or polycyclic heterocycles having at least one non-aromatic ring (saturated or partially saturated ring), wherein one or more of the ring-forming carbon atoms of the heterocycloalkyl is replaced by a heteroatom selected from N, O, S, and B, and wherein the ring-forming carbon atoms and heteroatoms of a heterocycloalkyl group can be optionally substituted by one or more oxo or sulfide (e.g., C(O), S(O), C(S), or $S(O)_2$, etc). Heterocycloalkyl groups include monocyclic and polycyclic (e.g., having 2, 3, or 4 fused rings) systems. Included in heterocycloalkyl are monocyclic and polycyclic 3-14-, 4-14-, 3-10-, 4-10-, 5-10-, 4-7-, 5-7-, 5-6-, 5- or 6-membered heterocycloalkyl groups. Heterocycloalkyl groups can also include spirocycles and bridged rings (e.g., a 5-14 membered bridged biheterocycloalkyl ring having one or more ring-forming carbon atoms replaced by a heteroatom independently selected from N, O, S, and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Example heterocycloalkyl groups include pyrrolidonyl, pyrrolidin-2-one, 1,3-isoxazolidin-2-one, pyranyl, tetrahydropyran, oxetanyl, azetidinyl, morpholinyl, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, 1,2,3,4-tetrahydroisoquinoline, benzazapene, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxaadamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like. In some embodiments, the heterocycloalkyl group is pyrrolidonyl, pyrrolidin-2-one, 1,3-isoxazolidin-2-one, pyranyl, tetrahydropuran, oxetanyl, azetidinyl, morpholinyl, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, or azepanyl.

In some embodiments, the heterocycloalkyl group contains 3 to 14 ring-forming atoms, 4 to 14 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S, and B and having one or more oxidized ring members. In some embodiments, the heterocycloalkyl is a monocyclic or bicyclic 4-10 membered heterocycloalkyl having 1, 2, 3, or 4 heteroatoms independently selected from N, O, S, and B and having one or more oxidized ring members.

As used herein, an "alkyl linking group" is a bivalent straight chain or branched alkyl linking group ("alkylene group"). For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-diyl, propan-1,2-diyl, propan-1,1-diyl and the like.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

As used herein, the term "independently selected from" means feat each occurrence of a variable or substituent are independently selected at each occurrence from the applicable list.

The compounds described herein can be asymmetric (e.g., having one or more stereocenters). All stereoisomers, such as enantiomers and diastereomers, are intended unless otherwise indicated. Compounds of fee present disclosure feat contain asymmetrically substituted carbon atoms can be isolated in optically active or racemic forms. Methods on how to prepare optically active forms from optically inactive starting materials are known in fee art, such as by resolution of racemic mixtures or by stereoselective synthesis. Many geometric isomers of olefins, C=N double bonds, and fee like can also be present in fee compounds described herein, and all such stable isomers are contemplated in fee present invention. Cis and tram geometric isomers of fee compounds of fee present disclosure are described and may be isolated as a mixture of isomers or as separated isomeric forms. In some embodiments, the compound has fee (R)-configuration. In some embodiments, the compound has fee (S)-configuration. The Formulas (e.g., Formula (I), (II), etc.) provided herein include stereoisomers of the compounds.

Resolution of racemic mixtures of compounds can be carried out by any of numerous methods known in fee art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or fee various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

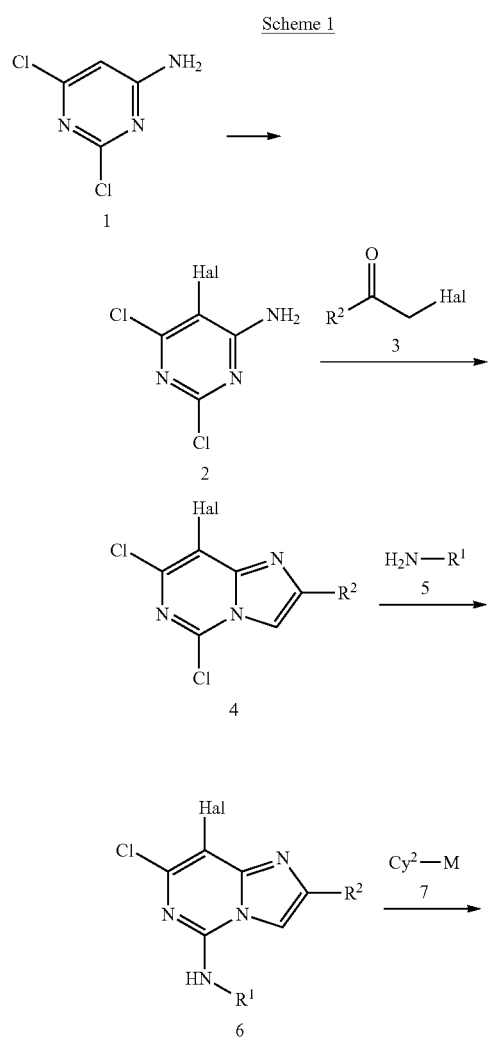

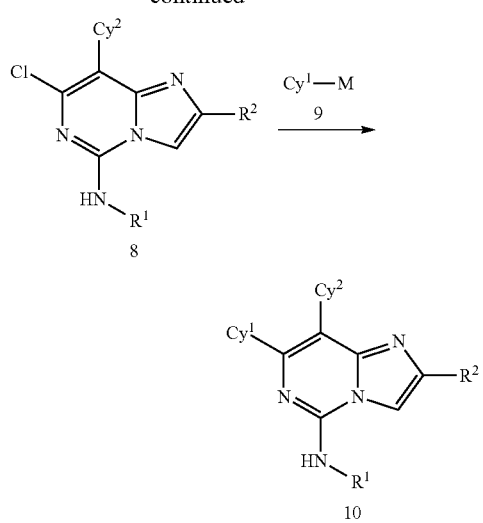

Compound of formula 10 can be prepared via the synthetic route as outlined in Scheme 1. The commercially available starting material 1 can undergo a halogenation reaction, such as electrophilic aromatic substitution ($S_EAr$), with an appropriate reagent, such as N-bromosuccinimide (NBS), to afford compound 2 (Hal is a halide, such as F, Cl, Br, or I). Condensation of compound 2 with a carbonyl adduct of formula 3 at elevated temperature can generate the bicyclic compound 4. Selective chloride displacement of compound 4 via either nucleophilic substitution, or a coupling reaction, with compound 5 can deliver compound 6. Compound 6 can then be selectively coupled to an adduct of formula 7, in which M is a boronic acid, a boronic ester or an appropriately substituted metal [e.g., M is $B(OR)_2$, $Sn(Alkyl)_3$, Zn-Hal, etc.], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), to give a derivative of formula 8. Introduction of $Cy^1$ can then be achieved by the coupling of compound 8 with an adduct of formula 9, using similar conditions as described for the preparation of compound 8 from compound 6, to afford compound 10.

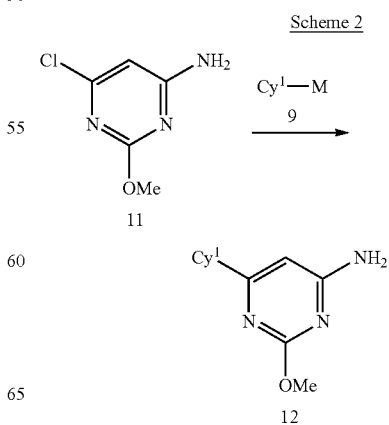

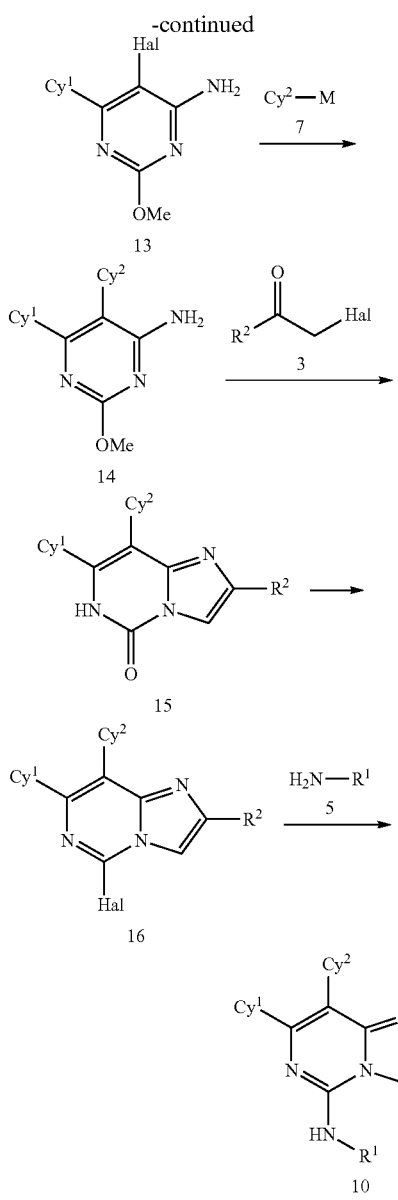

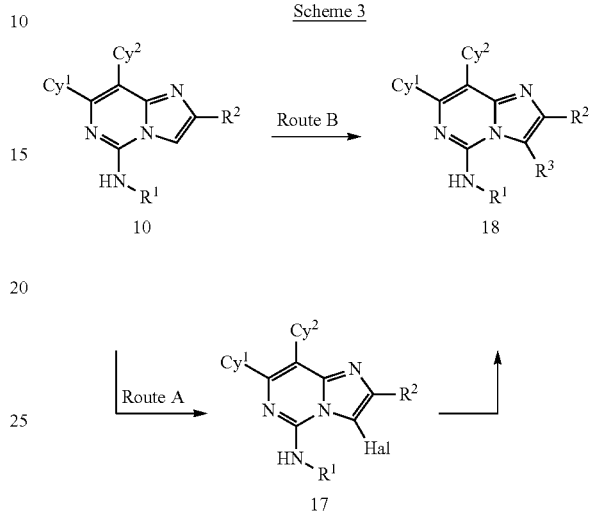

temperature can generate the bicyclic compound 15. Treatment of compound 15 with an appropriate reagent, such as phosphoryl chloride ($POCl_3$), at elevated temperature can afford the halide adduct 16. Displacement of the halogen in compound 16 via nucleophilic substitution, or a coupling reaction, with adduct 5 can then afford compound 10.

Compound 18 can be prepared via the synthetic route (Route A) as outlined in Scheme 3. Compound 10 can first undergo a halogenation reaction, such as electrophilic aromatic substitution ($S_EAr$), with an appropriate reagent, such as N-bromosuccinimide (NBS), to afford compound 17 (Hal is a halide, such as F, Cl, Br, or I). $R^3$ can then be introduced either via nucleophilic substitution, or a coupling reaction, to afford compound 18. Alternatively, compound 10 can undergo a direct chemical transformation, such as electrophilic substitution, to generate compound 18 (Route B).

Alternatively, compound of formula 10 can be prepared via the synthetic route as outlined in Scheme 2. The commercially available starting material 11 can undergo a coupling reaction with an adduct of formula 9, in which M is a boronic acid, a boronic ester or an appropriately substituted metal [e.g., M is $B(OR)_2$, $Sn(Alkyl)_3$, Zn-Hal, etc.], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), to give a derivative of formula 12. Compound 12 can undergo a halogenation reaction, such as electrophilic aromatic substitution ($S_EAr$), with an appropriate reagent, such as N-bromosuccinimide (NBS), to afford compound 13 (Hal is a halide, such as F, Cl, Br, or I). Coupling of compound 13 with an adduct of formula 7, using similar conditions as described for the preparation of compound 12 from compound 11, can afford compound 14. Condensation of compound 14 with a carbonyl adduct of formula 3 at elevated

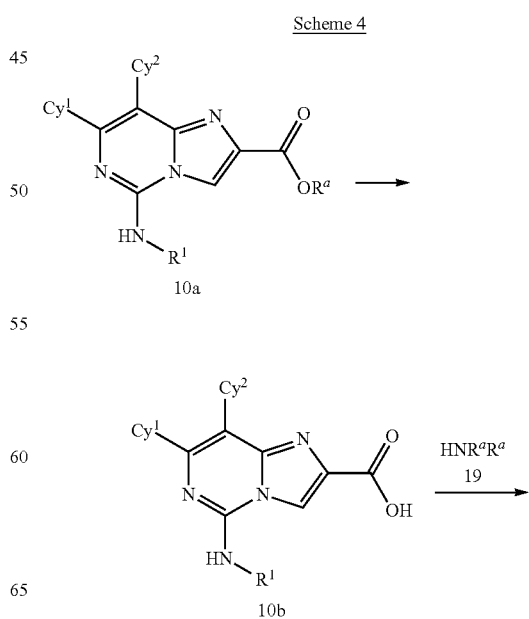

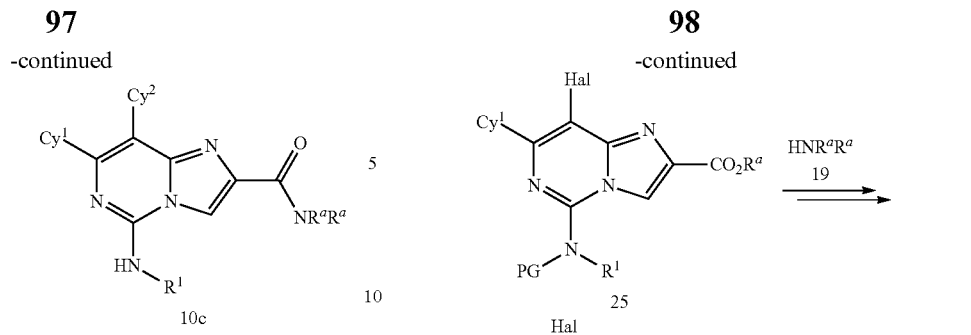

Compound 10c can be prepared via the synthetic route as outlined in Scheme 4 starting from compound 10a, which can be prepared as described in either Scheme 1 or Scheme 2. Ester hydrolysis of compound 10a using an appropriate reagent, such as lithium hydroxide (LiOH), can deliver carboxylic acid 10b, which can then be coupled with amine 19 using an appropriate coupling reagent (such as HATU, BOP, or PyBOP) to afford compound 10c.

Scheme 5

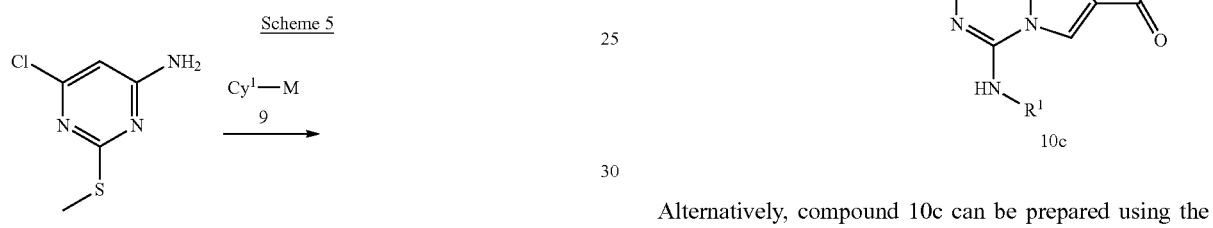

Alternatively, compound 10c can be prepared using the synthetic route as outlined in Scheme 5. The commercially available starting material 20 can undergo a coupling reaction with an adduct of formula 9, in which M is a boronic acid, a boronic ester or an appropriately substituted metal [e.g., M is $B(OR)_2$, $Sn(Alkyl)_3$, Zn-Hal, etc.], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), to give a derivative of formula 21. Compound 21 can then be subjected to a halogenation reaction, such as electrophilic aromatic substitution ($S_EAr$), with an appropriate reagent, such as N-bromosuccinimide (NBS), to afford compound 22 (Hal is a halide, such as F, Cl, Br, or I). Condensation of compound 22 with a carbonyl adduct of formula 3a at elevated temperature can generate the bicyclic compound of formula 23. Oxidation of compound 23 with an appropriate oxidant, such as mCPBA, followed by nucleophilic substitution with a protected amine adduct 24 can deliver compound 25. Ester hydrolysis of compound 25 in the presence of an appropriate reagent, such as lithium hydroxide (LiOH), can generate the corresponding carboxylic acid, which can then be coupled with an amine adduct of formula 19, using an appropriate coupling reagent (such as HATU, BOP, or PyBOP), to afford compound 26. Alternatively, compound 26 can be accessed by reacting compound 25 directly with amine adduct 19 at elevated temperature. Finally, introduction of $Cy^2$ can be achieved by the coupling of compound 26 with an adduct of formula 7, using similar conditions as described for the preparation of compound 21 from compound 20. The protecting group (PG) can then be removed under appropriate conditions to afford compound 10c. Alternatively, compound 10c can also be prepared by first removal of the protecting group (PG) in compound 26, followed by the coupling reaction with adduct 7.

Scheme 6

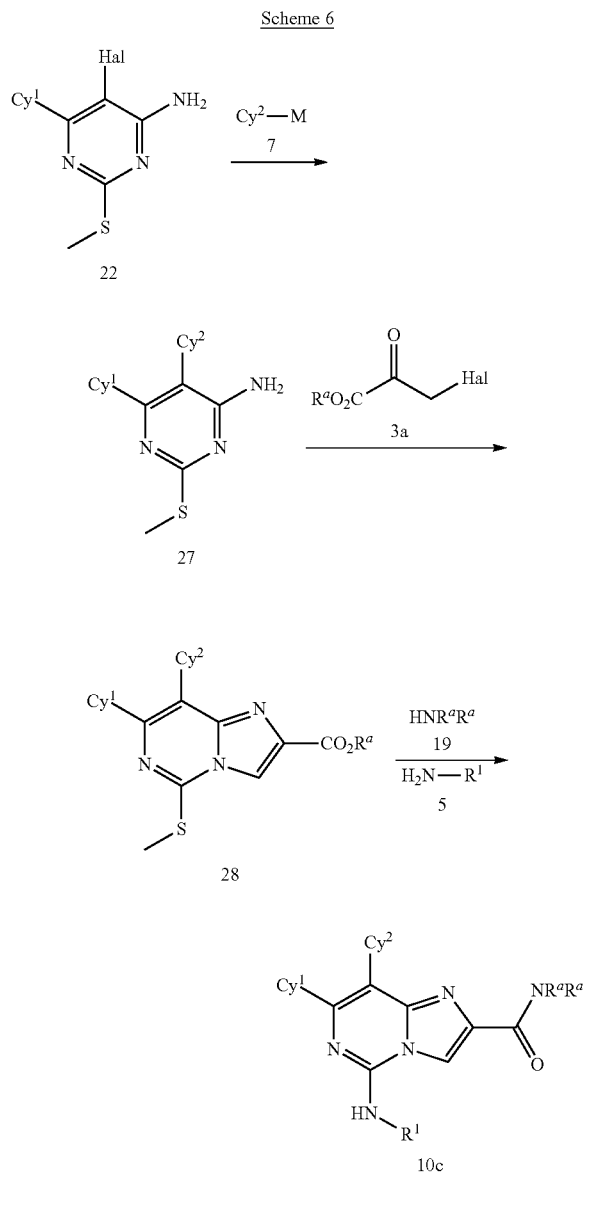

Scheme 7

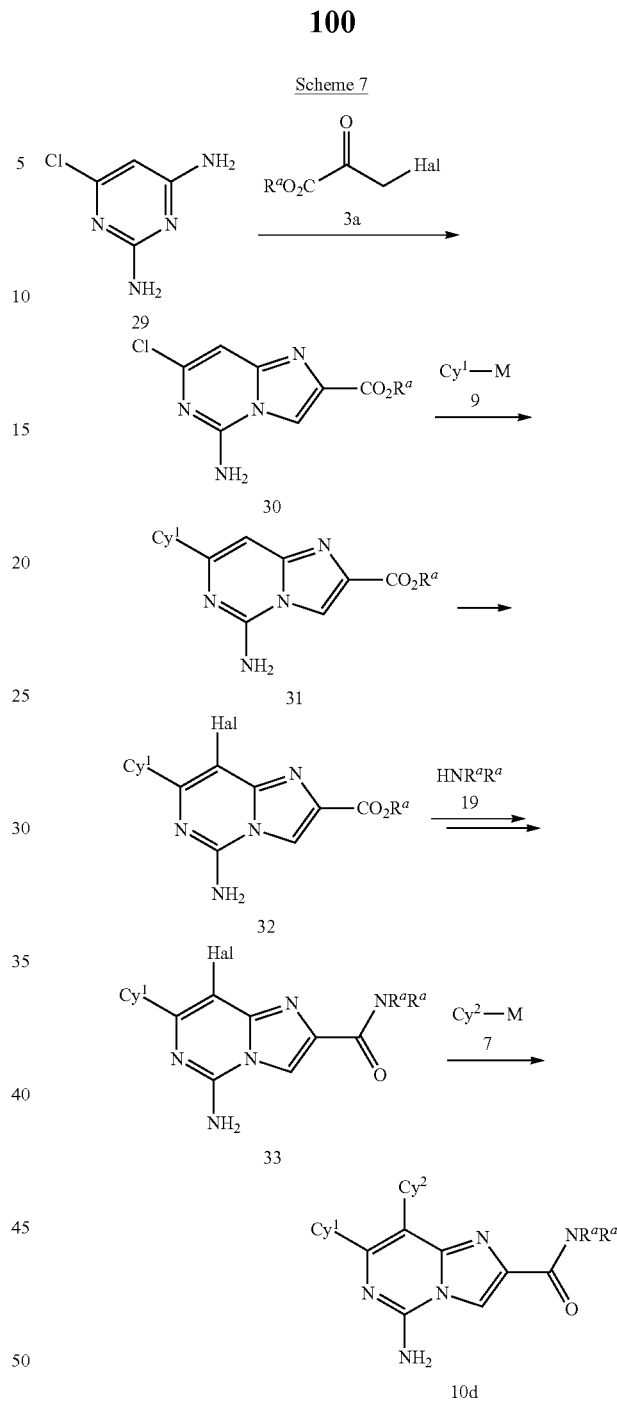

Compound 10c can also be prepared using the synthetic route as outlined in Scheme 6. Compound 22 (prepared as described in Scheme 5) can first undergo a coupling reaction with an adduct of formula 7, in which M is a boronic acid, a boronic ester or an appropriately substituted metal [e.g., M is $B(OR)_2$, $Sn(Alkyl)_3$, Zn-Hal, etc.], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), to give a derivative of formula 27. Condensation of compound 27 with a carbonyl adduct of formula 3a at elevated temperature can generate the bicyclic compound of formula 28. Compound 28 can then react with amine 19 and amine 5, in either order, to afford Compound 10c.

Compounds 10d can be prepared using the synthetic route as outlined in Scheme 7. Condensation of commercially available starting material 29 with a carbonyl adduct of formula 3a at elevated temperature can generate the bicyclic compound of formula 30. Compound 30 can then undergo a coupling reaction with an adduct of formula 9, in which M is a boronic acid, a boronic ester or an appropriately substituted metal [e.g., M is $B(OR)_2$, $Sn(Alkyl)_3$, Zn-Hal, etc.], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), to give a derivative of formula 31. Compound 31 can then be subjected to a halogenation reaction, such as electrophilic aromatic substitution (S$_E$Ar), with an appropriate reagent, such as N-bromosuccinimide (NBS), to afford compound 32 (Hal is a halide, such as F, Cl, Br, or I). Ester hydrolysis of compound 32 in the presence of an appropriate reagent, such as lithium hydroxide (LiOH), can generate the corresponding carboxylic acid, which can then be coupled with an amine adduct of formula 19, using an appropriate coupling reagent (such as HATU, BOP, or PyBOP), to afford compound 33. Alternatively, compound 33 can be accessed by reacting compound 32 directly with amine adduct 19 at elevated temperature. Introduction of Cy$^2$ can then be achieved by the coupling of compound 33 with an adduct of formula 7, using similar conditions as described for the preparation of compound 31 from compound 30, to afford compound 10d.

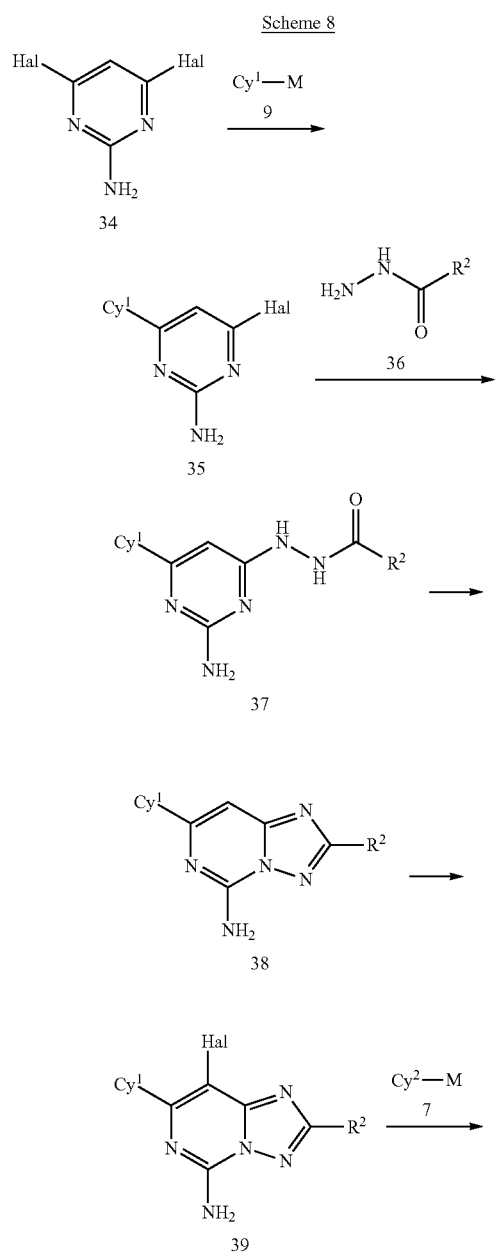

Scheme 8

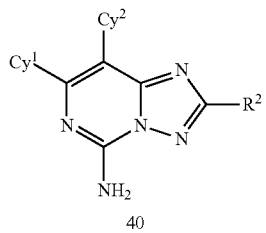

40

Compounds of formula 40 can be synthesized via the synthetic route outlined in Scheme 8. Starting material 34 first undergoes a cross-coupling reaction with reagent 9 to generate compound 35, in which M is a boronic acid, boronic ester or an appropriately substituted metal [e.g., M is B(OR)$_2$, Sn(Alkyl)$_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst). A nucleophilic aromatic substitution (S$_N$Ar) reaction of compound 35 with hydrazide 36 then affords compound 37, which undergoes a cyclization reaction at elevated temperature in the presence of a suitable reagent, such as N,O-bis(trimethylsilyl)acetamide, to produce bicycle 38. Halogenation of 38 with an appropriate reagent, such as N-bromosuccinimide (NBS), affords compound 39. The final product 40 can be prepared by a cross-coupling reaction between compound 39 and a derivative of formula 7, using similar procedures as described for the preparation of compound 35 from starting material 34. At various stages during this synthetic sequence, the R$^2$ group can be further functionalized as seen appropriate.

Scheme 9

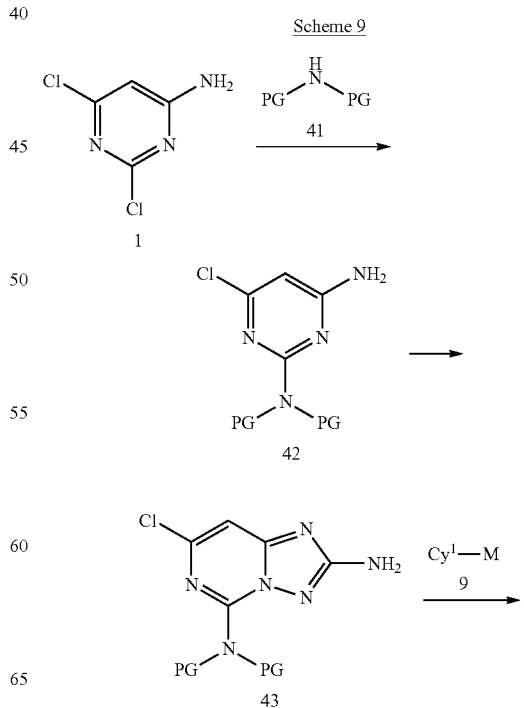

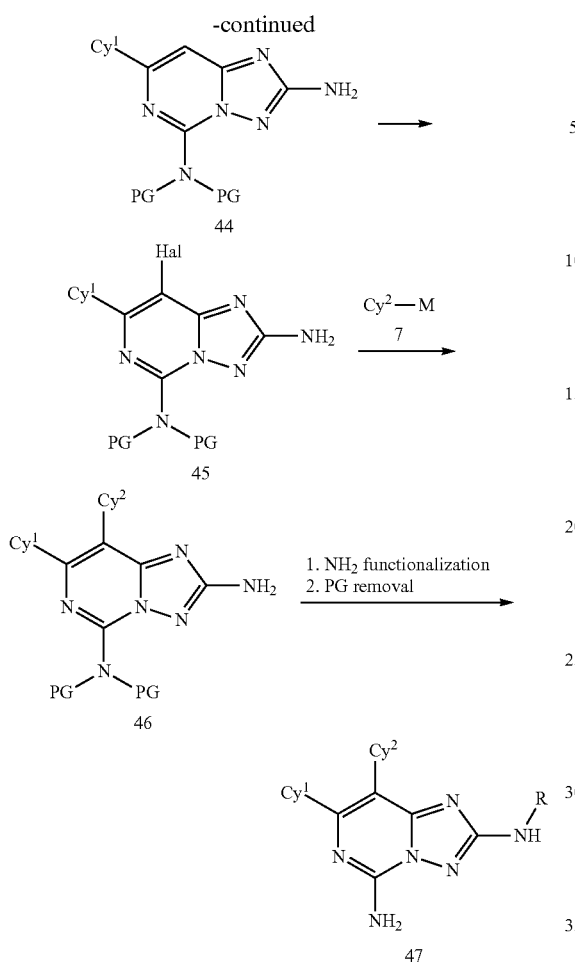

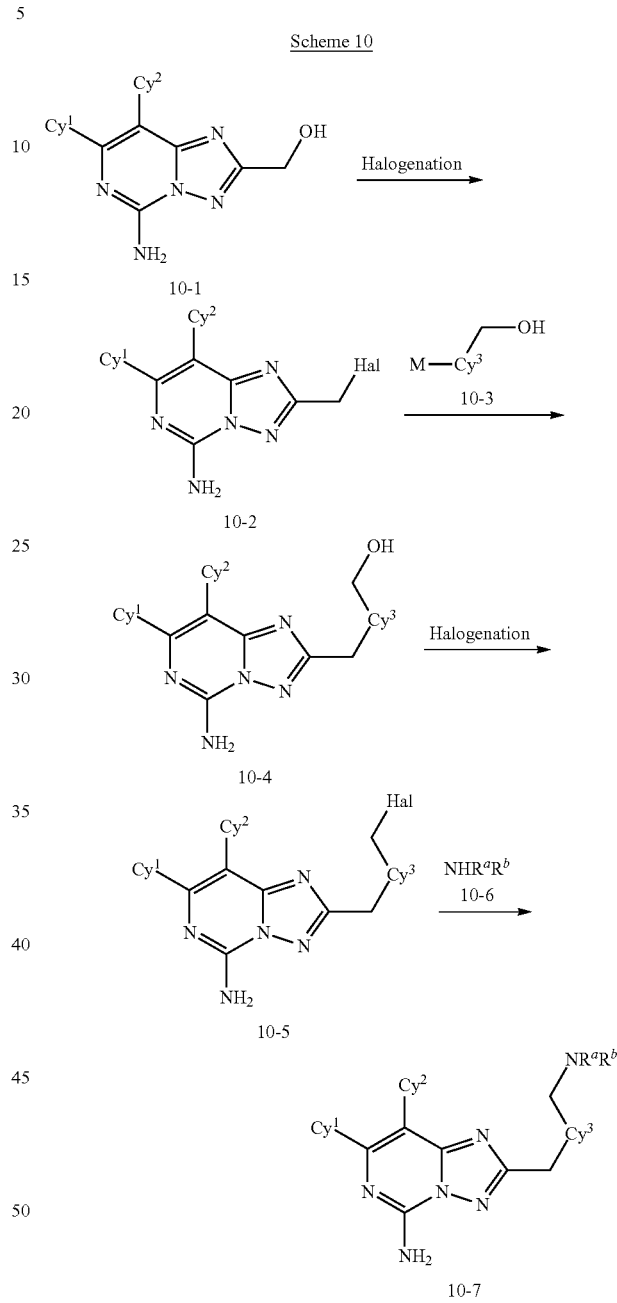

suitable hydride source), or Strecker reaction conditions (e.g., in the presence of a suitable cyanide source), followed by protecting group removal to afford product 47.

Scheme 10

Compounds of formula 47 can be synthesized via the synthetic route outlined in Scheme 9. Selective nucleophilic aromatic substitution ($S_NAr$) reaction of starting material 1 with amine 41 (PG represents a suitable protecting group, such as 4-methoxybenzyl) affords compound 42. Compound 42 can then be cyclized to intermediate 43 via appropriate chemical transformations, such as a two-step sequence using O-ethyl carbonisothiocyanatidate and hydroxylamine hydrochoride. A cross-coupling reaction between 43 and a reagent of formula 9, in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), will generate intermediate 44. Halogenation of 44 using a suitable reagent, such as N-bromosuccinimide (NBS), gives compound 45. A cross-coupling reaction between 45 and a derivative of formula 7, using similar procedures as described for the preparation of compound 44 from compound 43, generates intermediate 46. The amino group of 46 can then be functionalized using suitable chemical transformations, such as Buchwald-Hartwig coupling conditions in the presence of a palladium catalyst (e.g., chloro(2-dicyclohexylphosphino-2',4',6'-triisopropyl-1,1'-biphenyl)[2-(2'-amino-1,1'-biphenyl)] palladium(II)) and a base (e.g., sodium tert-butoxide), or reductive animation conditions (e.g., in the presence of a Compounds of formula 10-7 can be synthesized via the synthetic route outlined in Scheme 10. Advanced intermediate 10-1 (which can be prepared using synthetic procedures as outlined in Scheme 8) first undergoes a halogenation reaction (using an suitable reagent, such as thionyl chloride) to generate compound 10-2 (Hal is a halide, such as F, Cl, Br, or I). Compound 10-2 can then be subjected to a cross-coupling reaction with reagents of formula 10-3, in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), to afford compound 10-4. The hydroxyl group in 10-4 can then be converted to a halogen to provide compound 10-5 (using similar procedures as described for the conversion of 10-1 to 10-2). Product 10-7 can then be prepared from intermediate 10-5 and reagents of formula 10-6, using an appropriate transformation, such as a nucleophilic substitution ($S_N2$) reaction.

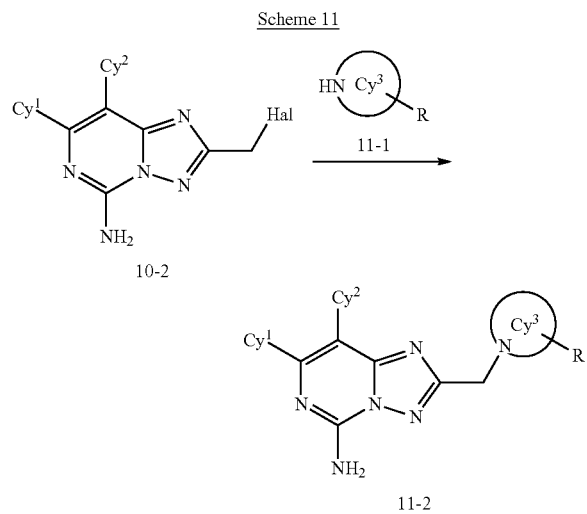

Scheme 11

Compounds of formula 11-2 can be synthesized via the synthetic route outlined in Scheme 11. Intermediate 10-2 (which can be prepared using synthetic procedures as outlined in Scheme 10, Hal is a halide, such as F, Cl, Br, or I) can undergo a nucleophic substitution reaction ($S_N2$) with reagent of formula 11-1, to afford compound 11-2.

Methods of Use

The compounds of the present disclosure can modulate the activity of adenosine receptors, such as subtypes A2A and A2B receptors. Accordingly, the compounds, salts or stereoisomers described herein can be used in methods of inhibiting adenosine receptors (e.g., A2A and/or A2B receptors) by contacting the receptor with any one or more of the compounds, salts, or compositions described herein. In some embodiments, the compounds or salts can be used in methods of inhibiting activity of an adenosine receptor in an individual/patient in need of the inhibition by administering an effective amount of a compound or salt of described herein. In some embodiments, modulating is inhibiting. In some embodiments, the contacting is in vivo. In some embodiments, the contacting is ex vivo or in vitro.

The compounds or salts described herein can be selective. By "selective," it is meant that the compound binds to or inhibits an adenosine receptor with greater affinity or potency, respectively, compared to at least one other receptor, kinase, etc. The compounds of the present disclosure can also be dual antagonists (i.e., inhibitors) of adenosine receptors, e.g., A2A and A2B adenosine receptors.

Another aspect of the present disclosure pertains to methods of treating an adenosine receptor associated disease or disorder in an individual (e.g., patient) by administering to the individual in need of such treatment a therapeutically effective amount or dose of one or more compounds of the present disclosure or a pharmaceutical composition thereof.

An adenosine receptor associated disease or disorder can include any disease, disorder or condition that is directly or indirectly linked to expression or activity of the adenosine receptor, including overexpression and/or abnormal activity levels.

The compounds of the present disclosure are useful in the treatment of diseases related to the activity of adenosine receptors including, for example, cancer, inflammatory diseases, cardiovascular diseases, neurodegenerative diseases, immunomodulatory disorders, central nerve system diseases, and diabetes.

Based on the compelling roles of adenosine, e.g., A2A, A2B, receptors in multiple immunosuppressive mechanisms, developing inhibitors can boost the immune system to suppress tumor progression. Adenosine receptor inhibitors can be used to treat, alone or in combination with other therapies, bladder cancer, lung cancer (e.g., non-small cell lung cancer (NSCLC), lung metastasis), melanoma (e.g., metastatic melanoma), breast cancer, cervical cancer, ovarian cancer, colorectal cancer, pancreatic cancer, esophageal cancer, prostate cancer, kidney cancer, skin cancer, thyroid cancer, liver cancer, uterine cancer, head and neck cancer, and renal cell carcinoma (Antonioli, L. et al., *Nature Reviews Cancer*, 2013, 13, 842-857). See also, https://globenewswire.com/news-release/2017/04/04/954192/0/en/Corvus-Pharmaceuticals-Announces-Interim-Results-from-Ongoing-Phase-1-1b-Study-Demonstrating-Safety-and-Clinical-Activity-of-Lead-Checkpoint-Inhibitor-CPI-444-in-Patients-with-Adva.html; Cekic C. et al., *J Immunol*, 2012, 188:198-205; Iannone, R. et al., *Am. J. Cancer Res.* 2014, 4:172-181 (study shows that both A2A and CD73 blockade enhance the antitumor activity of anti-CTLA-4 mAb therapy in a B16F10 murine melanoma model); Iannone, R. et al., *Neoplasia*, 2013, 15:1400-1410 and Beavis Pa., et al., *Proc Natl Acad Sci. USA*, 2013, 110:14711-14716 (study shows that A2A and CD73 blockade decreased metastasis in 4T1 breast tumor model with has high CD73 expression). In some embodiments, the prostate cancer is metastatic castrate-resistant prostate carcinoma (mCRPC). In some embodiments, the colorectal cancer is colorectal carcinoma (CRC).

In some embodiments, the disease or disorder is lung cancer (e.g., non-small cell lung cancer), melanoma, pancreatic cancer, breast cancer, head and neck squamous cell carcinoma, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibro sarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is mesothelioma or adrenocarcinoma. In some embodiments, the disease or disorder is mesothelioma. In some embodiments, the disease or disorder is adrenocarcinoma.

MDSC (myeloid-derived suppressor cells) are a heterogenous group of immune cells from the myeloid lineage (a family of cells that originate from bone marrow stem cells). MDSCs strongly expand in pathological situations such as chronic infections and cancer, as a result of an altered haematopoiesis. MDSCs are discriminated from other myeloid cell types in which they possess strong immuno-suppressive activities rather than immunostimulatory properties. Similar to other myeloid cells, MDSCs interact with other immune cell types including T cells, dendritic cells, macrophages and natural killer cells to regulate their functions. In some embodiments, the compounds, etc. described herein can be used in methods related to cancer tissue (e.g., tumors) with high infiltration of MDSCs, including solid tumors with high basal level of macrophage and/or MDSC infiltration.

In some embodiments, the compounds of the disclosure can be used in treating pulmonary inflammation, including bleomycin-induced pulmonary fibrosis and injury related to adenosine deaminase deficiency (Baraldi, et al., *Chem. Rev.,* 2008, 108, 238-263).

In some embodiments, the compounds of the disclosure can be used as a treatment for inflammatory disease such as allergic reactions (e.g., A2B adenosine receptor dependent allergic reactions) and other adenosine receptor dependent immune reactions. Further inflammatory diseases that can be treated by compounds of the disclosure include respiratory disorders, sepsis, reperfusion injury, and thrombosis.

In some embodiments, the compounds of the disclosure can be used as a treatment for cardiovascular disease such as coronary artery disease (myocardial infarction, angina pectoris, heart failure), cerebrovascular disease (stroke, transient ischemic attack), peripheral artery disease, and aortic atherosclerosis and aneurysm. Atherosclerosis is an underlying etiologic factor in many types of cardiovascular disease. Atherosclerosis begins in adolescence with fatty streaks, which progress to plaques in adulthood and finally results in thrombotic events that cause occlusion of vessels leading to clinically significant morbidity and mortality. Antagonists to the A2B adenosine receptor and A2A adenosine receptor may be beneficial in preventing atherosclerotic plaque formation (Eisenstein, A. et al., *J. Cell Physiol.,* 2015, 230(12), 2891-2897).

In some embodiments, the compounds of the disclosure can be used as a treatment for disorders in motor activity; deficiency caused by degeneration of the striatonigral dopamine system; and Parkinson's disease; some of the motivational symptoms of depression (Collins, L. E. et al. *Pharmacol. Biochem. Behav.,* 2012, 100, 498-505.).

In some embodiments, the compounds of the disclosure can be used as a treatment for diabetes and related disorders, such as insulin resistance. Diabetes affects the production of adenosine and the expression of A2B adenosine receptors (A2BRs) that stimulate IL-6 and CRP production, insulin resistance, and the association between A2BR gene single-nucleotide polymorphisms (ADORA2B SNPs) and inflammatory markers. The increased A2BR signaling in diabetes may increase insulin resistance in part by elevating pro-inflammatory mediators. Selective A2BR blockers may be useful to treat insulin resistance (Figler, R. A. et al. *Diabetes,* 2011, 60(2), 669-679).

It is believed that compounds provided herein, e.g., compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient", used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

In some embodiments, A2A and A2B dual inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Compounds of the present disclosure can be used in combination with one or more immune checkpoint inhibitors. Exemplary immune checkpoint inhibitors include inhibitors against immune checkpoint molecules such as CD20, CD28, CD40, CD122, CD96, CD73, CD47, GITR, CSF1R, JAK, PI3K delta, PI3K gamma, TAM, arginase, HPK1, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the A2A and A2B dual inhibitors provided herein can be used in combination with one or more agonists of immune checkpoint molecules, e.g., OX40, CD27, OX40, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122 or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675, 206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, orTSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40 L fusion protein. In some embodiments, the anti-OX40 antibody is MEDI0562, MOXR-0916, PF-04518600, GSK3174998, or BMS-986178. In some embodiments, the OX40 L fusion protein is MEDI6383.

In some embodiments, the inhibitor of an immune checkpoint molecule is an inhibitor of CD20, e g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3, tumor specific antigens (e.g., CD70), or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer. Examples of diseases and indications treatable with combination therapies include those as described herein.

The compounds of the present disclosure can be used in combination with one or more additional pharmaceutical agents such as, for example, chemotherapeutics, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF and FAK kinase inhibitors. The one or more additional pharmaceutical agents can be administered to a patient simultaneously or sequentially.

For example, the compounds as disclosed herein can be combined with one or more inhibitors of the following kinases for the treatment of cancer and other diseases or disorders described herein: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Non-limiting examples of inhibitors that can be combined with the compounds of the present disclosure for treatment of cancer and other diseases and disorders described herein include an FGFR inhibitor (FGFR1, FGFR2, FGFR3 or FGFR4, e g., INCB54828, INCB62079 and INCB63904), a JAK inhibitor (JAK1 and/or JAK2, e g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a Pirn inhibitor, a CSFIR inhibitor, a TAM receptor tyrosine kinases (Tyro-3, Axl, and Mer), a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA™, (gefitinib), TARCEVA™, (erlotinib), antibodies to EGFR, GLEEVEC™, intron, ara-C, adriamycin, cytoxan, gemcitabine, uracil mustard, chlormethylne, ifosfamide, melphalan, chlorambucil, pipobroman, triethylenemelamine, triethylenethylophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™,™ (oxaliplatin), pentostatine, vinblastine, vincristine, vindesine, bleomycin, dactinomycin, daunorubicin, doxorubicin, epirubicin, idarubicin, mithramycin, deoxycofbrmycin, mitomycin-C, L-asparaginase, teniposide 17.alpha-.-ethylnylestradiol, diethylstilbestrol, testosterone, prednisone, fluoxymesterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethylmide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™, (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101, 731.

The compounds of the present disclosure can further be used in combination with other methods of treating cancers, for example by chemotherapy, irradiation therapy, tumortargeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, streptozocin, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib, and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Fh-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a PI3K inhibitor of the present disclosure with an additional agent.

In some embodiments, the compounds of the disclosure can be used in combination with an inhibitor of JAK or PI3Kδ.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV).

In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HTV, Hepatitis (A, B, & C), Influenza, Herpes, *Giardia*, Malaria, *Leishmania, Staphylococcus aureus, Pseudomonas Aeruginosa.*

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, comovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Pathogenic fungi causing infections treatable by methods of the disclosure include, but are not limited to, *Candida (albicans, krusei, glabrata, tropicalis,* etc.), *Cryptococcus neoformans, Aspergillus (fumigatus, niger,* etc.), Genus Mucorales *(mucor, absidia,* rhizophus), *Sporothrix schenkii, Blastomyces dermatitidis, Paracoccidioides brasiliensis, Coccidioides immitis* and *Histoplasma capsulatum.* Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis.*

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders.

The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating A2A and/or A2B receptors in tissue samples, including human, and for identifying A2A and/or A2B antagonists by inhibition binding of a labeled compound. Substitution of one or more of the atoms of the compounds of the present disclosure can also be useful in generating differentiated ADME (Adsorption, Distribution, Metabolism and Excretion.) Accordingly, the present disclosure includes adenosine receptor (e.g., A2A and/or A2B) assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups in any of the disclosed Formulas, e.g., Formula (I), can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of any "alkyl", "alkenyl", "alkynyl", "aryl", "phenyl", "cycloalkyl", "heterocycloalkyl", or "heteroaryl" substituents or "—$C_{1-6}$ alkyl-", "alkylene", "alkenylene" and "alkynylene" linking groups, as described herein, are each optionally replaced by a deuterium atom.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances, (see e.g., A. Kerekes et. al. J. Med. Chem 2011, 54, 201-210; R. Xu et. al. J. Label Compd. Radiopharm. 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro adenosine receptor labeling and competition assays, compounds that incorporate $^{3}$H, $^{14}$C, $^{82}$Br, $^{123}$I, $^{131}$I or $^{35}$S can be useful. For radio-imaging applications $^{11}$C, $^{18}$F, $^{123}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from the group consisting of $^{3}$H, $^{14}$C, $^{123}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind an adenosine receptor by monitoring its concentration variation when contacting with the adenosine receptor, through tracking of the labeling. For example, a test compound (labeled) can be evaluated for its ability to reduce binding of another compound which is known to bind to an adenosine receptor (i.e., standard compound). Accordingly, the ability of a test compound to compete with the standard compound for binding to the adenosine receptor directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of adenosine receptor-associated diseases or disorders (such as, e.g., cancer, an inflammatory disease, a cardiovascular disease, or a neurodegenerative disease) which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of an adenosine receptor (e.g., A2A and/or A2B) according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Haque, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 µm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 30×100 mm or Waters XBridge™ $C_{18}$ 5 µm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, J. Comb. Chem., 6, 874-883 (2004)).

pH=10 purifications: Waters XBridge™ $C_{18}$ 5 µm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

Separation of some of the racemic compounds into enantiopure samples were prepared on preparative scale by chiral-phase high performance liquid chromatography under the following conditions: Instrument: Agilent 1100 Prep HPLC; Column: Phenomenex Lux Cellulose-4, 21.2×250 mm, 5 μm; eluting with isocratic mobile phase 45% EtOH in hexanes with a flow rate of 20 mL/minute.

Example 1. 3-(5-Amino-8-(2,6-dimethylpyridin-4-yl)imidazo[1,2-c]pyrimidin-7-yl)benzonitrile

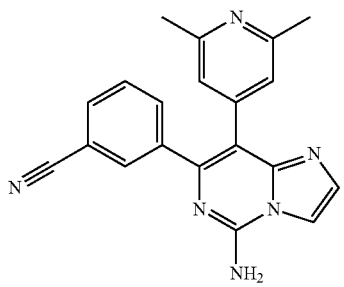 [SMILES: Cc1cc(-c2c(-c3cccc(C#N)c3)nc(N)n3ccnc23)cc(C)n1]

Step 1: 5-Bromo-2,6-dichloropyrimidin-4-amine

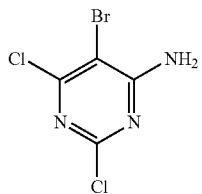

To a solution of 2,6-dichloropyrimidin-4-amine (Combi-Blocks, cat #OR-0412) (10 g, 61 mmol) in DMF (50 mL) at 0° C. was added N-bromosuccinimide (11 g, 61 mmol). The reaction mixture was stirred for 16 h at room temperature before water (100 mL) was added. The resulting precipitate was collected by filtration, and then dried to give the desired product (13.1 g, 88%), which was used in the next step without further purification. LC-MS calculated for $C_4H_3BrCl_2N_3$ (M+H)$^+$: m/z=241.9; found 241.8.

Step 2: 8-Bromo-5,7-dichloroimidazo[1,2-c]pyrimidine

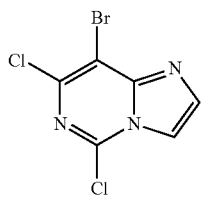 [SMILES: Clc1nc(Cl)n2ccnc2c1Br]

2-Bromo-1,1-diethoxyethane (11 mL, 70 mmol) was added to a mixture of 5-bromo-2,6-dichloropyrimidin-4-amine (2.0 g, 8.2 mmol) in MeCN (25 mL). The resulting mixture was stirred at 120° C. for 1 h then cooled to room temperature and concentrated under reduced pressure. The residue was triturated with EtOAc to give the desired product as the HBr salt (2.4 g, 84%), which was used in the next step without further purification. LC-MS calculated for $C_6H_3BrCl_2N_3$ (M+H)$^+$: m/z=265.9; found 265.8.

Step 3: 8-Bromo-7-chloroimidazo[1,2-c]pyrimidin-5-amine

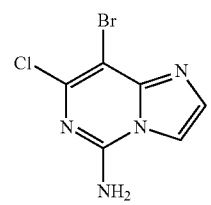 [SMILES: Nc1nc(Cl)c(Br)c2nccn12]

To a solution of 8-bromo-5,7-dichloroimidazo[1,2-c]pyrimidine hydrobromide (2.2 g, 6.3 mmol) in THF (30 mL) was added concentrated ammonium hydroxide (57 mL, 14 M). The reaction mixture was stirred at room temperature for 16 h before the volatiles were removed under reduced pressure. The resulting solid was collected by filtration, washed with water (100 mL) and then dried to give foe desired product (0.75 g, 48%), which was used in the next step without further purification. LC-MS calculated for $C_6H_5BrClN_4$ (M+H)$^+$: m/z=246.9; found 247.0.

Step 4: 7-Chloro-8-(2,6-dimethylpyridin-4-yl)imidazo[1,2-c]pyrimidin-5-amine

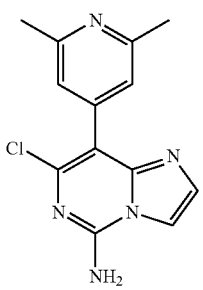 [SMILES: Cc1cc(-c2c(Cl)nc(N)n3ccnc23)cc(C)n1]

[1,1'-Bis(diphenylphosphino)ferrocene]dichloropalladium(II) (7.3 mg, 10 mol %) was added to a mixture of 8-bromo-7-chloroimidazo[1,2-c]pyrimidin-5-amine (25 mg, 0.10 mmol), 2,6-dimethyl-4-(4,4,5,5-tetramethyl-1,3,2-dioxaborolan-2-yl)pyridine (35 mg, 0.15 mmol), and sodium carbonate (32 mg, 0.30 mmol) in THF (0.36 mL) and water (0.07 mL). The mixture was purged with nitrogen, and then stirred at 70° C. for 16 h. The reaction mixture was cooled to room temperature and concentrated under reduced pressure. The crude product was purified by flash chromatography on a silica gel column eluting with 0 to 15% MeOH/DCM to give the desired product, which was used in the next step without further purification. LC-MS calculated for $C_{13}H_{13}ClN_5$ (M+H)$^+$: m/z=274.1; found 274.1.

Step 5: 3-(5-Amino-8-(2,6-dimethylpyridin-4-yl)imidazo[1,2-c]pyrimidin-7-yl)benzonitrile To a microwave vial was added 7-chloro-8-(2,6-dimethylpyridin-4-yl)imidazo[1,2-c]pyrimidin-5-amine (40 mg, 0.15 mmol), (3-cyanophenyl)boronic acid (64 mg, 0.44 mmol), tripotassium phosphate (120 mg, 0.59 mmol), DMF (2.4 mL), water (0.60 mL) and [1,1'-bis(diphenylphosphino)ferrocene]dichloropalladium(II) (11 mg, 10 mol %). The reaction solution was purged with nitrogen, and then the microwave vial was sealed and heated in a microwave reactor at 120° C. for 20 min. The reaction mixture was cooled to room temperature, filtered through a Celite plug with 50% EtOAc/DCM, and then concentrated under reduced pressure. The crude product was purified by prep-LCMS (pH=2, MeCN/water with TFA) to give the desired product as the TFA salt. LC-MS calculated for $C_{20}H_{17}N_6$ $(M+H)^+$: m/z=341.2; found 341.1.

Example 2. 7-(2,3-Dihydro-1H-pyrrolo[2,3-b]pyridin-5-yl)-8-(2,6-dimethylpyridin-4-yl)imidazo[1,2-c]pyrimidin-5-amine

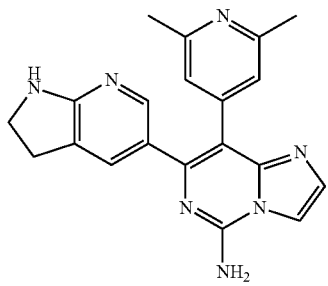 [SMILES: Cc1cc(-c2c(-c3cnc4c(c3)CCN4)nc(N)n3ccnc23)cc(C)n1]

This compound was prepared using similar procedures as described for Example 1, with (2,3-dihydro-1H-pynolo[2,3-b]pyridin-5-yl)boronic acid replacing (3-cyanophenyl)boronic acid in Step 5. The product was purified by prep-LCMS (pH=10, MeCN/water with NH₄OH) to give the desired product as the free base. LC-MS calculated for $C_{20}H_{20}N_7$ $(M+H)^+$: m/z=358.2; found 358.2.

Example 3. 8-(2,6-Dimethylpyridin-4-yl)-3-(morpholinomethyl)-7-phenylimidazo[1,2-c]pyrimidin-5-amine

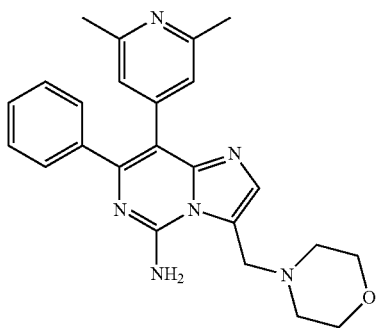 [SMILES: Cc1cc(-c2c(-c3ccccc3)nc(N)n3c(CN4CCOCC4)cnc23)cc(C)n1]

To a mixture of 8-(2,6-dimethylpyridin-4-yl)-7-phenylimidazo[1,2-c]pyrimidin-5-amine (prepared using similar procedures as described in Example 1, with phenylboronic acid replacing (3-cyanophenyl)boronic acid in Step 5) (25 mg, 0.08 mmol) and morpholine (9.5 µL, 0.16 mmol) was added (diacetoxyiodo)benzene (51 mg, 0.16 mmol). The reaction mixture was stirred at 50° C. for 2 h, and the product was purified by prep-LCMS (pH=2, MeCN/water with TFA) to give the desired product as the TFA salt. LC-MS calculated for $C_{24}H_{27}N_6O$ $(M+H)^+$: m/z=415.2; found 415.2.

Example 4. 7-(3-Methoxyphenyl)-8-(pyridin-4-yl)imidazo[1,2-c]pyrimidin-5-amine

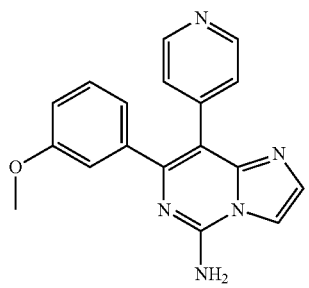 [SMILES: COc1cccc(-c2nc(N)n3ccnc3c2-c2ccncc2)c1]

[1,1'-bis(dicyclohexylphosphino)ferrocene]dichloropalladium(II) (6.1 mg, 10 mol %) was added to a mixture of 8-bromo-7-chloroimidazo[1,2-c]pyrimidin-5-amine (prepared in Example 1, Step 3) (20 mg, 0.08 mmol), pyridin-4-ylboronic acid (12 mg, 0.10 mmol), and cesium carbonate (79 mg, 0.24 mmol) in tert-butanol (0.45 mL) and water (0.09 mL). The solution was purged with nitrogen, stirred at 75° C. for 2 h, and cooled to room temperature. Cesium carbonate (53 mg, 0.24 mmol), [1,1'-bis(dicyclohexylphosphino)ferrocene]dichloropalladium(II) (3.1 mg, 5 mol %), and (3-methoxyphenyl)boronic acid (18 mg, 0.12 mmol) were then added. The reaction mixture was stirred at 105° C. for 4 h, and cooled to room temperature. The mixture was filtered through a Celite plug with 50% EtOAc/DCM and concentrated under reduced pressure. The product was purified by prep-LCMS (pH=2, MeCN/water with TFA) to give the desired product as the TFA salt. LC-MS calculated for $C_{18}H_{16}N_5O$ $(M+H)^+$: m/z=318.1; found 318.2.

Example 5. 7,8-Di(pyridin-4-yl)imidazo[1,2-c]pyrimidin-5-amine

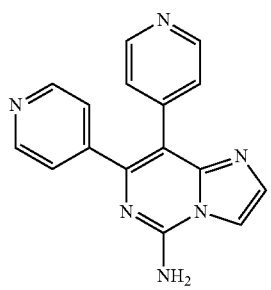 [SMILES: Nc1nc(-c2ccncc2)c(-c2ccncc2)c2nccn12]

This compound was prepared using similar procedures as described for Example 4, with pyridin-4-ylboronic acid replacing (3-methoxyphenyl)boronic acid. The product was purified by prep-LCMS (pH=2, MeCN/water with TFA) to give the desired product as the TFA salt. LC-MS calculated for $C_{16}H_{13}N_6$ $(M+H)^+$: m/z=289.1; found 289.1.

Example 6. 7-(2-Methylfuran-3-yl)-8-(pyridin-4-yl)imidazo[1,2-c]pyrimidin-5-amine

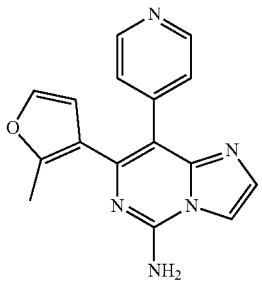 [SMILES: Cc1occc1-c1nc(N)n2ccnc2c1-c1ccncc1]

This compound was prepared using similar procedures as described for Example 4, with 4,4,5,5-tetramethyl-2-(2-methylfuran-3-yl)-1,3,2-dioxaborolane replacing (3-methoxyphenyl)boronic acid. In addition, the reaction mixture was stirred at 105° C. for 20 h. The product was purified by prep-LCMS (pH=2, MeCN/water with TFA) to give the desired product as the TFA salt. LC-MS calculated for $C_{16}H_{14}N_5O$ (M+H)$^+$: m/z=292.1; found 292.1.

Example 7. 7-(2-Fluorophenyl)-8-(pyridin-4-yl)imidazo[1,2-c]pyrimidin-5-amine

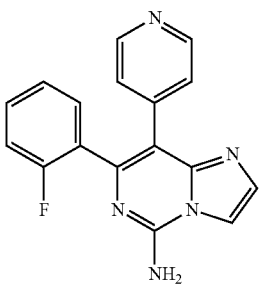 [SMILES: Nc1nc(-c2ccccc2F)c(-c2ccncc2)c2nccn12]

This compound was prepared using similar procedures as described for Example 4, with (2-fluorophenyl)boronic acid replacing (3-methoxyphenyl)boronic acid. The product was purified by prep-LCMS (pH=2, MeCN/water with TFA) to give the desired product as the TFA salt. LC-MS calculated for $C_{17}H_{13}FN_5$ (M+H)$^+$: m/z=306.1; found 306.1.

Example 8. 7-(Benzofuran-2-yl)-8-(pyridin-4-yl)imidazo[1,2-c]pyrimidin-5-amine

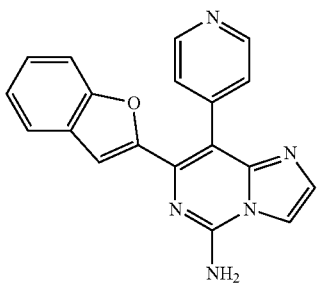 [SMILES: Nc1nc(-c2cc3ccccc3o2)c(-c2ccncc2)c2nccn12]

This compound was prepared using similar procedures as described for Example 4, with benzofuran-2-ylboronic acid replacing (3-methoxyphenyl)boronic acid. The product was purified by prep-LCMS (pH=2, MeCN/water with TFA) to give the desired product as the TFA salt. LC-MS calculated for $C_{19}H_{14}N_5O$ (M+H)$^+$: m/z=328.1; found 328.1.

Example 9. 7-(1-Methyl-1H-pyrazol-4-yl)-8-(2-methylpyridin-4-yl)imidazo[1,2-c]pyrimidin-5-amine

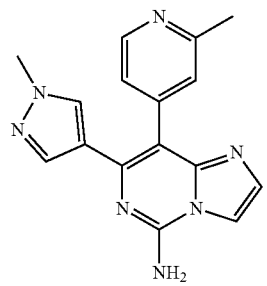 [SMILES: Cc1cc(-c2c(-c3cnn(C)c3)nc(N)n3ccnc23)ccn1]

Step 1: 7-Chloro-8-(2-methylpyridin-4-yl)imidazo[1,2-c]pyrimidin-5-amine

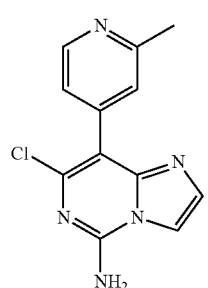

[1,1'-bis(dicyclohexylphosphino)ferrocene]dichloropalladium(II) (110 mg, 10 mol %) was added to a mixture of 8-bromo-7-chloroimidazo[1,2-c]pyrimidin-5-amine (prepared in Example 1, Step 3) (370 mg, 1.5 mmol), 2-methy-4-(4,4,5,5-tetramethyl-1,3,2-dioxaborolan-2-yl)pyridine (490 mg, 2.2 mmol), and cesium carbonate (1.5 g, 4.5 mmol) in tert-butanol (8.3 mL) and water (1.7 mL). The solution was purged with nitrogen, and then stirred at 75° C. for 5 h. The reaction mixture was cooled to room temperature and filtered through a Celite plug with EtOAc. The filtrate was concentrated under reduced pressure. The crude product was purified by flash chromatography on a silica gel column eluting with 0-10% MeOH/DCM to give the desired product, which was used in the next step without further purification. LC-MS calculated for $C_{12}H_{11}ClN_5$ (M+H)$^+$: m/z=260.1; found 260.0.

Step 2: 7-(1-Methyl-1H-pyrazol-4-yl)-8-(2-methylpyridin-4-yl)imidazo[1,2-c]pyrimidin-5-amine To a microwave vial was added 7-chloro-8-(2-methylpyridin-4-yl)imidazo[1,2-c]pyrimidin-5-amine (43 mg, 0.17 mmol), 1-methyl-4-(4,4,5,5-tetramethyl-1,3,2-dioxaborolan-2-yl)-1H-pyrazole (100 mg, 0.50 mmol), tripotassium phosphate (140 mg, 0.66 mmol), DMF (1.3 mL), water (0.33 mL) and [1,1'-bis(diphenylphosphino)ferrocene]dichloropalladium(II) (12 mg, 10 mol %). The reaction solution was purged with nitrogen, and then the microwave vial was sealed and heated in a microwave reactor at 120° C. for 20 min. The reaction mixture was cooled to room temperature and filtered through a Celite plug with 50% EtOAc/DCM, then concentrated under reduced pressure. The product was purified by prep-LCMS (pH=10, MeCN/water with NH$_4$OH) to give the desired product as the free base. LC-MS calculated for C$_{16}$H$_{16}$N$_7$ (M+H)$^+$: m/z=306.1; found 306.1.

Example 10. 8-(2-Methylpyridin-4-yl)-2,7-diphenylimidazo[1,2-c]pyrimidin-5-amine

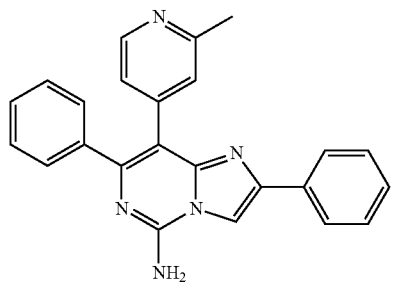 [SMILES: Cc1cc(-c2c(-c3ccccc3)nc(N)n3cc(-c4ccccc4)nc23)ccn1]

Step 1: 2-Methoxy-6-phenylpyrimidin-4-amine

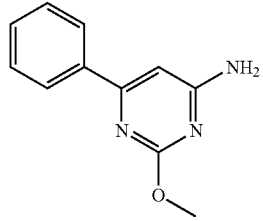

Bis(di-tert-butyl(4-dimethylaminophenyl)phosphine)dichloropalladium(II) (0.89 g, 5 mol %) was added to a mixture of 6-chloro-2-methoxypyrimidin-4-amine (Ark Pharm, Inc, cat #AK-25131) (4.0 g, 25 mmol), phenylboronic acid (4.6 g, 38 mmol) and cesium carbonate (16 g, 50 mmol) in toluene (130 mL) and water (13 mL). The solution was purged with nitrogen, and then stirred at 115° C. for 16 h. The reaction mixture was cooled to room temperature, filtered through a Celite plug with DCM and concentrated under reduced pressure. Water (100 mL) was added to the residue and the resulting solid was collected by filtration, and then dried to give the desired product (5.0 g, 99%), which was used in the next step without further purification. LC-MS calculated for C$_{11}$H$_{12}$N$_3$O (M+H)$^+$: m/z=202.1; found 202.0.

Step 2: 5-Bromo-2-methoxy-6-phenylpyrimidin-4-amine

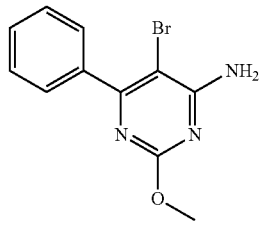 [SMILES: COc1nc(N)c(Br)c(-c2ccccc2)n1]

To a solution of 2-methoxy-6-phenylpyrimidin-4-amine (5.1 g, 25 mmol) in DMSO (51 mL), MeCN (27 mL) and water (1.7 mL) at 0° C. was added N-bromosuccinimide (4.5 g, 25 mmol). The reaction mixture was stirred for 2 h at room temperature before water (100 mL) was added. The resulting precipitate was collected by filtration then dried to give the desired product (5.2 g, 73%), which was used in the next step without further purification. LC-MS calculated for C$_{11}$H$_{11}$BrN$_3$O (M+H)$^+$: m/z=280.0; found 280.0.

Step 3: 2-Methoxy-5-(2-methylpyridin-4-yl)-6-phenylpyrimidin-4-amine

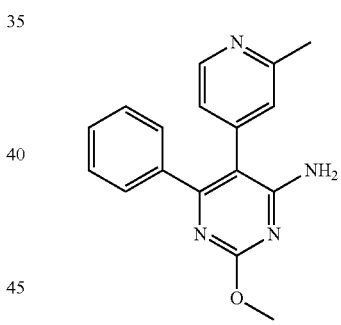

[1,1'-bis(dicyclohexylphosphino)ferrocene]dichloropalladium(II) (0.41 g, 10 mol %) was added to a mixture of 5-bromo-2-methoxy-6-phenylpyrimidin-4-amine (1.5 g, 5.4 mmol), 2-methyl-4-(4,4,5,5-tetramethyl-1,3,2-dioxaborolan-2-yl)pyridine (1.8 g, 8.0 mmol), and cesium carbonate (3.5 g, 11 mmol) in tert-butanol (20 mL) and water (3.9 mL). The solution was purged with nitrogen, and then stirred at 120° C. for 1.5 h. The reaction mixture was cooled to room temperature, filtered through a Celite plug with DCM and concentrated under reduced pressure. Water (100 mL) was added to the residue and the resulting solid was collected by filtration then dried to give the desired product (1.02 g, 65%), which was used in the next step without further purification. LC-MS calculated for C$_{17}$H$_{17}$N$_4$O (M+H)$^+$: m/z=293.1; found 293.1.

Step 4: 8-(2-Methylpyridin-4-yl)-2,7-diphenylimidazo[1,2-c]pyrimidin-5(6H)-one

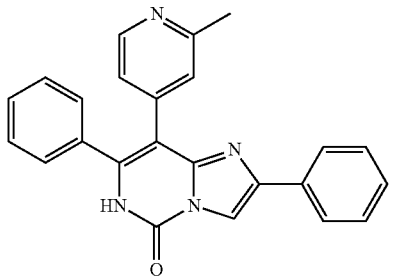 [SMILES: Cc1cc(-c2c(-c3ccccc3)[nH]c(=O)n3cc(-c4ccccc4)nc23)ccn1]

To 2-methoxy-5-(2-methylpyridin-4-yl)-6-phenylpyrimidin-4-amine (100 mg, 0.34 mmol) in acetic acid (1.4 mL) was added 2-bromo-1-phenylethan-1-one (170 mg, 0.86 mmol). The reaction mixture was stirred at 120° C. for 20 h. After cooling to room temperature the volatiles were removed under reduced pressure. The resulting solid was washed with Et$_2$O, collected by filtration and then dried to give the crude product, which was used in the next step without further purification. LC-MS calculated for C$_{24}$H$_{19}$N$_4$O (M+H)$^+$: m/z=379.2; found 379.1.

Step 5: 5-Chloro-8-(2-methylpyridin-4-yl)-2,7-diphenylimidazo[1,2-c]pyrimidine

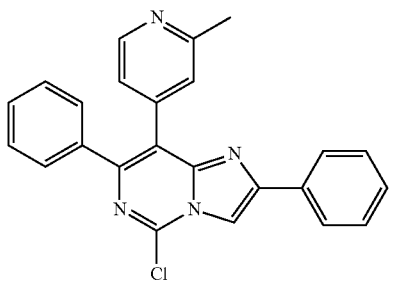 [SMILES: Cc1cc(-c2c(-c3ccccc3)nc(Cl)n3cc(-c4ccccc4)nc23)ccn1]

To a stirred solution of 8-(2-methylpyridin-4-yl)-2,7-diphenylimidazo[1,2-c]pyrimidin-5(6H)-one acetate (150 mg, 0.34 mmol) and POCl$_3$ (0.25 mL, 2.6 mmol) in toluene (1.3 mL) at 0° C. was added dropwise N,N-diisopropylethylamine (0.26 mL, 1.5 mmol). The resulting solution was slowly heated to 120° C. over 1 h, and then stirred at 120° C. for 16 h. After cooling to room temperature the volatiles were removed under reduced pressure. The resulting residue was diluted with 1 N HCl (2.0 mL) and water (20 mL), and extracted with DCM (5×20 mL). The organic layers were combined, dried over Na$_2$SO$_4$, filtered and concentrated under reduced pressure. The resulting crude product mixture was used in the next step without further purification. LC-MS calculated for C$_{24}$H$_{18}$ClN$_4$ (M+H)$^+$: m/z=397.1; found 397.1.

Step 6: 8-(2-Methylpyridin-4-yl)-2,7-diphenylimidazo[1,2-c]pyrimidin-5-amine

This compound was prepared using a similar procedure as described for Example 1, Step 3, with 5-chloro-8-(2-methylpyridin-4-yl)-2,7-diphenylimidazo[1,2-c]pyrimidine replacing 8-bromo-5,7-dichloroimidazo[1,2-c]pyrimidine hydrobromide. The product was purified by prep-LCMS (pH=2, MeCN/water with TFA) to give the desired product as the TFA salt. LC-MS calculated for C$_{24}$H$_{20}$N$_5$ (M+H)$^+$: m/z=378.2; found 378.1.

Example 11. Ethyl 5-amino-8-(2-methylpyridin-4-yl)-7-phenylimidazo[1,2-c]pyrimidine-2-carboxylate

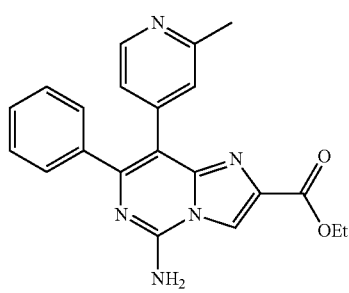 [SMILES: CCOC(=O)c1cn2c(N)nc(-c3ccccc3)c(-c3ccnc(C)c3)c2n1]

This compound was prepared using similar procedures as described for Example 10, with ethyl 3-bromo-2-oxopropanoate replacing 2-bromo-1-phenylethan-1-one in Step 4. The product was purified by prep-LCMS (pH=10, MeCN/water with NH$_4$OH) to give the desired product as the free base. LC-MS calculated for C$_{21}$H$_{20}$N$_5$O$_2$ (M+H)$^+$: m/z=374.2; found 374.0.

Example 12. Methyl 5-(5-amino-7-phenyl-8-(pyridin-4-yl)imidazo[1,2-c]pyrimidin-2-yl)isoxazole-3-carboxylate

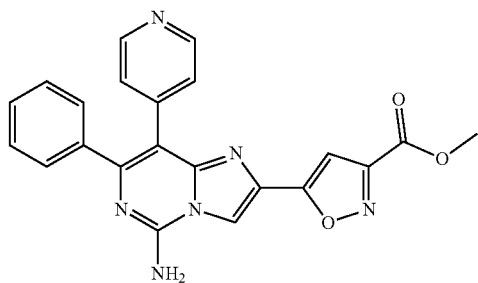 [SMILES: COC(=O)c1cc(-c2cn3c(N)nc(-c4ccccc4)c(-c4ccncc4)c3n2)on1]

Step 1: Ethyl 5-(5-oxo-7-phenyl-8-(pyridin-4-yl)-5,6-dihydroimidazo[1,2-c]pyrimidin-2-yl)isoxazole-3-carboxylate

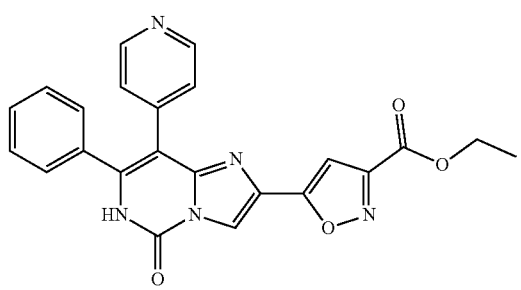 [SMILES: CCOC(=O)c1cc(-c2cn3c(=O)[nH]c(-c4ccccc4)c(-c4ccncc4)c3n2)on1]

To a mixture of 2-methoxy-6-phenyl-5-(pyridin-4-yl)pyrimidin-4-amine (prepared using similar procedures as described in Example 10, Step 1-3, with pyridin-4-ylboronic acid replacing 2-methyl-4-(4,4,5,5-tetramethyl-1,3,2-dioxaborolan-2-yl)pyridine in Step 3) (50 mg, 0.18 mmol) in 2-propanol (0.54 mL) was added ethyl 5-(2-bromoacetyl)isoxazole-3-carboxylate (Combi-Blocks, cat #SS-6738) (71 mg, 0.27 mmol). The reaction mixture was stirred at 110° C. for 4 h. After cooling to room temperature the volatiles were removed under reduced pressure. The resulting solid was washed with EtOAc, collected by filtration, and then dried to give the crude product as the HBr salt, which was used in the next step without further purification. LC-MS calculated for $C_{23}H_{18}N_5O_4$ (M+H)$^+$: m/z=428.1; found 428.0.

Step 2: Ethyl 5-(5-chloro-7-phenyl-8-(pyridin-4-yl)imidazo[1,2-c]pyrimidin-2-yl)isoxazole-3-carboxylate

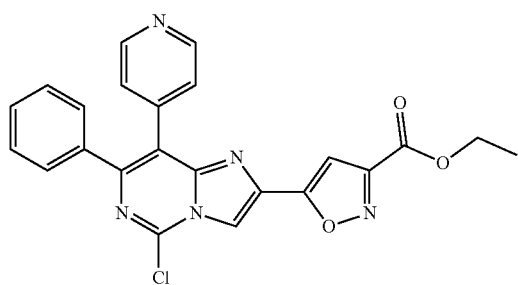 [SMILES: CCOC(=O)c1cc(-c2cn3c(Cl)nc(-c4ccccc4)c(-c4ccncc4)c3n2)on1]

To a stirred solution of ethyl 5-(5-oxo-7-phenyl-8-(pyridin-4-yl)-5,6-dihydroimidazo[1,2-c]pyrimidin-2-yl)isoxazole-3-carboxylate hydrobromide (72 mg, 0.14 mmol) in MeCN (0.53 mL) was added POCl$_3$ (0.54 mL, 5.8 mmol). The resulting solution was stirred at 120° C. for 16 h. After cooling to room temperature the volatiles were removed under reduced pressure. To the residue was slowly added ice water (20 mL) and the slurry was stirred for 20 min. The resulting solid was collected by filtration then dried to give the crude product, which was used in the next step without further purification. LC-MS calculated for $C_{23}H_{17}ClN_5O_3$ (M+H)$^+$: m/z=446.1; found 446.0.

Step 3: Methyl 5-(5-amino-7-phenyl-8-(pyridin-4-yl)imidazo[1,2-c]pyrimidin-2-yl)isoxazole-3-carboxylate To a solution of ethyl 5-(5-chloro-7-phenyl-8-(pyridin-4-yl)imidazo[1,2-c]pyrimidin-2-yl)isoxazole-3-carboxylate (70 mg, 0.16 mmol) in THF (0.70 mL) and MeOH (0.10 mL) was added concentrated ammonium hydroxide (1.4 mL, 14 M). The reaction mixture was stirred at room temperature for 16 h before the volatiles were removed under reduced pressure. The product was purified by prep-LCMS (pH=2, MeCN/water with TFA) to give the desired product as the TFA salt. LC-MS calculated for $C_{22}H_{17}N_6O_3$ (M+H)$^+$: m/z=413.1; found 413.1.

Example 13. 3-(4-Ethoxyphenyl)-8-(2-methylpyridin-4-yl)-7-phenylimidazo[1,2-c]pyrimidin-5-amine

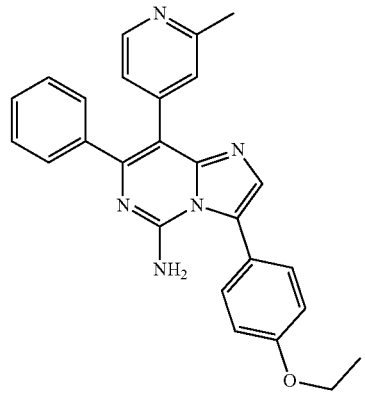 [SMILES: CCOc1ccc(-c2cnc3c(-c4ccnc(C)c4)c(-c4ccccc4)nc(N)n23)cc1]

Step 1: 8-(2-Methylpyridin-4-yl)-7-phenylimidazo[1,2-c]pyrimidin-5(6H)-one

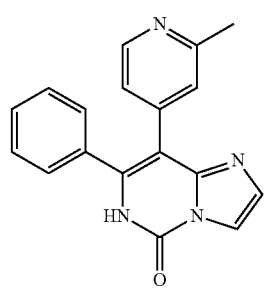 [SMILES: Cc1cc(-c2c(-c3ccccc3)[nH]c(=O)n3ccnc23)ccn1]

To a mixture of 2-methoxy-5-(2-methylpyridin-4-yl)-6-phenylpyrimidin-4-amine (from Example 10, Step 3) (400 mg, 1.4 mmol) in 2-propanol (4.2 mL) was added 2-chloroacetaldehyde (2.0 mL, 7 M in water). The reaction mixture was stirred at 110° C. for 4 h. After cooling to room temperature the volatiles were removed under reduced pressure. The resulting residue was triturated with EtOAc to give the title compound as the HCl salt (395 mg, 85%), which was used in the next step without further purification. LC-MS calculated for $C_{18}H_{15}N_4O$ (M+H)$^+$: m/z=303.1; found 303.1.

Step 2: 8-(2-Methylpyridin-4-yl)-7-phenylimidazo[1,2-c]pyrimidin-5-amine

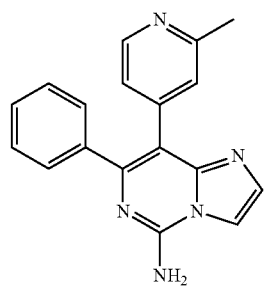 [SMILES: Cc1cc(-c2c(-c3ccccc3)nc(N)n3ccnc23)ccn1]

This compound was prepared using similar procedures as described for Example 10, Step 5-6, with 8-(2-methylpyridin-4-yl)-7-phenylimidazo[1,2-c]pyrimidin-5(6H)-one replacing 8-(2-methylpyridin-4-yl)-2,7-diphenylimidazo[1,2-c]pyrimidin-5(6H)-one in Step 5. The product was purified by prep-LCMS (pH=2, MeCN/water with TFA) to give the desired product as the TFA salt. LC-MS calculated for C$_{18}$H$_{16}$N$_5$ (M+H)$^+$: m/z=302.1; found 302.1.

Step 3: 3-Bromo-8-(2-methylpyridin-4-yl)-7-phenylimidazo[1,2-c]pyrimidin-5-amine

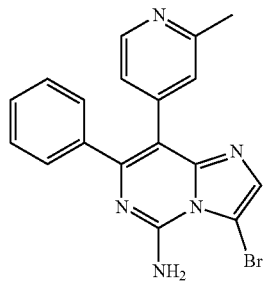 [SMILES: Cc1cc(-c2c(-c3ccccc3)nc(N)n3c(Br)cnc23)ccn1]

To a mixture of 8-(2-methylpyridin-4-yl)-7-phenylimidazo[1,2-c]pyrimidin-5-amine 2,2,2-trifluoroacetate (31 mg, 0.08 mmol) and sodium bicarbonate (14 mg, 0.17 mmol) in MeOH (0.31 mL) and water (0.31 mL) was added bromine (5.8 µL, 0.11 mmol) dropwise at 0° C. The reaction mixture was stirred at room temperature for 16 h. The resulting solution was concentrated under reduced pressure to give the crude product, which was used in the next step without further purification. LC-MS calculated for C$_{18}$H$_{15}$BrN$_5$ (M+H)$^+$: m/z=380.1; found 380.1.

Step 4: 3-(4-Ethoxyphenyl)-8-(2-methylpyridin-4-yl)-7-phenylimidazo[1,2-c]pyrimidin-5-amine To a microwave vial was added 3-Bromo-8-(2-methylpyridin-4-yl)-7-phenylimidazo[1,2-c]pyrimidin-5-amine (3 mg, 0.01 mmol), (4-ethoxyphenyl)boronic acid (4 mg, 0.02 mmol), tripotassium phosphate (7 mg, 0.03 mmol), DMF (2.4 mL), water (0.60 mL) and [1,1'-bis(diphenylphosphino)ferrocene]dichloropalladium(II) (2 mg, 25 mol %). The reaction solution was purged with nitrogen, and then the microwave vial was sealed and heated in a microwave reactor at 120° C. for 20 min. The reaction mixture was cooled to room temperature and filtered through a Celite plug with 50% EtOAc/DCM, then concentrated under reduced pressure. The crude product was purified by prep-LCMS (pH=2, MeCN/water with TFA) to give the desired product as the TFA salt. LC-MS calculated for C$_{26}$H$_{24}$N$_5$O (M+H)$^+$: m/z=422.2; found 422.2.

Example 14. 5-Amino-8-(2-methylpyridin-4-yl)-7-phenylimidazo[1,2-c]pyrimidine-2-carboxamide

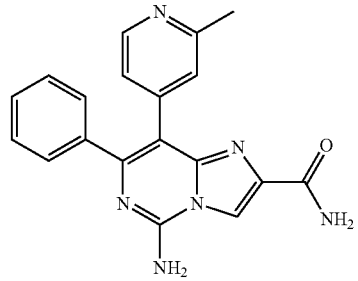 [SMILES: Cc1cc(-c2c(-c3ccccc3)nc(N)n3cc(C(N)=O)nc23)ccn1]

Step 1: 5-Amino-8-(2-methylpyridin-4-yl)-7-phenylimidazo[1,2-c]pyrimidine-2-carboxylic acid

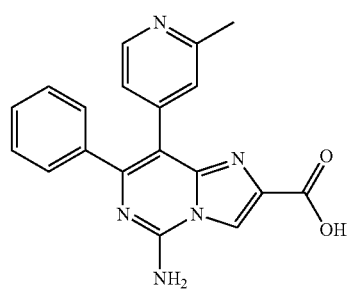 [SMILES: Cc1cc(-c2c(-c3ccccc3)nc(N)n3cc(C(=O)O)nc23)ccn1]

To a stirred solution of ethyl 5-amino-8-(2-methylpyridin-4-yl)-7-phenylimidazo[1,2-c]pyrimidine-2-carboxylate (prepared in Example 11) (66 mg, 0.18 mmol) in THF (0.90 mL) was added lithium hydroxide monohydrate (15 mg, 0.36 mmol) and water (0.90 mL). The resulting mixture was stirred at 50° C. for 16 h. After cooling to room temperature, 1 N HCl (0.38 mL) and water (0.9 mL) were added to give a precipitate which was removed by filtration. The filtrate was concentrated to give the crude product, which was used in the next step without further purification. LC-MS calculated for C$_{19}$H$_{16}$N$_5$O$_2$ (M+H)$^+$: m/z=346.1; found 346.1.

Step 2: 5-Amino-8-(2-methylpyridin-4-yl)-7-phenylimidazo[1,2-c]pyrimidine-2-carboxamide To a solution of 5-amino-8-(2-methylpyridin-4-yl)-7-phenylimidazo[1,2-c]pyrimidine-2-carboxylic acid (48 mg, 0.14 mmol) in DMF (0.87 mL) was added HATU (63 mg, 0.17 mmol) and triethylamine (39 µL, 0.28 mmol). The reaction mixture was stirred at room temperature for 30 min before ammonium chloride (8.0 mg, 0.15 mmol) was added and the solution continued stirring at room temperature for 1.5 h. The mixture was diluted with EtOAc (5.0 mL) and washed with saturated aqueous sodium bicarbonate solution (5.0 mL) and brine (5.0 mL). The organic layer were dried over Na$_2$SO$_4$, filtered and concentrated under reduced pressure. The product was purified by prep-LCMS (pH=2, MeCN/water with TFA) to give the desired product as the TFA salt. LC-MS calculated for C$_{19}$H$_{17}$N$_6$O (M+H)$^+$: m/z=345.1; found 345.1.

Example 15. 5-Amino-8-(1-carbamoyl-1,2,3,6-tetra-hydropyridin-4-yl)-N-ethyl-7-phenylimidazo[1,2-c]pyrimidine-2-carboxamide

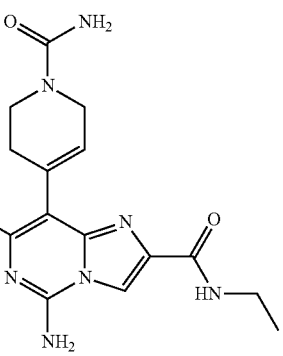

Step 1: 2-(Methylthio)-6-phenylpyrimidin-4-amine

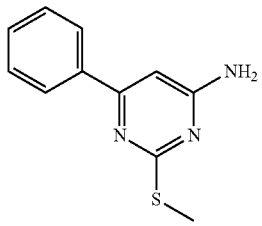

A mixture of 6-chloro-2-(methylthio)pyrimidin-4-amine (Combi-Blocks Catalog, #ST-1384) (10.0 g, 56.9 mmol), phenylboronic acid (8.33 g, 68.3 mmol), and bis(di-tert-butyl(4-dimethylaminophenyl)phosphine)dichloropalladium(II) (1.01 g, 1.42 mmol) in 1,4-dioxane (50 mL) and water (10 mL) was added cesium carbonate (37.1 g, 114.0 mmol). The reaction mixture was purged with nitrogen and then stirred at 100° C. for 12 h. After being cooled to room temperature, the reaction mixture was diluted with EtOAc, washed with brine, dried over Na$_2$SO$_4$, filtered and concentrated under reduced pressure. Light yellow solid precipitated from the solution, which was filtered and dried to obtain the desired product. LC-MS calculated for C$_{11}$H$_{12}$N$_3$S (M+H)$^+$: m/z=218.1; found 218.1.

Step 2: 5-Bromo-2-(methylthio)-6-phenylpyrimidin-4-amine

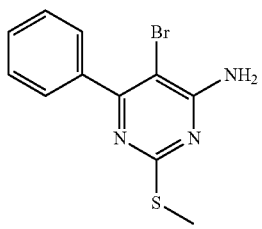 [SMILES: CSc1nc(N)c(Br)c(-c2ccccc2)n1]

To a stirred solution of 2-(methylthio)-6-phenylpyrimidin-4-amine (2.5 g, 11.5 mmol) in DMF (50 mL) was added N-bromosuccinimide (2.05 g, 11.5 mmol). The resulting mixture was stirred at room temperature for 2 h before water (200 mL) was added. Light yellow solid precipitated from the solution, which was filtered and dried to obtain the desired product. LC-MS calculated for C$_{11}$H$_{11}$BrN$_3$S (M+H)$^+$: m/z=296.0; found 296.0.

Step 3: Ethyl 8-bromo-5-(methylthio)-7-phenylimidazo[1,2-c]pyrimidine-2-carboxylate

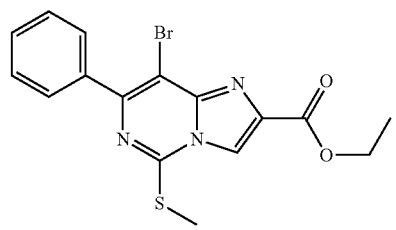 [SMILES: CCOC(=O)c1cn2c(SC)nc(-c3ccccc3)c(Br)c2n1]

To a solution of 5-bromo-2-(methylthio)-6-phenylpyrimidin-4-amine (3.69 g, 12.5 mmol) in 1,2-dimethoxyethane (40 mL) was added ethyl 3-bromo-2-oxopropanoate (4.69 mL, 37.4 mmol). The mixture was heated to 110° C. for 12 h. After being cooled to room temperature, the reaction mixture was washed with saturated NaHCO$_3$ solution and brine, dried over Na$_2$SO$_4$, filtered, and concentrated under reduced pressure to afford light brown solid as the desired product. LC-MS calculated for C$_{16}$H$_{15}$BrN$_3$O$_2$S (M+H)$^+$: m/z=392.0; found 392.0.

Step 4: Ethyl 8-bromo-5-(2,4-dimethoxybenzylamino)-7-phenylimidazo[1,2-c]pyrimidine-2-carboxylate

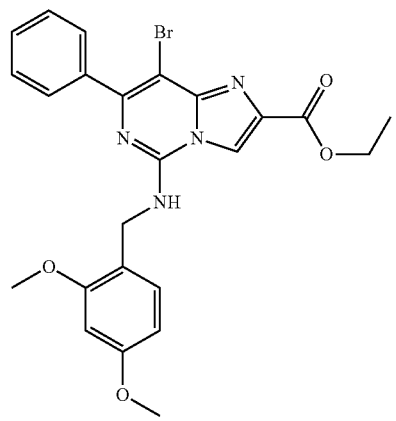 [SMILES: CCOC(=O)c1cn2c(NCc3ccc(OC)cc3OC)nc(-c3ccccc3)c(Br)c2n1]

In a 500 mL round bottom flask, ethyl 8-bromo-5-(methylthio)-7-phenylimidazo[1,2-c]pyrimidine-2-carboxylate (2.1 g, 5.35 mmol) was dissolved in 100 mL of DCM. To this solution, 3-chloroperbenzoic acid (mCPBA) (2.28 g, 10.2 mmol) in DCM (30 mL) was added dropwise through an addition funnel at 0° C. After addition, the reaction mixture was allowed to warm to room temperature and stirred for 4 h. The reaction was then quenched by adding saturated NaHCO$_3$ solution and the resulting two layers were separated. The organic layer was washed with brine, dried over Na$_2$SO$_4$, and filtrated. To this filtrate, (2,4-dimethoxyphenyl)methanamine (1.61 mL, 10.7 mmol) was added dropwise at room temperature. The resulting mixture was stirred for 2 h, and concentrated under reduced pressure. The resulting residue was purified by flash chromatography on a silica gel column eluting with 0 to 100% EtOAc in hexanes to afford the desired product. LC-MS calculated for C$_{24}$H$_{24}$BrN$_4$O$_4$ (M+H)$^+$: m/z=511.1; found 511.1.

Step 5: 8-Bromo-5-(2,4-dimethoxybenzylamino)-N-ethyl-7-phenylimidazo[1,2-c]pyrimidine-2-carboxamide

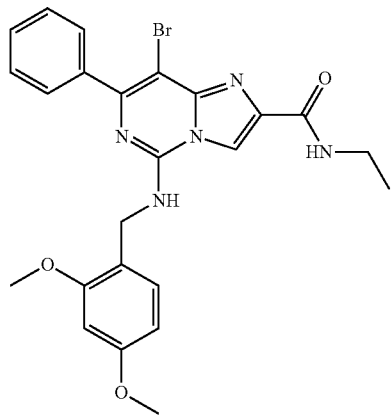 [SMILES: CCNC(=O)c1cn2c(NCc3ccc(OC)cc3OC)nc(-c3ccccc3)c(Br)c2n1]

Ethyl 8-bromo-5-(2,4-dimethoxybenzylamino)-7-phenylimidazo[1,2-c]pyrimidine-2-carboxylate (1.80 g, 3.5 mmol) in MeOH (20 mL), THF (20 mL), and water (10 mL) was added LiOH (0.34 g, 14.1 mmol) in one portion. The reaction mixture was stirred at 45° C. for 2 h, cooled to room temperature, and concentrated under reduced pressure. The resulting residue was dissolved in DMF (30 mL), followed by addition of ethanamine (2 M solution in THF, 3.52 mL, 7.04 mmol), N-ethyl-N-isopropylpropan-2-amine (1.84 mL, 10.6 mmol), and (benzotriazol-1-yloxy)tripyrrolidinophosphonium hexafluorophosphate (PyBOP) (3.66 g, 7.04 mmol). The reaction mixture was stirred at room temperature overnight before 100 mL of water was added. The resulting solid was collected and dried to afford the desired product as a yellow solid. LC-MS calculated for C$_{24}$H$_{25}$BrN$_5$O$_3$ (M+H)$^+$: m/z=510.1; found 510.1.

Step 6: tert-Butyl 4-(5-(2,4-dimethoxybenzylamino)-2-(ethylcarbamoyl)-7-phenylimidazo[1,2-c]pyrimidin-8-yl)-5,6-dihydropyridine-1(2H)-carboxylate

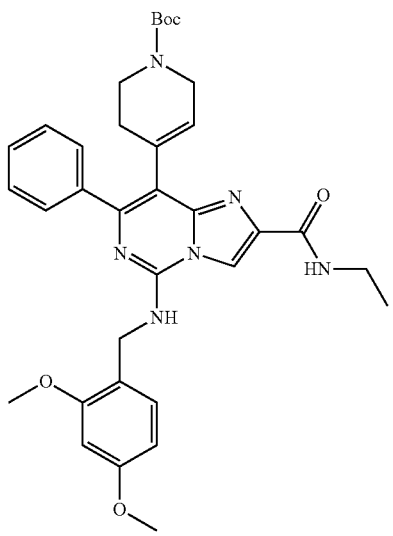 [SMILES: CCNC(=O)c1cn2c(NCc3ccc(OC)cc3OC)nc(-c3ccccc3)c(C3=CCN(C(=O)OC(C)(C)C)CC3)c2n1]

A mixture of 8-bromo-5-(2,4-dimethoxybenzylamino)-N-ethyl-7-phenylimidazo[1,2-c]pyrimidine-2-carboxamide (20.0 mg, 0.039 mmol), tert-butyl 4-(4,4,5,5-tetramethyl-1,3,2-dioxaborolan-2-yl)-3,6-dihydropyridine-1 (2H)-carboxylate (14.5 mg, 0.047 mmol), XPhos Pd G2 (2.0 mg, 2.5 µmol), and Cs$_2$CO$_3$ (38.2 mg, 0.12 mmol) in 1,4-dioxane (1 mL) and water (0.2 mL) was degassed and stirred at 90° C. for 2 h. The reaction mixture was then cooled to room temperature, and concentrated under reduced pressure. The resulting residue was purified by flash chromatography on a silica gel column eluting with 0 to 100% EtOAc in hexanes to afford the desired product. LC-MS calculated for C$_{34}$H$_{41}$N$_6$O$_5$(M+H)$^+$: m/z=613.3; found 613.3.

Step 7: 5-Amino-8-(1-carbamoyl-1,2,3,6-tetrahydropyridin-4-yl)-N-ethyl-7-phenylimidazo[1,2-c]pyrimidine-2-carboxamide In a 10 mL reaction vial, tert-butyl 4-(5-(2,4-dimethoxybenzylamino)-2-(ethylcarbamoyl)-7-phenylimidazo[1,2-c]pyrimidin-8-yl)-5,6-dihydropyridine-1 (2H)-carboxylate (20.0 mg, 0.033 mmol) was dissolved in 1 mL of TFA. The reaction mixture was stirred at 70° C. for 10 min, cooled to room temperature, concentrated and quenched with saturated NaHCO$_3$ solution. The resulting mixture was extracted with 3:1 DCM/IPA, and the combined organic layers were washed with brine, dried over Na$_2$SO$_4$, filtered and concentrated under reduced pressure. The resulting residue was dissolved in DCM (1 mL), and isocyanatotrimethylsilane (7.5 mg, 0.065 mmol) was added. The resulting mixture was stirred for 4 h, concentrated and purified by prep-LC-MS (pH=2, MeCN/water with TFA) to give the desired product as the TFA salt. LC-MS calculated for C$_{21}$H$_{24}$N$_7$O$_2$ (M+H)$^+$: m/z=406.2; found 406.2.

Example 16. 5-Amino-8-(1-carbamoylpiperidin-4-yl)-N-ethyl-7-phenylimidazo[1,2-c]pyrimidine-2-carboxamide

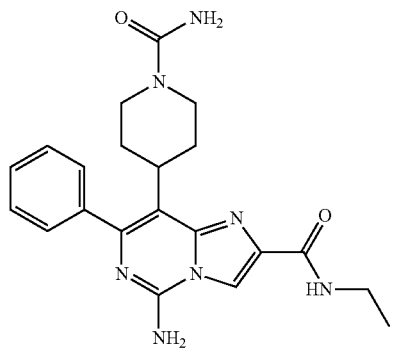 [SMILES: CCNC(=O)c1cn2c(N)nc(-c3ccccc3)c(C3CCN(C(N)=O)CC3)c2n1]

In a 10 mL reaction vial, 5-amino-8-(1-carbamoyl-1,2,3,6-tetrahydropyridin-4-yl)-W-ethyl-7-phenylimidazo[1,2-c]pyrimidine-2-carboxamide TFA salt (prepared in Example 15) (10.0 mg, 0.020 mmol) and palladium hydroxide on carbon (10 wt %, 3.7 mg, 2.3 μmol) were dissolved in 1 mL of MeOH. The reaction mixture was then stirred at 50° C. for 5 h under 1 atm of $H_2$. After completion, the reaction mixture was filtered and purified by prep-LC-MS (pH=2, MeCN/water with TFA) to give the desired product as the TFA salt. LC-MS calculated for $C_{21}H_{26}N_7O_2$ $(M+H)^+$: m/z=408.2; found 408.2.

Example 17. 5-Amino-7-(3-cyanophenyl)-JV-ethyl-3-(2-hydroxyethoxy)-8-(2-methoxypyridin-4-yl)imidazo[1,2-c]pyrimidine-2-carboxamide

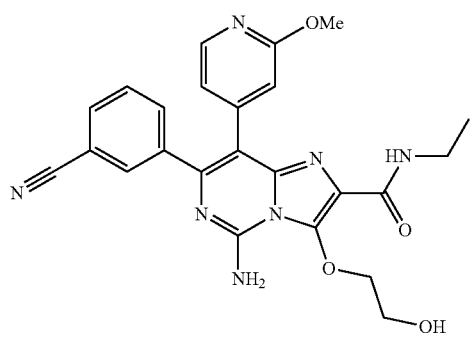 [SMILES: CCNC(=O)c1nc2c(-c3ccnc(OC)c3)c(-c3cccc(C#N)c3)nc(N)n2c1OCCO]

Step 1: 3-(6-Amino-2-(methylthio)pyrimidin-4-yl)benzonitrile

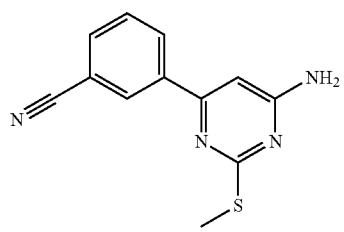 [SMILES: CSc1nc(N)cc(-c2cccc(C#N)c2)n1]

Bis(di-tert-butyl(4-dimethylaminophenyl)phosphine)dichloropalladium(II) (1.0 g, 5 mol %) was added to a mixture of 6-chloro-2-(methylthio)pyrimidin-4-amine (Combi-Blocks, cat #ST-1384) (5.0 g, 29 mmol), (3-cyanophenyl)boronic acid (8.4 g, 57 mmol) and cesium carbonate (37 g, 114 mmol) in toluene (100 mL) and water (10 mL). The mixture was purged with nitrogen, and then stirred at 115° C. for 16 h. The reaction mixture was cooled to room temperature, filtered through a Celite plug with DCM and concentrated under reduced pressure. Water (200 mL) was added to the residue and the resulting solid was collected by filtration, and then dried to give the desired product (6.5 g, 94%), which was used in the next step without further purification. LC-MS calculated for $(M+H)^+$: m/z=243.1; found 243.2.

Step 2: 3-(6-Amino-5-bromo-2-(methylthio)pyrimidin-4-yl)benzonitrile

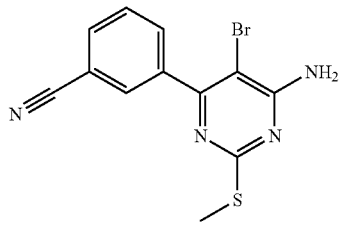 [SMILES: CSc1nc(N)c(Br)c(-c2cccc(C#N)c2)n1]

To a solution of 3-(6-amino-2-(methylthio)pyrimidin-4-yl)benzonitrile (6.5 g, 27 mmol) in DMSO (55 mL), MeCN (30 mL) and water (1.8 mL) at 0° C. was added N-bromosuccinimide (4.8 g, 27 mmol). The reaction mixture was stirred for 2 h at room temperature before water (200 mL) was added. The resulting precipitate was collected by filtration, and then dried to give the desired product (8.6 g, 99%), which was used in the next step without further purification. LC-MS calculated for $C_{12}H_{10}BrN_4S$ $(M+H)^+$: m/z=321.0; found 321.1.

Step 3: Ethyl 8-bromo-7-(3-cyanophenyl)-5-(methylthio)imidazo[1,2-c]pyrimidine-2-carboxylate

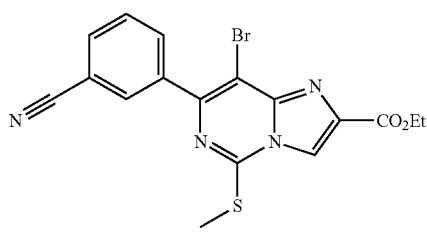 [SMILES: CCOC(=O)c1cn2c(SC)nc(-c3cccc(C#N)c3)c(Br)c2n1]

To a solution of 3-(6-amino-5-bromo-2-(methylthio)pyrimidin-4-yl)benzonitrile (2.0 g, 6.2 mmol) in DME (26 mL) was added ethyl 3-bromo-2-oxopropanoate (2.3 mL, 19 mmol). The reaction mixture was stirred at 110° C. for 3 h before the volatiles were removed under reduced pressure. The resulting solid was collected by filtration, washed with $Et_2O$ (100 mL), and dried to give the desired product as HBr salt (1.4 g, 54%). LC-MS calculated for $C_{17}H_{14}BrN_4O_2S$ $(M+H)^+$: m/z=417.0; found 417.0.

Step 4: Ethyl 8-bromo-7-(3-cyanophenyl)-5-(2,4-dimethoxybenzylamino)imidazo[1,2-c]pyrimidine-2-carboxylate

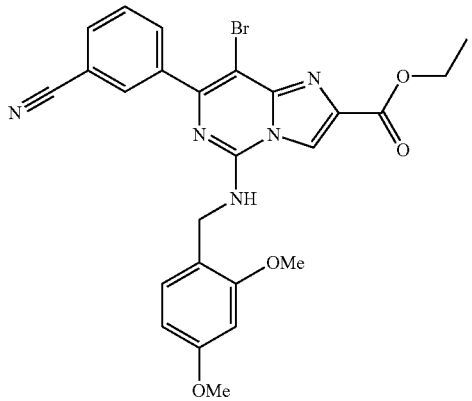 [SMILES: CCOC(=O)c1cn2c(NCc3ccc(OC)cc3OC)nc(-c3cccc(C#N)c3)c(Br)c2n1]

To a solution of ethyl 8-bromo-7-(3-cyanophenyl)-5-(methylthio)imidazo[1,2-c]pyrimidine-2-carboxylate hydrobromide (1.4 g, 3.4 mmol) in DCM (170 ml) at 0° C. was added a solution of mCPBA (1.6 g, 6.4 mmol, 70%) in DCM (15 mL) dropwise. The solution was stirred at room temperature for 2 h. Following complete consumption of starting material, (2,4-dimethoxyphenyl)methanamine (1.02 ml, 6.8 mmol) in DCM (15 mL) was added and the suspension was stirred for 2 h. The reaction mixture was then washed with saturated NaHCO$_3$ solution (100 mL), water (100 mL), and brine (50 mL). The organic layer was dried over MgSO$_4$, filtered and concentrated under reduced pressure. The resulting material was purified by column chromatography eluting with 0-100% EtOAc/hexanes to give the desired product (1.4 g, 54%). LC-MS calculated for $C_{25}H_{23}BrN_5O_4$(M+H)$^+$: m/z=536.1; found 536.2.

Step 5: Ethyl 7-(3-cyanophenyl)-5-(2,4-dimethoxybenzylamino)-8-(2-methoxypyridin-4-yl)imidazo[1,2-c]pyrimidine-2-carboxylate

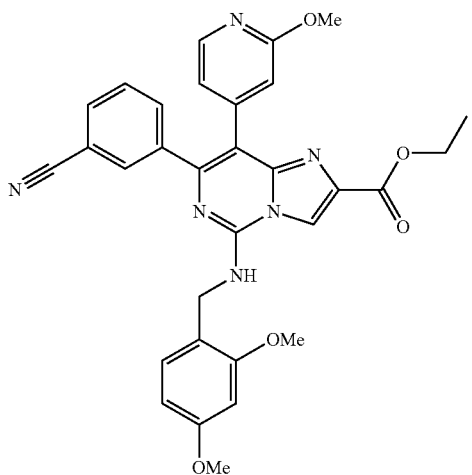 [SMILES: CCOC(=O)c1cn2c(NCc3ccc(OC)cc3OC)nc(-c3cccc(C#N)c3)c(-c3ccnc(OC)c3)c2n1]

[1,1'-bis(dicyclohexylphosphino)ferrocene]dichloropalladium(II) (230 mg, 10 mol %) was added to a mixture of ethyl 8-bromo-7-(3-cyanophenyl)-5-(2,4-dimethoxybenzylamino)imidazo[1,2-c]pyrimidine-2-carboxylate (1.7 g, 3.1 mmol), 2-methoxypyridin-4-ylboronic acid (570 mg, 3.7 mmol), and cesium carbonate (1.7 g, 5.2 mmol) in tert-butanol (13 mL) and water (2.6 mL). The reaction mixture was purged with nitrogen, and stirred at 120° C. for 3 h. The reaction mixture was then cooled to room temperature, filtered through a Celite plug with DCM and concentrated under reduced pressure. The resulting material was purified by column chromatography eluting with 0-100% EtOAc/hexanes to give the desired product (370 mg). LC-MS calculated for $C_{31}H_{29}N_6O_5$ (M+H)$^+$: m/z=565.2; found 565.4.

Step 6: 5-Amino-7-(3-cyanophenyl)-N-ethyl-8-(2-methoxypyridin-4-yl)imidazo[1,2-c]pyrimidine-2-carboxamide

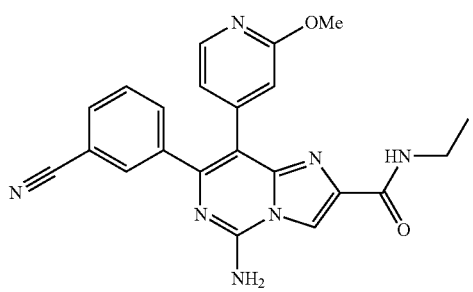 [SMILES: CCNC(=O)c1cn2c(N)nc(-c3cccc(C#N)c3)c(-c3ccnc(OC)c3)c2n1]

To ethyl 7-(3-cyanophenyl)-5-(2,4-dimethoxybenzylamino)-8-(2-methoxypyridin-4-yl)imidazo[1,2-c]pyrimidine-2-carboxylate (370 mg, 0.65 mmol) was added ethanamine (3.3 mL, 2 M in MeOH). The solution was stirred at 85° C. in a sealed vial for 16 h, cooled to room temperature and the volatiles were removed under reduced pressure. TFA (2.0 mL) was added to the residue and the mixture was stirred at 100° C. for 10 min in a sealed vial. The reaction mixture was then cooled to room temperature, and the volatiles were removed under reduced pressure.

The product was purified by column chromatography eluting with 0-10% MeOH/DCM containing 0.5% triethylamine. LC-MS calculated for $C_{22}H_{20}N_7O_2$ (M+H)$^+$: m/z=414.2; found 414.3.

Step 7: 5-Amino-3-bromo-7-(3-cyanophenyl)-N-ethyl-8-(2-methoxypyridin-4-yl)imidazo[1,2-c]pyrimidine-2-carboxamide

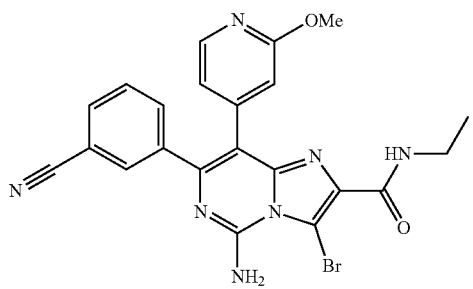 [SMILES: CCNC(=O)c1nc2c(-c3ccnc(OC)c3)c(-c3cccc(C#N)c3)nc(N)n2c1Br]

To a solution of 5-amino-7-(3-cyanophenyl)-W-ethyl-8-(2-methoxypyridin-4-yl)imidazo[1,2-c]pyrimidine-2-carboxamide (110 mg, 0.27 mmol) in DMF (0.5 mL) at 0° C. was added N-bromosuccinimide (47 mg, 0.27 mmol). The reaction mixture was stirred for 2 h at room temperature before water (1.0 mL) was added. The resulting precipitate was collected by filtration, and dried to give the desired product, which was used in the next step without further purification. LC-MS calculated for $C_{22}H_{19}BrN_7O_2$ (M+H)$^+$: m/z=492.1; found 492.1.

Step 8: 5-Amino-7-(3-cyanophenyl)-N-ethyl-3-(2-hydroxyethoxy)-8-(2-methoxypyridin-4-yl)imidazo[1,2-c]pyrimidine-2-carboxamide To a reaction vial was added copper(I) iodide (1.2 mg, 6.1 µmol), 3,4,7,8-tetramethyl-1,10-phenanthroline (2.9 mg, 0.01 mmol), 5-amino-3-bromo-7-(3-cyanophenyl)-W-ethyl-8-(2-methoxypyridin-4-yl)imidazo[1,2-c]pyrimidine-2-carboxamide (30 mg, 0.06 mmol), and cesium carbonate (30 mg, 0.09 mmol). The reaction vial was flushed with nitrogen and fitted with a rubber septum. Toluene (0.2 mL) and ethane-1,2-diol (0.17 mL, 3.1 mmol) were added and the rubber septum was replaced with a Teflon-lined cap. The reaction mixture was stirred at 110° C. for 24 h, cooled to room temperature, diluted with ethyl acetate (2 mL), and filtered through a plug of silica gel. The filtrate was concentrated and purified by prep-LCMS (pH=2, MeCN/water with TFA) to give the desired product as the TFA salt. LC-MS calculated for $C_{24}H_{24}N_7O_4$ (M+H)$^+$: m/z=474.2; found 474.2.

Example 18. 5-Amino-7-(3-cyanophenyl)-N-ethyl-8-(2-methoxypyridin-4-yl)-3-methylimidazo[1,2-c]pyrimidine-2-carboxamide

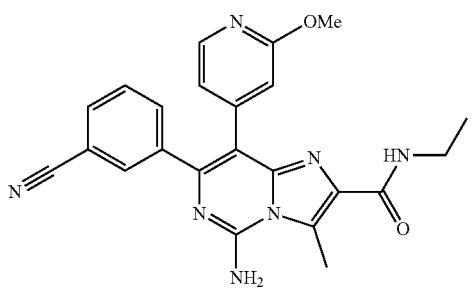 [SMILES: CCNC(=O)c1nc2c(-c3ccnc(OC)c3)c(-c3cccc(C#N)c3)nc(N)n2c1C]

To a mixture of 5-amino-3-bromo-7-(3-cyanophenyl)-N-ethyl-8-(2-methoxypyridin-4-yl)imidazo[1,2-c]pyrimidine-2-carboxamide (prepared in Example 17, Step 7) (40 mg, 0.08 mmol) and [1,1'-Bis(diphenylphosphino)ferrocene]dichloropalladium(II), complex with dichloromethane (3.3 mg, 4.1 µmol) in 1,4-dioxane (0.50 mL) under nitrogen atmosphere was added dimethylzinc in toluene (0.27 mL, 1.2 M) dropwise. The resulting mixture was stirred at 90° C. overnight, cooled to room temperature, diluted with DCM (5 mL) and filtered through a Celite plug. The filtrate was concentrated under reduced pressure and the crude material was purified by prep-LCMS (pH=2, MeCN/water with TFA) to give the desired product as the TFA salt. LC-MS calculated for $C_{23}H_{22}N_7O_2$(M+H)$^+$: m/z=428.2; found 428.2.

Example 19. 5-Amino-7-(3-cyanophenyl)-N-ethyl-8-(2-methoxypyridin-4-yl)-3-(pyridin-2-yl)imidazo[1,2-c]pyrimidine-2-carboxamide

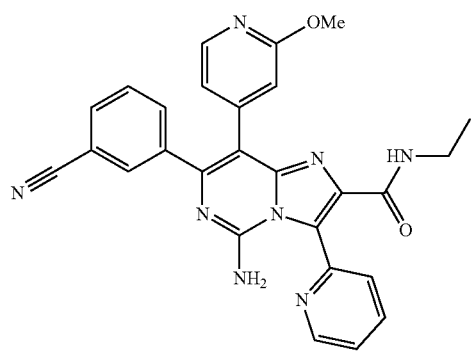 [SMILES: CCNC(=O)c1nc2c(-c3ccnc(OC)c3)c(-c3cccc(C#N)c3)nc(N)n2c1-c1ccccn1]

Bis(triphenylphosphine)palladium(II) chloride (4.3 mg, 6.1 µmol) was added to a mixture of 5-amino-3-bromo-7-(3-cyanophenyl)-N-ethyl-8-(2-methoxypyridin-4-yl)imidazo[1,2-c]pyrimidine-2-carboxamide (prepared in Example 17, Step 7) (30 mg, 0.06 mmol) and 2-(tributylstannyl)pyridine (0.05 mL, 0.12 mmol) in DMF (0.5 mL). The reaction mixture was purged with nitrogen and then stirred at 100° C. for 5 h. After cooling to room temperature, the mixture was diluted with DCM (5 mL) and filtered through a Celite plug. The filtrate was concentrated under reduced pressure and the crude material was purified by prep-LCMS (pH=2, MeCN/water with TFA) to give the desired product as the TFA salt. LC-MS calculated for $C_{27}H_{23}N_8O_2$ (M+H)$^+$: m/z=491.2; found 491.2.

Example 20. 5-Amino-3-bromo-8-(2,6-dimethylpyridin-4-yl)-N-ethyl-7-phenylimidazo[1,2-c]pyrimidine-2-carboxamide

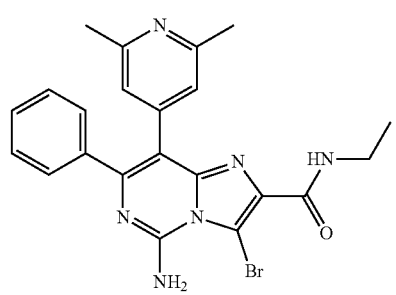 [SMILES: CCNC(=O)c1nc2c(-c3cc(C)nc(C)c3)c(-c3ccccc3)nc(N)n2c1Br]

Step 1: Ethyl 5-(2,4-dimethoxybenzylamino)-8-(2,6-dimethylpyridin-4-yl)-7-phenylimidazo[1,2-c]pyrimidine-2-carboxylate

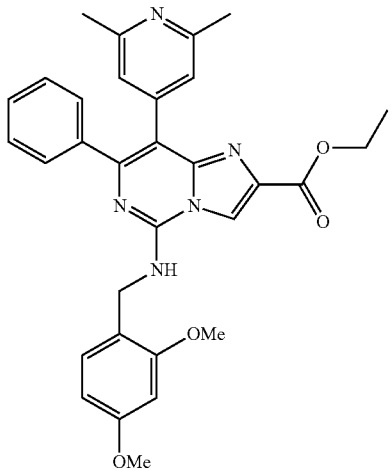 [SMILES: CCOC(=O)c1cn2c(NCc3ccc(OC)cc3OC)nc(-c3ccccc3)c(-c3cc(C)nc(C)c3)c2n1]

[1,1'-bis(dicyclohexylphosphino)ferrocene]dichloropalladium(II) (400 mg, 10 mol %) was added to a mixture of ethyl 8-bromo-5-((2,4-dimethoxybenzyl)amino)-7-phenylimidazo[1,2-c]pyrimidine-2-carboxylate (prepared in Example 15, Step 4) (2.7 g, 5.3 mmol), (2,6-dimethylpyridin-4-yl)boronic acid (1.2 g, 7.9 mmol), and cesium carbonate (3.4 g, 11 mmol) in tert-butanol (20 mL) and water (3.8 mL). The mixture was purged with nitrogen, and then stirred at 120° C. for 1.5 h. The reaction mixture was cooled to room temperature, filtered through a Celite plug with DCM and concentrated under reduced pressure. The resulting material was purified by column chromatography eluting with 0-20% MeOH/DCM to give the desired product (2.8 g, 99%). LC-MS calculated for $C_{31}H_{32}N_5O_4$ (M+H)$^+$: m/z=538.2; found 538.3.

Step 2: 5-(2,4-Dimethoxybenzylamino)-8-(2,6-dimethylpyridin-4-yl)-7-phenylimidazo[1,2-c]pyrimidine-2-carboxylic acid

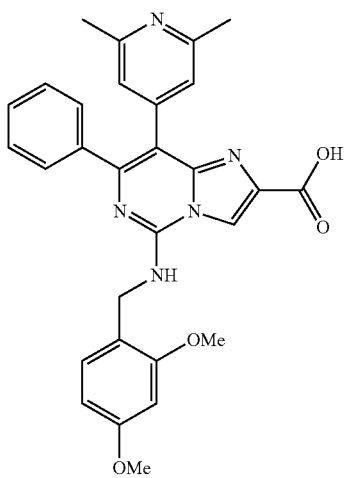 [SMILES: COc1ccc(CNc2nc(-c3ccccc3)c(-c3cc(C)nc(C)c3)c3nc(C(=O)O)cn23)c(OC)c1]

To a solution of ethyl 5-(2,4-dimethoxybenzylamino)-8-(2,6-dimethylpyridin-4-yl)-7-phenylimidazo[1,2-c]pyrimidine-2-carboxylate (1.0 g, 1.9 mmol) in THF (3.9 mL) was added lithium hydroxide (0.18 g, 7.4 mmol) and water (3.9 mL). The resulting mixture was stirred at 50° C. for 16 h. After cooling to room temperature, water (2.0 mL) was added and the pH was adjusted using 1 N HCl to pH 2. The resulting precipitate was collected by filtration, washed with water and dried to afford the crude product, which was used in the next step without further purification. LC-MS calculated for $C_{29}H_{28}N_5O_4$ (M+H)$^+$: m/z=510.2; found 510.2.

Step 3: 5-Amino-8-(2,6-dimethylpyridin-4-yl)-N-ethyl-7-phenylimidazo[1,2-c]pyrimidine-2-carboxamide

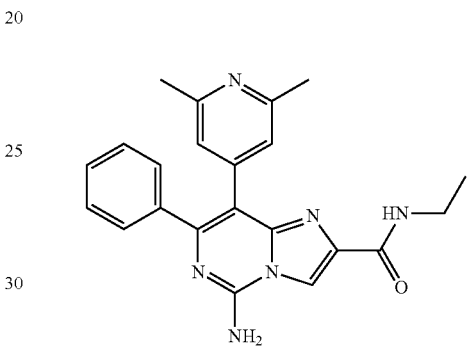

To a solution of 5-(2,4-dimethoxybenzylamino)-8-(2,6-dimethylpyridin-4-yl)-7-phenylimidazo[1,2-c]pyrimidine-2-carboxylic acid (0.95 g, 1.9 mmol) in DMF (17 mL) was added triethylamine (0.78 mL, 5.6 mmol). The solution was stirred for 5 min before the addition of BOP (1.2 g, 2.8 mmol) and ethanamine (9.3 mL, 2 M in THF). The reaction mixture was then stirred at room temperature for 30 min, quenched with water (20 mL), and extracted with EtOAc (5×30 mL). The combined organic layers were washed with water (50 mL) and brine (30 mL), dried with MgSO$_4$, and concentrated under reduced pressure. To the resulting residue was added TFA (3.0 mL), and the reaction mixture was stirred at 100° C. for 10 min. After cooling to room temperature, the volatiles were removed under reduced pressure to afford the crude product, which was used in the next step without further purification. LC-MS calculated for $C_{22}H_{23}N_6O$ (M+H)$^+$: m/z=387.2; found 387.3.

Step 4: 5-Amino-3-bromo-8-(2,6-dimethylpyridin-4-yl)-N-ethyl-7-phenylimidazo[1,2-c]pyrimidine-2-carboxamide To a solution of 5-amino-8-(2,6-dimethylpyridin-4-yl)-N-ethyl-7-phenylimidazo[1,2-c]pyrimidine-2-carboxamide (700 mg, 1.8 mmol) in DMSO (3.6 mL)/MeCN (1.9 mL)/water (0.12 mL) at 0° C. was added N-bromosuccinimide (320 mg, 1.8 mmol). The reaction mixture was stirred for 2 h at room temperature, at which point water (20 mL) was added and the desired product was collected by filtration. The product was purified by prep-LCMS (pH=2, MeCN/ water with TFA) to give the desired product as the TFA salt. LC-MS calculated for $C_{22}H_{22}BrN_6O$ (M+H)$^+$: m/z=465.1; found 465.1.

Example 21. 5-Amino-3-cyano-8-(2,6-dimethylpyridin-4-yl)-N-ethyl-7-phenylimidazo[1,2-c]pyrimidine-2-carboxamide

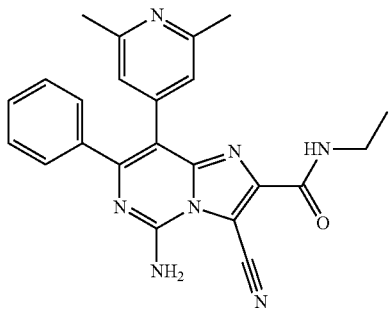 [SMILES: CCNC(=O)c1nc2c(-c3cc(C)nc(C)c3)c(-c3ccccc3)nc(N)n2c1C#N]

To a microwave vial was added copper(I) cyanide (8.7 mg, 0.10 mmol) and 5-amino-3-bromo-8-(2,6-dimethylpyridin-4-yl)-N-ethyl-7-phenylimidazo[1,2-c]pyrimidine-2-carboxamide (prepared in Example 20) (30 mg, 0.06 mmol) in DMF (0.30 mL). The vial was flushed with nitrogen and sealed before being heated in a microwave reactor at 180° C. for 10 min. After cooling to room temperature, the reaction mixture was diluted with NH$_4$OH (1 mL) and H$_2$O (1 mL), and extracted with EtOAc (3×5 mL). The combined organic layers were dried over MgSO$_4$, filtered, and concentrated under reduced pressure. The resulting material was purified by prep-LCMS (pH=2, MeCN/water with TFA) to give the desired product as the TFA salt. LC-MS calculated for $C_{23}H_{22}N_7O$ (M+H)$^+$: m/z=412.2; found 412.2.

Example 22. 8-(2,6-Dimethylpyridin-4-yl)-N-ethyl-5-(ethylamino)-7-phenylimidazo[1,2-c]pyrimidine-2-carboxamide

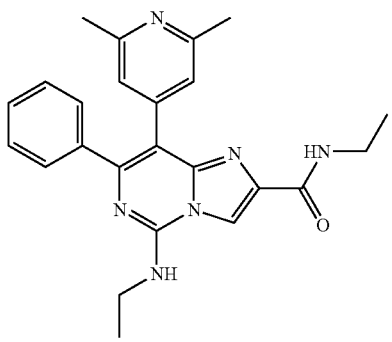 [SMILES: CCNC(=O)c1cn2c(NCC)nc(-c3ccccc3)c(-c3cc(C)nc(C)c3)c2n1]

Step 1: 5-(2,6-Dimethylpyridin-4-yl)-2-(methylthio)-6-phenylpyrimidin-4-amine

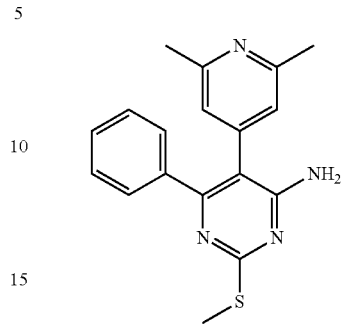

[1,1'-bis(dicyclohexylphosphino)ferrocene]dichloropalladium(II) (510 mg, 10 mol %) was added to a mixture of 5-bromo-2-(methylthio)-6-phenylpyrimidin-4-amine (prepared in Example 15, Step 2) (2.0 g, 6.8 mmol), (2,6-dimethylpyridin-4-yl)boronic acid (1.5 g, 10 mmol), and cesium carbonate (4.4 g, 14 mmol) in tert-butanol (25 mL) and water (5.0 mL). The mixture was purged with nitrogen, and then stirred at 120° C. for 2 h. The reaction mixture was coded to room temperature and filtered through a Celite plug. The filtrate was concentrated under reduced pressure and purified by flash chromatography on a silica gel column eluting with 0-100% EtOAc/hexanes to give the desired product (440 mg, 20%). LC-MS calculated for $C_{18}H_{19}N_4S$ (M+H)$^+$: m/z=323.1; found 323.1.

Step 2: Ethyl 8-(2,6-dimethylpyridin-4-yl)-5-(methylthio)-7-phenylimidazo[1,2-c]pyrimidine-2-carboxylate

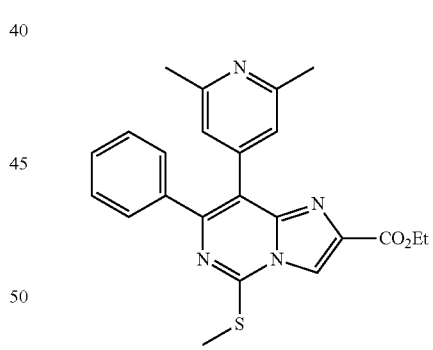

To a solution of 5-(2,6-dimethylpyridin-4-yl)-2-(methylthio)-6-phenylpyrimidin-4-amine (800 mg, 2.5 mmol) in DME (10 mL) was added ethyl 3-bromo-2-oxopropanoate (0.93 mL, 7.4 mmol). The reaction mixture was stirred at 110° C. for 2 h before the volatiles were removed under reduced pressure. The resulting residue was diluted with DCM (20 mL), washed with saturated NaHCO$_3$ solution (20 mL), water (20 mL) and brine (10 mL), dried over MgSO$_4$, filtered, and concentrated under reduced pressure. The resulting material was purified by column chromatography eluting with 0-20% MeOH/DCM to give the desired product (1.0 g, 99%). LC-MS calculated for $C_{23}H_{23}N_4O_2S$ (M+H)$^+$: m/z=419.2; found 419.1.

Step 3: 8-(2,6-Dimethylpyridin-4-yl)-N-ethyl-5-(ethylamino)-7-phenylimidazo[1,2-c]pyrimidine-2-carboxamide Ethyl 8-(2,6-dimethylpyridin-4-yl)-5-(methylthio)-7-phenylimidazo[1,2-c]pyrimidine-2-carboxylate (100 mg, 0.24 mmol) was suspended in a solution of ethanamine (1.2 mL, 2 M in MeOH) and heated at reflux for 16 h. After cooling to room temperature, the solvent was removed under reduced pressure and the resulting material was purified by prep-LCMS (pH=2, MeCN/water with TFA) to give the desired product as the TFA salt. LC-MS calculated for $C_{24}H_{27}N_6O$ $(M+H)^+$: m/z=415.2; found 415.1.

Example 23. 4-(5-Amino-2-(ethylcarbamoyl)-7-phenylimidazo[1,2-c]pyrimidin-8-yl)-2,6-dimethylpyridine 1-oxide

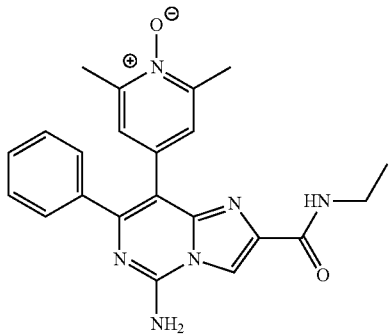 [SMILES: CCNC(=O)c1cn2c(N)nc(-c3ccccc3)c(-c3cc(C)[n+]([O-])c(C)c3)c2n1]

Step 1: 4-(2-(Ethoxycarbonyl)-5-(methylsulfonyl)-7-phenylimidazo[1,2-c]pyrimidin-8-yl)-2,6-dimethylpyridine 1-oxide

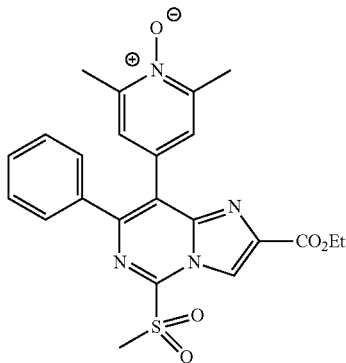 [SMILES: CCOC(=O)c1cn2c(S(C)(=O)=O)nc(-c3ccccc3)c(-c3cc(C)[n+]([O-])c(C)c3)c2n1]

To a mixture of ethyl 8-(2,6-dimethylpyridin-4-yl)-5-(methylthio)-7-phenylimidazo[1,2-c]pyrimidine-2-carboxylate (prepared in Example 22, Step 2) (50 mg, 0.12 mmol) in DCM (10 mL) at 0° C. was added mCPBA (88 mg, 0.36 mmol). The resulting solution was stirred at room temperature for 3 h, and then the volatiles were removed under reduced pressure. The resulting residue was taken up in EtOAc (20 mL), washed with a mixture of saturated $Na_2S_2O_3$ solution (10 mL) and saturated $NaHCO_3$ solution (10 mL), and then brine (10 mL). The organic layer was dried over $MgSO_4$ and concentrated under reduced pressure to afford the crude product, which was used in the next step without further purification. LC-MS calculated for $C_{23}H_{23}N_4O_5S$ $(M+H)^+$: m/z=467.1; found 467.1.

Step 2: 4-(5-Amino-2-(ethoxycarbonyl)-7-phenylimidazo[1,2-c]pyrimidin-8-yl)-2,6-dimethylpyridine 1-oxide

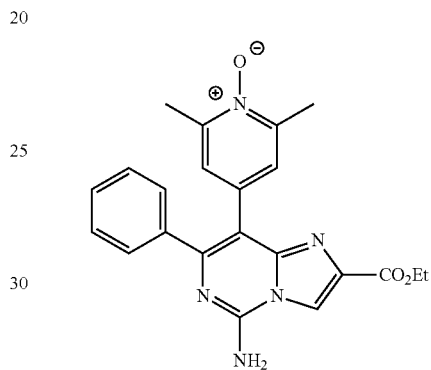

To a solution of 4-(2-(ethoxycarbonyl)-5-(methylsulfonyl)-7-phenylimidazo[1,2-c]pyrimidin-8-yl)-2,6-dimethylpyridine 1-oxide (54 mg, 0.12 mmol) in acetonitrile (1.0 mL) was added concentrated ammonium hydroxide (0.09 mL, 14 M). The reaction mixture was stirred at room temperature for 30 min before the volatiles were removed under reduced pressure. The resulting material was purified by prep-LCMS (pH=10, MeCN/water with $NH_4OH$) to give the desired product as the free base. LC-MS calculated for $C_{22}H_{22}N_5O_3$ $(M+H)^+$: m/z=404.2; found 404.2.

Step 3: 4-(5-Amino-2-(ethylcarbamoyl)-7-phenylimidazo[1,2-c]pyrimidin-8-yl)-2,6-dimethylpyridine 1-oxide 4-(5-Amino-2-(ethoxycarbonyl)-7-phenylimidazo[1,2-c]pyrimidin-8-yl)-2,6-dimethylpyridine 1-oxide (15 mg, 0.03 mmol) was suspended in a solution of ethanamine (1.0 mL, 2 M in methanol) and heated at reflux for 1 h. After cooling to room temperature, the solvent was removed under reduced pressure and the product was purified by prep-LCMS (pH=2, MeCN/water with TFA) to give the desired product as the TFA salt. LC-MS calculated for $C_{22}H_{23}N_6O_2$ $(M+H)^+$: m/z=403.2; found 403.1.

Example 24. 3-(5-Amino-8-(1-ethyl-6-oxo-1,6-dihydropyridin-3-yl)-2-(3-hydroxyazetidine-1-carbonyl)imidazo[1,2-c]pyrimidin-7-yl)benzonitrile

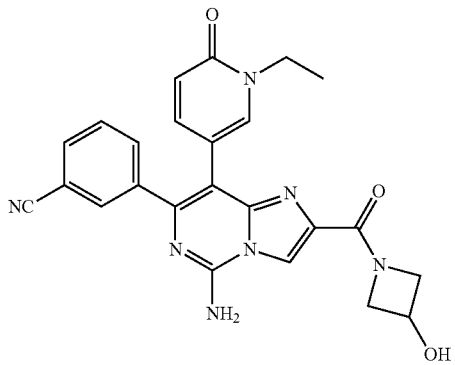 [SMILES: CCn1cc(-c2c(-c3cccc(C#N)c3)nc(N)n3cc(C(=O)N4CC(O)C4)nc23)ccc1=O]

Step 1: 3-(8-Bromo-5-(2,4-dimethoxybenzylamino)-2-(3-hydroxyazetidine-1-carbonyl)imidazo[1,2-c]pyrimidin-7-yl)benzonitrile

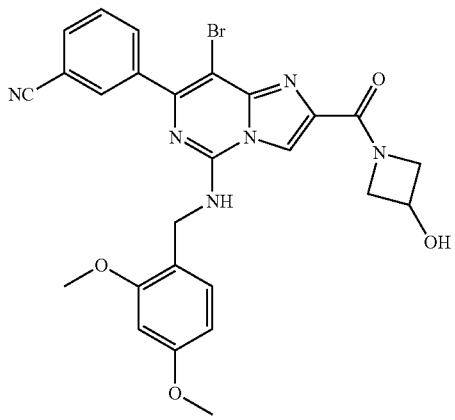 [SMILES: COc1ccc(CNc2nc(-c3cccc(C#N)c3)c(Br)c3nc(C(=O)N4CC(O)C4)cn23)c(OC)c1]

Ethyl 8-bromo-7-(3-cyanophenyl)-5-(2,4-dimethoxybenzylamino)imidazo[1,2-c]pyrimidine-2-carboxylate (prepared in Example 17, Step 4) (100 mg, 0.186 mmol) in MeOH (2 mL), THF (2 mL), and water (1 mL) was added LiOH (17.9 mg, 0.75 mmol). The reaction mixture was stirred at 45° C. for 2 h, and the solvent was removed under reduced pressure. The resulting residue was dissolved in DMF (3 mL), followed by the addition of azetidin-3-ol (27.3 mg, 0.37 mmol), N-ethyl-N-isopropylpropan-2-amine (98 µL, 0.56 mmol), and HATU (142 mg, 0.37 mmol). The reaction mixture was stirred at room temperature overnight before 10 mL of water was added. The precipitated solid was collected and dried to afford the desired product as a yellow solid. LC-MS calculated for $C_{26}H_{24}BrN_6O_4$ (M+H)$^+$: m/z=563.1; found 563.1.

Step 2: 3-(5-Amino-8-(1-ethyl-6-oxo-1,6-dihydropyridin-3-yl)-2-(3-hydroxyazetidine-1-carbonyl)imidazo[1,2-c]pyrimidin-7-yl)benzonitrile A mixture of 3-(8-bromo-5-(2,4-dimethoxybenzylamino)-2-(3-hydroxyazetidine-1-carbonyl)imidazo[1,2-c]pyrimidin-7-yl)benzonitrile (20 mg, 0.048 mmol), 1-ethyl-5-(4,4,5,5-tetramethyl-1,3,2-dioxaborolan-2-yl)pyridin-2(1H)-one (14.5 mg, 0.058 mmol), XPhos Pd G2 (2.0 mg, 2.5 µmol), and $Cs_2CO_3$ (47 mg, 0.15 mmol) in 1,4-dioxane (1 mL) and water (0.2 mL) was degassed and sealed. The reaction was stirred at 90° C. for 2 h, cooled to room temperature, and concentrated. To the resulting residue, 1 mL of TFA was added, and the resulting mixture was stirred at 70° C. for 30 min. After completion, the reaction mixture was concentrated, diluted with methanol, and purified with prep-LC-MS (pH=2, MeCN/water with TFA) to give the desired product as a TFA salt. LC-MS calculated for $C_{24}H_{22}N_7O_3$ (M+H)$^+$: m/z=456.2; found 456.2.

Example 25. 5-Amino-7-(3-cyanophenyl)-8-(1-ethyl-6-oxo-1,6-dihydropyridin-3-yl)-N-(1-(2-hydroxyethyl)-1H-pyrazol-4-yl)imidazo[1,2-c]pyrimidine-2-carboxamide

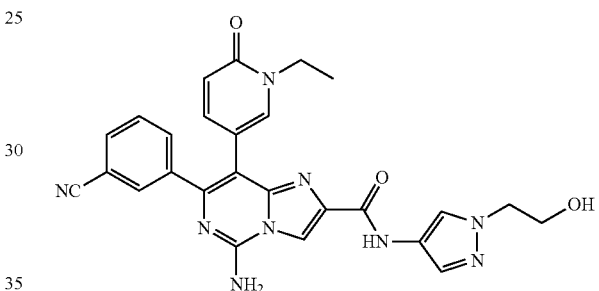

This compound was prepared using similar procedures as described for Example 24 with 2-(4-amino-1H-pyrazol-1-yl)ethanol (AstaTech Product List #50515) replacing azetidin-3-ol in Step 1. The product was purified by prep-LC-MS (pH=2, MeCN/water with TFA) to give the desired product as a TFA salt. LC-MS calculated for $C_{26}H_{24}N_9O_3$ (M+H)$^+$: m/z=510.2; found 510.2.

Example 26. 5-Amino-7-(3-cyanophenyl)-N-ethyl-8-(pyridin-4-yl)imidazo[1,2-c]pyrimidine-2-carboxamide

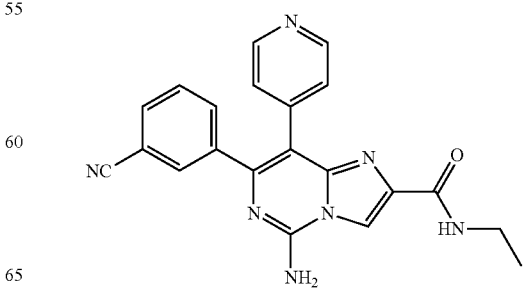

Step 1: Ethyl 5-amino-7-chloroimidazo[1,2-c]pyrimidine-2-carboxylate

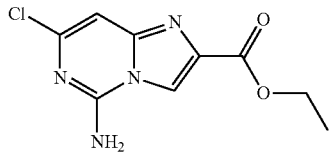 [SMILES: CCOC(=O)c1cn2c(N)nc(Cl)cc2n1]

A solution of 6-chloropyrimidine-2,4-diamine (2 g, 13.8 mmol) and ethyl 3-bromo-2-oxopropanoate (2.6 ml, 20.8 mmol) in DME (50 ml) was stirred at 70° C. overnight. After completion, the reaction was cooled to room temperature and the solid was collected by filtration. The crude solid was dissolved in hot methanol (25 mL) and the desired product was recrystallized by slowly cooling the solution to room temperature. The product was filtered, washed with EtOAc, and dried to give the desired product. LC-MS calculated for $C_9H_{10}ClN_4O_2$ (M+H)$^+$: m/z=241.0; found 241.1.

Step 2: Ethyl 5-amino-7-(3-cyanophenyl)imidazo[1,2-c]pyrimidine-2-carboxylate

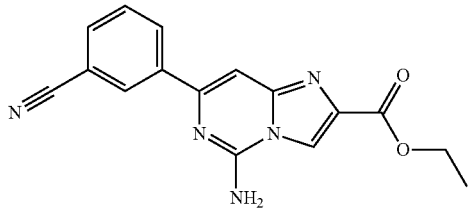 [SMILES: CCOC(=O)c1cn2c(N)nc(-c3cccc(C#N)c3)cc2n1]

A mixture of ethyl 5-amino-7-chloroimidazo[1,2-c]pyrimidine-2-carboxylate (0.60 g, 2.49 mmol), (3-cyanophenyl)boronic acid (0.44 g, 2.99 mmol), XPhos Pd G2 (0.098 g, 0.125 mmol) and sodium carbonate (0.53 g, 4.99 mmol) in 1,4-dioxane (50 mL) and water (5.0 mL) was purged with nitrogen and then stirred at 100° C. for 1 h. After being cooled to room temperature, the reaction mixture diluted with EtOAc, washed with brine, dried over Na$_2$SO$_4$, filtered, and concentrated under reduced pressure. Light yellow solid precipitated from the solution, which was filtered and dried to afford the desired product. LC-MS calculated for $C_{16}H_{14}N_5O_2$ (M+H)$^+$: m/z=308.1; found 308.1.

Step 3: Ethyl 5-amino-8-bromo-7-(3-cyanophenyl)imidazo[1,2-c]pyrimidine-2-carboxylate

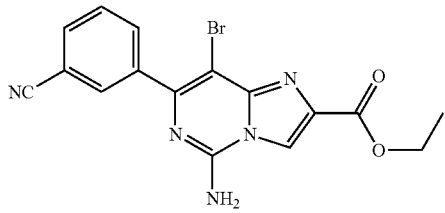 [SMILES: CCOC(=O)c1cn2c(N)nc(-c3cccc(C#N)c3)c(Br)c2n1]

To a solution of ethyl 5-amino-7-(3-cyanophenyl)imidazo[1,2-c]pyrimidine-2-carboxylate (2.3 g, 7.48 mmol) in DMF (50 ml) was slowly added a solution of N-bromosuccinimide (1.33 g, 7.48 mmol) in DMF (5.0 mL) at 0° C. The reaction mixture was then stirred at room temperature for 2 h before water (100 mL) was added. The resulting light yellow solid was collected by filtration and dried to obtain the desired product (2.3 g, 80%). LC-MS calculated for $C_{16}H_{13}BrN_5O_2$ (M+H)$^+$: m/z=386.0; found 386.0.

Alternatively, this compound can be prepared using the following procedure: to a solution of ethyl 8-bromo-7-(3-cyanophenyl)-5-(methylthio)imidazo[1,2-c]pyrimidine-2-carboxylate (prepared in Example 17, Step 3) (2.40 g, 5.75 mmol) in DCM (100 mL) was added a solution mCPBA (77%, 1.93 g, 8.63 mmol) in DCM (30 mL) this solution was dried over anhydrous magnesium sulfate through an addition funnel at room temperature for 30 minutes. The reaction mixture was then stirred for 4 h, and quenched by bubbling NH$_3$ gas via cannula for 1 h. The reaction mixture was then concentrated under reduced pressure to give a crude mixture, which was poured into a saturated NaHCO$_3$ solution (150 mL). The resulting solid was collected by filtration, washed with water and hexanes, and dried to afford the desired product as a brown solid (1.9 g, 86%). LC-MS calculated for $C_{16}H_{13}BrN_5O_2$ (M+H)$^+$: m/z=386.0; found 386.0.

Step 4: 5-Amino-8-bromo-7-(3-cyanophenyl)-N-ethylimidazo[1,2-c]pyrimidine-2-carboxamide

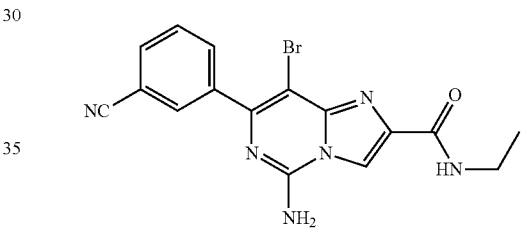

To a mixture of ethyl 5-amino-8-bromo-7-(3-cyanophenyl)imidazo[1,2-c]pyrimidine-2-carboxylate (1.00 g, 2.59 mmol) in MeOH (20 mL), THF (20 mL), and water (10 mL) was added LiOH (124 mg, 5.18 mmol). The reaction mixture was stirred at room temperature for 2 h, and the solvent was removed under reduced pressure. The resulting residue was dissolved in DMF (30 mL), followed by the addition of ethylamine solution (2.1 mL, 25.9 mmol, 70% in water), triethyl amine (1.08 mL, 7.77 mmol), and BOP (2.29 g, 5.18 mmol). The reaction mixture was stirred at room temperature overnight before 100 mL of water was added. The resulting solid was collected by filtration and dried to afford the desired product as a yellow solid (0.77 g). LC-MS calculated for $C_{16}H_{14}BrN_6O$ (M+H)$^+$: m/z=385.0; found 385.1.

Step 5: 5-Amino-7-(3-cyanophenyl)-N-ethyl-8-(pyridin-4-yl)imidazo[1,2-c]pyrimidine-2-carboxamide A mixture of 5-amino-8-bromo-7-(3-cyanophenyl)-N-ethylimidazo[1,2-c]pyrimidine-2-carboxamide (10.0 mg, 0.026 mmol), pyridin-4-ylboronic acid (4.8 mg, 0.039 mmol), XPhos Pd G2 (2.0 mg, 2.51 µmol), and Na$_2$CO$_3$ (8.3 mg, 0.078 mmol) in 1,4-dioxane (1.5 mL) and water (0.15 mL) was degassed and sealed. The reaction mixture was stirred at 110° C. for 1 h, coded to room temperature, diluted with MeOH, and purified with prep-LC-MS (pH=2, MeCN/ water with TFA) to give the desired product as a TFA salt. LC-MS calculated for $C_{21}H_{18}N_7O$ $(M+H)^+$: m/z=384.2; found 384.2.

Example 27. 5-Amino-7-(3-cyanophenyl)-N-ethyl-8-(3-methylpyridin-4-yl)imidazo[1,2-c]pyrimidine-2-carboxamide

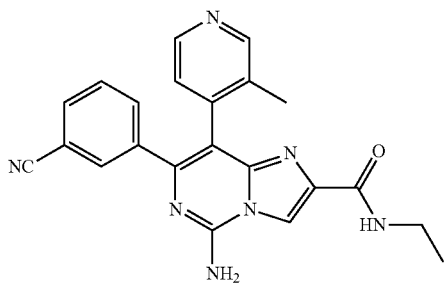 [SMILES: CCNC(=O)c1cn2c(N)nc(-c3cccc(C#N)c3)c(-c3ccncc3C)c2n1]

This compound was prepared using similar procedures as described for Example 26 with 3-methylpyridin-4-ylboronic acid replacing pyridin-4-ylboronic acid in Step 5. The product was purified by prep-LC-MS (pH=2, MeCN/water with TFA) to give the desired product as a TFA salt. LC-MS calculated for $C_{22}H_{20}N_7O$ $(M+H)^+$: m/z=398.2; found 398.2.

Example 28. 5-Amino-7-(3-cyanophenyl)-N-ethyl-8-(3-fluoropyridin-4-yl)imidazo[1,2-c]pyrimidine-2-carboxamide

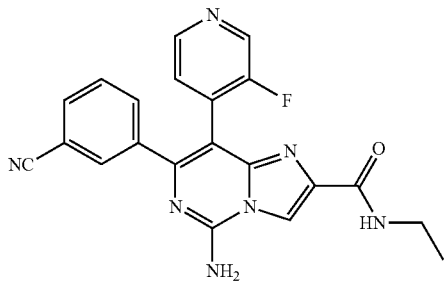 [SMILES: CCNC(=O)c1cn2c(N)nc(-c3cccc(C#N)c3)c(-c3ccncc3F)c2n1]

This compound was prepared using similar procedures as described for Example 26 with 3-fluoropyridin-4-ylboronic acid replacing pyridin-4-ylboronic acid in Step 5. The product was purified by prep-LC-MS (pH=2, MeCN/water with TFA) to give the desired product as a TFA salt. LC-MS calculated for $C_{21}H_{17}FN_7O$ $(M+H)^+$: m/z=402.1; found 402.2.

Example 29. 5-Amino-7-(3-cyanophenyl)-N-ethyl-8-(3-chloropyridin-4-yl)imidazo[1,2-c]pyrimidine-2-carboxamide

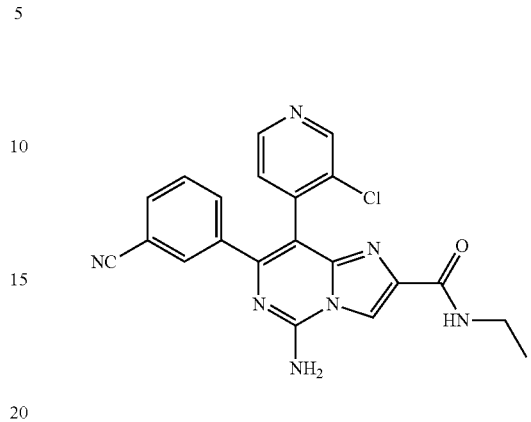

This compound was prepared using similar procedures as described for Example 26 with 3-chloropyridin-4-ylboronic acid replacing pyridin-4-ylboronic acid in Step 5. The product was purified by prep-LC-MS (pH=2, MeCN/water with TFA) to give the desired product as a TFA salt. LC-MS calculated for $C_{21}H_{14}ClN_7O$ $(M+H)^+$: m/z=418.1; found 418.2.

Example 30. 5-Amino-7-(3-cyanophenyl)-N-ethyl-8-(3-methoxypyridin-4-yl)imidazo[1,2-c]pyrimidine-2-carboxamide

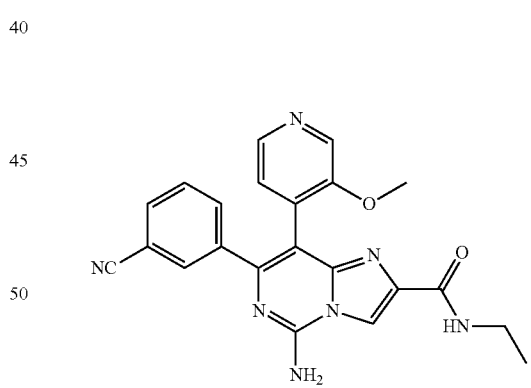

This compound was prepared using similar procedures as described for Example 26 with 3-methoxypyridin-4-ylboronic acid replacing pyridin-4-ylboronic acid in Step 5. The product was purified by prep-LC-MS (pH=2, MeCN/water with TFA) to give the desired product as a TFA salt. LC-MS calculated for $C_{22}H_{20}N_7O_2$ $(M+H)^+$: m/z=414.2; found 414.2.

Example 31. 5-Amino-7-(3-cyanophenyl)-N-ethyl-8-(3-cyanopyridin-4-yl)imidazo[1,2-c]pyrimidine-2-carboxamide

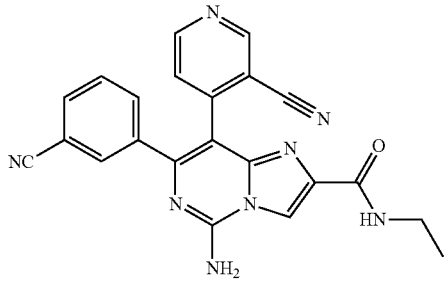 [SMILES: CCNC(=O)c1cn2c(N)nc(-c3cccc(C#N)c3)c(-c3ccncc3C#N)c2n1]

This compound was prepared using similar procedures as described for Example 26 with 4-(4,4,5,5-tetramethyl-1,3,2-dioxaborolan-2-yl)nicotinonitrile replacing pyridin-4-ylboronic acid in Step 5. The product was purified by prep-LC-MS (pH=2, MeCN/water with TFA) to give the desired product as a TFA salt. LC-MS calculated for $C_{22}H_{17}N_8O$ (M+H)$^+$: m/z=409.2; found 409.2.

Example 32. 5-Amino-8-(4-carbamoylphenyl)-7-(3-cyanophenyl)-N-ethylimidazo[1,2-c]pyrimidine-2-carboxamide

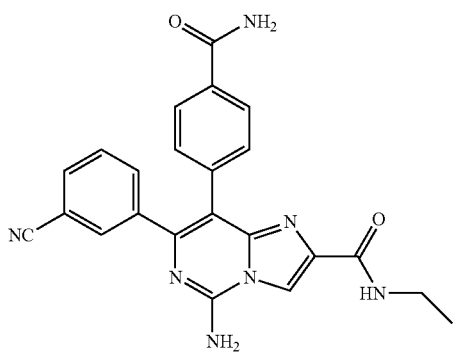 [SMILES: CCNC(=O)c1cn2c(N)nc(-c3cccc(C#N)c3)c(-c3ccc(C(N)=O)cc3)c2n1]

This compound was prepared using similar procedures as described for Example 26 with (4-carbamoylphenyl)boronic acid replacing pyridin-4-ylboronic acid in Step 5. The product was purified by prep-LC-MS (pH=2, MeCN/water with TFA) to give the desired product as a TFA salt. LC-MS calculated for $C_{23}H_{20}N_7O_2$ (M+H)$^+$: m/z=426.2; found 426.2.

Example 33. 5-Amino-7-(3-cyanophenyl)-N-ethyl-8-(pyrazolo[1,5-a]pyridin-3-yl)imidazo[1,2-c]pyrimidine-2-carboxamide

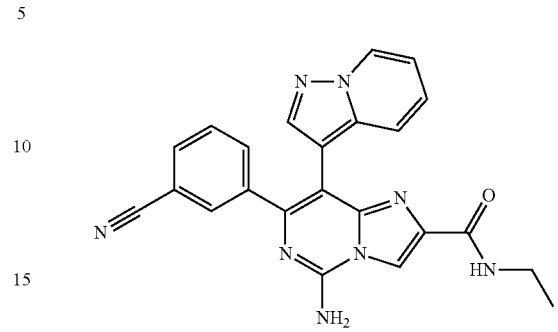

This compound was prepared using similar procedures as described for Example 26 with 3-(4,4,5,5-tetramethyl-1,3,2-dioxaborolan-2-yl)pyrazolo[1,5-a]pyridine replacing pyridin-4-ylboronic acid in Step 5. The product was purified by prep-LC-MS (pH=2, MeCN/water with TFA) to give the desired product as a TFA salt. LC-MS calculated for $C_{23}H_{19}N_8O$ (M+H)$^+$: m/z=423.2; found 423.2.

Example 34. 5-Amino-7-(3-cyanophenyl)-N-ethyl-8-(5-methyl-1H-pyrazol-4-yl)imidazo[1,2-c]pyrimidine-2-carboxamide

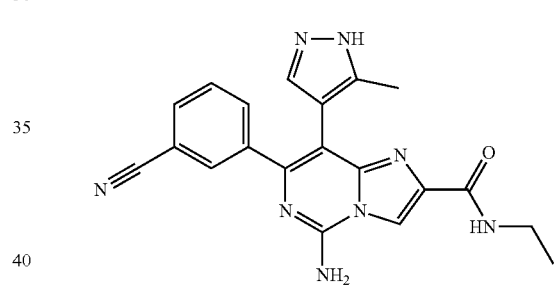

This compound was prepared using similar procedures as described for Example 26 with 5-methyl-4-(4,4,5,5-tetramethyl-1,3,2-dioxaborolan-2-yl)-1H-pyrazole replacing pyridin-4-ylboronic acid in Step 5. The product was purified by prep-LC-MS (pH=2, MeCN/water with TFA) to give the desired product as a TFA salt. LC-MS calculated for $C_{20}H_{19}N_8O$ (M+H)$^+$: m/z=387.2; found 387.2.

Example 35. 5-Amino-7-(3-cyanophenyl)-N-ethyl-8-(1-ethyl-1H-pyrazol-5-yl)imidazo[1,2-c]pyrimidine-2-carboxamide

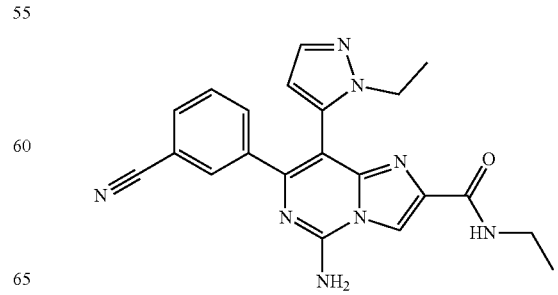

This compound was prepared using similar procedures as described for Example 26 with 1-ethyl-5-(4,4,5,5-tetramethyl-1,3,2-dioxaborolan-2-yl)-1H-pyrazole replacing pyridin-4-ylboronic acid in Step 5. The product was purified by prep-LC-MS (pH=2, MeCN/water with TFA) to give the desired product as a TFA salt. LC-MS calculated for $C_{21}H_{21}N_8O$ (M+H)$^+$: m/z=401.2; found 401.2.

Example 36. 5-Amino-7-(3-cyanophenyl)-N-ethyl-8-(1-isopropyl-1H-pyrazol-5-yl)imidazo[1,2-c]pyrimidine-2-carboxamide

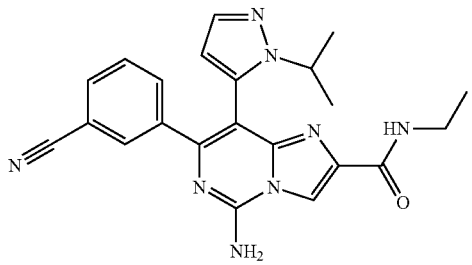 [SMILES: CCNC(=O)c1cn2c(N)nc(-c3cccc(C#N)c3)c(-c3ccnn3C(C)C)c2n1]

This compound was prepared using similar procedures as described for Example 26 with 1-isopropyl-5-(4,4,5,5-tetramethyl-1,3,2-dioxaborolan-2-yl)-1H-pyrazole replacing pyridin-4-ylboronic acid in Step 5. The product was purified by prep-LC-MS (pH=2, MeCN/water with TFA) to give the desired product as a TFA salt. LC-MS calculated for $C_{22}H_{23}N_8O$ (M+H)$^+$: m/z=415.2; found 415.2.

Example 37. 5-Amino-7-(3-cyanophenyl)-N-ethyl-8-(1-propyl-1H-pyrazol-5-yl)imidazo[1,2-c]pyrimidine-2-carboxamide

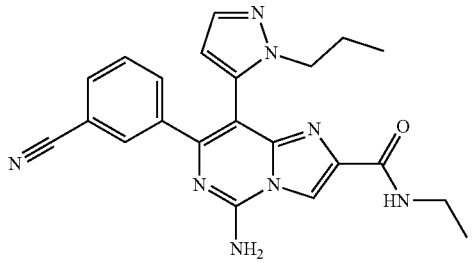 [SMILES: CCCn1nccc1-c1c(-c2cccc(C#N)c2)nc(N)n2cc(C(=O)NCC)nc12]

This compound was prepared using similar procedures as described for Example 26 with 1-propyl-5-(4,4,5,5-tetramethyl-1,3,2-dioxaborolan-2-yl)-1H-pyrazole replacing pyridin-4-ylboronic acid in Step 5. The product was purified by prep-LC-MS (pH=2, MeCN/water with TFA) to give the desired product as a TFA salt. LC-MS calculated for $C_{22}H_{23}N_8O$ (M+H)$^+$: m/z=415.2; found 415.2.

Example 38. 5-Amino-7-(3-cyanophenyl)-N-ethyl-8-(pyrimidin-4-yl)imidazo[1,2-c]pyrimidine-2-carboxamide

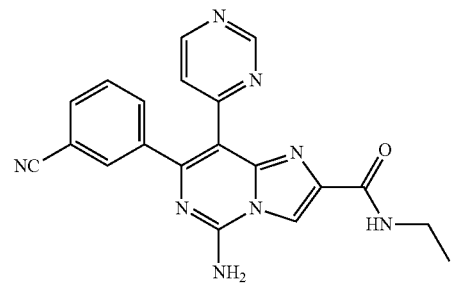

A mixture of 5-amino-8-bromo-7-(3-cyanophenyl)-N-ethylimidazo[1,2-c]pyrimidine-2-carboxamide (prepared in Example 26, Step 4) (50 mg, 0.13 mmol), 4-(tributylstannyl)pyrimidine (96 mg, 0.260 mmol), tetrakis(triphenylphosphine)palladium(0) (15.0 mg, 0.013 mmol), copper(I) chloride (15.4 mg, 0.156 mmol) and lithium chloride (6.6 mg, 0.156 mmol) in THF (2 mL) was degassed and sealed. The reaction mixture was stirred at 80° C. for 12 h, cooled to room temperature, and concentrated under reduced pressure. The resulting residue was purified by prep-LC-MS (pH=2, MeCN/water with TFA) to give the desired product as a TFA salt. LC-MS calculated for $C_{20}H_{17}N_8O$ (M+H)$^+$: m/z=385.2; found 385.2.

Example 39. 5-Amino-7-(3-cyanophenyl)-8-(2,3-dihydro-[1,4]dioxino[2,3-b]pyridin-8-yl)-N-ethylimidazo[1,2-c]pyrimidine-2-carboxamide

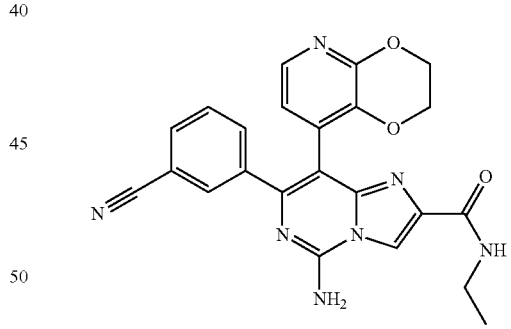

A mixture of 5-amino-8-bromo-7-(3-cyanophenyl)-N-ethylimidazo[1,2-c]pyrimidine-2-carboxamide (prepared in Example 26, Step 4) (72 mg, 0.19 mmol), (2,3-dihydro-[1,4]dioxino[2,3-b]pyridin-8-yl)boronic acid (33.8 mg, 0.19 mmol), cesium carbonate (122 mg, 0.37 mmol) and [1,1'-bis(dicyclohexylphosphino)ferrocene]dichloropalladium(II) (14.1 mg, 0.019 mmol) in dioxane (2.0 mL) and water (0.2 mL) was stirred at 120° C. for 1 h under microwave irradiation. The reaction mixture was then cooled to room temperature, and directly purified by prep-LC-MS (pH=2, MeCN/water with TFA) to give the desired product as a TFA salt. LC-MS calculated for $C_{23}H_{20}N_7O_3$(M+H)$^+$: m/z=442.2; found 442.3.

Example 40. 5-Amino-7-(3-cyanophenyl)-8-cyclopropyl-N-ethylimidazo[1,2-c]pyrimidine-2-carboxamide

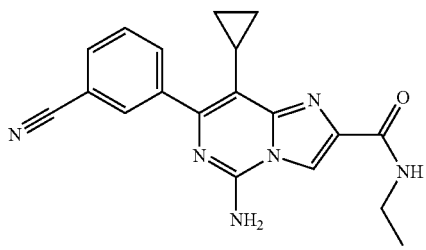 [SMILES: CCNC(=O)c1cn2c(N)nc(-c3cccc(C#N)c3)c(C3CC3)c2n1]

A mixture of 5-amino-8-bromo-7-(3-cyanophenyl)-N-ethylimidazo[1,2-c]pyrimidine-2-carboxamide (prepared in Example 26, Step 4) (72 mg, 0.19 mmol), cyclopropylboronic acid (32.1 mg, 0.37 mmol), cesium carbonate (122 mg, 0.37 mmol) and [1,1'-bis(dicyclohexylphosphino)ferrocene]dichloropalladium (II) (14.1 mg, 0.019 mmol) in dioxane (2.0 mL) and water (0.2 mL) was stirred at 80° C. for 1 h under microwave irradiation. The reaction mixture was then cooled to room temperature, and directly purified by prep-LC-MS (pH=2, MeCN/water with TFA) to give the desired product as a TFA salt. LC-MS calculated for $C_{19}H_{19}N_6O$ (M+H)$^+$: m/z=347.2; found 347.3.

Example 41. 3-(5-Amino-2-(pyridin-2-ylmethyl)-8-(pyrimidin-4-yl)-[1,2,4]triazolo[1,5-c]pyrimidin-7-yl)benzonitrile

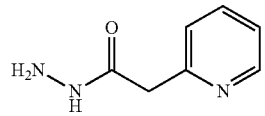

Step 1: 3-(2-Amino-6-chloropyrimidin-4-yl)benzonitrile

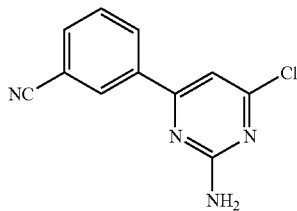 [SMILES: N#Cc1cccc(-c2cc(Cl)nc(N)n2)c1]

A mixture of 4,6-dichloropyrimidin-2-amine (2.5 g, 15.2 mmol), (3-cyanophenyl)boronic acid (2.02 g, 13.7 mmol), tetrakis(triphenylphosphine)palladium(0) (1.06 g, 0.92 mmol) and sodium carbonate (3.23 g, 30.5 mmol) in 1,4-dioxane (60 mL), and water (5 mL) was degassed with nitrogen, then the resulting mixture was heated and stirred at 60° C. for two days. After cooled to room temperature (r.t.), the mixture was concentrated, diluted with water, and extracted with DCM (30 mL×3). The combined organic layers were dried over MgSO$_4$, filtered, and concentrated. The resulting residue was purified by flash chromatography on a silica gel column eluting with 8% EtOAc in dichloromethane to afford the desired product. LCMS calculated for $C_{11}H_8ClN_4$ (M+H)$^+$: 231.0. Found: 231.0.

Step 2: 2-(Pyridin-2-yl)acetohydrazide

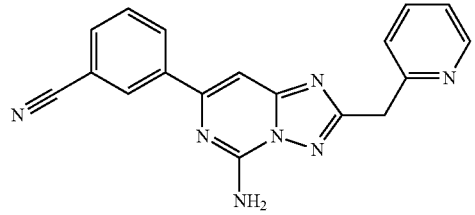 [SMILES: N#Cc1cccc(-c2cc3nc(Cc4ccccn4)nn3c(N)n2)c1]

Hydrazine (4.15 mL, 132 mmol) was added to a ethanol (66 mL) solution of methyl 2-(pyridin-2-yl)acetate (10 g, 66.2 mmol) at r.t. The mixture was heated and stirred at 85° C. for 4 h, and then cooled to r.t. White solid was formed upon standing, which was collected via filtration and used in next step without further purification. LCMS calculated for $C_7H_{10}N_3O$ (M+H)$^+$: 152.1. Found: 152.0.

Step 3: 3-(5-Amino-2-(pyridin-2-ylmethyl)-[1,2,4]triazolo[1,5-c]pyrimidin-7-yl)benzonitrile 2-(pyridin-2-yl)acetohydrazide (2.62 g, 17.34 mmol) was added to a ethanol (35 mL) solution of 3-(2-amino-6-chloropyrimidin-4-yl)benzonitrile (4.00 g, 17.34 mmol) at r.t. After being heated and stirred at reflux for 2 h, the reaction mixture was cooled to r.t., and concentrated. The resulting residue was taken into N,O-bis(trimethylsilyl)acetamide (20 mL) and stirred at 120° C. for 7 h. The mixture was then cooled to r.t., poured onto ice, and allowed to stir at r.t. for 1 h. The resulting solid was collected by filtration, and taken into 20 mL of 1 N HCl solution. The resulting mixture was stirred at r.t. for 1 h, filtered, and the aqueous layer was neutralized by addition of saturated NaHCO$_3$ solution. The resulting precipitate was collected by filtration, and dried to obtain the desired product as a brown solid. LCMS calculated for $C_{18}H_{14}N_7$ (M+H)$^+$: 328.1; found 328.1.

Step 4: 3-(5-Amino-8-bromo-2-(pyridin-2-ylmethyl)-[1,2,4]triazolo[1,5-c]pyrimidin-7-yl)benzonitrile

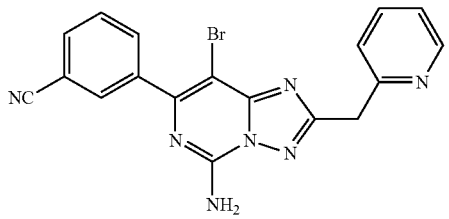 [SMILES: N#Cc1cccc(-c2nc(N)n3nc(Cc4ccccn4)nc3c2Br)c1]

To a mixture of 3-(5-amino-2-(pyridin-2-ylmethyl)-[1,2,4]triazolo[1,5-c]pyrimidin-7-yl)benzonitrile (2 g, 6.11 mmol) in DMF (12 mL) at −30° C. was added NBS (1.09 g, 6.11 mmol) portion-wise. The reaction mixture was allowed to slowly warm to 0° C., resulting a homogenous solution. After stirring at 0° C. for 1 h, the reaction mixture was diluted with saturated NaHCO$_3$ solution and the resulting solid was collected by filtration. The solid was then purified by flash chromatography on a silica gel column eluting with 0 to 10% MeOH in DCM to afford the desired product. LCMS calculated for $C_{18}H_{13}BrN_7$ (M+H)$^+$: 406.0; found 406.0.

Step 5: 3-(5-Amino-2-(pyridin-2-ylmethyl)-8-(pyrimidin-4-yl)-[1,2,4]triazolo[1,5-c]pyrimidin-7-yl)benzonitrile Pd(Ph$_3$P)$_4$ (284 mg, 0.246 mmol) was added to a mixture of 4-(tributylstannyl)pyrimidine (1090 mg, 2.95 mmol), 3-(5-amino-8-bromo-2-(pyridin-2-ylmethyl)-[1,2,4]triazolo[1,5-c]pyrimidin-7-yl)benzonitrile (1000 mg, 2.46 mmol), and copper(I) chloride (244 mg, 2.46 mmol) in 1,4-dioxane (12 mL). The reaction mixture was purged with N$_2$ and stirred at 80° C. for 7 h. The resulting mixture was cooled to r.t., concentrated, diluted with DCM (50 mL) and washed with saturated NH$_4$OH solution. The organic layer was dried over Na$_2$SO$_4$, concentrated, and purified by preparative LC-MS (pH 2, acetonitrile/water with TFA) to afford the product as a TFA salt. LCMS calculated for $C_{22}H_{16}N_9$ (M+H)$^+$: 406.2; found 406.2. $^1$H NMR (500 MHz, DMSO) δ 8.95 (s, 1H), 8.83 (d, J=5.3 Hz, 1H), 8.59 (d, J=5.1 Hz, 1H), 7.96 (m, 1H), 7.88 (d, J=5.1 Hz, 1H), 7.82 (d, J=7.6 Hz, 1H), 7.76 (s, 1H), 7.60-7.53 (m, 2H), 7.53-7.48 (m, 1H), 7.48-7.42 (m, 1H), 4.49 (s, 2H).

Example 42. 3-(5-Amino-8-(1-ethyl-1H-pyrazol-5-yl)-2-(pyridin-2-ylmethyl)-[1,2,4]triazolo[1,5-c]pyrimidin-7-yl)benzonitrile

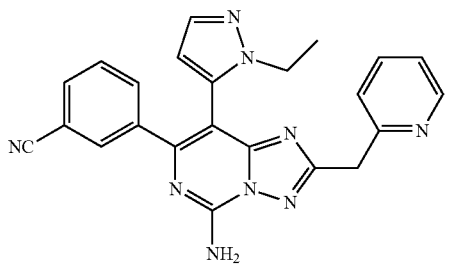

A mixture of 3-(5-amino-8-bromo-2-(pyridin-2-ylmethyl)-[1,2,4]triazolo[1,5-c]pyrimidin-7-yl)benzonitrile (from Example 41, Step 4) (50 mg, 0.123 mmol), 1-ethyl-5-(4,4,5,5-tetramethyl-1,3,2-dioxaborolan-2-yl)-1H-pyrazole (54.7 mg, 0.246 mmol), chloro(2-dicyclohexylphosphino-2',4',6'-triisopropyl-1,1'-biphenyl)[2-(2'-amino-1,1'-biphenyl)]palladium(II) (9.68 mg, 0.012 mmol), and sodium carbonate (13.0 mg, 0.123 mmol) in 1,4-dioxane (1119 µL) and water (112 µL) was stirred at 100° C. for 1 h. The resulting mixture was cooled to r.t., concentrated, and purified by preparative LC-MS (pH 2, acetonitrile/water with TFA) to afford the product as a TFA salt. LCMS calculated for $C_{23}H_{20}N_9$ (M+H)$^+$: 422.2; found 422.2.

Example 43. 3-(5-Amino-8-(1-propyl-1H-pyrazol-5-yl)-2-(pyridin-2-ylmethyl)-[1,2,4]triazolo[1,5-c]pyrimidin-7-yl)benzonitrile

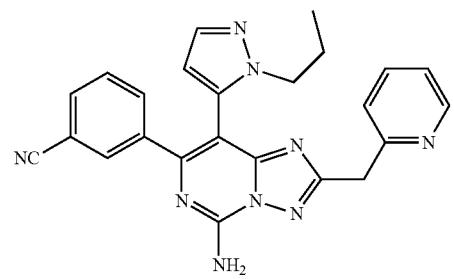 [SMILES: CCCn1nccc1-c1c(-c2cccc(C#N)c2)nc(N)n2nc(Cc3ccccn3)nc12]

This compound was prepared using similar procedures as described for Example 42 with 1-propyl-5-(4,4,5,5-tetramethyl-1,3,2-dioxaborolan-2-yl)-1H-pyrazole replacing 1-ethyl-5-(4,4,5,5-tetramethyl-1,3,2-dioxaborolan-2-yl)-1H-pyrazole. The final material was purified by preparative LC-MS (pH 2, acetonitrile/water with TFA) to afford the product as a TFA salt. LCMS calculated for $C_{24}H_{22}N_9$ (M+H)$^+$: 436.2; found 436.2.

Example 44. 3-(5-Amino-2-(pyridin-2-ylmethyl)-8-(quinolin-5-yl)-[1,2,4]triazolo[1,5-c]pyrimidin-7-yl)benzonitrile

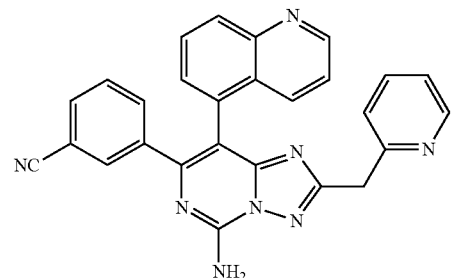

This compound was prepared using similar procedures as described for Example 42 with 5-(4,4,5,5-tetramethyl-1,3,2-dioxaborolan-2-yl)quinoline replacing 1-ethyl-5-(4,4,5,5-tetramethyl-1,3,2-dioxaborolan-2-yl)-1H-pyrazole. The final material was purified by preparative LC-MS (pH 2, acetonitrile/water with TFA) to afford the product as a TFA salt. LCMS calculated for $C_{27}H_{19}N_8$ (M+H)$^+$: 455.2; found 455.2.

Example 45. 3-(5-Amino-8-(5-fluoropyrimidin-4-yl)-2-(hydroxy(phenyl)methyl)-[1,2,4]triazolo[1,5-c]pyrimidin-7-yl)benzonitrile

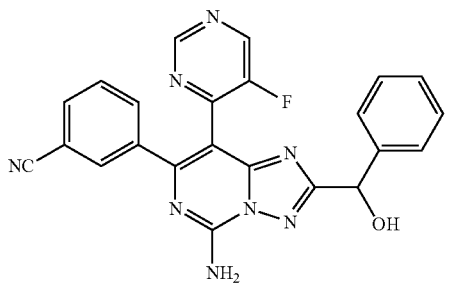 [SMILES: N#Cc1cccc(-c2nc(N)n3nc(C(O)c4ccccc4)nc3c2-c2ncncc2F)c1]

Step 1: 3-(5-Amino-8-bromo-2-(hydroxy(phenyl)methyl)-[1,2,4]triazolo[1,5-c]pyrimidin-7-yl)benzonitrile

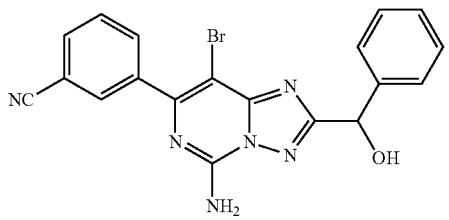 [SMILES: N#Cc1cccc(-c2nc(N)n3nc(C(O)c4ccccc4)nc3c2Br)c1]

This compound was prepared using similar procedures as described for Example 41, Step 1 to Step 4, with 2-hydroxy-2-phenylacetohydrazide replacing 2-(pyridin-2-yl)acetohydrazide in Step 3. LCMS calculated for $C_{19}H_{14}BrN_6O$ (M+H)$^+$: 421.0; found 421.0.

Step 2: 5-Fluoro-4-(trimethylstannyl)pyrimidine

Pd(Ph$_3$P)$_4$ (43.6 mg, 0.038 mmol) and 1,1,1,2,2,2-hexamethyldistannane (124 mg, 0.377 mmol) were successively added to a mixture of 4-chloro-5-fluoropyrimidine (50 mg, 0.377 mmol) in 1,4-dioxane (1886 µL) under a nitrogen atmosphere. The reaction mixture was then stirred at reflux overnight, cooled to r.t., and filtered. The filtrate was used in next step without further purification.

Step 3: 3-(5-Amino-8-(5-fluoropyrimidin-4-yl)-2-(hydroxy(phenyl)methyl)-[1,2,4]triazolo[1,5-c]pyrimidin-7-yl)benzonitrile This compound was prepared using similar procedures as described for Example 41, Step 5, with 5-fluoro-4-(trimethylstannyl)pyrimidine replacing 4-(tributylstannyl)pyrimidine, and with 3-(5-amino-8-bromo-2-(hydroxy(phenyl)methyl)-[1,2,4]triazolo[1,5-c]pyrimidin-7-yl)benzonitrile replacing 3-(5-amino-8-bromo-2-(pyridin-2-ylmethyl)-[1,2,4]triazolo[1,5-c]pyrimidin-7-yl)benzonitrile. The final material was purified by preparative LC-MS (pH 2, acetonitrile/water with TFA) to afford the product as a TFA salt. LCMS calculated for $C_{23}H_{16}FN_8O$ (M+H)$^+$: 439.1; found 439.1.

Example 46. 3-(5-Amino-8-(5-fluoropyrimidin-4-yl)-2-(pyridin-2-ylmethyl)-[1,2,4]triazolo[1,5-c]pyrimidin-7-yl)benzonitrile

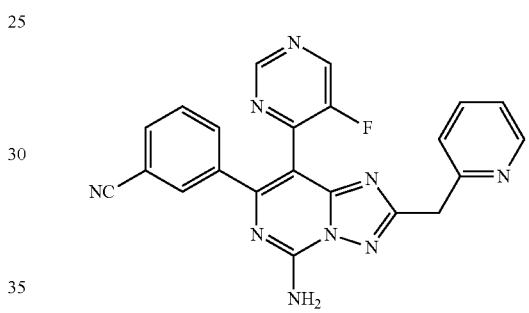

This compound was prepared using similar procedures as described for Example 41, with 5-fluoro-4-(trimethylstannyl)pyrimidine (from Example 45, Step 2) replacing 4-(tributylstannyl)pyrimidine. The final material was purified by preparative HPLC (pH 2, acetonitrile/water with TFA) to afford the product as a TFA salt. LCMS calculated for $C_{22}H_{15}FN_9$ (M+H)$^+$: 424.1; found 424.2.

Example 47. 3-(5-Amino-2-((2-hydroxyethylamino)(phenyl)methyl)-8-(pyridin-4-yl)-[1,2,4]triazolo[1,5-c]pyrimidin-7-yl)benzonitrile

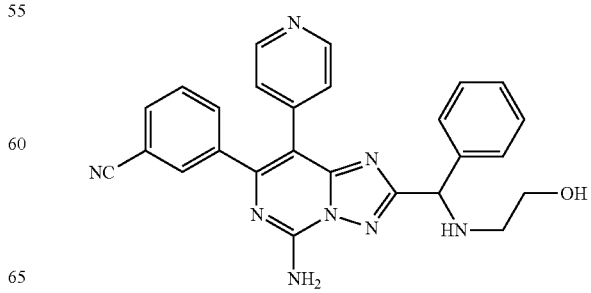

Step 1: 3-(5-Amino-8-bromo-2-(chloro(phenyl)methyl)-[1,2,4]triazolo[1,5-c]pyrimidin-7-yl)benzonitrile

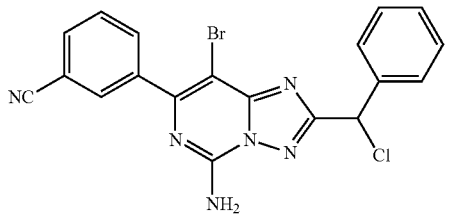

Thionyl chloride (87 µL, 1.19 mmol) was added to 3-(5-amino-8-bromo-2-(hydroxy(phenyl)methyl)-[1,2,4]triazolo[1,5-c]pyrimidin-7-yl)benzonitrile (from Example 45, Step 1) (10 mg, 0.024 mmol) at r.t. After stirring for 30 min, the reaction mixture was concentrated, and the resulting residue was used in the next step without further purification.

LCMS calculated for $C_{19}H_{13}BrClN_6$ (M+H)$^+$: 441.0; found 441.0.

Step 2: 3-(5-Amino-8-bromo-2-((2-hydroxyethylamino)(phenyl)methyl)-[1,2,4]triazolo[1,5-c]pyrimidin-7-yl)benzonitrile

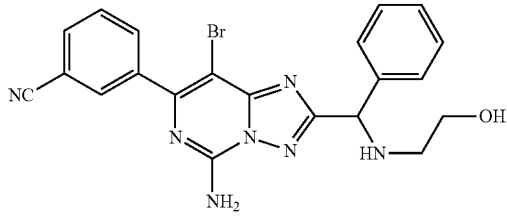 [SMILES: N#Cc1cccc(-c2nc(N)n3nc(C(NCCO)c4ccccc4)nc3c2Br)c1]

2-aminoethan-1-ol (4.35 mg, 0.071 mmol) was added to a DMF (237 µL) solution of 3-(5-amino-8-bromo-2-(chloro(phenyl)methyl)-[1,2,4]triazolo[1,5-c]pyrimidin-7-yl)benzonitrile (10 mg, 0.024 mmol). The reaction mixture was stirred at r.t. overnight, concentrated, and used in the next step without further purification. LCMS calculated for $C_{21}H_{19}BrN_7O$ (M+H)$^+$: 464.1; found 464.2.

Step 3: 3-(5-Amino-2-((2-hydroxyethylamino)(phenyl)methyl)-8-(pyridin-4-yl)-[1,2,4]triazolo[1,5-c]pyrimidin-7-yl)benzonitrile A mixture of 3-(5-amino-8-bromo-2-(((2-hydroxyethyl)amino)(phenyl)methyl)-[1,2,4]triazolo[1,5-c]pyrimidin-7-yl)benzonitrile (10 mg, 0.022 mmol), pyridin-4-ylboronic acid (6.0 mg, 0.043 mmol), chloro(2-dicyclohexylphosphino-2',4',6'-triisopropyl-1,1'-biphenyl)[2-(2'-amino-1,1'-biphenyl)]palladium(II) (1.70 mg, 2.15 µmol), and sodium carbonate (2.3 mg, 0.022 mmol) in 1,4-dioxane (196 µL) and water (19.6 µL) was heated and stirred at 100° C. for 1 h. The reaction mixture was then cooled to r.t., concentrated, purified by preparative LC-MS (pH 2, acetonitrile/water with TFA) to afford the product as a TFA salt. LCMS calculated for $C_{26}H_{23}N_8O$ (M+H)$^+$: 463.2; found 463.2.

Example 48. 3-(5-Amino-2-(cyclohexylmethyl)-8-(1-ethyl-1H-pyrazol-5-yl)-[1,2,4]triazolo[1,5-c]pyrimidin-7-yl)benzonitrile

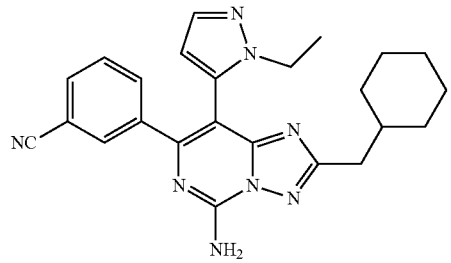 [SMILES: CCn1nccc1-c1c(-c2cccc(C#N)c2)nc(N)n2nc(CC3CCCCC3)nc12]

Step 1: 3-(5-Amino-8-bromo-2-(cyclohexylmethyl)-[1,2,4]triazolo[1,5-c]pyrimidin-7-yl)benzonitrile

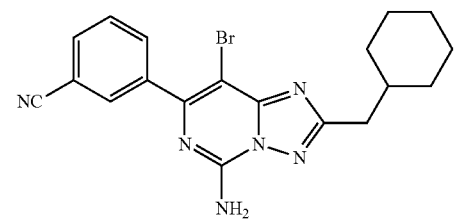 [SMILES: N#Cc1cccc(-c2nc(N)n3nc(CC4CCCCC4)nc3c2Br)c1]

This compound was prepared using similar procedures as described for Example 41, Step 1 to Step 4, with 2-cyclohexylacetohydrazide replacing 2-(pyridin-2-yl)acetohydrazide in Step 3.

LCMS calculated for $C_{19}H_{20}BrN_6$ (M+H)$^+$: 411.1; found 411.1.

Step 2: 3-(5-Amino-2-(cyclohexylmethyl)-8-(1-ethyl-1H-pyrazol-5-yl)-[1,2,4]triazolo[1,5-c]pyrimidin-7-yl)benzonitrile This compound was prepared using similar procedures as described for Example 42, with 3-(5-amino-8-bromo-2-(cyclohexylmethyl)-[1,2,4]triazolo[1,5-c]pyrimidin-7-yl)benzonitrile replacing 3-(5-amino-8-bromo-2-(pyridin-2-ylmethyl)-[1,2,4]triazolo[1,5-c]pyrimidin-7-yl)benzonitrile. The final material was purified by preparative LC-MS (pH 2, acetonitrile/water with TFA) to afford the product as a TFA salt. LCMS calculated for $C_{24}H_{27}N_8$ (M+H)$^+$: 427.2; found 427.2.

Example 49. 3-(5-Amino-2-(2-fluorobenzyl)-8-(pyrimidin-4-yl)-[1,2,4]triazolo[1,5-c]pyrimidin-7-yl)benzonitrile

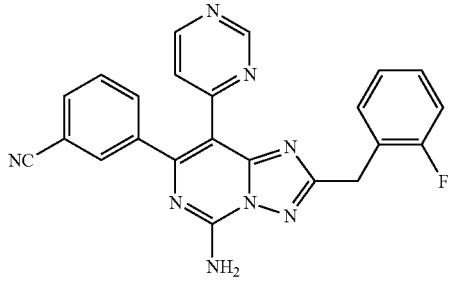 [SMILES: N#Cc1cccc(-c2nc(N)n3nc(Cc4ccccc4F)nc3c2-c2ccncn2)c1]

This compound was prepared using similar procedures as described for Example 41, with 2-(2-fluorophenyl)acetohydrazide replacing 2-(pyridin-2-yl)acetohydrazide in Step 3. The final material was purified by preparative LC-MS (pH 2, acetonitrile/water with TFA) to afford the product as a TFA salt. LCMS calculated for $C_{23}H_{16}FN_8$ $(M+H)^+$: 423.2; found 423.2.

Example 50. 3-(5-Amino-2-((2-fluorophenyl)(hydroxy)methyl)-8-(pyrimidin-4-yl)-[1,2,4]triazolo[1,5-c]pyrimidin-7-yl)benzonitrile

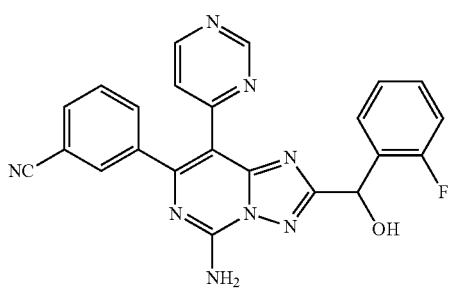 [SMILES: N#Cc1cccc(-c2nc(N)n3nc(C(O)c4ccccc4F)nc3c2-c2ccncn2)c1]

This compound was prepared using similar procedures as described for Example 41, with 2-(2-fluorophenyl)-2-hydroxyacetohydrazide replacing 2-(pyridin-2-yl)acetohydrazide in Step 3. The final material was purified by preparative LC-MS (pH 2, acetonitrile/water with TFA) to afford the product as a TFA salt. LCMS calculated for $C_{23}H_{16}FN_8O$ $(M+H)^+$: 439.1; found 439.1.

Example 51. 3-(5-Amino-2-((6-methylpyridin-2-yl)methyl)-8-(pyrimidin-4-yl)-[1,2,4]triazolo[1,5-c]pyrimidin-7-yl)benzonitrile

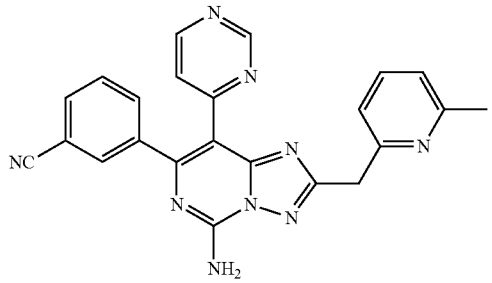 [SMILES: Cc1cccc(Cc2nc3c(-c4ccncn4)c(-c4cccc(C#N)c4)nc(N)n3n2)n1]

Step 1: 2-(6-14 ethylpyridin-2-yl)acetohydrazide

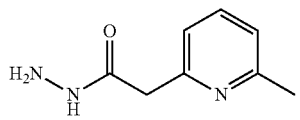

This compound was prepared using similar procedures as described for Example 41, Step 2, with ethyl 2-(6-methylpyridin-2-yl)acetate replacing methyl 2-(pyridin-2-yl)acetate. LCMS calculated for $C_8H_{12}N_3O$ $(M+H)^+$: 166.1; found 166.1.

Step 2: 3-(5-Amino-2-((6-methylpyridin-2-yl)methyl)-8-(pyrimidin-4-yl)-[1,2,4]triazolo[1,5-c]pyrimidin-7-yl)benzonitrile This compound was prepared using similar procedures as described for Example 41, with 2-(6-methylpyridin-2-yl)acetohydrazide replacing 2-(pyridin-2-yl)acetohydrazide in Step 3. The final material was purified by preparative LC-MS (pH 2, acetonitrile/water with TFA) to afford the product as a TFA salt. LCMS calculated for $C_{23}H_{18}N_9$ $(M+H)^+$: 420.2; found 420.2.

Example 52. 3-(5-Amino-8-(1-ethyl-1H-pyrazol-5-yl)-2-((3-fluoropyridin-2-yl)methyl)-[1,2,4]triazolo[1,5-c]pyrimidin-7-yl)benzonitrile

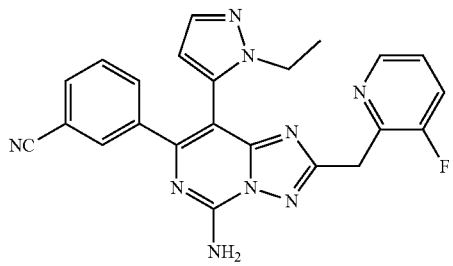 [SMILES: CCn1nccc1-c1c(-c2cccc(C#N)c2)nc(N)n2nc(Cc3ncccc3F)nc12]

Step 1: 2-(3-Fluoropyridin-2-yl)acetohydrazide

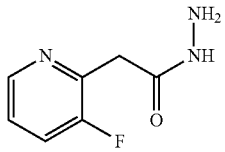 [SMILES: NNC(=O)Cc1ncccc1F]

Hunig's base (169 µL, 0.967 mmol) was added to a DMF (2149 µL) solution of 2-(3-fluoropyridin-2-yl)acetic acid (100 mg, 0.645 mmol), tert-butyl hydrazinecarboxylate (102 mg, 0.774 mmol), and BOP (428 mg, 0.967 mmol) at r.t. The reaction mixture was stirred at r.t. for 2 h, concentrated, and purified by flash chromatography on a silica gel column eluting with 0 to 10% MeOH in DCM. The purified intermediate tert-butyl 2-(2-(3-fluoropyridin-2-yl)acetyl)hydrazinecarboxylate was then treated with TFA (0.5 mL), stirred at r.t. overnight, concentrated, and diluted with ether. The resulting white precipitate was collected by filtration, and used in next step without further purification. LCMS calculated for $C_7H_9FN_3O$ (M+H)$^+$: 170.1; found 170.1.

Step 2: 3-(5-Amino-8-bromo-2-((3-fluoropyridin-2-yl)methyl)-[1,2,4]triazolo[1,5-c]pyrimidin-7-yl)benzonitrile

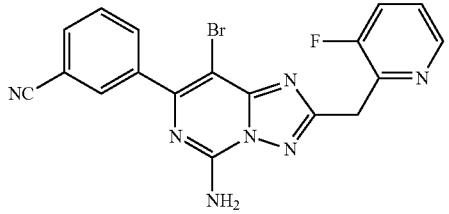 [SMILES: N#Cc1cccc(-c2nc(N)n3nc(Cc4ncccc4F)nc3c2Br)c1]

This compound was prepared using similar procedures as described for Example 41, Step 1 to Step 4, with 2-(3-fluoropyridin-2-yl)acetohydrazide replacing 2-(pyridin-2-yl)acetohydrazide in Step 3. LCMS calculated for $C_{18}H_{12}BrFN_7$ (M+H)$^+$: 424.0; found 424.0.

Step 3: 3-(5-Amino-8-(1-ethyl-1H-pyrazol-5-yl)-2-((3-fluoropyridin-2-yl)methyl)-[1,2,4]triazolo[1,5-c]pyrimidin-7-yl)benzonitrile This compound was prepared using similar procedures as described for Example 42 with 3-(5-amino-8-bromo-2-((3-fluoropyridin-2-yl)methyl)-[1,2,4]triazolo[1,5-c]pyrimidin-7-yl)benzonitrile replacing 3-(5-amino-8-bromo-2-(pyridin-2-ylmethyl)-[1,2,4]triazolo[1,5-c]pyrimidin-7-yl)benzonitrile. The final material was purified by preparative LC-MS (pH 2, acetonitrile/water with TFA) to afford the product as a TFA salt. LCMS calculated for $C_{25}H_{19}FN_9$ (M+H)$^+$: 440.2; found 440.2.

Example 53. 3-(5-Amino-8-(1-ethyl-1H-pyrazol-5-yl)-2-((3-methoxypyridin-2-yl)methyl)-[1,2,4]triazolo[1,5-c]pyrimidin-7-yl)benzonitrile

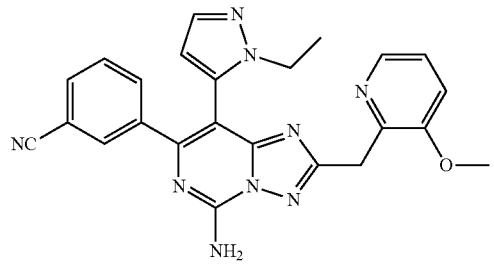 [SMILES: CCn1nccc1-c1c(-c2cccc(C#N)c2)nc(N)n2nc(Cc3ncccc3OC)nc12]

This compound was prepared using similar procedures as described for Example 52, with 2-(3-methoxypyridin-2-yl)acetic acid replacing 2-(3-fluoropyridin-2-yl)acetic acid in Step 1. The final material was purified by preparative LC-MS (pH 2, acetonitrile/water with TFA) to afford the product as a TFA salt. LCMS calculated for $C_{24}H_{22}N_9O$ (M+H)$^+$: 452.2; found 452.2.

Example 54. 3-(5-Amino-2-(2-(1-methyl-1H-pyrazol-4-yl)benzyl)-8-(pyrimidin-4-yl)-[1,2,4]triazolo[1,5-c]pyrimidin-7-yl)benzonitrile

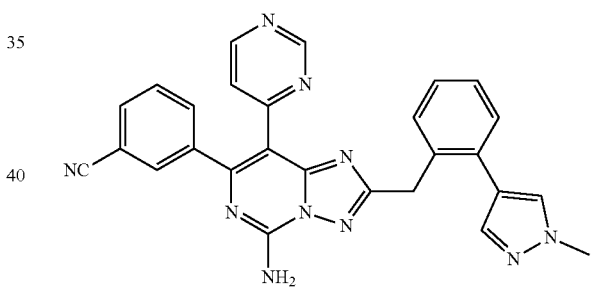

Step 1: 3-(5-Amino-2-(2-bromobenzyl)-[1,2,4]triazolo[1,5-c]pyrimidin-7-yl)benzonitrile

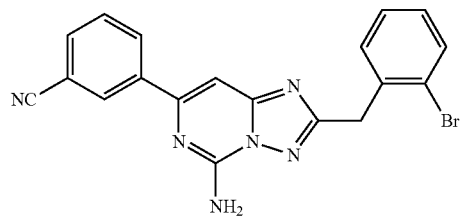 [SMILES: N#Cc1cccc(-c2cc3nc(Cc4ccccc4Br)nn3c(N)n2)c1]

This compound was prepared using similar procedures as described for Example 41, Step 1 to Step 3, with 2-(2-bromophenyl)acetohydrazide replacing 2-(pyridin-2-yl)acetohydrazide in Step 3. LCMS calculated for $C_{19}H_{14}BrN_6$ (M+H)$^+$: 405.0; found 405.0.

Step 2: 3-(5-Amino-2-(2-bromobenzyl)-8-iodo-[1,2,4]triazolo[1,5-c]pyrimidin-7-yl)benzonitrile

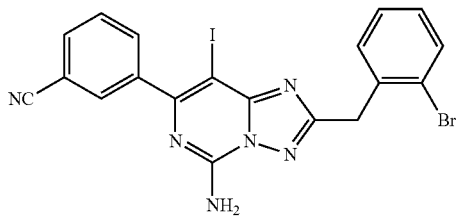 [SMILES: N#Cc1cccc(-c2nc(N)n3nc(Cc4ccccc4Br)nc3c2I)c1]

NIS (153 mg, 0.679 mmol) was added to a DMF (3084 μL) solution of 3-(5-amino-2-(2-bromobenzyl)-[1,2,4]triazolo[1,5-c]pyrimidin-7-yl)benzonitrile (250 mg, 0.617 mmol) at r.t. After stirring at 50° C. for 1 h, the reaction mixture was cooled to r.t., diluted with water and the resulting precipitate was collected by filtration. The brown solid was dissolved in DCM and purified by flash chromatography on a silica gel column eluting with 0 to 50% EtOAc in DCM to afford the desired product. LCMS calculated for $C_{19}H_{13}BrIN_6$ (M+H)$^+$: 531.0; found 531.0.

Step 3: 3-(5-Amino-2-(2-bromobenzyl)-8-(pyrimidin-4-yl)-[1,2,4]triazolo[1,5-c]pyrimidin-7-yl)benzonitrile

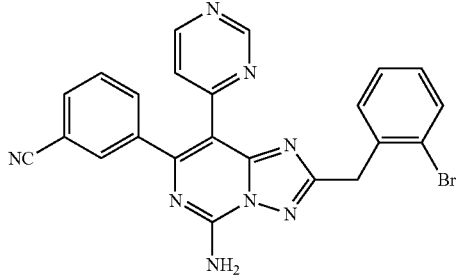 [SMILES: N#Cc1cccc(-c2nc(N)n3nc(Cc4ccccc4Br)nc3c2-c2ccncn2)c1]

This compound was prepared using similar procedures as described for Example 41, Step 5, with 3-(5-amino-2-(2-bromobenzyl)-8-iodo-[1,2,4]triazolo[1,5-c]pyrimidin-7-yl)benzonitrile replacing 3-(5-amino-8-bromo-2-(pyridin-2-ylmethyl)-[1,2,4]triazolo[1,5-c]pyrimidin-7-yl)benzonitrile. The final material was purified by flash chromatography on a silica gel column eluting with 0 to 15% MeOH in DCM to afford the desired product. LCMS calculated for $C_{23}H_{16}BrN_8$ (M+H)$^+$: 483.1; found 483.1.

Step 4: 3-(5-Amino-2-(2-(1-methyl-1H-pyrazol-4-yl)benzyl)-8-(pyrimidin-4-yl)-[1,2,4]triazolo[1,5-c]pyrimidin-7-yl)benzonitrile A mixture of 3-(5-amino-2-(2-bromobenzyl)-8-(pyrimidin-4-yl)-[1,2,4]triazolo[1,5-c]pyrimidin-7-yl)benzonitrile (10 mg, 0.021 mmol), (1-methyl-1H-pyrazol-4-yl)boronic acid (5.2 mg, 0.041 mmol), PdCl$_2$(dppf)-CH$_2$Cl$_2$ adduct (1.7 mg, 2.07 μmol), and sodium carbonate (2.2 mg, 0.021 mmol) in 1,4-dioxane (172 μL) and water (35 μL) was purged with N$_2$ and stirred at 90° C. for 1 h. The reaction mixture was cooled to r.t., concentrated, and purified by preparative LC-MS (pH 2, acetonitrile/water with TFA) to afford the product as a TFA salt. LCMS calculated for $C_{27}H_{21}N_{10}$ (M+H)$^+$: 485.2; found 485.1.

Example 55. 3-(5-Amino-2-(benzo[d]isoxazol-3-ylmethyl)-8-(1-ethyl-1H-pyrazol-5-yl)-[1,2,4]triazolo[1,5-c]pyrimidin-7-yl)benzonitrile

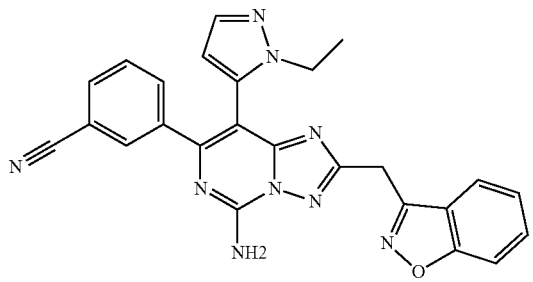 [SMILES: CCn1nccc1-c1c(-c2cccc(C#N)c2)nc(N)n2nc(Cc3noc4ccccc34)nc12]

Step 1: 3-(5-Amino-2-(benzo[d]isoxazol-3-ylmethyl)-8-bromo-[1,2,4]triazolo[1,5-c]pyrimidin-7-yl)benzonitrile

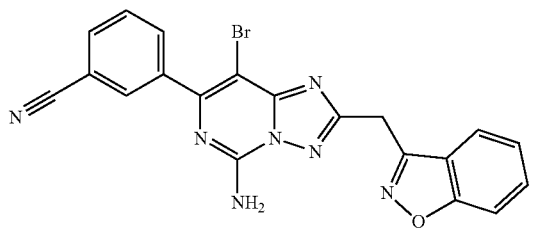 [SMILES: N#Cc1cccc(-c2nc(N)n3nc(Cc4noc5ccccc45)nc3c2Br)c1]

This compound was prepared using similar procedures as described in Example 41, Step 1 to Step 4, with 2-(benzo[d]isoxazol-3-yl)acetohydrazide in place of 2-(pyridin-2-yl)acetohydrazide in Step 3. LCMS calculated for $C_{20}H_{13}BrN_7O$ (M+H)$^+$: 446.3. Found: 446.1.

Step 2: 3-(5-Amino-2-(benzo[d]isoxazol-3-ylmethyl)-8-(1-ethyl-1H-pyrazol-5-yl)-[1,2,4]triazolo[1,5-c]pyrimidin-7-yl)benzonitrile A vial was charged with 3-(5-amino-2-(benzo[d]isoxazol-3-ylmethyl)-8-bromo-[1,2,4]triazolo[1,5-c]pyrimidin-7-yl)benzonitrile (24 mg, 0.054 mmol), (1-ethyl-1H-pyrazol-5-yl)boronic acid (17 mg, 0.12 mmol), XPhos Pd G2 (4.3 mg, 0.0054 mmol), K$_3$PO$_4$ (23 mg, 0.11 mmol), dioxane (1 mL) and water (0.2 mL). The reaction mixture was then heated and stirred at 80° C. for 1 h, cooled to r.t., diluted with saturated NH$_4$Cl solution (1 mL), and extracted with EtOAc (5 mL). The organic phase was separated, dried over Na$_2$SO$_4$, concentrated, and purified by preparative LC-MS (pH 2, acetonitrile/water with TFA) to afford the product as a TFA salt. LCMS calculated for $C_{25}H_{20}N_9O$ (M+H)$^+$: 462.2. Found: 462.2.

Example 56. 3-(5-Amino-8-(1-ethyl-1H-pyrazol-5-yl)-2-((1-methyl-1H-indazol-3-yl)methyl)-[1,2,4]triazolo[1,5-c]pyrimidin-7-yl)benzonitrile

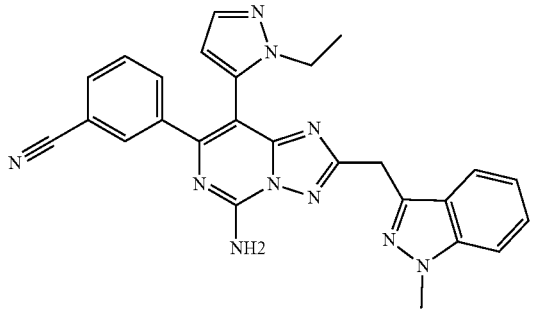 [SMILES: CCn1nccc1-c1c(-c2cccc(C#N)c2)nc(N)n2nc(Cc3nn(C)c4ccccc34)nc12]

Step 1: Ethyl 5-amino-8-bromo-7-(3-cyanophenyl)-[1,2,4]triazolo[1,5-c]pyrimidine-2-carboxylate

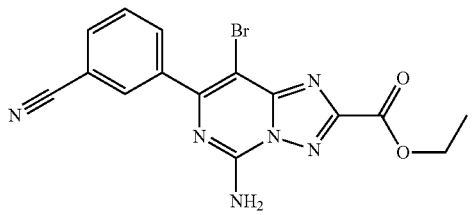 [SMILES: CCOC(=O)c1nc2c(Br)c(-c3cccc(C#N)c3)nc(N)n2n1]

This compound was prepared using the same procedures as described in Example 41, Step 1 to Step 4, with ethyl 2-hydrazinyl-2-oxoacetate in place of 2-(pyridin-2-yl)acetohydrazide in Step 3. LCMS calculated for $C_{15}H_{12}BrN_6O_2$ (M+H)$^+$: 387.2. Found: 387.0.

Step 2: 3-(5-Amino-8-bromo-2-(hydroxymethyl)-[1,2,4]triazolo[1,5-c]pyrimidin-7-yl)benzonitrile

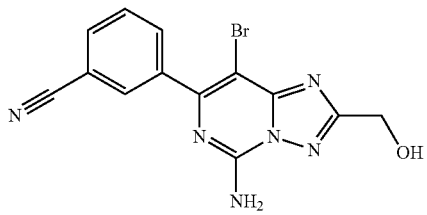 [SMILES: N#Cc1cccc(-c2nc(N)n3nc(CO)nc3c2Br)c1]

To a solution of ethyl 5-amino-8-bromo-7-(3-cyanophenyl)-[1,2,4]triazolo[1,5-c]pyrimidine-2-carboxylate (77 mg, 0.20 mmol) in THF (5 mL) at 0° C. was added LiBH$_4$ solution (0.2 mL, 2.0 M in THF) dropwise. The reaction mixture was stirred at r.t. for 10 min, then quenched by adding water (1 mL) and saturated Rochelle salt solution (5 mL). After stirring for another 2 h, the organic layer was separated, and the aqueous layer was extracted with EtOAc (3×5 mL). The combined organic layers were washed with brine, dried over Na$_2$SO$_4$, to afford the crude product, which was used in next step without further purification.

Step 3: 3-(5-Amino-8-(1-ethyl-1H-pyrazol-5-yl)-2-(hydroxymethyl)-[1,2,4]triazolo[1,5-c]pyrimidin-7-yl)benzonitrile To the crude 3-(5-amino-8-bromo-2-(hydroxymethyl)-[1,2,4]triazolo[1,5-c]pyrimidin-7-yl)benzonitrile from previous step was added (1-ethyl-1H-pyrazol-5-yl)boronic acid (47 mg, 0.34 mmol), XPhos Pd G2 (13 mg, 0.017 mmol), K$_3$PO$_4$ (71 mg, 0.34 mmol), dioxane (3 mL) and water (0.6 mL). The reaction mixture was heated and stirred at 90° C. for 1 h, cooled to r.t., diluted with saturated NH$_4$Cl solution (3 mL), and extracted with EtOAc (15 mL). The organic phase was separated, dried over Na$_2$SO$_4$, concentrated, and purified by flash chromatography (0 to 70% EtOAc in dichloromethane) to give the desired product (40 mg, 55%). LCMS calculated for $C_{18}H_{17}N_8O$ (M+H)$^+$: 361.1. Found: 361.1.

Step 4: 3-(5-Amino-2-(chloromethyl)-8-(1-ethyl-1H-pyrazol-5-yl)-[1,2,4]triazolo[1,5-c]pyrimidin-7-yl)benzonitrile 3-(5-Amino-8-(1-ethyl-1H-pyrazol-5-yl)-2-(hydroxymethyl)-[1,2,4]triazolo[1,5-c]pyrimidin-7-yl)benzonitrile (40 mg, 0.11 mmol) was dissolved in MeCN (2 mL). SOCl$_2$ (0.02 mL, 0.27 mmol) was added to the solution dropwise at r.t. The reaction mixture was stirred at r.t. for 30 min, quenched with saturated NaHCO$_3$ solution, and extracted with EtOAc (5×5 mL). the combined organic layers were dried over Na$_2$SO$_4$, and concentrated to afford the crude product, which was used in the next step without further purification.

Step 5: 3-(5-Amino-8-(1-ethyl-1H-pyrazol-5-yl)-2-((1-methyl-1H-indazol-3-yl)methyl)-[1,2,4]triazolo[1,5-c]pyrimidin-7-yl)benzonitrile A vial was charged with 3-(5-amino-2-(chloromethyl)-8-(1-ethyl-1H-pyrazol-5-yl)-[1,2,4]triazolo[1,5-c]pyrimidin-7-yl)benzonitrile (16 mg, 0.042 mmol), 1-methyl-3-(4,4,5,5-tetramethyl-1,3,2-dioxaborolan-2-yl)-1H-indazole (32 mg, 0.12 mmol), XPhos Pd G2 (3.3 mg, 0.0042 mmol), Cs₂CO₃ (41 mg, 0.13 mmol), and dioxane (1 mL). The reaction mixture was heated and stirred at 90° C. for 1 h, cooled to r.t., diluted with saturated NH₄Cl solution, and extracted with EtOAc (5 mL). The organic phase was separated, dried over Na₂SO₄, concentrated, and purified by preparative LC-MS (pH 2, acetonitrile/water with TFA) to afford the product as a TFA salt (2 mg, 10%). LCMS calculated for $C_{26}H_{23}N_{10}$ (M+H)⁺: 475.2. Found: 475.1.

Example 57. 3-(5-Amino-2-((3-hydroxyazetidin-1-yl)methyl)-8-(pyrimidin-4-yl)-[1,2,4]triazolo[1,5-c]pyrimidin-7-yl)benzonitrile

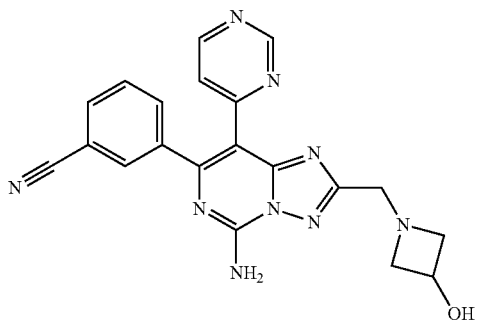 [SMILES: N#Cc1cccc(-c2nc(N)n3nc(CN4CC(O)C4)nc3c2-c2ccncn2)c1]

Step 1: 3-(5-Amino-2-(hydroxymethyl)-8-(pyrimidin-4-yl)-[1,2,4]triazolo[1,5-c]pyrimidin-7-yl)benzonitrile

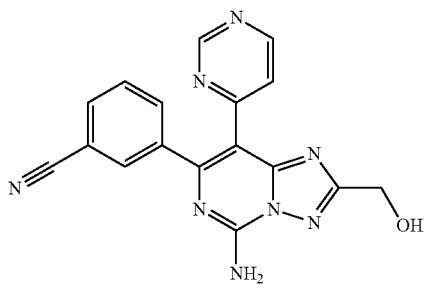 [SMILES: N#Cc1cccc(-c2nc(N)n3nc(CO)nc3c2-c2ccncn2)c1]

This compound was prepared using similar procedures as described for Example 41 Step 5 with 3-(5-amino-8-bromo-2-(hydroxymethyl)-[1,2,4]triazolo[1,5-c]pyrimidin-7-yl)benzonitrile (Example 56, Step 2) replacing 3-(5-amino-8-bromo-2-(pyridin-2-ylmethyl)-[1,2,4]triazolo[1,5-c]pyrimidin-7-yl)benzonitrile. LCMS calculated for $C_{17}H_{13}N_8O$ (M+H)⁺: 345.1; found 345.1.

Step 2: (5-Amino-7-(3-cyanophenyl)-8-(pyrimidin-4-yl)-[1,2,4]triazolo[1,5-c]pyrimidin-2-yl)methyl methanesulfonate

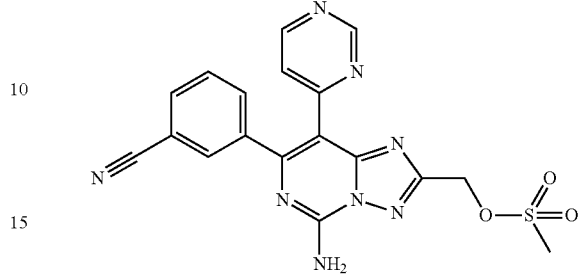

Methanesulfonyl chloride (11.3 μL, 0.145 mmol) was added to a mixture of 3-(5-amino-2-(hydroxymethyl)-8-(pyrimidin-4-yl)-[1,2,4]triazolo[1,5-c]pyrimidin-7-yl)benzonitrile (50 mg, 0.145 mmol) and pyridine (23.5 μL, 0.290 mmol) in DCM (4.0 mL) at 0° C. The reaction mixture was stirred at r.t. for 30 min, quenched with saturated NaHCO₃ solution, and extracted with EtOAc (3×10 mL). The combined organic layers were dried over MgSO₄, and concentrated to afford the desired product. LCMS calculated for $C_{18}H_{15}N_8O_3S$ (M+H)⁺: 423.1; found 423.1.

Step 3: 3-(5-Amino-2-((3-hydroxyazetidin-1-yl)methyl)-8-(pyrimidin-4-yl)-[1,2,4]triazolo[1,5-c]pyrimidin-7-yl)benzonitrile A mixture of (5-amino-7-(3-cyanophenyl)-8-(pyrimidin-4-yl)-[1,2,4]triazolo[1,5-c]pyrimidin-2-yl)methyl methanesulfonate (10.0 mg, 0.024 mmol), azetidin-3-ol hydrochloride (3.9 mg, 0.036 mmol), and DIPEA (8.3 μL, 0.047 mmol) in DMF (0.5 mL) was stirred at 90° C. until completion. The reaction mixture was then cooled to r.t., and directly purified by preparative LC-MS (pH 10, acetonitrile/water with NH₄OH) to give the desired product. LCMS calculated for $C_{20}H_{18}N_9O$ (M+H)⁺: 400.2; found 400.2.

Example 58. 3-(5-Amino-8-(3-methylpyridin-4-yl)-2-(pyridin-2-ylmethyl)-[1,2,4]triazolo[1,5-c]pyrimidin-7-yl)benzonitrile

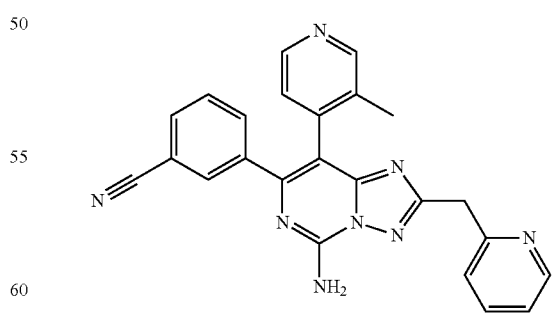

This compound was prepared using similar procedures as described in Example 42 using 3-methylpyridin-4-ylboronic acid in place of 1-ethyl-5-(4,4,5,5-tetramethyl-1,3,2-dioxaborolan-2-yl)-1H-pyrazole. The final material was purified by preparative LC-MS (pH 2, acetonitrile/water with TFA)

Example 59. 3-(5-Amino-8-(2-methoxy-6-methylpyridin-4-yl)-2-(pyridin-2-ylmethyl)-[1,2,4]triazolo[1,5-c]pyrimidin-7-yl)benzonitrile

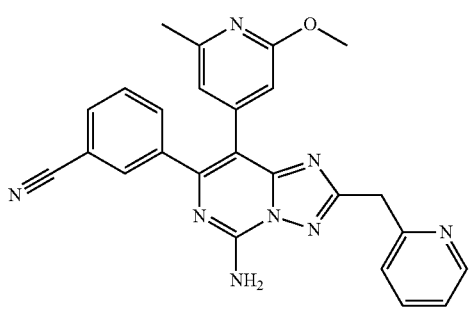 [SMILES: COc1cc(-c2c(-c3cccc(C#N)c3)nc(N)n3nc(Cc4ccccn4)nc23)cc(C)n1]

This compound was prepared using similar procedures as described in Example 42 using 2-methoxy-6-methylpyridin-4-ylboronic acid in place of 1-ethyl-5-(4,4,5,5-tetramethyl-1,3,2-dioxaborolan-2-yl)-1H-pyrazole. The final material was purified by preparative LC-MS (pH 2, acetonitrile/water with TFA) to afford the product as a TFA salt. LCMS calculated for $C_{25}H_{21}N_8O$ (M+H)$^+$: 449.2; Found: 449.3.

Example 60. 3-(5-Amino-8-(pyrazolo[1,5-b]pyridazin-3-yl)-2-(pyridin-2-ylmethyl)-[1,2,4]triazolo[1,5-c]pyrimidin-7-yl)benzonitrile

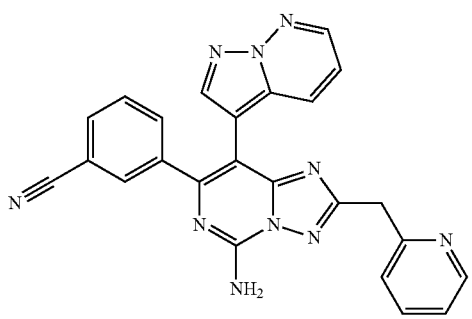 [SMILES: N#Cc1cccc(-c2nc(N)n3nc(Cc4ccccn4)nc3c2-c2cnn3ncccc23)c1]

This compound was prepared using similar procedures as described in Example 42 using 3-(4,4,5,5-tetramethyl-1,3,2-dioxaborolan-2-yl)pyrazolo[1,5-b]pyridazine in place of 1-ethyl-5-(4,4,5,5-tetramethyl-1,3,2-dioxaborolan-2-yl)-1H-pyrazole. The final material was purified by preparative LC-MS (pH 2, acetonitrile/water with TFA) to afford the product as a TFA salt. LCMS calculated for $C_{24}H_{17}N_{10}$ (M+H)$^+$: 445.2; Found: 445.3.

Example 61. 3-(5-Amino-8-(4-methyloxazol-5-yl)-2-(pyridin-2-ylmethyl)-[1,2,4]triazolo[1,5-c]pyrimidin-7-yl)benzonitrile

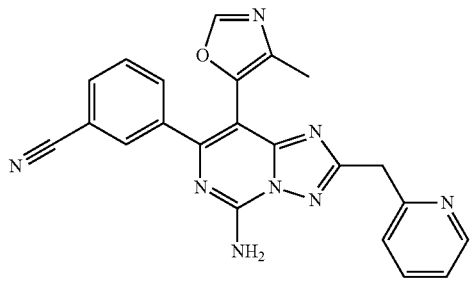 [SMILES: Cc1ncoc1-c1c(-c2cccc(C#N)c2)nc(N)n2nc(Cc3ccccn3)nc12]

Step 1: 4-Methyl-5-(4,4,5,5-tetramethyl-1,3,2-dioxaborolan-2-yl)oxazole

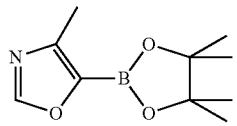

To a mixture of (1,5-cyclooctadiene)(methoxy)iridium(I) dimer (20 mg, 0.030 mmol) in pentane (2 mL) under $N_2$ gas was added 4,4,5,5-tetramethyl-1,3,2-dioxaborolane (0.22 mL, 1.5 mmol) at r.t. After stirring for 15 min, 4,4'-di-tert-butyl-2,2'-dipyridyl was added and the resulting mixture was stirred for another 15 min before a solution of 3-methyloxazole (83 mg, 1.0 mmol) in $Et_2O$ (2 mL) was added. The reaction mixture was then stirred at r.t. for 2 h, and concentrated to afford the crude product, which was used in the next step without further purification. LC-MS calculated for $C_{10}H_{17}BNO_3$ (M+H)$^+$: m/z=210.1; found 210.1.

Step 2: 3-(5-Amino-8-(4-methyloxazol-5-yl)-2-(pyridin-2-ylmethyl)-[1,2,4]triazolo[1,5-c]pyrimidin-7-yl)benzonitrile This compound was prepared using similar procedures as described in Example 42 using 4-methyl-5-(4,4,5,5-tetramethyl-1,3,2-dioxaborolan-2-yl)oxazole in place of 1-ethyl-5-(4,4,5,5-tetramethyl-1,3,2-dioxaborolan-2-yl)-1H-pyrazole. The final material was purified by preparative LC-MS (pH 2, acetonitrile/water with TFA) to afford the product as a TFA salt. LCMS calculated for $C_{22}H_{17}N_8O$ (M+H)$^+$: 409.1. Found: 409.2.

Example 62. 3-(5-Amino-8-(4-(hydroxymethyl)-2-methyloxazol-5-yl)-2-(pyridin-2-ylmethyl)-[1,2,4]triazolo[1,5-c]pyrimidin-7-yl)benzonitrile

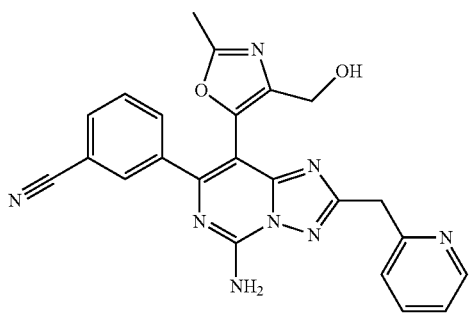 [SMILES: Cc1nc(CO)c(-c2c(-c3cccc(C#N)c3)nc(N)n3nc(Cc4ccccn4)nc23)o1]

Step 1: 4-((tert-Butyldimethylsilyloxy)methyl)-2-methyloxazole

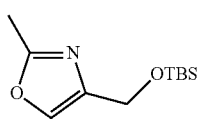

To a solution of (2-methyloxazol-4-yl)methanol (1.0 g, 8.84 mmol) and imidazole (0.90 g, 13.3 mmol) in DCM (20 ml) was added TBSCl (1.5 g, 9.7 mmol). The reaction mixture was stirred at r.t. for 2 h, and concentrated. The resulting residue was then diluted with Et$_2$O (20 mL), washed with saturated NH$_4$Cl solution and brine, dried over MgSO$_4$, and concentrated to afford the crude product which was used in the next step without further purification. LC-MS calculated for C$_{11}$H$_{22}$NO$_2$Si (M+H)$^+$: m/z=228.1; found 228.1.

Step 2: 4-((tert-Butyldimethylsilyloxy)methyl)-2-methyl-5-(4,4,5,5-tetramethyl-1,3,2-dioxaborolan-2-yl)oxazole

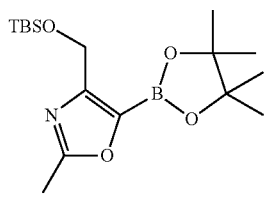

This compound was prepared using similar procedures as described in Example 61, Step 1, using 4-((tert-butyldimethylsilyloxy)methyl)-2-methyloxazole in place of 3-methyloxazole. LCMS calculated for C$_{17}$H$_{33}$BNO$_4$Si (M+H)$^+$: 354.2. Found: 354.2.

Step 3: 3-(5-Amino-8-(4-((tert-butyldimethylsilyloxy)methyl)-2-methyloxazol-5-yl)-2-(pyridin-2-ylmethyl)-[1,2,4]triazolo[1,5-c]pyrimidin-7-yl)benzonitrile

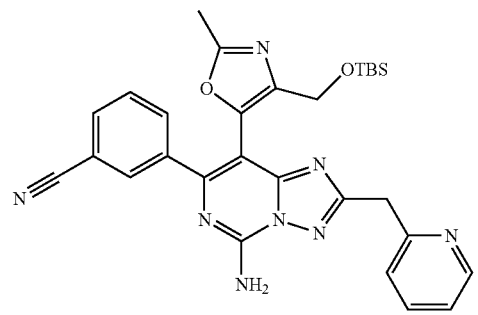 [SMILES: Cc1nc(CO[Si](C)(C)C(C)(C)C)c(-c2c(-c3cccc(C#N)c3)nc(N)n3nc(Cc4ccccn4)nc23)o1]

This compound was prepared using similar procedures as described of Example 42 using 4-((tert-butyldimethylsilyloxy)methyl)-2-methyl-5-(4,4,5,5-tetramethyl-1,3,2-dioxaborolan-2-yl)oxazole in place of 1-ethyl-5-(4,4,5,5-tetramethyl-1,3,2-dioxaborolan-2-yl)-1H-pyrazole. The crude material from this step was used in the next step without further purification. LCMS calculated for C$_{29}$H$_{33}$N$_8$O$_2$Si (M+H)$^+$: 553.2. Found: 553.2.

Step 4: 3-(5-Amino-8-(4-(hydroxymethyl)-2-methyloxazol-5-yl)-2-(pyridin-2-ylmethyl)-[1,2,4]triazolo[1,5-c]pyrimidin-7-yl)benzonitrile The crude material from previous step was treated with TFA (0.5 mL) and stirred for 0.5 h at 100° C. The reaction mixture was cooled to r.t., diluted with MeOH, and purified by preparative LC-MS (pH 2, acetonitrile/water with TFA) to afford the product as a TFA salt.

LCMS calculated for C$_{23}$H$_{19}$N$_8$O$_2$ (M+H)$^+$: 439.2; Found: 439.3.

Example 63. 3-(5-Amino-8-(4-(methoxymethyl)-2-methyloxazol-5-yl)-2-(pyridin-2-ylmethyl)-[1,2,4]triazolo[1,5-c]pyrimidin-7-yl)benzonitrile

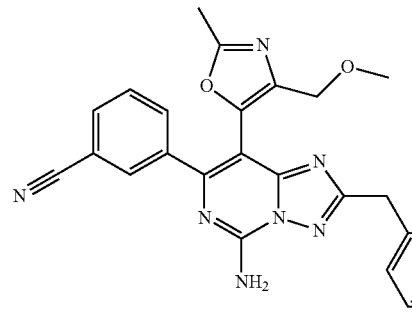

Step 1: 4-(Methoxymethyl)-2-methyloxazole

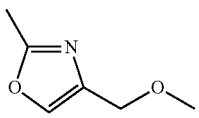

To a solution of (2-methyloxazol-4-yl)methanol (113 mg, 1.0 mmol) in THF (10 ml) was added NaH (48 mg, 60 wt %, 1.2 mmol) at 0° C. After stirring for 0.5 h, iodomethane (170 mg, 1.2 mmol) was added. The reaction mixture was stirred at r.t. for 2 h, diluted with $Et_2O$ (20 mL), washed with saturated $NH_4Cl$ solution and brine, dried over $MgSO_4$, and concentrated to give the crude product which was used in the next step without further purification. LC-MS calculated for $C_6H_{10}NO_2$ $(M+H)^+$: m/z=128.1; found 128.1.

Step 2: 4-(Methoxymethyl)-2-methyl-5-(4,4,5,5-tetramethyl-1,3,2-dioxaborolan-2-yl)oxazole

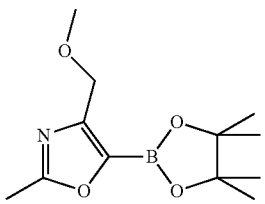

This compound was prepared using similar procedures as described of Example 61, Step 1, using 4-(methoxymethyl)-2-methyloxazole in place of 3-methyloxazole. LCMS calculated for $C_{12}H_{21}BNO_4$ $(M+H)^+$: 254.2; Found: 254.2.

Step 3: 3-(5-Amino-8-(4-(methoxymethyl)-2-methyloxazol-5-yl)-2-(pyridin-2-ylmethyl)-[1,2,4]triazolo[1,5-c]pyrimidin-7-yl)benzonitrile This compound was prepared using similar procedures as described in Example 42 using 4-(methoxymethyl)-2-methyl-5-(4,4,5,5-tetramethyl-1,3,2-dioxaborolan-2-yl)oxazole in place of 1-ethyl-5-(4,4,5,5-tetramethyl-1,3,2-dioxaborolan-2-yl)-1H-pyrazole. The final material was purified by preparative LC-MS (pH 2, acetonitrile/water with TFA) to afford the product as a TFA salt. LCMS calculated for $C_{24}H_{21}N_8O_2$ $(M+H)^+$: 453.2. Found: 453.2.

Examples 64-65. (S)-3-(5-amino-2-(hydroxy(phenyl)methyl)-8-(pyrimidin-4-yl)-[1,2,4]triazolo[1,5-c]pyrimidin-7-yl)benzonitrile (Example 64) & (R)-3-(5-amino-2-(hydroxy(phenyl)methyl)-8-(pyrimidin-4-yl)-[1,2,4]triazolo[1,5-c]pyrimidin-7-yl)benzonitrile (Example 65)

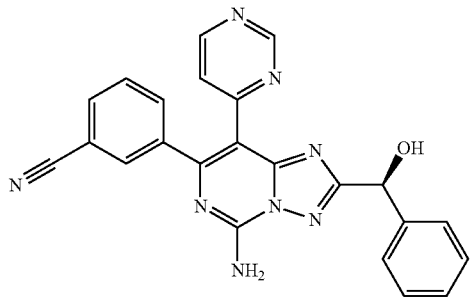

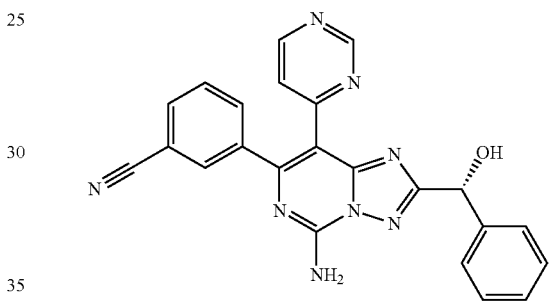

These compounds were prepared using similar procedures as described for Example 41, with 2-hydroxy-2-phenylacetohydrazide (Alfa Aesar-L11653) replacing 2-(pyridin-2-yl)acetohydrazide in Step 3. The two enantiomers were first separated by chiral HPLC using a Phenomenex Lux Cellulose-4 column (21.2×250 mm, 5 μm particle size) eluting with an isocratic mobile phase 45% EtOH in hexanes with a flow rate of 20 mL/minute. The retention times of Peak 1 (Example 64) and Peak 2 (Example 65) were 9.47 min and 14.42 min, respectively. Following their separation, the enantiomers were individually purified by prep-LCMS (pH=2, MeCN/water with TFA) to give the desired products both as TFA salt. For both products, LC-MS calculated for $C_{23}H_{17}N_8O$ $(M+H)^+$: m/z=421.2; found 421.3.

Alternatively, Example 64 could be prepared using similar procedures as described for Example 41, with methyl (S)-(+)-mandelate (Sigma-Aldrich-251542) replacing methyl 2-(pyridin-2-yl)acetate in Step 2. The crude material was purified by prep-LCMS (pH=2, MeCN/water with TFA) to give the desired product as a TFA salt. LC-MS calculated for $C_{23}H_{17}N_8O$ $(M+H)^+$: m/z=421.2; found 421.3.

Example 65 could be prepared using similar procedures as described for Example 41, with methyl (R)-(−)-mandelate (Sigma-Aldrich-251550) replacing methyl 2-(pyridin-2-yl)acetate in Step 2. The crude material was purified by prep-LCMS (pH=2, MeCN/water with TFA) to give the desired product as a TFA salt. LC-MS calculated for $C_{23}H_{17}N_8O$ $(M+H)^+$: m/z=421.2; found 421.3.

Example 66. 3-(5-Amino-2-benzoyl-8-(pyrimidin-4-yl)-[1,2,4]triazolo[1,5-c]pyrimidin-7-yl)benzonitrile

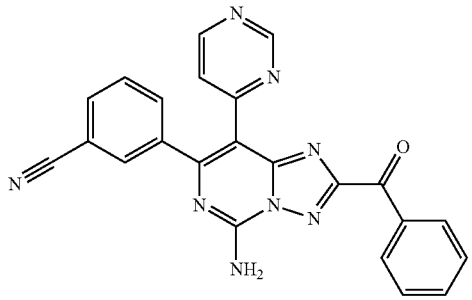 [SMILES: N#Cc1cccc(-c2nc(N)n3nc(C(=O)c4ccccc4)nc3c2-c2ccncn2)c1]

To solution of 3-(5-amino-2-(hydroxy(phenyl)methyl)-8-(pyrimidin-4-yl)-[1,2,4]triazolo[1,5-c]pyrimidin-7-yl)benzonitrile (from Example 64) (370 mg, 0.87 mmol) in acetonitrile (7.2 mL) and DMF (1.4 mL) was added tetrakisacetonitrile copper(I) triflate (65 mg, 0.17 mmol), 4,4'-dimethoxy-2,2'-bipyridine (38 mg, 0.17 mmol), 9-azabicyclo[3.3.1]nonane N-oxyl (5.8 mg, 0.04 mmol), and 1-methyl-1H-imidazole (28 µL, 0.35 mmol). The reaction mixture was stirred for 30 min open to air at r.t., and then volatiles were removed under reduced pressure. The crude material was purified by prep-LCMS (pH=2, MeCN/water with TFA) to give the desired product as a TFA salt. LC-MS calculated for $C_{23}H_{15}N_8O$ (M+H)$^+$: m/z=419.1; found 419.3.

Example 67. 3-(5-Amino-8-(1-ethyl-1H-pyrazol-5-yl)-2-(1-phenylcyclopropyl)-[1,2,4]triazolo[1,5-c]pyrimidin-7-yl)benzonitrile

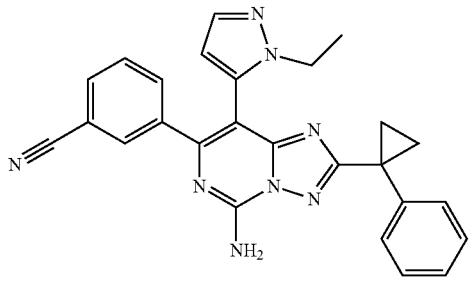 [SMILES: CCn1nccc1-c1c(-c2cccc(C#N)c2)nc(N)n2nc(C3(c4ccccc4)CC3)nc12]

Step 1: 3-(5-Amino-8-bromo-2-(1-phenylcyclopropyl)-[1,2,4]triazolo[1,5-c]pyrimidin-7-yl)benzonitrile

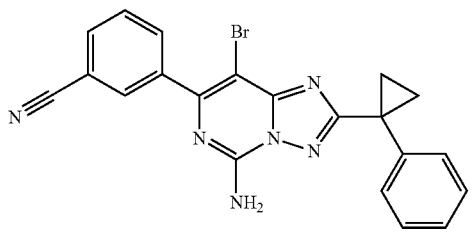 [SMILES: N#Cc1cccc(-c2nc(N)n3nc(C4(c5ccccc5)CC4)nc3c2Br)c1]

To a solution of 3-(5-amino-2-(1-phenylcyclopropyl)-[1,2,4]triazolo[1,5-c]pyrimidin-7-yl)benzonitrile (prepared using similar procedures as described for Example 41, Step 1 to Step 4, with 1-phenylcyclopropane-1-carbohydrazide replacing 2-(pyridin-2-yl)acetohydrazide in Step 3) (380 mg, 1.1 mmol) in DMF (2.1 mL) was slowly added NBS (190 mg, 1.1 mmol) at 0° C. The reaction mixture was then stirred at r.t. for 30 min before water (10 mL) was added. The resulting solid was collected by filtration, and dried to obtain the desired product. LC-MS calculated for $C_{21}H_{16}BrN_6$ (M+H)$^+$: m/z=431.0; found 431.2.

Step 2: 3-(5-Amino-8-(1-ethyl-1H-pyrazol-5-yl)-2-(1-phenylcyclopropyl)-[1,2,4]triazolo[1,5-c]pyrimidin-7-yl)benzonitrile A mixture of 3-(5-amino-8-bromo-2-(1-phenylcyclopropyl)-[1,2,4]triazolo[1,5-c]pyrimidin-7-yl)benzonitrile (20 mg, 0.046 mmol), 1-ethyl-5-(4,4,5,5-tetramethyl-1,3,2-dioxaborolan-2-yl)-1H-pyrazole (10 mg, 0.046 mmol), XPhos Pd G2 (7.0 mg, 9.3 µmol), and $Na_2CO_3$ (20 mg, 0.19 mmol) in 1,4-dioxane (0.50 mL) and water (0.05 mL) was flushed with nitrogen and sealed. The reaction mixture was stirred at 110° C. for 1 h, cooled to room temperature, diluted with methanol, and purified with prep-LC-MS (pH=2, MeCN/water with TFA) to give the desired product as a TFA salt. LC-MS calculated for $C_{26}H_{23}N_8$ (M+H)$^+$: m/z=447.2; found 447.3.

Example 68. 2-((7-(3-Cyanophenyl)-2-(hydroxy(phenyl)methyl)-8-(pyrimidin-4-yl)-[1,2,4]triazolo[1,5-c]pyrimidin-5-yl)amino)nicotinonitrile

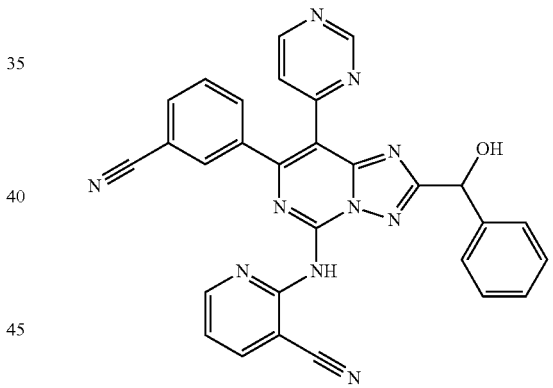

Step 1: 2-((8-Bromo-7-(3-cyanophenyl)-2-(hydroxy(phenyl)methyl)-[1,2,4]triazolo[1,5-c]pyrimidin-5-yl)amino)nicotinonitrile

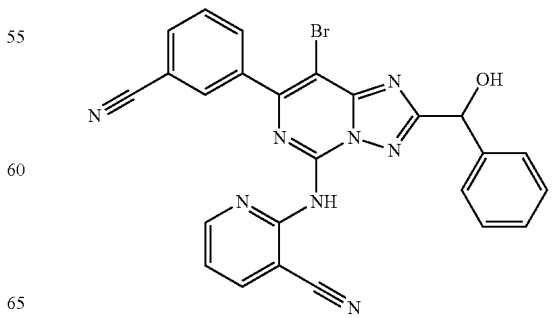

To a solution of 3-(5-amino-8-bromo-2-(hydroxy(phenyl) methyl)-[1,2,4]triazolo[1,5-c]pyrimidin-7-yl)benzonitrile (from Example 45, Step 1) (50 mg, 0.12 mmol) in THF (0.60 mL) was slowly added sodium hydride (7.1 mg, 0.18 mmol, 60 wt %) at 0° C. The reaction mixture was then stirred at r.t. for 30 min before 2-fluoronicotinonitrile (23 mg, 0.19 mmol) was added. The reaction mixture was then stirred at reflux for 2 h, quenched with water (5 mL), and extracted with EtOAc (5×5 mL). The combined organic layers were washed with water and brine, dried with $MgSO_4$, and concentrated. The resulting material was purified by column chromatography eluting with 0-20% MeOH/DCM to give the desired product. LC-MS calculated for $C_{25}H_{16}BrN_8O$ $(M+H)^+$: m/z=523.0; found 523.0.

Step 2: 2-((7-(3-Cyanophenyl)-2-(hydroxy(phenyl) methyl)-8-(pyrimidin-4-yl)-[1,2,4]triazolo[1,5-c] pyrimidin-5-yl)amino)nicotinonitrile A mixture of 2-((8-bromo-7-(3-cyanophenyl)-2-(hydroxy (phenyl)methyl)-[1,2,4]triazolo[1,5-c]pyrimidin-5-yl) amino)nicotinonitrile (25 mg, 0.05 mmol), 4-(tributylstannyl)pyrimidine (17 µL, 0.05 mmol), tetrakis (triphenylphosphine)palladium(0) (5.6 mg, 4.9 µmol), copper(I) iodide (1.9 mg, 9.8 µmol) and cesium fluoride (15 mg, 0.10 mmol) in dioxane (0.50 mL) was heated and stirred at 140° C. for 60 min in a microwave reactor. The reaction mixture was then cooled to r.t., filtered through a Celite plug (washed with DCM), and concentrated. The resulting residue was purified by prep-LC-MS (pH=2, MeCN/water with TFA) to give the desired product as a TFA salt. LC-MS calculated for $C_{29}H_{19}N_{10}O$ $(M+H)^+$: m/z=523.2; found 523.2.

Example 69. 3-(5-Amino-2-((cyano(phenyl)methyl) amino)-8-(pyrimidin-4-yl)-[1,2,4]triazolo[1,5-c]pyrimidin-7-yl)benzonitrile

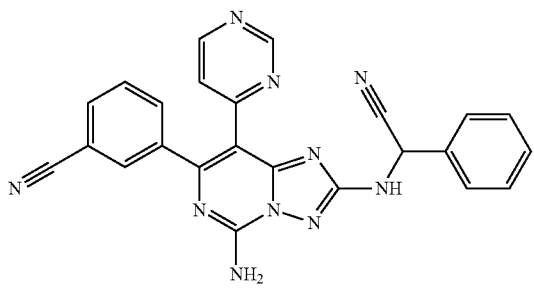 [SMILES: N#Cc1cccc(-c2nc(N)n3nc(NC(C#N)c4ccccc4)nc3c2-c2ccncn2)c1]

Step 1: 6-Chloro-$N^2$,$N^2$-bis(4-methoxybenzyl)pyrimidine-2,4-diamine

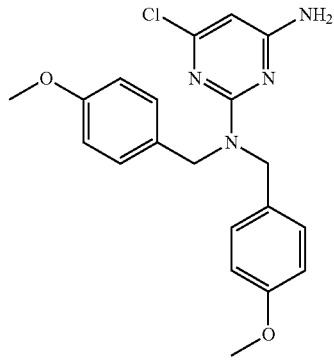 [SMILES: COc1ccc(CN(Cc2ccc(OC)cc2)c2nc(N)cc(Cl)n2)cc1]

To a solution of 2,6-dichloropyrimidin-4-amine (5.0 g, 31 mmol) in 2-propanol (31 mL) was added N,N-diisopropylethylamine (6.4 ml, 37 mmol) and bis(4-methoxybenzyl) amine (7.9 g, 31 mmol). The resulting solution was stirred at 100° C. for 16 h, cooled to r.t., diluted with water (100 mL), and extracted with EtOAc (100 mL). The organic layer was washed with water and brine, dried over anhydrous sodium sulfate, and concentrated to yield the crude product, which was used in the next step without further purification. LC-MS calculated for $C_{20}H_{22}ClN_4O_2$ $(M+H)^+$: 385.1; found 385.1.

Step 2: 7-Chloro-$N^5$,$N^5$-bis(4-methoxybenzyl)-[1,2,4]triazolo[1,5-c]pyrimidine-2,5-diamine

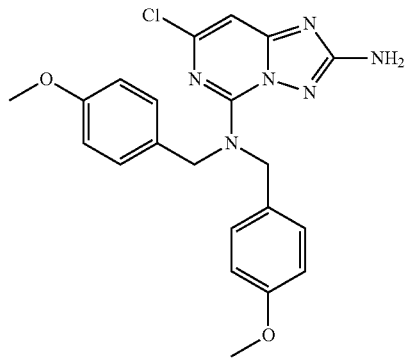 [SMILES: COc1ccc(CN(Cc2ccc(OC)cc2)c2nc(Cl)cc3nc(N)nn23)cc1]

O-ethyl carbonisothiocyanatidate (3.1 mL, 26 mmol) was added to a 1,4-dioxane (5.0 mL) solution of 6-chloro-$N^2$, $N^2$-bis(4-methoxybenzyl)pyrimidine-2,4-diamine (1.0 g, 2.6 mmol) at r.t. The reaction mixture was then stirred at 90° C. overnight, cooled to r.t., and concentrated. The resulting material was dissolved in methanol (12 mL) and ethanol (12 mL), and N,N-diisopropylethylamine (0.91 mL, 5.2 mmol) was added, followed by hydroxylamine hydrochoride (0.54 g, 7.8 mmol). The reaction mixture was stirred at 45° C. for 2 h, cooled to r.t., and concentrated. The resulting material was taken into EtOAc, washed with water, dried over anhydrous sodium sulfate, and concentrated. The crude material was then purified by silica gel chromatography eluting with 0% to 50% EtOAc in hexanes to afford the product. LC-MS calculated for $C_{21}H_{22}ClN_6O_2$ $(M+H)^+$: 425.1; found 425.2.

Step 3: 3-(2-Amino-5-(bis(4-methoxybenzyl)amino)-[1,2,4]triazolo[1,5-c]pyrimidin-7-yl)benzonitrile

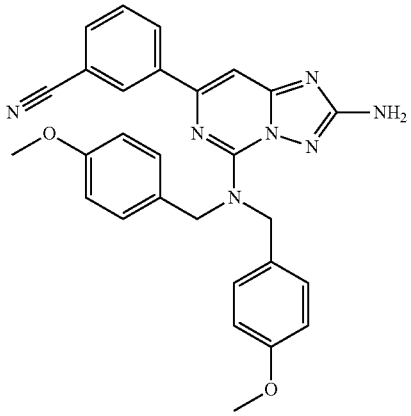 [SMILES: COc1ccc(CN(Cc2ccc(OC)cc2)c2nc(-c3cccc(C#N)c3)cc3nc(N)nn23)cc1]

Chloro(2-dicyclohexylphosphino-2',4',6'-tri-i-propyl-1,1'-biphenyl)(2'-amino-1,1'-biphenyl-2-yl) palladium(II) (330 mg, 0.42 mmol) was added to a mixture of (3-cyanophenyl)boronic acid (460 mg, 3.2 mmol), 7-chloro-$N^5,N^5$-bis(4-methoxybenzyl)-[1,2,4]triazolo[1,5-c]pyrimidine-2,5-diamine (890 mg, 2.1 mmol), and sodium carbonate (890 mg, 8.4 mmol) in 1,4-dioxane (8.8 mL) and water (1.8 mL). The mixture was purged with $N_2$ and stirred at 95° C. overnight. The reaction mixture was then cooled to r.t., concentrated, and purified by silica gel chromatography eluting with 0% to 50% EtOAc in DCM to afford the desired product. LC-MS calculated for $C_{28}H_{26}N_7O_2$ (M+H)$^+$: 492.2; found 492.2.

Step 4: 3-(2-Amino-5-(bis(4-methoxybenzyl)amino)-8-bromo-[1,2,4]triazolo[1,5-c]pyrimidin-7-yl)benzonitrile

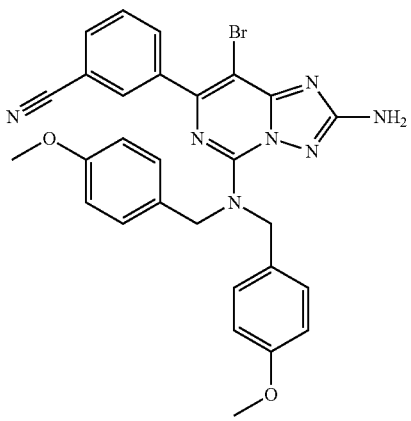 [SMILES: COc1ccc(CN(Cc2ccc(OC)cc2)c2nc(-c3cccc(C#N)c3)c(Br)c3nc(N)nn23)cc1]

To a solution of 3-(2-amino-5-(bis(4-methoxybenzyl)amino)-[1,2,4]triazolo[1,5-c]pyrimidin-7-yl)benzonitrile (330 mg, 0.66 mmol) in DMF (1.4 mL) was slowly added NBS (120 mg, 0.66 mmol) at 0° C. The reaction mixture was then stirred at r.t. for 30 min before water (10 mL) was added. The resulting solid was collected by filtration, and dried to obtain the desired product. LC-MS calculated for $C_{28}H_{25}BrN_7O_2$ (M+H)$^+$: m/z=570.1; found 570.2.

Step 5: 3-(2-Amino-5-(bis(4-methoxybenzyl)amino)-8-(pyrimidin-4-yl)-[1,2,4]triazolo[1,5-c]pyrimidin-7-yl)benzonitrile

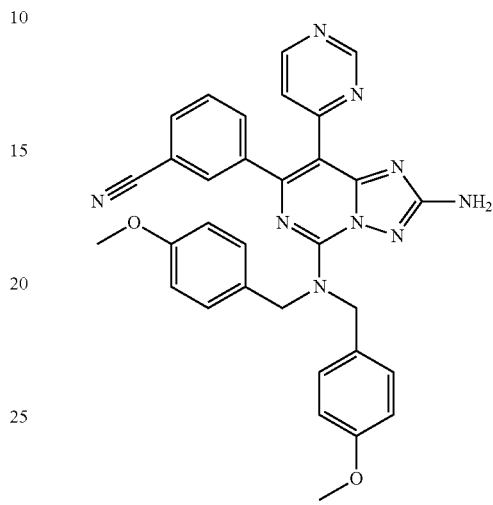

A mixture of 3-(2-amino-5-(bis(4-methoxybenzyl)amino)-8-bromo-[1,2,4]triazolo[1,5-c]pyrimidin-7-yl)benzonitrile (350 mg, 0.61 mmol), 4-(tributylstannyl)pyrimidine (210 µL, 0.67 mmol), tetrakis(triphenylphosphine)palladium(0) (70 mg, 0.060 mmol), copper(I) iodide (23 mg, 0.12 mmol) and cesium fluoride (180 mg, 1.2 mmol) in dioxane (4.7 mL) was heated and stirred at 140° C. for 30 min in a microwave reactor. The reaction mixture was then cooled to r.t., filtered through a Celite plug (washed with DCM), and concentrated. The resulting material was purified by silica gel column chromatography eluting with 0-20% MeOH/DCM to give the desired product. LC-MS calculated for $C_{32}H_{28}N_9O_2$ (M+H)$^+$: m/z=570.2; found 570.3.

Step 6: 3-(5-Amino-2-((cyano(phenyl)methyl)amino)-8-(pyrimidin-4-yl)-[1,2,4]triazolo[1,5-c]pyrimidin-7-yl)benzonitrile A mixture of 3-(2-amino-5-(bis(4-methoxybenzyl)amino)-8-(pyrimidin-4-yl)-[1,2,4]triazolo[1,5-c]pyrimidin-7-yl)benzonitrile (20 mg, 0.04 mmol) and benzaldehyde (7.2 µL, 0.070 mmol) in DCM (0.20 mL) and methanol (0.20 mL) were heated and stirred at 100° C. for 5 min. The reaction mixture was cooled to r.t. and trimethylsilyl cyanide (19 µL, 0.14 mmol) was added. After stirring at 100° C. for 30 min, the reaction mixture was cooled to r.t., diluted with EtOAc, washed with water and brine, dried over anhydrous sodium sulfate, and concentrated. Trifluoroacetic acid (1.0 mL) was then added to the resulting residue and the mixture was stirred at 100° C. for 30 min, cooled to r.t., and concentrated. The resulting residue was purified by prep-LC-MS (pH=2, MeCN/water with TFA) to give the desired product as a TFA salt. LC-MS calculated for $C_{24}H_{17}N_{10}$ (M+H)$^+$: m/z=445.2; found 445.2.

Example 70. 3-(5-Amino-8-(pyridin-4-yl)-2-(tetrahydrofuran-3-yl)-[1,2,4]triazolo[1,5-c]pyrimidin-7-yl)benzonitrile

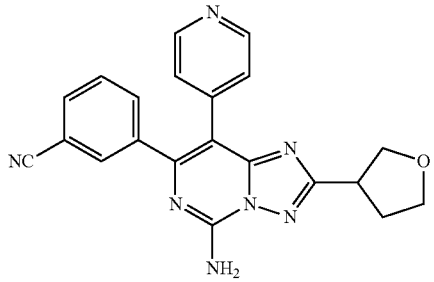 [SMILES: N#Cc1cccc(-c2nc(N)n3nc(C4CCOC4)nc3c2-c2ccncc2)c1]

Step 1: 3-(5-Amino-8-bromo-2-(tetrahydrofuran-3-yl)-[1,2,4]triazolo[1,5-c]pyrimidin-7-yl)benzonitrile

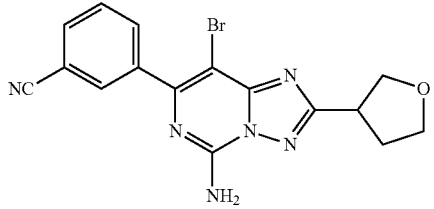 [SMILES: N#Cc1cccc(-c2nc(N)n3nc(C4CCOC4)nc3c2Br)c1]

This compound was prepared using similar procedures as described for Example 41, Step 1 to Step 4, with tetrahydrofuran-3-carbohydrazide replacing 2-(pyridin-2-yl)acetohydrazide in Step 3. LCMS calculated for $C_{16}H_{14}BrN_6O$ (M+H)$^+$: 385.0; found 385.0.

Step 2: 3-(5-Amino-8-(pyridin-4-yl)-2-(tetrahydrofuran-3-yl)-[1,2,4]triazolo[1,5-c]pyrimidin-7-yl)benzonitrile A mixture of 3-(5-amino-8-bromo-2-(tetrahydrofuran-3-yl)-[1,2,4]triazolo[1,5-c]pyrimidin-7-yl)benzonitrile (15 mg, 0.039 mmol), pyridin-4-ylboronic acid (10 mg, 0.078 mmol), chloro(2-dicyclohexylphosphino-2',4',6'-triisopropyl-1,1-biphenyl) [2-(2'-amino-1,1'-biphenyl)]palladium(II) (3.1 mg, 3.89 µmol), and sodium carbonate (12.4 mg, 0.117 mmol) in 1,4-dioxane (1.0 mL) and water (0.2 mL) was purged with $N_2$ and stirred at 90° C. overnight. The reaction mixture was then cooled to r.t., concentrated, and purified by prep-LC-MS (pH=2, MeCN/water with TFA) to give the desired product as a TFA salt. LC-MS calculated for $C_{21}H_{18}N_7O$ (M+H)$^+$: m/z=384.1; found 384.1.

Example 71. 3-(5-Amino-2-(phenyl(pyridin-2-yloxy)methyl)-8-(pyrimidin-4-yl)-[1,2,4]triazolo[1,5-c]pyrimidin-7-yl)benzonitrile

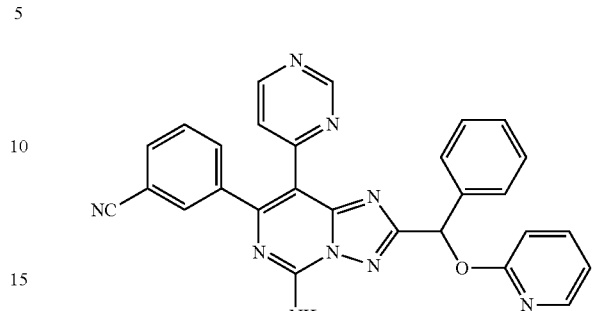

Step 1: 3-(5-Amino-8-bromo-2-(phenyl(pyridin-2-yloxy)methyl)-[1,2,4]triazolo[1,5-c]pyrimidin-7-yl)benzonitrile

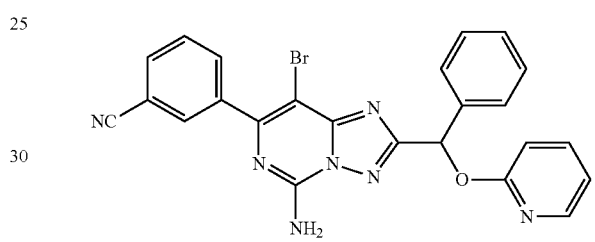

To a solution of 3-(5-amino-8-bromo-2-(hydroxy(phenyl)methyl)-[1,2,4]triazolo[1,5-c]pyrimidin-7-yl)benzonitrile (from Example 45, Step 1) (110 mg, 0.261 mmol) in DCM (2 mL) was added thionyl chloride (0.057 mL, 0.783 mmol). The reaction solution was stirred at r.t. for 1 h, and concentrated. The resulting residue was dissolved in DMF (1 mL), and added potassium carbonate (108 mg, 0.783 mmol) and pyridin-2-ol (49.7 mg, 0.522 mmol). The reaction mixture was then stirred at 90° C. for 2 h, cooled to r.t., quenched with water, and extracted with DCM. The combined organic layers were dried over MgSO$_4$, concentrated, and purified by flash chromatography on a silica gel column eluting with 50% EtOAc in dichloromethane to afford the desired product. LCMS calculated for $C_{24}H_{17}BrN_7O$ (M+H)$^+$: 498.1. Found: 498.1.

Step 2: 3-(5-Amino-2-(phenyl(pyridin-2-yloxy)methyl)-8-(pyrimidin-4-yl)-[1,2,4]triazolo[1,5-c]pyrimidin-7-yl)benzonitrile To a mixture of 3-(5-amino-8-bromo-2-(phenyl(pyridin-2-yloxy)methyl)-[1,2,4]triazolo[1,5-c]pyrimidin-7-yl)benzonitrile (15 mg, 0.030 mmol), 4-(tributylstannyl)pyrimidine (22.2 mg, 0.060 mmol), and lithium chloride (5.1 mg, 0.120 mmol) in 1,4-dioxane (100 µL) was added dichlorobis(triphenylphosphine)-palladium(II) (2.1 mg, 3.01 µmol) and copper(I) chloride (11.9 mg, 0.120 mmol). The resulting mixture was purged with $N_2$ and stirred at 100° C. overnight. The reaction mixture was then cooled to r.t., concentrated, and purified by prep-LC-MS (pH=2, MeCN/water with TFA) to give the desired product as a TFA salt. LC-MS calculated for $C_{28}H_{20}N_9O$ (M+H)$^+$: m/z=498.2; found 498.1.

Example 72. 3-(5-Amino-2-(2-fluoro-6-(((3R,4R)-3-fluoro-4-hydroxypyrrolidin-1-yl)methyl)benzyl)-8-(pyrimidin-4-yl)-[1,2,4]triazolo[1,5-c]pyrimidin-7-yl)benzonitrile

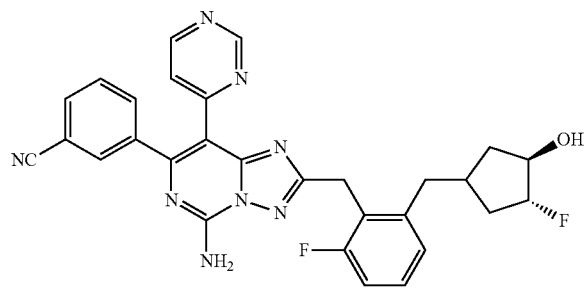 [SMILES: N#Cc1cccc(-c2nc(N)n3nc(Cc4c(F)cccc4CC4C[C@@H](O)[C@H](F)C4)nc3c2-c2ccncn2)c1]

Step 1: 3-(5-Amino-2-(hydroxymethyl)-[1,2,4]triazolo[1,5-c]pyrimidin-7-yl)benzonitrile

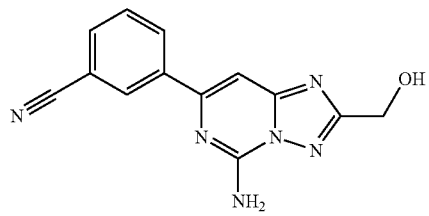 [SMILES: N#Cc1cccc(-c2cc3nc(CO)nn3c(N)n2)c1]

2-Hydroxyacetohydrazide (2.34 g, 26.01 mmol) was added to a ethanol (35 mL) solution of 3-(2-amino-6-chloropyrimidin-4-yl)benzonitrile (4.00 g, 17.34 mmol) (Example 41, Step 1) at r.t. After being heated and stirred at reflux for 2 h, the reaction mixture was cooled to r.t., and concentrated. The resulting residue was taken into N,O-bis(trimethylsilyl)acetamide (20 mL) and stirred at 120° C. for 7 h. The mixture was then cooled to r.t., poured onto ice, and allowed to stir at r.t. for 1 h. The resulting solid was collected by filtration, and taken into 20 mL of 1 N HCl solution. The resulting mixture was stirred at r.t. for 1 h, filtered, and the aqueous layer was neutralized by addition of saturated NaHCO$_3$ solution. The resulting precipitate was collected by filtration, and dried to obtain the desired product as a brown solid. LCMS calculated for $C_{13}H_{11}N_6O$ (M+H)$^+$: 267.1; found 267.1.

Step 2: 3-(5-Amino-8-bromo-2-(hydroxymethyl)-[1,2,4]triazolo[1,5-c]pyrimidin-7-yl)benzonitrile

To a mixture of 3-(5-amino-2-(hydroxymethyl)-[1,2,4]triazolo[1,5-c]pyrimidin-7-yl)benzonitrile (1.0 g, 3.76 mmol) in DMF (12 mL) at −30° C. was added NBS (0.67 g, 3.76 mmol) portion-wise. The reaction mixture was allowed to slowly warm to 0° C., resulting a homogenous solution. After stirring at 0° C. for 1 h, the reaction mixture was diluted with saturated NaHCO$_3$ solution and the desired product was collected by filtration and dried. LCMS calculated for $C_{13}H_{10}BrN_6O$ (M+H)$^+$: 345.0; found 345.0.

Step 3: 3-(5-Amino-2-(hydroxymethyl)-8-(pyrimidin-4-yl)-[1,2,4]triazolo[1,5-c]pyrimidin-7-yl)benzonitrile

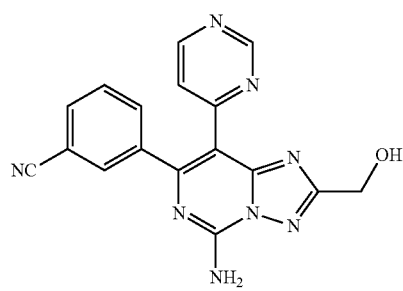 [SMILES: N#Cc1cccc(-c2nc(N)n3nc(CO)nc3c2-c2ccncn2)c1]

Tetrakis(triphenylphosphine)palladium(0) (0.067 g, 0.058 mmol) was added to a mixture of 4-(tributylstannyl)pyrimidine (0.321 g, 0.869 mmol), 3-(5-amino-8-bromo-2-(hydroxymethyl)-[1,2,4]triazolo[1,5-c]pyrimidin-7-yl)benzonitrile (0.20 g, 0.579 mmol), CsF (0.176 g, 1.159 mmol), and copper(I)iodide (0.022 g, 0.116 mmol) in 1,4-dioxane (5.0 mL). The reaction mixture was purged with N$_2$ and stirred at 80° C. for 7 h. The resulting mixture was cooled to r.t., concentrated and purified by flash column chromatography eluting with 0% to 10% methanol in DCM to afford the product. LC-MS calculated for $C_{17}H_{13}N_8O$ (M+H)$^+$: 345.1; found 345.1.

Step 4: 3-(5-Amino-2-(chloromethyl)-8-(pyrimidin-4-yl)-[1,2,4]triazolo[1,5-c]pyrimidin-7-yl)benzonitrile

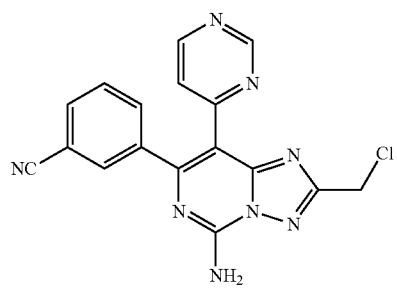 [SMILES: N#Cc1cccc(-c2nc(N)n3nc(CCl)nc3c2-c2ccncn2)c1]

To a mixture of 3-(5-amino-2-(hydroxymethyl)-8-(pyrimidin-4-yl)-[1,2,4]triazolo[1,5-c]pyrimidin-7-yl)benzonitrile (0.1 g, 0.290 mmol) in Acetonitrile (10 ml) was added thionyl chloride (0.212 ml, 2.90 mmol) at r.t. The reaction mixture was stirred at r.t. for 5 h, concentrated, and purified by flash chromatography eluting with 0% to 5% methanol in DCM to afford the product. LC-MS calculated for $C_{17}H_{12}ClN_8$ (M+H)$^+$: 363.1; found 363.1.

Step 5: 3-(5-Amino-2-(2-fluoro-6-(hydroxymethyl) benzyl)-8-(pyrimidin-4-yl)-[1,2,4]triazolo[1,5-c] pyrimidin-7-yl)benzonitrile

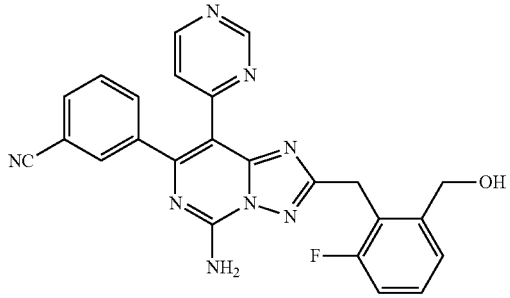 [SMILES: N#Cc1cccc(-c2nc(N)n3nc(Cc4c(F)cccc4CO)nc3c2-c2ccncn2)c1]

A mixture of 3-(5-amino-2-(chloromethyl)-8-(pyrimidin-4-yl)-[1,2,4]triazolo[1,5-c]pyrimidin-7-yl)benzonitrile (0.2 g, 0.55 mmol), (2-fluoro-6-(hydroxymethyl)phenyl)boronic acid (0.141 g, 0.827 mmol), chloro(2-dicyclohexylphosphino-2',4',6'-tri-i-propyl-1,1'-biphenyl)(2'-amino-1,1'-biphenyl-2-yl) palladium(II) (0.551 mmol) and Na$_2$CO$_3$ (0.117 g, 1.10 mmol) in Dioxane (30 mL) and water (3.0 mL) was stirred at 110° C. for 2 h. The resulting mixture was cooled to r.t., and diluted with water (20 mL). The resulting solid was collected by filtration, and dried to afford the product. LCMS calculated for C$_{24}$H$_{18}$FN$_8$O (M+H)$^+$: 453.2; found 453.2.

Step 6: 3-(5-Amino-2-(2-(chloromethyl)-6-fluorobenzyl)-8-(pyrimidin-4-yl)-[1,2,4]triazolo[1,5-c] pyrimidin-7-yl)benzonitrile

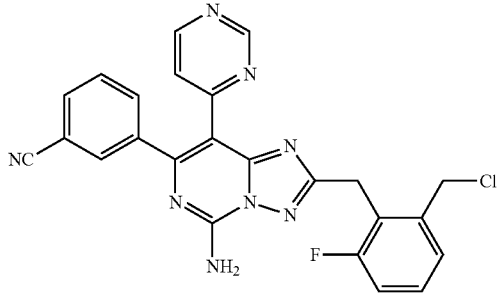 [SMILES: N#Cc1cccc(-c2nc(N)n3nc(Cc4c(F)cccc4CCl)nc3c2-c2ccncn2)c1]

To a mixture of 3-(5-Amino-2-(2-fluoro-6-(hydroxymethyl)benzyl)-8-(pyrimidin-4-yl)-[1,2,4]triazolo[1,5-c]pyrimidin-7-yl)benzonitrile (0.2 g, 0.290 mmol) in acetonitrile (10 ml) was added thionyl chloride (0.212 ml, 2.90 mmol) at r.t. The reaction mixture was stirred at r.t. for 5 h, concentrated, and purified by flash chromatography eluting with 0% to 5% methanol in DCM to afford the product. LC-MS calculated for C$_{24}$H$_{17}$ClFN$_8$ (M+H)$^+$: 471.1; found 471.1.

Step 7: 3-(5-Amino-2-(2-fluoro-6-(((3R,4R)-3-fluoro-4-hydroxypyrrolidin-1-yl)methyl)benzyl)-8-(pyrimidin-4-yl)-[1,2,4]triazolo[1,5-c]pyrimidin-7-yl)benzonitrile A mixture of 3-(5-amino-2-(2-(chloromethyl)-6-fluorobenzyl)-8-(pyrimidin-4-yl)-[1,2,4]triazolo[1,5-c]pyrimidin-7-yl)benzonitrile (10 mg, 0.021 mmol), (3R,4R)-4-fluoropyrrolidin-3-ol hydrochloride (4.51 mg, 0.032 mmol) and Cs$_2$CO$_3$ (20.7 mg, 0.064 mmol) in DMF (1 mL) was stirred at 100° C. for 10 min. The reaction mixture was then cooled to r.t., diluted with methanol (4 mL), and purified by preparative LC-MS (pH 2, acetonitrile/water with TFA) to afford the product as a TFA salt. LCMS calculated for C$_{24}$H$_{18}$F$_8$O (M+H)$^+$: 540.2; found 540.2.

Example 73. 1-(2-((5-Amino-7-(3-cyanophenyl)-8-(pyrimidin-4-yl)-[1,2,4]triazolo[1,5-c]pyrimidin-2-yl)methyl)-3-fluorobenzyl)piperidine-4-carboxylic acid

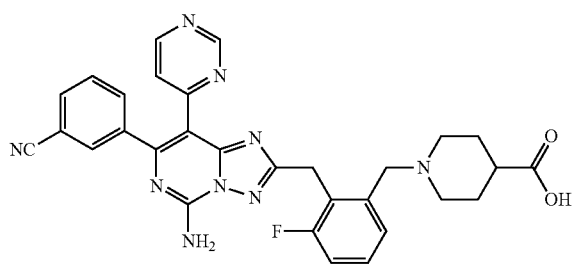 [SMILES: N#Cc1cccc(-c2nc(N)n3nc(Cc4c(F)cccc4CN4CCC(C(=O)O)CC4)nc3c2-c2ccncn2)c1]

Step 1: Methyl 1-(2-((5-amino-7-(3-cyanophenyl)-8-(pyrimidin-4-yl)-[1,2,4]triazolo[1,5-c]pyrimidin-2-yl)methyl)-3-fluorobenzyl)piperidine-4-carboxylate

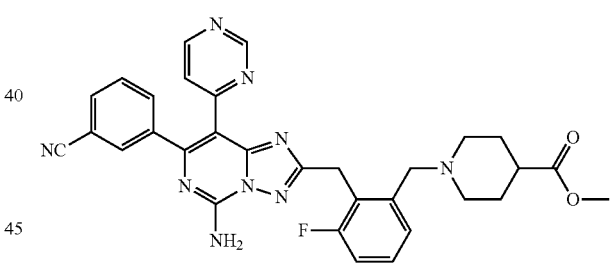

This compound was prepared using similar procedures, on the same scale, as described for Example 72, with methyl piperidine-4-carboxylate replacing (3R,4R)-4-fluoropyrrolidin-3-ol hydrochloride in Step 7. LCMS calculated for C$_{3-6}$H$_{29}$FN$_9$O$_2$ (M+H)$^+$: 578.2; found 578.2.

Step 2: 1-(2-((5-Amino-7-(3-cyanophenyl)-8-(pyrimidin-4-yl)-[1,2,4]triazolo[1,5-c]pyrimidin-2-yl)methyl)-3-fluorobenzyl)piperidine-4-carboxylic acid The product from the previous step was treated with LiOH (2.5 mg, 0.106 mmol) in water (2.0 mL), and stirred at r.t. for 1.5 h. The mixture was diluted with methanol (5 mL) and purified by preparative LC-MS (pH 2, acetonitrile/water with TFA) to afford the product as a TFA salt. LCMS calculated for C$_{30}$H$_{27}$FN$_9$O$_2$ (M+H)$^+$: 564.2; found 564.2.

Example 74. N-(2-((5-Amino-7-(3-cyanophenyl)-8-(pyrimidin-4-yl)-[1,2,4]triazolo[1,5-c]pyrimidin-2-yl)methyl)-3-fluorobenzyl)-N-methylmethanesulfonamide

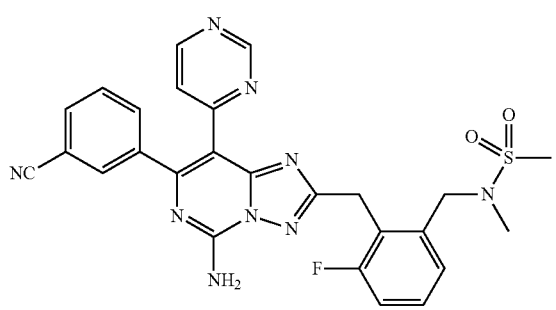 [SMILES: CN(Cc1cccc(F)c1Cc1nc2c(-c3ccncn3)c(-c3cccc(C#N)c3)nc(N)n2n1)S(C)(=O)=O]

This compound was prepared using similar procedures as described for Example 72, with N-methylmethanesulfonamide replacing (3R,4R)-4-fluoropyrrolidin-3-ol hydrochloride in Step 7. The product was purified by preparative LC-MS (pH 2, acetonitrile/water with TFA) to afford the product as a TFA salt. LCMS calculated for $C_{26}H_{23}FN_9O_2S$ (M+H)$^+$: 544.2; found 544.2.

Example 75. 3-(5-Amino-2-(2-((2,5-dioxoimidazolidin-1-yl)methyl)-6-fluorobenzyl)-8-(pyrimidin-4-yl)-[1,2,4]triazolo[1,5-c]pyrimidin-7-yl)benzonitrile

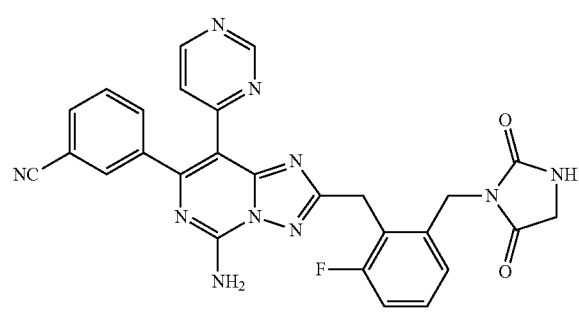 [SMILES: N#Cc1cccc(-c2nc(N)n3nc(Cc4c(F)cccc4CN4C(=O)CNC4=O)nc3c2-c2ccncn2)c1]

This compound was prepared using similar procedures as described for Example 72, with hydantoin replacing (3R,4R)-4-fluoropyrrolidin-3-ol hydrochloride in Step 7. The product was purified by preparative LC-MS (pH 2, acetonitrile/water with TFA) to afford the product as a TFA salt. LCMS calculated for $C_{27}H_{20}FN_{10}O_2$ (M+H)$^+$: 535.2; found 535.2.

Example 76. 3-(5-Amino-2-((2,6-difluorophenyl)(hydroxy)methyl)-8-(pyrimidin-4-yl)-[1,2,4]triazolo[1,5-c]pyrimidin-7-yl)benzonitrile (Peak 1)

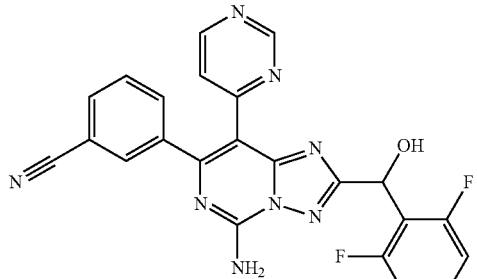

Step 1: Methyl 2-(2,6-difluorophenyl)-2-hydroxyacetate

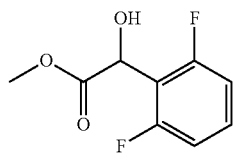

Concentrated sulfuric acid (1.42 mL, 27 mmol) was added to a methanol (45 mL) solution of 2,6-difluoromandelic acid (5 g, 27 mmol) at 0° C. The mixture was stirred at r.t. for 4 h before being concentrated. To the resulting slurry was added saturated NaHCO$_3$ solution (30 mL). The resulting mixture was extracted with DCM (3×20 mL). The combined organic layers were washed with water, dried over Mg$_2$SO$_4$, filtered, and concentrated to afford the crude product, which was used in the next step without further purification. LC-MS calculated for $C_{11}H_{12}F_2NO_3$ (M+H+MeCN)$^+$: m/z=244.1; found 244.2.

Step 2: 3-(5-Amino-2-((2,6-difluorophenyl)(hydroxy)methyl)-8-(pyrimidin-4-yl)-[1,2,4]triazolo[1,5-c]pyrimidin-7-yl)benzonitrile This compound was prepared using similar procedures as described for Example 41, with methyl 2-(2,6-difluorophenyl)-2-hydroxyacetate replacing methyl 2-(pyridin-2-yl)acetate in Step 2. The two enantiomers were separated by chiral SFC using a Phenomenex Lux Cellulose-1 column (21.2×250 mm, 5 μm particle size) eluting with an isocratic mobile phase 25% MeOH in CO$_2$ with a flow rate of 80 mL/minute. Peak 1 was isolated, and further purified by prep-LCMS (pH=2, MeCN/water with TFA) to give the desired product as a TFA salt. LC-MS calculated for $C_{23}H_{15}F_2N_8O$ (M+H)$^+$: m/z=457.1; found 457.1. $^1$H NMR (500 MHz, DMSO) δ 8.94 (d, J=1.3 Hz, 1H), 8.81 (d, 5.2 Hz, 1H), 7.85 (dd, J=5.3, 1.4 Hz, 1H), 7.81 (dt, 0.7=7.4, 1.5 Hz, 1H), 7.76 (t, J=1.7 Hz, 1H), 7.55 (dt, 7.8, 1.5 Hz, 1H), 7.49 (t, J=7.8 Hz, 1H), 7.44 (tt, J=8.4, 6.4 Hz, 1H), 7.09 (t, J=8.3 Hz, 2H), 6.27 (s, 1H).

Example 77. 3-(5-Amino-2-((2,6-difluorophenyl)(hydroxy)methyl)-8-(pyrimidin-4-yl)-[1,2,4]triazolo[1,5-c]pyrimidin-7-yl)benzonitrile (Peak 2)

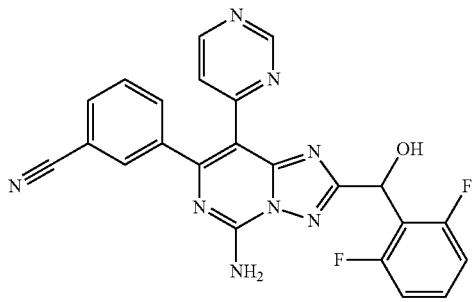 [SMILES: N#Cc1cccc(-c2nc(N)n3nc(C(O)c4c(F)cccc4F)nc3c2-c2ccncn2)c1]

This compound was prepared using the same procedures as described for Example 76. The two enantiomers were separated by chiral SFC using a Phenomenex Lux Cellulose-1 column (21.2×250 mm, 5 μm particle size) eluting with an isocratic mobile phase 25% MeOH in CO₂ with a flow rate of 80 mL/minute. Peak 2 was isolated, and further purified by prep-LCMS (pH=2, MeCN/water with TFA) to give the desired product as a TFA salt. LC-MS calculated for $C_{23}H_{15}F_2N_8O$ (M+H)⁺: m/z=457.1; found 457.1. ¹H NMR (500 MHz, DMSO) δ 8.94 (d, J=1.3 Hz, 1H), 8.81 (d, 5.2 Hz, 1H), 7.85 (dd, 5.3, 1.4 Hz, 1H), 7.81 (dt, J=7.4, 1.5 Hz, 1H), 7.76 (t, J=1.7 Hz, 1H), 7.55 (dt, 7.8, 1.5 Hz, 1H), 7.49 (t, J=7.8 Hz, 1H), 7.44 (tt, J=8.4, 6.4 Hz, 1H), 7.09 (t, J=8.3 Hz, 2H), 6.27 (s, 1H).

Examples 78A-78B. 3-(5-Amino-2-((5-(pyridin-2-yl)-2H-tetrazol-2-yl)methyl)-8-(pyrimidin-4-yl)-[1,2,4]triazolo[1,5-c]pyrimidin-7-yl)benzonitrile (Example 78A) and 3-(5-Amino-2-((5-(pyridin-2-yl)-1H-tetrazol-1-yl)methyl)-8-(pyrimidin-4-yl)-[1,2,4]triazolo[1,5-c]pyrimidin-7-yl)benzonitrile (Example 78B)

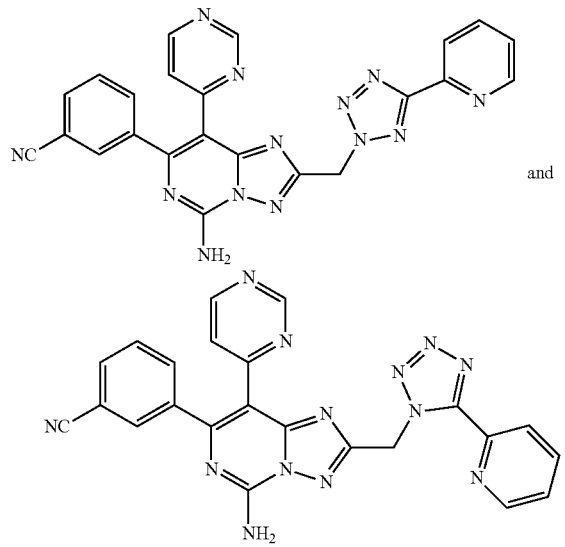

A mixture of 3-(5-amino-2-(chloromethyl)-8-(pyrimidin-4-yl)-[1,2,4]triazolo[1,5-c]pyrimidin-7-yl)benzonitrile (10 mg, 0.028 mmol) (From Example 72, Step 4), 2-(1H-tetrazol-5-yl)pyridine (8.1 mg, 0.055 mmol) and Cs₂CO₃ (20.7 mg, 0.064 mmol) in DMF (1 mL) was stirred at 100° C. for 10 min. The reaction mixture was then cooled to r.t., diluted with methanol (4 mL), and purified by preparative LC-MS (pH 2, acetonitrile/water with TFA) to afford the mixture of products (1.5:1 ratio of Example 78A:Example 78B) as TFA salts. LCMS calculated for $C_{23}H_{16}N_{13}$ (M+H)+: 474.2; found 474.2. Example 78A: ¹H NMR (500 MHz, DMSO) δ 8.99 (d, J=1.4 Hz, 1H), 8.85 (d, J=5.3 Hz, 1H), 8.80-8.71 (m, 1H), 8.71-8.39 (b, 2H), 8.18 (d, J=7.7, 1.1 Hz, 1H), 8.04 (t, J=7.8, 1.8 Hz, 1H), 7.85 (m, 2H), 7.80-7.76 (m, 1H), 7.62-7.55 (m, 2H), 7.53 (t, J=7.8 Hz, 1H), 6.39 (s, 2H).

Examples 79A-79B. 3-(2-((5-(1H-Pyrazol-1-yl)-2H-tetrazol-2-yl)methyl)-5-amino-8-(pyrimidin-4-yl)-[1,2,4]triazolo[1,5-c]pyrimidin-7-yl)benzonitrile (Example 79A) and 3-(2-((5-(1H-Pyrazol-1-yl)-1H-tetrazol-1-yl)methyl)-5-amino-8-(pyrimidin-4-yl)-[1,2,4]triazolo[1,5-c]pyrimidin-7-yl)benzonitrile (Example 79B)

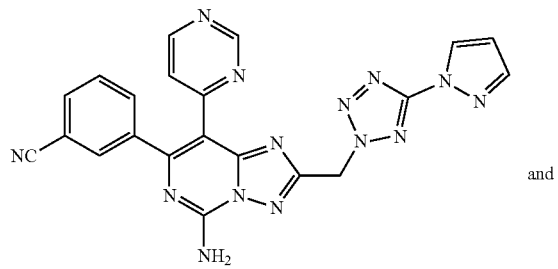

and

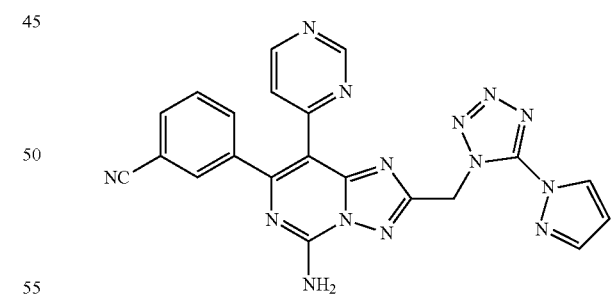

This title mixture of compounds was prepared using similar procedures as described for Example 78, with 5-(1H-pyrazol-1-yl)-1H-tetrazole replacing 2-(1H-tetrazol-5-yl)pyridine. The products were purified by preparative LC-MS (pH 2, acetonitrile/water with TFA) to afford the products as TFA salts. LCMS calculated for $C_{21}H_{15}N_{14}$ (M+H)⁺: 463.2; found 463.2.

Examples 80A-80B. 3-(5-Amino-8-(pyrimidin-4-yl)-2-((5-(thiazol-4-yl)-2H-tetrazol-2-yl)methyl)-[1,2,4]triazolo[1,5-a]pyridin-7-yl)benzonitrile (Example 80A) and 3-(5-Amino-8-(pyrimidin-4-yl)-2-((5-(thiazol-4-yl)-1H-tetrazol-1-yl)methyl)-[1,2,4]triazolo[1,5-c]pyrimidin-7-yl)benzonitrile (Example 80IB)

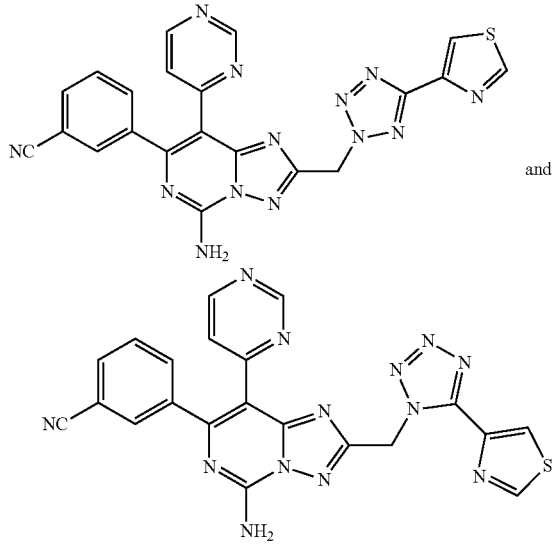

and

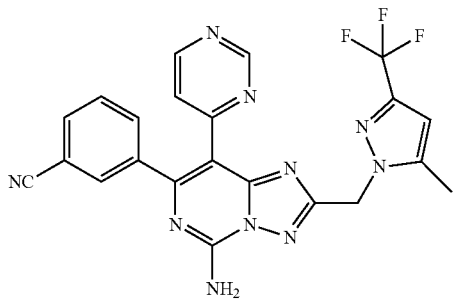 [SMILES: Cc1cc(C(F)(F)F)nn1Cc1nc2c(-c3ccncn3)c(-c3cccc(C#N)c3)nc(N)n2n1]

The title mixture of compounds was prepared using similar procedures as described for Example 78, with 4-(1H-tetrazol-5-yl)thiazole replacing 2-(1H-tetrazol-5-yl)pyridine. The products were purified by preparative LC-MS (pH 2, acetonitrile/water with TFA) to afford the products as TFA salts. LCMS calculated for $C_{21}H_{14}N_{13}S$ (M+H)$^+$: 480.1; found 480.1.

Example 81. 3-(5-Amino-2-((5-methyl-3-(trifluoromethyl)-1H-pyrazol-1-yl)methyl)-8-(pyrimidin-4-yl)-[1*2,4]triazolo[1,5-c]pyrimidin-7-yl)benzonitrile

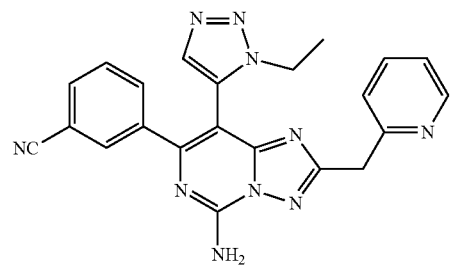 [SMILES: CCn1nncc1-c1c(-c2cccc(C#N)c2)nc(N)n2nc(Cc3ccccn3)nc12]

This compound was prepared using similar procedures as described for Example 78, with 5-methyl-3-(trifluoromethyl)-1H-pyrazole replacing 2-(1H-tetrazol-5-yl)pyridine. The product was purified by preparative LC-MS (pH 2, acetonitrile/water with TFA) to afford the product as a TFA salt. LCMS calculated for $C_{22}H_{16}F_3N_{10}$ (M+H)$^+$: 477.2; found 477.1.

Example 82. 3-(5-Amino-8-(4-ethyloxazol-5-yl)-2-(pyridin-2-ylmethyl)-[1,2,4]triazolo[1,5-c]pyrimidin-7-yl)benzonitrile

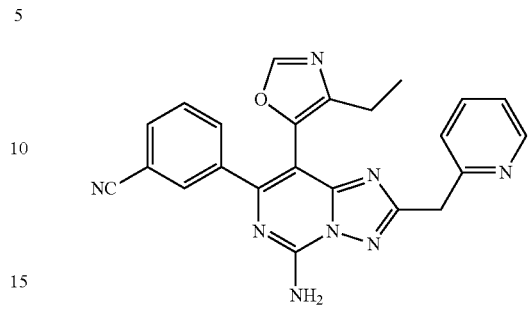

This compound was prepared using similar procedures as described for Example 42 with 4-ethyl-5-(4,4,5,5-tetramethyl-1,3,2-dioxaborolan-2-yl)oxazole replacing 1-ethyl-5-(4,4,5,5-tetramethyl-1,3,2-dioxaborolan-2-yl)-1H-pyrazole. The final material was purified by preparative LC-MS (pH 2, acetonitrile/water with TFA) to afford the product as a TFA salt. LCMS calculated for $C_{23}H_{19}N_8O$ (M+H)$^+$: 423.2; found 423.2.

Example 83. 3-(5-Amino-8-(1-ethyl-1H-1,2,3-triazol-5-yl)-2-(pyridin-2-ylmethyl)-[1,2,4]triazolo[1,5-c]pyrimidin-7-yl)benzonitrile

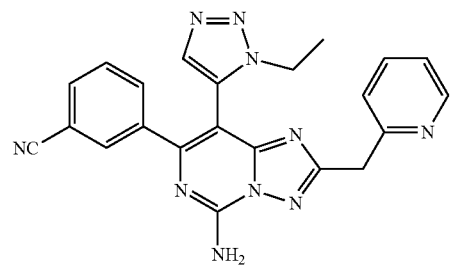 [SMILES: CCn1nncc1-c1c(-c2cccc(C#N)c2)nc(N)n2nc(Cc3ccccn3)nc12]

This compound was prepared using similar procedures as described for Example 41, Step 5, with 1-ethyl-5-(trimethylstannyl)-1H-1,2,3-triazole replacing 4-(tributylstannyl)pyrimidine. The final material was purified by preparative LC-MS (pH 2, acetonitrile/water with TFA) to afford the product as a TFA salt. LCMS calculated for $C_{22}H_{19}N_{10}$ (M+H)$^+$: 423.2; found 423.2

Example 84. 3-(5-Amino-8-(4-methyloxazol-5-yl)-2-((3-methylpyridin-2-yl)methyl)-[1,2,4]triazolo[1,5-c]pyrimidin-7-yl)benzonitrile

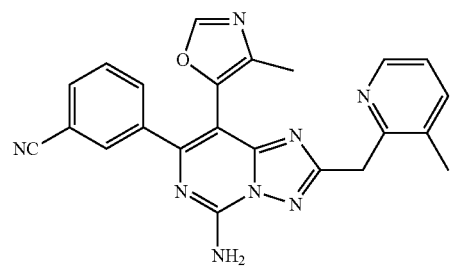 [SMILES: Cc1cccnc1Cc1nc2c(-c3ocnc3C)c(-c3cccc(C#N)c3)nc(N)n2n1]

Step 1: 3-(5-Amino-8-bromo-2-((3-methylpyridin-2-yl)methyl)-[1,2,4]triazolo[1,5-c]pyrimidin-7-yl)benzonitrile

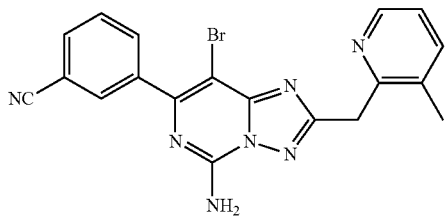 [SMILES: Cc1cccnc1Cc1nc2c(Br)c(-c3cccc(C#N)c3)nc(N)n2n1]

This compound was prepared using similar procedures as described for Example 41, Step 3 to Step 4, with 2-(3-methylpyridin-2-yl)acetohydrazide replacing 2-(pyridin-2-yl)acetohydrazide in Step 3. LCMS calculated for $C_{19}H_{15}BrN_7$ (M+H)$^+$: 420.1; found 420.1.

Step 2: 3-(5-Amino-8-(4-methyloxazol-5-yl)-2-((3-methylpyridin-2-yl)methyl)-[1,2,4]triazolo[1,5-c]pyrimidin-7-yl)benzonitrile This compound was prepared using similar procedures as described for Example 61, Step 2, with 3-(5-amino-8-bromo-2-((3-methylpyridin-2-yl)methyl)-[1,2,4]triazolo[1,5-c]pyrimidin-7-yl)benzonitrile replacing 3-(5-Amino-8-bromo-2-(pyridin-2-ylmethyl)-[1,2,4]triazolo[1,5-c]pyrimidin-7-yl)benzonitrile. The final material was purified by preparative LC-MS (pH 2, acetonitrile/water with TFA) to afford the product as a TFA salt. LCMS calculated for $C_{23}H_{19}N_8O$ (M+H)$^+$: 423.2; found 423.2.

Example 85. 3-(5-Amino-2-((3-fluoropyridin-2-yl)methyl)-8-(4-(hydroxymethyl)-2-methyloxazol-5-yl)-[1,2,4]triazolo[1,5-c]pyrimidin-7-yl)benzonitrile

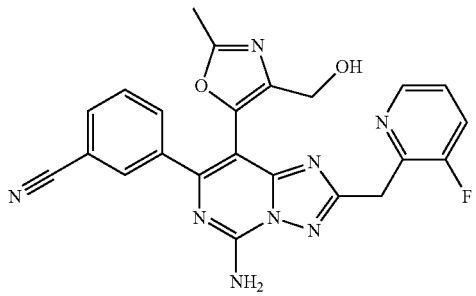 [SMILES: Cc1nc(CO)c(-c2c(-c3cccc(C#N)c3)nc(N)n3nc(Cc4ncccc4F)nc23)o1]

This compound was prepared using similar procedures as described for Example 62, Step 3 to Step 4, with 3-(5-Amino-8-bromo-2-((3-fluoropyridin-2-yl)methyl)-[1,2,4]triazolo[1,5-c]pyrimidin-7-yl)benzonitrile replacing 3-(5-Amino-8-bromo-2-(pyridin-2-ylmethyl)-[1,2,4]triazolo[1,5-c]pyrimidin-7-yl)benzonitrile in Step 3. The final material was purified by preparative LC-MS (pH 2, acetonitrile/water with TFA) to afford the product as a TFA salt. LCMS calculated for $C_{23}H_{18}FN_8O_2$ (M+H)$^+$: 457.2; found 457.2.

Example 86. 3-(5-Amino-2-(2-(((1,1-dioxidoisothiazolidin-2-yl)methyl)-6-fluorobenzyl)-8-(pyrimidin-4-yl)-[1,2,4]triazolo[1,5-c]pyrimidin-7-yl)benzonitrile

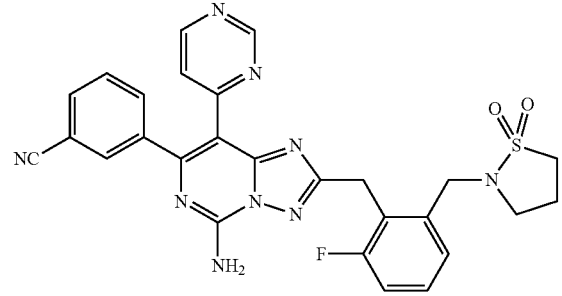 [SMILES: N#Cc1cccc(-c2nc(N)n3nc(Cc4c(F)cccc4CN4CCCS4(=O)=O)nc3c2-c2ccncn2)c1]

This compound was prepared using similar procedures as described for Example 72, with 1,2-thiazolidine 1,1-dioxide replacing (3R,4R)-4-fluoropyrrolidin-3-ol hydrochloride in Step 7. The product was purified by preparative LC-MS (pH 2, acetonitrile/water with TFA) to afford the product as a TFA salt. LCMS calculated for $C_{27}H_{23}FN_9O_2S$ (M+H)$^+$: 556.2; found 556.2.

Example 87. 3-(5-Amino-2-(2-fluoro-6-((3-methyl-2,5-dioxoimidazolidin-1-yl)methyl)benzyl)-8-(pyrimidin-4-yl)-[1,2,4]triazolo[1,5-c]pyrimidin-7-yl)benzonitrile

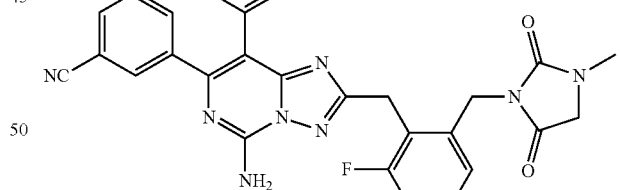

This compound was prepared using similar procedures as described for Example 72, with 1-methylimidazolidine-2,4-dione replacing (3R,4R)-4-fluoropyrrolidin-3-ol hydrochloride in Step 7. The product was purified by preparative LC-MS (pH 2, acetonitrile/water with TFA) to afford the product as a TFA salt. LCMS calculated for $C_{28}H_{22}FN_{10}O_2$ (M+H)$^+$: 549.2; found 549.2.

Example 88. 3-(5-Amino-2-((3-fluoropyridin-2-yl)methyl)-8-(pyrimidin-4-yl)-[1,2,4]triazolo[1,5-c]pyrimidin-7-yl)benzonitrile

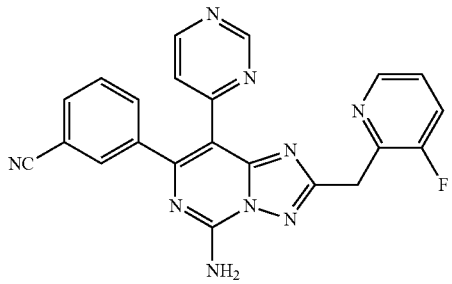 [SMILES: N#Cc1cccc(-c2nc(N)n3nc(Cc4ncccc4F)nc3c2-c2ccncn2)c1]

This compound was prepared using similar procedures as described for Example 41, Step 5, with 3-(5-amino-8-bromo-2-((3-fluoropyridin-2-yl)methyl)-[1,2,4]triazolo[1,5-c]pyrimidin-7-yl)benzonitrile (Example 52, Step 2) replacing 3-(5-amino-8-bromo-2-(pyridin-2-ylmethyl)-[1,2,4]triazolo[1,5-c]pyrimidin-7-yl)benzonitrile. The final material was purified by preparative LC-MS (pH 2, acetonitrile/water with TFA) to afford the product as a TFA salt. LCMS calculated for $C_{22}H_{15}FN_9$ (M+H)$^+$: 424.1; found 424.1.

Example 89. 3-(5-Amino-8-(4-methyloxazol-5-yl)-2-((6-(trifluoromethyl)pyridin-2-yl)methyl)-[1,2,4]triazolo[1,5-c]pyrimidin-7-yl)benzonitrile

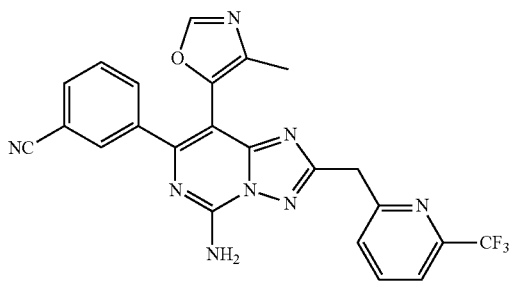 [SMILES: Cc1ncoc1-c1c(-c2cccc(C#N)c2)nc(N)n2nc(Cc3cccc(C(F)(F)F)n3)nc12]

Step 1: Ethyl 2-(6-(trifluoromethyl)pyridin-2-yl)acetate

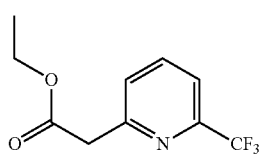

A THF (10.3 ml) solution of 2-methyl-6-(trifluoromethyl)pyridine (500 mg, 3.10 mmol) was cooled to −78° C., followed by addition of/J-butyllithium (1.49 ml, 3.72 mmol) dropwise. After 10 min, diethyl carbonate (0.564 ml, 4.65 mmol) was added in one portion. The mixture was allowed to stir at −78° C. for 30 min. The mixture was then diluted with aq. NH$_4$Cl and extracted with DCM. The combined organic layers were dried over MgSO$_4$, filtered, and concentrated. The resulting residue was purified by flash chromatography on a silica gel column eluting with 0 to 50% EtOAc in Hexanes to afford the desired product. LCMS calculated for $C_{10}H_{11}F_3NO_2$ (M+H)$^+$: 234.1. Found: 234.1.

Step 2: 3-(5-Amino-8-bromo-2-((6-(trifluoromethyl)pyridin-2-yl)methyl)-[1,2,4]triazolo[1,5-c]pyrimidin-7-yl)benzonitrile

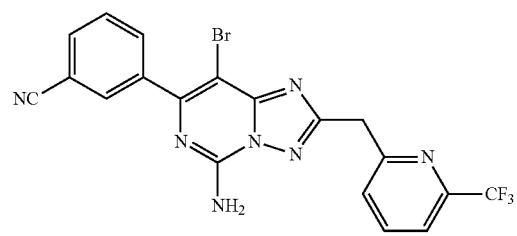 [SMILES: N#Cc1cccc(-c2nc(N)n3nc(Cc4cccc(C(F)(F)F)n4)nc3c2Br)c1]

This compound was prepared using similar procedures as described for Example 41, Step 1 to Step 4, with ethyl 2-(6-(trifluoromethyl)pyridin-2-yl)acetate replacing methyl 2-(pyridin-2-yl)acetate in Step 2. LCMS calculated for $C_{19}H_{12}BrF_3N_7$ (M+H)$^+$: 474.0; found 474.0.

Step 3: 3-(5-Amino-8-(4-methyloxazol-5-yl)-2-((6-(trifluoromethyl)pyridin-2-yl)methyl)-[1,2,4]triazolo[1,5-c]pyrimidin-7-yl)benzonitrile This compound was prepared using similar procedures as described for Example 42 with 3-(5-amino-8-bromo-2-((6-(trifluoromethyl)pyridin-2-yl)methyl)-[1,2,4]triazolo[1,5-c]pyrimidin-7-yl)benzonitrile replacing 3-(5-amino-8-bromo-2-(pyridin-2-ylmethyl)-[1,2,4]triazolo[1,5-c]pyrimidin-7-yl)benzonitrile, and with 4-methyl-5-(4,4,5,5-tetramethyl-1,3,2-dioxaborolan-2-yl)oxazole (Example 61, Step 1) replacing 1-ethyl-5-(4,4,5,5-tetramethyl-1,3,2-dioxaborolan-2-yl)-1H-pyrazole. The final material was purified by preparative LC-MS (pH 2, acetonitrile/water with TFA) to afford the product as a TFA salt. LCMS calculated for $C_{23}H_{16}F_3N_8O$ (M+H)$^+$: 477.1; found 477.2.

Example 90. 3-(5-Amino-8-(4-methyloxazol-5-yl)-2-(pyridin-2-ylmethyl)-[1,2,4]triazolo[1,5-c]pyrimidin-7-yl)-2-fluorobenzonitrile

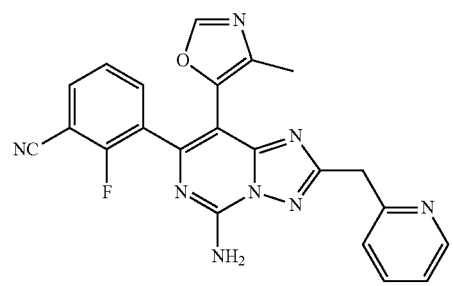 [SMILES: Cc1ncoc1-c1c(-c2cccc(C#N)c2F)nc(N)n2nc(Cc3ccccn3)nc12]

Step 1: 3-(5-Amino-8-bromo-2-(pyridin-2-ylmethyl)-[1,2,4]triazolo[1,5-c]pyrimidin-7-yl)-2-fluorobenzonitrile

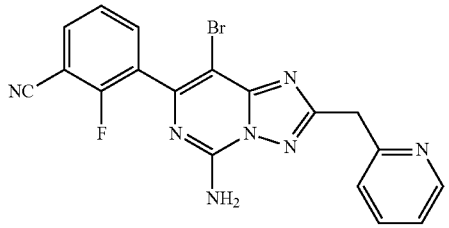 [SMILES: N#Cc1cccc(-c2nc(N)n3nc(Cc4ccccn4)nc3c2Br)c1F]

This compound was prepared using similar procedures as described for Example 41, Step 1 to Step 4, with (3-cyano-2-fluorophenyl)boronic acid replacing (3-cyanophenyl)boronic acid in Step 1. LCMS calculated for $C_{18}H_{12}BrFN_7$ (M+H)$^+$: 424.0; found 424.0.

Step 2: 3-(5-Amino-8-(4-methyloxazol-5-yl)-2-(pyridin-2-ylmethyl)-[1,2,4]triazolo[1,5-c]pyrimidin-7-yl)-2-fluorobenzonitrile This compound was prepared using similar procedures as described for Example 42 with 3-(5-amino-8-bromo-2-(pyridin-2-ylmethyl)-[1,2,4]triazolo[1,5-c]pyrimidin-7-yl)-2-fluorobenzonitrile replacing 3-(5-amino-8-bromo-2-(pyridin-2-ylmethyl)-[1,2,4]triazolo[1,5-c]pyrimidin-7-yl)benzonitrile, and with 4-methyl-5-(4,4,5,5-tetramethyl-1,3,2-dioxaborolan-2-yl)oxazole (Example 61, Step 1) replacing 1-ethyl-5-(4,4,5,5-tetramethyl-1,3,2-dioxaborolan-2-yl)-1H-pyrazole. The final material was purified by preparative LC-MS (pH 2, acetonitrile/water with TFA) to afford the product as a TFA salt. LCMS calculated for $C_{22}H_{16}FN_8O$ (M+H)$^+$: 427.1; found 427.2.

Example 91. 3-(5-Amino-2-((3-(hydroxymethyl)pyridin-2-yl)methyl)-8-(4-methyloxazol-5-yl)-[1,2,4]triazolo[1,5-c]pyrimidin-7-yl)benzonitrile

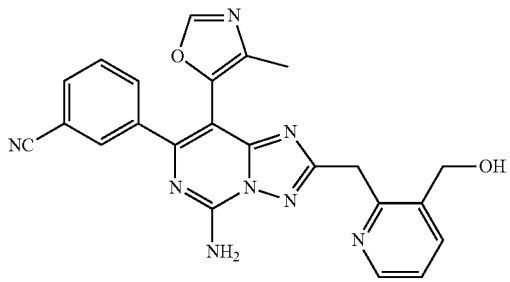 [SMILES: Cc1ncoc1-c1c(-c2cccc(C#N)c2)nc(N)n2nc(Cc3ncccc3CO)nc12]

Step 7: 3-(((tert-Butyldimethylsilyl)oxy)methyl)-2-methylpyridine

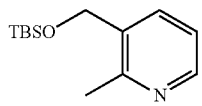

TBS-Cl (918 mg, 6.09 mmol) was added to a $CH_2Cl_2$ (20 ml) solution of (2-methylpyridin-3-yl)methanol (750 mg, 6.09 mmol) and imidazole (415 mg, 6.09 mmol) at rt. After stirring for 30 min, the mixture was diluted with water and extracted with DCM (×3). The combined organic layers were dried over $MgSO_4$, filtered, and concentrated. The resulting residue was purified by flash chromatography on a silica gel column eluting with 0 to 50% EtOAc in Hexanes to afford the desired product. LCMS calculated for $C_{13}H_{24}NOSi$ (M+H)$^+$: 238.2. Found: 238.2.

Step 2; Ethyl 2-(3-(((tert-butyldimethylsilyl)oxy)methyl)pyridin-2-yl)acetate

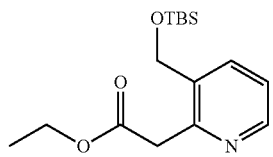 [SMILES: CCOC(=O)Cc1ncccc1CO[Si](C)(C)C(C)(C)C]

A THF (7.0 ml) solution 3-(((tert-butyldimethylsilyl)oxy)methyl)-2-methylpyridine (500 mg, 2.106 mmol) was cooled to −78° C., followed by addition of n-butyllithium (1095 µl, 2.74 mmol). After stirring for 1 h at −78° C., diethyl carbonate (765 µl, 6.32 mmol) was added in one portion. Then the mixture was allowed to slowly warm to room temperature and stirred overnight. The mixture was diluted with aq. $NH_4Cl$ and extracted with DCM (×3). The combined organic layers were dried over $MgSO_4$, filtered, and concentrated. The resulting residue was purified by flash chromatography on a silica gel column eluting with 0 to 50% EtOAc in Hexanes to afford the desired product. LCMS calculated for $C_{16}H_{28}NO_3Si$ (M+H)$^+$: 310.2. Found: 310.2.

Step 3: 3-(5-Amino-2-((3-(hydroxymethyl)pyridin-2-yl)methyl)-[1,2,4]triazolo[1,5-c]pyrimidin-7-yl)benzonitrile

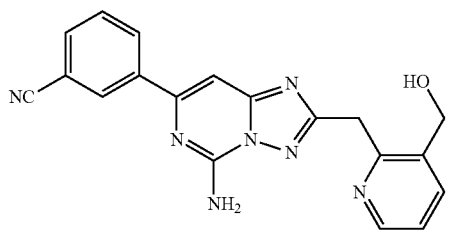 [SMILES: N#Cc1cccc(-c2cc3nc(Cc4ncccc4CO)nn3c(N)n2)c1]

This compound was prepared using similar procedures as described for Example 41, Step 1 to Step 3, with ethyl 2-(3-(((tert-butyldimethylsilyl)oxy)methyl)pyridin-2-yl)acetate replacing methyl 2-(pyridin-2-yl)acetate in Step 2. Then the corresponding product was taken into 3 mL of THF and treated with 3 mL of 6 N HCl solution. The mixture was allowed to stir at room temperature for 3 h. The mixture was diluted with water and extracted with DCM (×3). The combined organic layers were dried over $MgSO_4$, filtered, and concentrated. The resulting residue was purified by flash chromatography on a silica gel column eluting with 0 to 20% MeOH in DCM to afford the desired product. LCMS calculated for $C_{19}H_{16}N_7O$ (M+H)$^+$: 358.1. Found: 358.2.

Step 4: 3-(5-Amino-8-bromo-2-((3-(hydroxymethyl) pyridin-2-yl)methyl)-[1,2,4]triazolo[1,5-c]pyrimidin-7-yl)benzonitrile

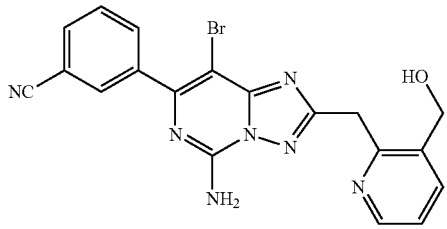 [SMILES: N#Cc1cccc(-c2nc(N)n3nc(Cc4ncccc4CO)nc3c2Br)c1]

This compound was prepared using similar procedures as described for Example 41, Step 4, with 3-(5-amino-2-((3-(hydroxymethyl)pyridin-2-yl)methyl)-[1,2,4]triazolo[1,5-c]pyrimidin-7-yl)benzonitrile replacing 3-(5-amino-2-(pyridin-2-ylmethyl)-[1,2,4]triazolo[1,5-c]pyrimidin-7-yl)benzonitrile. The resulting crude mixture was diluted with water and extracted with DCM (×3). The combined organic layers were dried over MgSO$_4$, filtered, and concentrated. The resulting residue was purified by flash chromatography on a silica gel column eluting with 0 to 15% MeOH in DCM to afford the desired product. LCMS calculated for C$_{19}$H$_{15}$BrN$_7$O (M+H)$^+$: 436.1.

Found: 436.0.

Step 5: 3-(5-Amino-2-((3-(hydroxymethyl)pyridin-2-yl)methyl)-8-(4-methyloxazol-5-yl)-[1,2,4]triazolo[1,5-c]pyrimidin-7-yl)benzonitrile This compound was prepared using similar procedures as described for Example 42, with 3-(5-amino-8-bromo-2-((3-(hydroxymethyl)pyridin-2-yl)methyl)-[1,2,4]triazolo[1,5-c]pyrimidin-7-yl)benzonitrile replacing 3-(5-amino-8-bromo-2-(pyridin-2-ylmethyl)-[1,2,4]triazolo[1,5-c]pyrimidin-7-yl)benzonitrile, and with 4-methyl-5-(4,4,5,5-tetramethyl-1,3,2-dioxaborolan-2-yl)oxazole (Example 61, Step 1) replacing 1-ethyl-5-(4,4,5,5-tetramethyl-1,3,2-dioxaborolan-2-yl)-1H-pyrazole. The final material was purified by preparative LC-MS (pH 2, acetonitrile/water with TFA) to afford the product as a TFA salt. LCMS calculated for C$_{23}$H$_{19}$N$_8$O$_2$ (M+H)$^+$: 439.2; found 439.2.

Example 92. 3-(5-Amino-2-((1-methyl-1H-pyrazol-3-yl)methyl)-8-(4-methyloxazol-5-yl)-[1,2,4]triazolo[1,5-c]pyrimidin-7-yl)benzonitrile

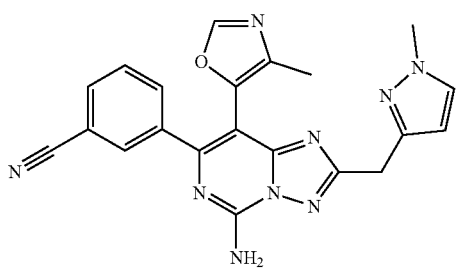 [SMILES: Cc1ncoc1-c1c(-c2cccc(C#N)c2)nc(N)n2nc(Cc3ccn(C)n3)nc12]

Step 1: Methyl 2-(1-methyl-1H-pyrazol-3-yl)acetate

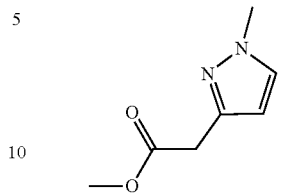

Acetyl chloride (0.355 ml, 4.99 mmol) was added to MeOH (3 ml) at 0° C. and then stirred for 20 min. To this mixture was added 2-(1-methyl-1H-pyrazol-3-yl)acetic acid (140 mg, 0.999 mmol) and then the mixture was stirred at rt overnight. The solvent was removed and the residue was used in the next step directly. LCMS calculated for C$_7$H$_{11}$N$_2$O$_2$ (M+H)$^+$: 155.1; found 155.1.

Step 2: 2-(i-Methyl-1H-pyrazol-3-yl)acetohydrazide

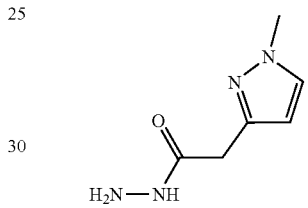

Hydrazine (0.061 ml, 1.946 mmol) was added to a solution of methyl 2-(1-methyl-1H-pyrazol-3-yl)acetate (0.15 g, 0.973 mmol) in ethanol (1.5 mL) at rt and then the reaction mixture was heated and stirred at 100° C. for 2 h. After cooling to rt, the resulting mixture was partially concentrated until solid presented. To this mixture diethyl ether (1.0 mL) was added and the resulting solid was collected by filtration, rinsed with ether, and dried to afford the desired product as a white solid, which was used in the next step without further purification. LCMS calculated for C$_6$H$_{11}$N$_4$O (M+H)$^+$: 155.1; found 155.2.

Step 3: 3-(5-Amino-2-((1-methyl-1H-pyrazol-3-yl)methyl)-[1,2,4]triazolo[1,5-c]pyrimidin-7-yl)benzonitrile

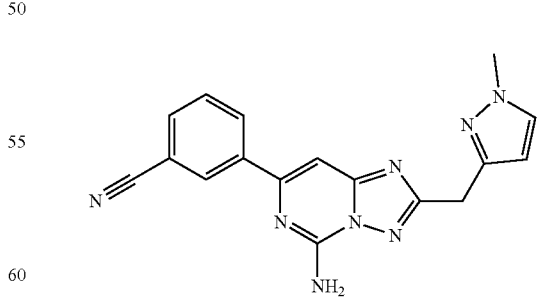

This compound was prepared using similar procedure as described for Example 41, Step 3, replacing 2-(pyridin-2-yl)acetohydrazide with 2-(1-methyl-1H-pyrazol-3-yl)acetohydrazide. LCMS calculated for C$_{17}$H$_{15}$N$_8$ (M+H)$^+$: 331.1; found 331.1.

Step 4: 3-(5-Amino-8-bromo-2-((1-methyl-1H-pyrazol-3-yl)methyl)-[1,2,4]triazolo[1,5-c]pyrimidin-7-yl)benzonitrile

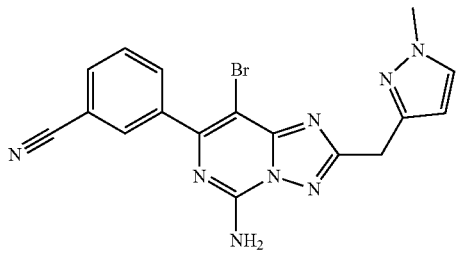 [SMILES: Cn1ccc(Cc2nc3c(Br)c(-c4cccc(C#N)c4)nc(N)n3n2)n1]

NBS (35.6 mg, 0.200 mmol) was added to a mixture of 3-(5-amino-2-((1-methyl-1H-pyrazol-3-yl)methyl)-[1,2,4]triazolo[1,5-c]pyrimidin-7-yl)benzonitrile (66.0 mg, 0.200 mmol) in DMSO (0.4 ml)/CH$_2$Cl$_2$ (0.4 ml) at −30° C. and the reaction mixture was stirred for 1 h. The low boiling point solvent was removed and to the residue was added water. The resulting solid was then collected by filtration, and dried to provide the product, which was used in the next step directly. LCMS calculated for C$_{17}$H$_{14}$BrN$_8$ (M+H)$^+$: 409.1; found 409.1.

Step 5: 3-(5-Amino-2-((1-methyl-1H-pyrazol-3-yl)methyl)-8-(4-methyloxazol-5-yl)-[1,2,4]triazolo[1,5-c]pyrimidin-7-yl)benzonitrile A mixture of 3-(5-amino-8-bromo-2-((1-methyl-1H-pyrazol-3-yl)methyl)-[1,2,4]triazolo[1,5-c]pyrimidin-7-yl)benzonitrile (10.0 mg, 0.024 mmol), 4-methyl-5-(4,4,5,5-tetramethyl-1,3,2-dioxaborolan-2-yl)oxazole (10.22 mg, 0.049 mmol), CsF (18.56 mg, 0.122 mmol) and chloro(1-t-butylindenyl)[2-(dicyclohexylphosphino)-2',4',6'-tri-i-propyl-1,1'-biphenyl]palladium(II) (1.355 mg, 2.443 µmol) in dioxane (0.5 mL)/water (0.1 mL) was first purged with nitrogen, and then heated and stirred at 105° C. for 2 h. The reaction mixture was then cooled to rt, and concentrated. The resulting mixture was diluted with acetonitrile/water and purified using prep-LCMS (pH 2, acetonitrile/water with TFA) to afford the desired product as its TFA salt. LC-MS calculated for C$_{21}$H$_{18}$N$_9$O (M+H)$^+$: m/z=412.2; found 412.2.

Example 93. 3-(5-Amino-2-((1-methyl-1H-pyrazol-3-yl)methyl)-8-(oxazol-5-yl)-[1,2,4]triazolo[1,5-c]pyrimidin-7-yl)benzonitrile

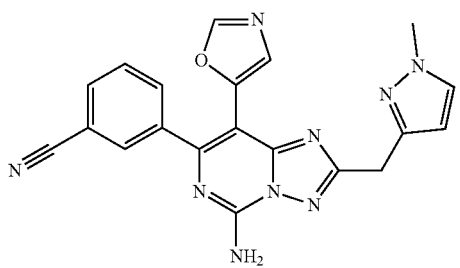 [SMILES: Cn1ccc(Cc2nc3c(-c4cnco4)c(-c4cccc(C#N)c4)nc(N)n3n2)n1]

This compound was prepared using similar procedures as described in Example 92, Step 5, replacing 4-methyl-5-(4, 4,5,5-tetramethyl-1,3,2-dioxaborolan-2-yl)oxazole with 5-(4,4,5,5-tetramethyl-1,3,2-dioxaborolan-2-yl)oxazole. LC-MS calculated for C$_{20}$H$_{16}$N$_9$O (M+H)$^+$: m/z=398.1; found 398.1.

Example 94. 3-(5-Amino-2-((3-methylpyridin-2-yl)methoxy)-8-(pyrimidin-4-yl)-[1,2,4]triazolo[1,5-c]pyrimidin-7-yl)benzonitrile

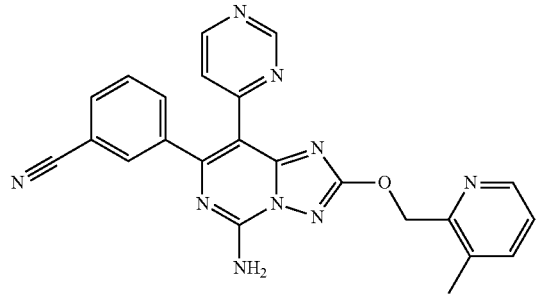 [SMILES: Cc1cccnc1COc1nc2c(-c3ccncn3)c(-c3cccc(C#N)c3)nc(N)n2n1]

Step 1: 3-(5-(Bis(4-methoxybenzyl)amino)-2-bromo-8-(pyrimidin-4-yl)-[1,2,4]triazolo[1,5-c]pyrimidin-7-yl)benzonitrile

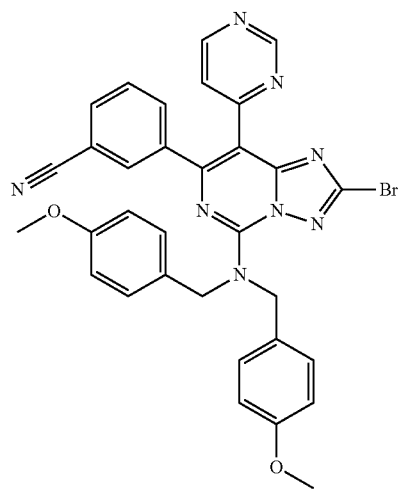 [SMILES: COc1ccc(CN(Cc2ccc(OC)cc2)c2nc(-c3cccc(C#N)c3)c(-c3ccncn3)c3nc(Br)nn23)cc1]

To a mixture of copper(II) bromide (91 mg, 0.407 mmol) and tert-butyl nitrite (0.054 ml, 0.407 mmol) in acetonitrile (3 mL) under nitrogen at 50° C. was added dropwise 3-(2-amino-5-(bis(4-methoxybenzyl)amino)-8-(pyrimidin-4-yl)-[1,2,4]triazolo[1,5-c]pyrimidin-7-yl)benzonitrile (100 mg, 0.203 mmol) (from Example 69, step 5) in acetonitrile (3 mL). The mixture was stirred at 50° C. for 2 hours. After cooling to room temperature, 1 N aqueous NH$_4$OH solution (20 mL) was added and the mixture was extracted three times with CH$_2$Cl$_2$ (20 mL). The combined organic layers were dried over sodium sulfate, filtered and concentrated. The crude material was purified by silica gel column chromatography eluting with 50-100% ethyl acetate/hexane to give the desired product. LC-MS calculated for C$_{32}$H$_{26}$BrN$_8$O$_2$ (M+H)$^+$: m/z=633.1; found 633.2.

Step 2: 3-(5-Amino-2-((3-methylpyridin-2-yl)methoxy)-8-(pyrimidin-4-yl)-[1,2,4]triazolo[1,5-c]pyrimidin-7-yl)benzonitrile A suspension of sodium hydride (60% in mineral oil, 3.8 mg, 0.095 mmol), 3-(5-(bis(4-methoxybenzyl)amino)-2-bromo-8-(pyrimidin-4-yl)-[1,2,4]triazolo[1,5-c]pyrimidin-7-yl)benzonitrile (20 mg, 0.032 mmol) and (3-methylpyridin-2-yl)methanol (9.1 µL, 0.095 mmol) in 1,4-dioxane (1 mL) was heated and stirred at 110° C. under nitrogen overnight. The reaction mixture was then cooled to rt, concentrated, and added TFA (1.0 mL). The resulting mixture was then stirred at 110° C. for 30 min, cooled to rt, diluted with acetonitrile, filtered and purified by preparative LC-MS (pH 2, acetonitrile/water with TFA) to give desired product as a TFA salt. LC-MS calculated for $C_{23}H_{18}N_9O$ $(M+H)^+$: m/z=436.2; found 436.2. $^1H$ NMR (600 MHz, DMSO) δ 8.97 (d, J=1.4 Hz, 1H), 8.88 (d, J=5.2 Hz, 1H), 8.58-8.52 (m, 1H), 7.97 (d, J=7.8 Hz, 1H), 7.88 (dd, 5.4, 1.4 Hz, 1H), 7.85 (dt, J=7.5, 1.5 Hz, 1H), 7.78 (t, J=1.8 Hz, 1H), 7.60-7.54 (m, 2H), 7.53 (t, J=7.8 Hz, 1H), 5.69 (s, 2H), 2.48 (s, 3H).

Example 95. 3-(5-Amino-2-((6-methylpyridin-2-yl)methoxy)-8-(pyrimidin-4-yl)-[1,2,4]triazolo[1,5-c]pyrimidin-7-yl)benzonitrile

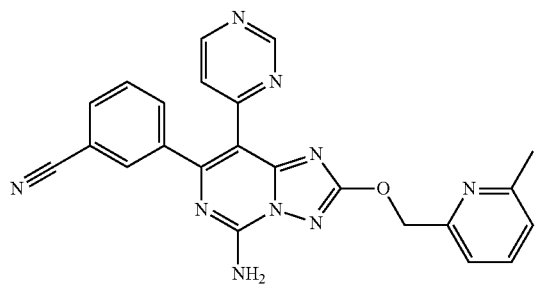 [SMILES: Cc1cccc(COc2nc3c(-c4ccncn4)c(-c4cccc(C#N)c4)nc(N)n3n2)n1]

This compound was prepared using similar procedures as described for Example 94, with (6-methylpyridin-2-yl)methanol replacing (3-methylpyridin-2-yl)methanol in Step 2. The crude was purified by preparative LC-MS (pH 2, acetonitrile/water with TFA) to afford the product as a TFA salt. LCMS calculated for $C_{23}H_{18}N_9O$ $(M+H)^+$: m/z=436.2; found 436.2.

Example 96. 2-((5-Amino-7-(3-cyanophenyl)-8-(pyrimidin-4-yl)-[1,2,4]triazolo[1,5-c]pyrimidin-2-yl)methoxy)benzonitrile

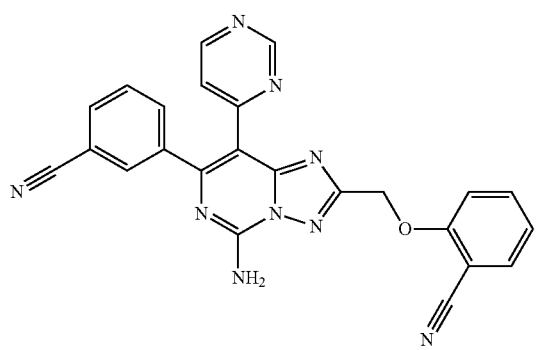 [SMILES: N#Cc1cccc(-c2nc(N)n3nc(COc4ccccc4C#N)nc3c2-c2ccncn2)c1]

A mixture of 3-(5-amino-2-(chloromethyl)-8-(pyrimidin-4-yl)-[1,2,4]triazolo[1,5-c]pyrimidin-7-yl)benzonitrile (20 mg, 0.055 mmol) (from Example 72, step 4), $Cs_2CO_3$ (35.9 mg, 0.110 mmol) and 2-hydroxybenzonitrile (13.1 mg, 0.110 mmol) in acetonitrile (1.0 mL) was heated and stirred at 70° C. for 1 h. The resulting mixture was then cooled to room temperature, diluted with methanol, filtered and purified by preparative LC-MS (pH 2, acetonitrile/water with TFA) to give the desired product as a TFA salt. LCMS calculated for $C_{24}H_{16}N_9O$ $(M+H)^+$: m/z=446.1; found 446.2.

Example 97. 3-(5-Amino-2-(((3-methylpyridin-2-yl)methyl)amino)-8-(pyrimidin-4-yl)-[1,2,4]triazolo[1,5-c]pyrimidin-7-yl)benzonitrile

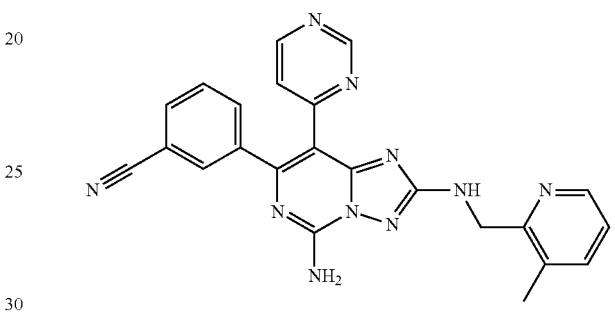

A mixture of Triethyl orthoformate (0.029 mL, 0.176 mmol), 3-(2-amino-5-(bis(4-methoxybenzyl)amino)-8-(pyrimidin-4-yl)-[1,2,4]triazolo[1,5-c]pyrimidin-7-yl)benzonitrile (20 mg, 0.035 mmol) (from Example 69, step 5), and 3-methylpicolinaldehyde (12.8 mg, 0.105 mmol) in EtOH (1 mL) was stirred at 120° C. overnight. The reaction mixture was then cooled to 0° C., and $NaBH_4$ (4.0 mg, 0.105 mmol) was added. After stirring at 0° C. for 1 h, the reaction mixture was quenched with a few drops of TFA and diluted with MeOH. The crude mixture was then purified by preparative LC-MS (pH 2, acetonitrile/water with TFA) to give the intermediate, which was then dissolved in TFA (1.0 mL). The resulting mixture was stirred at 120° C. for 25 min, cooled to rt, diluted with acetonitrile, and purified by preparative LC-MS (pH 2, acetonitrile/water with TFA) to give the desired product as a TFA salt. LCMS calculated for $C_{23}H_{19}N_{10}$ $(M+H)^+$: m/z=435.2; found 435.2.

Example A. Adenosine A2A Receptor Cyclic AMP GS Assay

Stably transfected HEK-293 cells expressing the human adenosine A2A receptor (Perkin Elmer) are maintained in MEM culture medium with 10% FBS and 400 µg/ml Genedcin (Life Technologies). 18 to 24 hours prior to assay, geneticin is removed from culture. The cisbio cAMP-GS Dynamic kit utilizing the FRET (Fluorescence Resonance Energy Transfer) technology is used to measure cAMP accumulation in the cells. Compounds of the present disclosure at an appropriate concentration are mixed with 10000 cells/well in white 96 well half area plates (Perkin Elmer) for 30 min at room temperature (RT) gently shaking. Agonist, CGS21680 (R&D Technologies) at 4 nM is added to each well for 60 min at RT gendy shaking. Detection reagents, d2-labeled cAMP (acceptor) and anti-cAMP cryptate (donor) are added to each well for 60 min at RT gently shaking. Plates are read on Pherastar (BMG Labtech), fluorescence ratio 665/620 is calculated and $EC_{50}$ determination is performed by fitting the curve of percent of control versus the log of the compound concentration using GraphPad Prism.

Example B. Adenosine A2B Receptor Cyclic AMP GS Assay

Stably transfected HEK-293 cells expressing the human adenosine A2B receptor (Perkin Elmer) were maintained in MEM culture medium with 10% FBS and 100 µg/ml Geneticin (Life Technologies). 18 to 24 hours prior to assay, geneticin was removed from culture. The cisbio cAMP-GS Dynamic kit utilizing the FRET (Fluorescence Resonance Energy Transfer) technology was used to measure cAMP accumulation in the cells. Compounds of the present disclosure at an appropriate concentration were mixed with 10000 cells/well in white 96 well half area plates (Perkin Elmer) for 30 min at RT gently shaking. Agonist, NECA (R&D Technologies) at 12 nM was added to each well for 60 min at RT gently shaking. Detection reagents, d2-labeled cAMP (acceptor) and anti-cAMP cryptate (donor) were added to each well for 60 min at RT gently shaking. Plates were read on Pherastar (BMG Labtech), fluorescence ratio 665/620 was calculated and $EC_{50}$ determination was performed by fitting the curve of percent of control versus the log of the compound concentration using GraphPad Prism. The $EC_{50}$ data obtained via this method are shown in Table 1.

Example C. A2A Tag-lite® HTRF Assay

Assays were conducted in black low volume 384-well polystyrene plates (Greiner 784076-25) in a final volume of 10 µL. Test compounds were first serially diluted in DMSO and 100 nl added to the plate wells before the addition of other reaction components. The final concentration of DMSO was 1%. Tag-lite® Adenosine A2A labeled cells (CisBio C1TT1A2A) were diluted 1:5 into Tag-lite buffer (CisBio LABMED) and spun 1200 g for 5 mins. The pellet was resuspended at a volume 10.4× the initial cell suspension volume in Tag-lite buffer, and Adenosine A2A Receptor Red antagonist fluorescent ligand (CisBio L0058RED) added at 12.5 nM final concentration. 10 ul of the cell and ligand mix was added to the assay wells and incubated at room temperature for 45 minutes before reading on a PHERAstar FS plate reader (BMG Labtech) with HTRF 337/620/665 optical module. Percent binding of the fluorescent ligand was calculated; where 100 nM of A2A antagonist control ZM 241385 (Tocris 1036) displaces the ligand 100% and 1% DMSO has 0% displacement. The % binding data versus the log of the inhibitor concentration was fitted to a one-site competitive binding model (GraphPad Prism version 7.02) where the ligand constant=12.5 nM and the ligand Kd=1.85 nM. The $K_i$ data obtained via this method are shown in Table 1.

Example D. A2B Fitter Binding Assay

Assays are conducted in deep well polypropylene plates (Greiner 786201) in a final volume of 550 µL. Test compounds are first serially diluted in DMSO and 5.5 ul is then added to the plate wells before the addition of other reaction components. The final concentration of DMSO is 3%. HEK293 cell membranes overexpressing the human adenosine receptor A2B (Perkin Elmer ES-113-M400UA) are diluted to 40 µg/ml in 50 mM HEPES pH 7.0, 5 mM $MgCl_2$, 1 mM EDTA (Assay buffer). [3H] 8-cyclopentyl-1,3-dipropylxanthine (Perkin Elmer NET974001MC) is diluted in assay buffer+22% DMSO to 24.2 nM, and then further diluted to 1 nM by addition to the diluted membranes. 545 µl of the membrane and ligand mix is added to the assay wells and incubated on a shaker at room temperature for 1 hour. The membrane mix is then filtered over a UniFilter GF/C filter plate (Perkin Elmer 6005174) pre-soaked in 50 mM HEPES pH 6.5, 5 mM $MgCl_2$ 1 mM EDTA 0.5% BSA and then washed with 5 ml ice cold 50 mM HEPES pH 6.5, 5 mM $MgCl_2$, 1 mM EDTA 0.2% BSA. 50 µl MicroScint™ cocktail (Perkin Elmer 6013621) is added and plates are read on a Topcount NXT FS (Perkin Elmer). Percent binding of the [3H] ligand is calculated, where 1000 nM of LUF 5834 (Tocris 4603) control displaces the ligand 100% and 3% DMSO has 0% displacement. The % binding data versus the log of the inhibitor concentration is fitted to a one-site competitive binding model (GraphPad Prism version 7.02) where the ligand constant=2 nM and the ligand Kd=13 nM.

Example E. A1 and A3 SPA Binding Assays

Both assays are conducted in white 384-well polystyrene plates (Greiner 781075) in a final volume of 50 µL. Inhibitors are first serially diluted in DMSO and 100 nL is added to the plate wells before the addition of other reaction components. The final concentration of DMSO is 2%.

Wheatgerm agglutinin-coated yttrium silicate SPA beads (Perkin Elmer RPNQ0023) and CHO-K1 cell membranes overexpressing each human adeonsine receptor are incubated in 50 mM HEPES pH 7.0, 5 mM $MgCl_2$, 1 mM EDTA (Assay buffer) on a rotary stirrer for 2 hours at 4° C. The beads are pelleted by centrifugation at 6000 g for one minute, and then the supernatant with unbound membrane is discarded. The beads are re-suspended to the original volume in assay buffer. Each radioligand is diluted in assay buffer+22% DMSO at 12.2× the final concentration, and then added to the SPA bead suspension. 50 µl of the SPA bead reaction mix is added to the assay wells and the plates shaken at 600 rpm for 1 hour at room temperature. The beads are then allowed to settle for 1 hour before reading on a Topcount NXT FS (Perkin Elmer). Percent binding of the radiolabeled ligand is calculated, where a control at >100× Ki displaces the ligand 100% and 2% DMSO has 0% displacement. The % binding data versus foe log of foe inhibitor concentration is fitted to a one-site competitive binding model (GraphPad Prism version 7.02). Assay conditions are provided in the table below.

| Assay Component | A1 | A3 |
| --- | --- | --- |
| SPA beads in Hepes buffer | 3 mg/ml | 1.25 mg/ml |
| Membrane | 60 µg/ml Perkin Elmer ES-010 | 20 µg/ml Perkin Elemer ES-012 |
| Radioligand | 1 nM [3H] DP-CPX (Perkin Elmer NET974) $K_D$ = 1 nM | 0.1 nM [125I] MECA (Perkin Elmer NEX312) $K_D$ = 0.8 nM |
| Control | 1 µM DPCPX (Tocris 0439) | 0.1 µM IB-MECA (Tocris 1066) |

TABLE 1

The $A_{2A}$_Ki data (Example C) and $A_{2B}$_cAMP_$EC_{50}$ data (Example B) are provided below.

| Ex. No. | $A_{2A}$_Ki (nM) | $A_{2B}$_cAMP_$EC_{50}$ (nM) |
|---|---|---|
| 1 | † | ††† |
| 2 | ††† | N/A |
| 3 | †† | N/A |
| 4 | † | † |
| 5 | †† | †† |
| 6 | †† | N/A |
| 7 | †† | †† |
| 8 | ††† | N/A |
| 9 | †† | N/A |
| 10 | † | ††† |
| 11 | †† | N/A |
| 12 | †† | N/A |
| 13 | †† | N/A |
| 14 | † | †† |
| 15 | † | ††† |
| 16 | † | ††† |
| 17 | † | †† |
| 18 | †† | †† |
| 19 | † | ††† |
| 20 | † | ††† |
| 21 | † | †††† |
| 22 | †† | †††† |
| 23 | † | N/A |
| 24 | † | † |
| 25 | † | ††† |
| 26 | † | † |
| 27 | † | †† |
| 28 | † | † |
| 29 | † | † |
| 30 | † | † |
| 31 | † | †† |
| 32 | † | ††† |
| 33 | † | ††† |
| 34 | † | † |
| 35 | † | † |
| 36 | † | †† |
| 37 | † | † |
| 38 | † | †† |
| 39 | † | †† |
| 40 | †† | †††† |
| 41 | † | † |
| 42 | † | † |
| 43 | † | † |
| 44 | † | †† |
| 45 | † | † |
| 46 | † | † |
| 47 | † | † |
| 48 | † | †† |
| 49 | † | † |
| 50 | † | † |
| 51 | † | †† |
| 52 | † | † |
| 53 | † | †† |
| 54 | † | † |
| 55 | † | † |
| 56 | † | †† |
| 57 | † | ††† |
| 58 | † | † |
| 59 | † | †† |
| 60 | † | †† |
| 61 | † | † |
| 62 | † | † |
| 63 | † | † |
| 64 | † | † |
| 65 | † | † |
| 66 | † | † |
| 67 | † | ††† |
| 68 | † | ††† |
| 69 | † | †† |
| 70 | † | †† |
| 71 | † | †† |
| 72 | † | †† |
| 73 | † | †† |
| 74 | † | † |
| 75 | † | † |
| 76 | † | † |
| 77 | † | †† |
| 78 | † | † |
| 79 | † | † |
| 80 | † | †† |
| 81 | † | † |
| 82 | † | † |
| 83 | † | †† |
| 84 | † | † |
| 85 | † | † |
| 86 | † | † |
| 87 | † | † |
| 88 | † | † |
| 89 | † | † |
| 90 | † | † |
| 91 | † | † |
| 92 | † | † |
| 93 | † | † |
| 94 | † | † |
| 95 | † | † |
| 96 | † | † |
| 97 | † | † |

† indicates $A_{2A}$_Ki or $A_{2B}$_cAMP_$EC_{50}$ ≤ 10 nM,
†† indicates $A_{2A}$_Ki or $A_{2B}$_cAMP_$EC_{50}$ > 10 nM but ≤ 100 nM,
††† indicates $A_{2A}$_Ki or $A_{2B}$_cAMP_$EC_{50}$ > 100 nM but ≤ 1 μM,
†††† indicates $A_{2A}$_Ki or $A_{2B}$_cAMP_$EC_{50}$ is greater than 1 μM.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula (I):

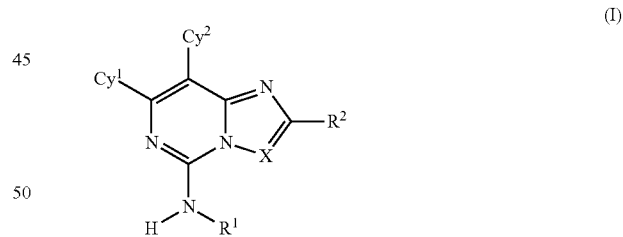

or a pharmaceutically acceptable salt thereof; wherein:

X is N;

$R^1$ is selected from H, $C_{1-6}$ alkyl, $C_{2-6}$ alkenyl, $C_{2-6}$ alkynyl, and $C_{1-6}$ haloalkyl;

$R^2$ is selected from $C_{1-6}$ alkyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, $C(O)R^{b2}$, $C(O)NR^{c2}R^{d2}$, $C(O)OR^{a2}$, and $NR^{c2}R^{d2}$, wherein the $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- are each optionally substituted with 1, 2, 3, 4, or 5 independently selected $R^C$ substituents; and wherein the $C_{1-6}$ alkyl of $R^2$ is substituted with 1, 2, 3, 4, or 5 independently selected $R^C$ substituent;

$Cy^1$ is 3-cyanophenyl;

$Cy^2$ is $C_{6-14}$ aryl, $C_{3-14}$ cycloalkyl, 5-14 membered heteroaryl, or 4-14 membered heterocycloalkyl, wherein the $C_{6-14}$ aryl, $C_{3-14}$ cycloalkyl, 5-14 membered heteroaryl, or 4-14 membered heterocycloalkyl is optionally substituted with 1, 2, 3, 4, 5, 6, 7, or 8 independently selected $R^F$ substituents;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a2}$, $R^{c2}$, and $R^{d2}$ are each optionally substituted with 1, 2, 3, 4, 5, 6, 7, or 8 independently selected $R^G$ substituents;

or any $R^{c2}$ and $R^{d2}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^G$ substituents;

each $R^{b2}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b2}$ are each optionally substituted with 1, 2, 3, 4, 5, 6, 7, or 8 independently selected $R^G$ substituents;

each $R^C$, $R^F$, and $R^G$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, $OS(O)_2R^{b4}$, $SF_5$, $P(O)R^{f4}R^{g4}$, $OP(O)(OR^{h4})(OR^{i4})$, $P(O)(OR^{h4})(OR^{i4})$, and $BR^{j4}R^{k4}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^C$, $R^F$, and $R^G$ are each optionally substituted with 1, 2, 3, 4, 5, 6, 7, or 8 independently selected $R^H$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a4}$, $R^{c4}$, and $R^{d4}$ are each optionally substituted with 1, 2, 3, 4, 5, 6, 7, or 8 independently selected $R^H$ substituents;

or, any $R^{c4}$ and $R^{d4}$ attached to the same N atom, together with the N atom to which they are attached, optionally form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^H$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b4}$ are each optionally substituted with 1, 2, 3, 4, 5, 6, 7, or 8 independently selected $R^H$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f4}$ and $R^{g4}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h4}$ and $R^{i4}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j4}$ and $R^{k4}$ is independently selected from OH, $C_{1-6}$ alkoxy, and $C_{1-6}$ haloalkoxy;

or, any $R^{j4}$ and $R^{k4}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^H$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, $OS(O)_2R^{b5}$, $SF_5$, $P(O)R^{f5}R^{g5}$, $OP(O)(OR^{h5})(OR^{i5})$, $P(O)(OR^{h5})(OR^{i5})$, and $BR^{j5}R^{k5}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^H$ are each optionally substituted with 1, 2, 3, or 4 independently selected $R^I$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a5}$, $R^{c5}$, and $R^{d5}$ are each optionally substituted with 1, 2, 3, or 4 independently selected R substituents;

or any $R^{c5}$ and $R^{d5}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected R substituents;

each $R^{b5}$ is independently selected from H, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b5}$ are each optionally substituted with 1, 2, 3, or 4 independently selected R substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f5}$ and $R^{g5}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h5}$ and $R^{i5}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j5}$ and $R^{k5}$ is independently selected from OH, $C_{1-6}$ alkoxy, and $C_{1-6}$ haloalkoxy;

or, any $R^{j5}$ and $R^{k5}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c5}R^{d6}$, $C(=NR^{e6})R^{b6}$, $C(=NR^{e6})NR^{c6}R^{d6}$, $NR^{c6}C(=NR^{e6})NR^{c6}R^{d6}$, $NR^{c6}C(=NR^{e6})R^{b6}$, $NR^{c6}S(O)R^{b6}$, $NR^{c6}S(O)NR^{c6}R^{d6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^I$ are each optionally substituted with 1, 2, 3, or 4 independently selected $R^J$ substituents;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a6}$, $R^{c6}$, and $R^{d6}$ are each optionally substituted with 1, 2, 3, or 4 independently selected R substituents;

or any $R^{c6}$ and $R^{d6}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected R substituents;

each $R^{b6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b6}$ are each optionally substituted with 1, 2, 3, or 4 independently selected R substituents;

each $R^{e6}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{f6}$ and $R^{g6}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h6}$ and $R^{i6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j6}$ and $R^{k6}$ is independently selected from OH, $C_{1-6}$ alkoxy, and $C_{1-6}$ haloalkoxy;

or, any $R^{j6}$ and $R^{k6}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$ $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^{c7}C(=NR^{e7})NR^{c7}R^{d7}$, $NR^{c7}C(=NR^{e7})R^{b7}$, $NR^{c7}S(O)R^{b7}$, $NR^{c7}S(O)NR^{c7}R^{d7}$, $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, $OS(O)_2R^{b7}$, $SF_5$, $P(O)R^{f7}R^{g7}$, $OP(O)(OR^{h7})(OR^{i7})$, $P(O)(OR^{h7})(OR^{i7})$, and $BR^{j7}R^{k7}$, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^J$ are each optionally substituted with 1, 2, 3, or 4 independently selected $R^K$ substituents;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{a7}$, $R^{c7}$, and $R^{d7}$ are each optionally substituted with 1, 2, 3, or 4 independently selected $R^K$ substituents;

or any $R^{c7}$ and $R^{d7}$ attached to the same N atom, together with the N atom to which they are attached, form a 5- or 6-membered heteroaryl or a 4-14 membered heterocycloalkyl group, wherein the 5- or 6-membered heteroaryl or 4-14 membered heterocycloalkyl group is optionally substituted with 1, 2, 3, or 4 independently selected $R^K$ substituents;

each $R^{b7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl- of $R^{b7}$ are each optionally substituted with 1, 2, 3, or 4 independently selected $R^K$ substituents;

each $R^{e7}$ is independently selected from H, OH, CN, $C_{1-6}$ alkyl, $C_{2-6}$ alkenyl, $C_{1-6}$ alkoxy, $C_{1-6}$ haloalkyl, $C_{1-6}$ haloalkoxy, $C_{2-6}$ alkynyl, $C_{6-14}$ aryl, $C_{3-14}$ cycloalkyl, 5-14 membered heteroaryl, and 4-14 membered heterocycloalkyl;

each $R^{f7}$ and $R^{g7}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{h7}$ and $R^{i7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

each $R^{j7}$ and $R^{k7}$ is independently selected from OH, $C_{1-6}$ alkoxy, and $C_{1-6}$ haloalkoxy;

or, any $R^{j7}$ and $R^{k7}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^K$ is independently selected from H, D, OH, halo, oxo, CN, C(O)OH, $NH_2$, $NO_2$, $SF_5$, $C_{1-6}$ alkyl, $C_{1-6}$ alkoxy, $C_{1-6}$ haloalkoxy, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-; and wherein any heteroaryl group of any of the above-recited substituents optionally comprises an N-oxide on any ring-forming nitrogen.

2. The compound of claim 1, or a pharmaceutically acceptable salt thereof; wherein:

each $R^J$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-, CN, $NO_2$, $OR^{a7}$, $SR^{a7}$, $NHOR^{a7}$, $C(O)R^{b7}$, $C(O)NR^{c7}R^{d7}$, $C(O)NR^{c7}(OR^{a7})$, $C(O)OR^{a7}$, $OC(O)R^{b7}$, $OC(O)NR^{c7}R^{d7}$, $NR^{c7}R^{d7}$ $NR^{c7}NR^{c7}R^{d7}$, $NR^{c7}C(O)R^{b7}$, $NR^{c7}C(O)OR^{a7}$, $NR^{c7}C(O)NR^{c7}R^{d7}$, $C(=NR^{e7})R^{b7}$, $C(=NR^{e7})NR^{c7}R^{d7}$, $NR^7C(=NR^{e7})$ $NR^{c7}R^{d7}$, $NR^{c7}C(=NR^{e7})R^{b7}$, $NR^7S(O)R^{b7}$, $NR^{c7}S(O)NR^{c7}R^{d7}$ $NR^{c7}S(O)_2R^{b7}$, $NR^{c7}S(O)(=NR^{e7})R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $OS(O)(=NR^{e7})R^{b7}$, $OS(O)_2R^{b7}$, $SF_5$, $P(O)R^{f7}R^{g7}$, $OP(O)(OR^{h7})(OR^{i7})$, $P(O)(OR^{h7})(OR^{i7})$, and $BR^{j7}R^{k7}$;

each $R^{a7}$, $R^{c7}$, and $R^{d7}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

or any $R^{c7}$ and $R^{d7}$ attached to the same N atom, together with the N atom to which they are attached, form a 5- or 6-membered heteroaryl or a 4-14-membered heterocycloalkyl group; and each $R^{b7}$ is independently selected from H, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-.

3. The compound of claim 1, or a pharmaceutically acceptable salt thereof; wherein:

each $R^I$ is independently selected from D, halo, oxo, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, (4-14 membered heterocycloalkyl)-$C_{1-6}$ alkyl-, CN, $NO_2$, $OR^{a6}$, $SR^{a6}$, $NHOR^{a6}$, $C(O)R^{b6}$, $C(O)NR^{c6}R^{d6}$, $C(O)NR^{c6}(OR^{a6})$, $C(O)OR^{a6}$, $OC(O)R^{b6}$, $OC(O)NR^{c6}R^{d6}$, $NR^{c6}R^{d6}$, $NR^{c6}NR^{c6}R^{d6}$, $NR^{c6}C(O)R^{b6}$, $NR^{c6}C(O)OR^{a6}$, $NR^{c6}C(O)NR^{c5}R^{d6}$, $C(=NR^{e6})R^{b6}$, $C(=NR^{e6})NR^{c6}R^{d6}$, $NR^{c6}C(=NR^{e6})$ $NR^{c6}R^{d6}$, $NR^{c6}C(=NR^{e6})R^{b6}$, $NR^{c6}S(O)R^{b6}$, $NR^{c6}S(O)NR^{c6}R^{d6}$, $NR^{c6}S(O)_2R^{b6}$, $NR^{c6}S(O)(=NR^{e6})R^{b6}$, $NR^{c6}S(O)_2NR^{c6}R^{d6}$, $S(O)R^{b6}$, $S(O)NR^{c6}R^{d6}$, $S(O)_2R^{b6}$, $S(O)_2NR^{c6}R^{d6}$, $OS(O)(=NR^{e6})R^{b6}$, $OS(O)_2R^{b6}$, $SF_5$, $P(O)R^{f6}R^{g6}$, $OP(O)(OR^{h6})(OR^{i6})$, $P(O)(OR^{h6})(OR^{i6})$, and $BR^{j6}R^{k6}$;

each $R^{a6}$, $R^{c6}$, and $R^{d6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-;

or any $R^{c6}$ and $R^{d6}$ attached to the same N atom, together with the N atom to which they are attached, form a 5- or 6-membered heteroaryl or a 4-14-membered heterocycloalkyl group; and each $R^{b6}$ is independently selected from H, $C_{1-6}$ alkyl, $C_{1-6}$ haloalkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, $C_{6-14}$ aryl-$C_{1-6}$ alkyl-, $C_{3-14}$ cycloalkyl-$C_{1-6}$ alkyl-, (5-14 membered heteroaryl)-$C_{1-6}$ alkyl-, and (4-14 membered heterocycloalkyl)-$C_{1-6}$ alkyl-.

4. The compound of claim 1, or a pharmaceutically acceptable salt thereof, wherein $Cy^2$ is $C_{6-14}$ aryl, wherein the $C_{6-14}$ aryl is optionally substituted with 1, 2, 3, or 4 independently selected $R^F$ substituents.

5. The compound of claim 1, or a pharmaceutically acceptable salt thereof, wherein $Cy^2$ is 5-14 membered heteroaryl, wherein the 5-14 membered heteroaryl is optionally substituted with 1, 2, 3, or 4 independently selected $R^F$ substituents.

6. The compound claim 1, or a pharmaceutically acceptable salt thereof, wherein $Cy^2$ is 4-14 membered heterocycloalkyl, wherein the 4-14 membered heterocycloalkyl is optionally substituted with 1, 2, 3, or 4 independently selected $R^F$ substituents.

7. The compound of claim 1, or a pharmaceutically acceptable salt thereof, wherein $Cy^2$ is selected from pyridinyl, tetrahydropyridinyl, piperidinyl, pyridine-N-oxide, oxo-dihydropyridinyl, phenyl, pyrazolo[1,5-a]pyridin-3-yl, pyrazolo[1,5-b]pyridazinyl, pyrazolyl, pyrimidinyl, quinolinyl, oxazolyl, 2,3-dihydro-[1,4]dioxino[2,3-b]pyridin-8-yl, and triazolyl each of which is optionally substituted with 1, 2, or 3 substituents selected from $C_{1-3}$ alkyl, $C_{1-3}$ alkyl-OH, halo, CN, $C_{1-3}$ alkoxy, and $C(O)NH_2$.

8. The compound of claim 1, or a pharmaceutically acceptable salt thereof, wherein the optionally substituted $Cy^2$ is selected from 2,6-dimethylpyridin-4-yl, pyridin-4-yl, 2-methylpyridin-4-yl, 1-carbamoyl-1,2,3,6-tetrahydropyridin-4-yl, 1-carbamoylpiperidin-4-yl, 2-methoxypyridin-4-yl, 2-methoxy-6-methylpyridin-4-yl, 2,6-dimethylpyridin-4-yl-1-oxide, 1-ethyl-6-oxo-1,6-dihydropyridin-3-yl, 3-methylpyridin-4-yl, 3-fluoropyridin-4-yl, 3-chloropyridin-4-yl, 3-methoxypyridin-4-yl, 3-cyanopyridin-4-yl, 4-carbamoylphenyl, pyrazolo[1,5-a]pyridin-3-yl, pyrazolo[1,5-b]pyridazin-3-yl, 5-methyl-1H-pyrazol-4-yl, 1-ethyl-1H-pyrazol-5-yl, 1-isopropyl-1H-pyrazol-5-yl, 1-propyl-1H-pyrazol-5-yl, pyrimidin-4-yl, 2,3-dihydro-[1,4]dioxino[2,3-b]pyridin-8-yl, quinolin-5-yl, 5-fluoropyrimidin-4-yl, oxazol-5-yl, 4-methyloxazol-5-yl, 4-ethyloxazol-5-yl, 4-(hydroxymethyl)-2-methyloxazol-5-yl, 4-(methoxymethyl)-2-methyloxazol-5-yl, 4-(hydroxymethyl)-2-methyloxazol-5-yl, 1-ethyl-1H-1,2,3-triazol-5-yl, and cyclopropyl.

9. The compound of claim 1, or a pharmaceutically acceptable salt thereof, wherein $R^1$ is selected from H and $C_{1-6}$ alkyl.

10. The compound of claim 1, or a pharmaceutically acceptable salt thereof, wherein $R^1$ is H or $C_{1-3}$ alkyl.

11. The compound of claim 1, for a pharmaceutically acceptable salt thereof, wherein $R^1$ is H or ethyl.

12. The compound of claim 1, or a pharmaceutically acceptable salt thereof, wherein $R^1$ is H.

13. The compound of claim 1, or a pharmaceutically acceptable salt thereof, wherein the optionally substituted $R^2$ is selected from pyridinylmethyl, hydroxy(phenyl)methyl, hydroxyethylamino(phenyl)ethyl, cyclohexylmethyl, fluorobenzyl, hydroxy(fluorophenyl)methyl, (methylpyridinyl)methyl, (fluoropyridinyl)methyl, (trifluoromethylpyridinyl)methyl, ((hydroxymethyl)pyridinyl)methyl, (methoxypyridinyl)methyl, (methylpyrazolyl)benzyl, (methylpyrazolyl)methyl, benzoisoxazolylmethyl, (methylindazolyl)methyl, (hydroxyazetidinyl)methyl, benzoyl, phenylcyclopropyl, (cyano(phenyl)methyl)amino, tetrahydrofuranyl, phenyl(pyridinyloxy)methyl, fluoro((fluorohydroxypyrrolidinyl)methyl)benzyl, ((carboxypiperidinyl)methyl)fluorobenzyl, fluoro((N-methylmethylsulfonamido)methyl)benzyl, ((dioxoimidazolidinyl)methyl)fluorobenzyl, (difluorophenyl)(hydroxy)methyl, (pyridinyl-1H-tetrazolyl)methyl, (pyrazolyl-1H-tetrazolyl)methyl, (thiazolyl-1H-tetrazolyl)methyl, (methyltrifluoromethylpyrazolyl)methyl, ((1,1-dioxidoisothiazolidinyl)methyl)fluorobenzyl, ((methyl-2,5-dioxoimidazolidinyl)methyl)benzyl, and (cyanophenoxy)methyl.

14. The compound of claim/or a pharmaceutically acceptable salt thereof, wherein the optionally substituted $R^2$ is selected from pyridin-2-ylmethyl, hydroxy(phenyl)methyl, (2-hydroxyethylamino)(phenyl)methyl, cyclohexylmethyl, 2-fluorobenzyl, (2-fluorophenyl)(hydroxy)methyl, (6-methylpyridin-2-yl)methyl, (3-fluoropyridin-2-yl)methyl, (3-methoxypyridin-2-yl)methyl, 2-(1-methyl-1H-pyrazol-4-yl)benzyl, benzo[d]isoxazol-3-ylmethyl, (1-methyl-1H-indazol-3-yl)methyl, (3-hydroxyazetidin-1-yl)methyl, benzoyl, 1-phenylcyclopropyl, (cyano(phenyl)methyl)amino, tetrahydrofuran-3-yl, phenyl(pyridin-2-yloxy)methyl, 2-fluoro-6-(((3R,4R)-3-fluoro-4-hydroxypyrrolidin-1-yl)methyl)benzyl, 2-((4-carboxypiperidin-1-yl)methyl)-6-fluorobenzyl, 2-fluoro-6-((N-methylmethylsulfonamido)methyl)benzyl, 2-((2,5-dioxoimidazolidin-1-yl)methyl)-6-fluorobenzyl, (2,6-difluorophenyl)(hydroxy)methyl, (5-(pyridin-2-yl)-1H-tetrazol-1-yl)methyl, (5-(1H-pyrazol-1-yl)-1H-tetrazol-1-yl)methyl, (5-(thiazol-4-yl)-1H-tetrazol-1-yl)methyl, (5-methyl-3-(trifluoromethyl)-1H-pyrazol-1-yl)methyl, (3-methylpyridin-2-yl)methyl, 2-((1,1-dioxidoisothiazolidin-2-yl)methyl)-6-fluorobenzyl, 2-fluoro-6-((3-methyl-2,5-dioxoimidazolidin-1-yl)methyl)benzyl, (6-(trifluoromethyl)pyridin-2-yl)methyl, (3-(hydroxymethyl)pyridin-2-yl)methyl, (1-methyl-1H-pyrazol-3-yl)methyl, (2-cyanophenoxy)methyl, and ((3-methylpyridin-2-yl)methyl)amino.

15. The compound of claim 1, or a pharmaceutically acceptable salt thereof, wherein each $R^C$ is independently selected from halo, $C_{1-6}$ alkyl, $C_{6-14}$ aryl, 5-14 membered heteroaryl, (4-14 membered heterocycloalkyl)-$C_{1-6}$ alkyl-, $OR^{a4}$, $C(O)OR^{a4}$, and $NR^{c4}R^{d4}$ wherein the $C_{1-6}$ alkyl, 5-14 membered heteroaryl, and (4-14 membered heterocycloalkyl)-$C_{1-6}$ alkyl- are optionally substituted with 1, 2, or 3 independently selected $R^H$ substituents.

16. The compound of claim 1, or a pharmaceutically acceptable salt thereof, wherein each $R^H$ is independently selected from halo, oxo, $C_{1-6}$ alkyl, $C_{1-6}$ haloalkyl, $OR^{a5}$, $C(O)OR^{a5}$, and $NR^{c5}S(O)_2R^{b5}$.

17. The compound of claim 1, or a pharmaceutically acceptable salt thereof;
wherein:
$R^1$ is selected from H and $C_{1-6}$ alkyl;
$R^2$ is selected from $C_{6-14}$ aryl, 5-14 membered heteroaryl, 4-14 membered heterocycloalkyl, $C_{6-14}$ aryl-$C_{1-6}$ alkyl-, (5-14 membered heteroaryl)-$C_{1-6}$ alkyl-, (4-14 membered heterocycloalkyl)-$C_{1-6}$ alkyl-, $NR^{c2}R^{d2}$, $C(O)R^{b2}$, $C(O)NR^{c2}R^{d2}$, and $C(O)OR^{a2}$, wherein the $C_{6-14}$ aryl, 5-14 membered heteroaryl, 4-14 membered heterocycloalkyl, $C_{6-14}$ aryl-$C_{1-6}$ alkyl-, (5-14 membered heteroaryl)-$C_{1-6}$ alkyl-, (4-14 membered heterocycloalkyl)-$C_{1-6}$ alkyl- of $R^2$ are each optionally substituted with 1, 2, 3, or 4 independently selected $R^c$ substituents;

$Cy^2$ is $C_{6-14}$ aryl, $C_{3-14}$ cycloalkyl, 5-14 membered heteroaryl or 4-14 membered heterocycloalkyl, wherein the $C_{6-14}$ aryl, $C_{3-14}$ cycloalkyl, 5-14 membered heteroaryl and 4-14 membered heterocycloalkyl of $Cy^2$ are each optionally substituted with 1, 2, 3, or 4 independently selected $R^F$ substituents;

each $R^{a2}$, $R^{c2}$, and $R^{d2}$ is independently selected from H, $C_{1-6}$ alkyl, $C_{2-6}$ alkenyl, $C_{2-6}$ alkynyl, $C_{6-14}$ aryl, $C_{6-14}$ aryl-$C_{1-6}$ alkyl-, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{6-14}$ aryl-$C_{1-6}$ alkyl-, $C_{3-14}$ cycloalkyl, 5-14 membered heteroaryl, and 4-14 membered heterocycloalkyl of $R^{a2}$, $R^{c2}$, and $R^{d2}$ are each optionally substituted with 1, 2, 3, or 4 independently selected $R^G$ substituents;

each $R^{b2}$ is independently selected from $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl are each optionally substituted with 1, 2, 3, or 4 independently selected $R^G$ substituents;

each $R^C$, $R^F$, and $R^G$ is independently selected from D, halo, oxo, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, 4-14 membered heterocycloalkyl, CN, $NO_2$, $OR^{a4}$, $SR^{a4}$, $NHOR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^4S(O)_2R^{b4}$, and $NR^{c4}S(O)_2NR^{c4}R^{d4}$ wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^C$, $R^F$, and $R^G$ are each optionally substituted with 1, 2, 3, or 4 independently selected $R^H$ substituents;

each $R^{a4}$, $R^{c4}$, and $R^{d4}$ is independently selected from H, $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl of $R^{a4}$, $R^{c4}$, and $R^{d4}$ are each optionally substituted with 1, 2, 3, or 4 independently selected $R^H$ substituents;

each $R^{b4}$ is independently selected from $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl, wherein the $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl are each optionally substituted with 1, 2, 3, or 4 independently selected $R^H$ substituents;

each $R^H$ is independently selected from D, halo, oxo, $C_{1-6}$ alkyl, CN, $NO_2$, $OR^{a5}$, $SR^{a5}$, $NHOR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, and $NR^{c5}S(O)_2NR^{c5}R^{d5}$; and each $R^{a5}$, $R^{c5}$, and $R^{d5}$ is independently selected from H, and $C_{1-6}$ alkyl;

each $R^{b5}$ is independently selected from $C_{1-6}$ alkyl, $C_{2-6}$ alkenyl, $C_{2-6}$ alkynyl, $C_{6-14}$ aryl, $C_{3-14}$ cycloalkyl, 5-14 membered heteroaryl, and 4-14 membered heterocycloalkyl; and each $R^{e5}$ is independently selected from H and $C_{1-6}$ alkyl.

18. The compound of claim 1, selected from:

3-(5-amino-2-(pyridin-2-ylmethyl)-8-(pyrimidin-4-yl)-[1,2,4]triazolo[1,5-c]pyrimidin-7-yl)benzonitrile;

3-(5-amino-8-(1-ethyl-1H-pyrazol-5-yl)-2-(pyridin-2-ylmethyl)-[1,2,4]triazolo[1,5-c]pyrimidin-7-yl)benzonitrile;

3-(5-amino-8-(1-propyl-1H-pyrazol-5-yl)-2-(pyridin-2-ylmethyl)-[1,2,4]triazolo[1,5-c]pyrimidin-7-yl)benzonitrile;

3-(5-amino-2-(pyridin-2-ylmethyl)-8-(quinolin-5-yl)-[1,2,4]triazolo[1,5-c]pyrimidin-7-yl)benzonitrile;

3-(5-amino-8-(5-fluoropyrimidin-4-yl)-2-(hydroxy(phenyl)methyl)-[1,2,4]triazolo[1,5-c]pyrimidin-7-yl)benzonitrile;

3-(5-amino-8-(5-fluoropyrimidin-4-yl)-2-(pyridin-2-ylmethyl)-[1,2,4]triazolo[1,5-c]pyrimidin-7-yl)benzonitrile;

3-(5-amino-2-((2-hydroxyethylamino)(phenyl)methyl)-8-(pyridin-4-yl)-[1,2,4]triazolo[1,5-c]pyrimidin-7-yl)benzonitrile;

3-(5-amino-2-(cyclohexylmethyl)-8-(1-ethyl-1H-pyrazol-5-yl)-[1,2,4]triazolo[1,5-c]pyrimidin-7-yl)benzonitrile;

3-(5-amino-2-(2-fluorobenzyl)-8-(pyrimidin-4-yl)-[1,2,4]triazolo[1,5-c]pyrimidin-7-yl)benzonitrile;

3-(5-amino-2-((2-fluorophenyl)(hydroxy)methyl)-8-(pyrimidin-4-yl)-[1,2,4]triazolo[1,5-c]pyrimidin-7-yl)benzonitrile;

3-(5-amino-2-((6-methylpyridin-2-yl)methyl)-8-(pyrimidin-4-yl)-[1,2,4]triazolo[1,5-c]pyrimidin-7-yl)benzonitrile;

3-(5-amino-8-(1-ethyl-1H-pyrazol-5-yl)-2-((3-fluoropyridin-2-yl)methyl)-[1,2,4]triazolo[1,5-c]pyrimidin-7-yl)benzonitrile;

3-(5-amino-8-(1-ethyl-1H-pyrazol-5-yl)-2-((3-methoxypyridin-2-yl)methyl)-[1,2,4]triazolo[1,5-c]pyrimidin-7-yl)benzonitrile;

3-(5-amino-2-(2-(1-methyl-1H-pyrazol-4-yl)benzyl)-8-(pyrimidin-4-yl)-[1,2,4]triazolo[1,5-c]pyrimidin-7-yl)benzonitrile;

3-(5-amino-2-(benzo[d]isoxazol-3-ylmethyl)-8-(1-ethyl-1H-pyrazol-5-yl)-[1,2,4]triazolo[1,5-c]pyrimidin-7-yl)benzonitrile;

3-(5-amino-8-(1-ethyl-1H-pyrazol-5-yl)-2-((1-methyl-1H-indazol-3-yl)methyl)-[1,2,4]triazolo[1,5-c]pyrimidin-7-yl)benzonitrile;

3-(5-amino-2-((3-hydroxyazetidin-1-yl)methyl)-8-(pyrimidin-4-yl)-[1,2,4]triazolo[1,5-c]pyrimidin-7-yl)benzonitrile;

3-(5-amino-8-(3-methylpyridin-4-yl)-2-(pyridin-2-ylmethyl)-[1,2,4]triazolo[1,5-c]pyrimidin-7-yl)benzonitrile;

3-(5-amino-8-(2-methoxy-6-methylpyridin-4-yl)-2-(pyridin-2-ylmethyl)-[1,2,4]triazolo[1,5-c]pyrimidin-7-yl)benzonitrile;

3-(5-amino-8-(pyrazolo[1,5-b]pyridazin-3-yl)-2-(pyridin-2-ylmethyl)-[1,2,4]triazolo[1,5-c]pyrimidin-7-yl)benzonitrile;

3-(5-amino-8-(4-methyloxazol-5-yl)-2-(pyridin-2-ylmethyl)-[1,2,4]triazolo[1,5-c]pyrimidin-7-yl)benzonitrile;

3-(5-amino-8-(4-(hydroxymethyl)-2-methyloxazol-5-yl)-2-(pyridin-2-ylmethyl)-[1,2,4]triazolo[1,5-c]pyrimidin-7-yl)benzonitrile;

3-(5-amino-8-(4-(methoxymethyl)-2-methyloxazol-5-yl)-2-(pyridin-2-ylmethyl)-[1,2,4]triazolo[1,5-c]pyrimidin-7-yl)benzonitrile;

(S)-3-(5-amino-2-(hydroxy(phenyl)methyl)-8-(pyrimidin-4-yl)-[1,2,4]triazolo[1,5-c]pyrimidin-7-yl)benzonitrile;

(R)-3-(5-amino-2-(hydroxy(phenyl)methyl)-8-(pyrimidin-4-yl)-[1,2,4]triazolo[1,5-c]pyrimidin-7-yl)benzonitrile;

3-(5-amino-2-benzoyl-8-(pyrimidin-4-yl)-[1,2,4]triazolo[1,5-c]pyrimidin-7-yl)benzonitrile;

3-(5-amino-8-(1-ethyl-1H-pyrazol-5-yl)-2-(1-phenylcyclopropyl)-[1,2,4]triazolo[1,5-c]pyrimidin-7-yl)benzonitrile;

3-(5-amino-2-((cyano(phenyl)methyl)amino)-8-(pyrimidin-4-yl)-[1,2,4]triazolo[1,5-c]pyrimidin-7-yl)benzonitrile;

3-(5-amino-8-(pyridin-4-yl)-2-(tetrahydrofuran-3-yl)-[1,2,4]triazolo[1,5-c]pyrimidin-7-yl)benzonitrile; and 3-(5-amino-2-(phenyl(pyridin-2-yloxy)methyl)-8-(pyrimidin-4-yl)-[1,2,4]triazolo[1,5-c]pyrimidin-7-yl)benzonitrile;

or a pharmaceutically acceptable salt thereof.

19. The compound of claim 1, selected from:

3-(5-amino-2-(2-fluoro-6-(((3R,4R)-3-fluoro-4-hydroxypyrrolidin-1-yl)methyl)benzyl)-8-(pyrimidin-4-yl)-[1,2,4]triazolo[1,5-c]pyrimidin-7-yl)benzonitrile;

1-(2-((5-amino-7-(3-cyanophenyl)-8-(pyrimidin-4-yl)-[1,2,4]triazolo[1,5-c]pyrimidin-2-yl)methyl)-3-fluorobenzyl)piperidine-4-carboxylic acid;

N-(2-((5-amino-7-(3-cyanophenyl)-8-(pyrimidin-4-yl)-[1,2,4]triazolo[1,5-c]pyrimidin-2-yl)methyl)-3-fluorobenzyl)-N-methylmethanesulfonamide;

3-(5-amino-2-(2-((2,5-dioxoimidazolidin-1-yl)methyl)-6-fluorobenzyl)-8-(pyrimidin-4-yl)-[1,2,4]triazolo[1,5-c]pyrimidin-7-yl)benzonitrile; and 3-(5-amino-2-((2,6-difluorophenyl)(hydroxy)methyl)-8-(pyrimidin-4-yl)-[1,2,4]triazolo[1,5-c]pyrimidin-7-yl)benzonitrile;

or a pharmaceutically acceptable salt thereof.

20. The compound of claim 1, selected from:

3-(5-amino-2-((5-(pyridin-2-yl)-1H-tetrazol-1-yl)methyl)-8-(pyrimidin-4-yl)-[1,2,4]triazolo[1,5-c]pyrimidin-7-yl)benzonitrile;

3-(2-((5-(1H-pyrazol-1-yl)-1H-tetrazol-1-yl)methyl)-5-amino-8-(pyrimidin-4-yl)-[1,2,4]triazolo[1,5-c]pyrimidin-7-yl)benzonitrile;

3-(5-amino-8-(pyrimidin-4-yl)-2-((5-(thiazol-4-yl)-1H-tetrazol-1-yl)methyl)-[1,2,4]triazolo[1,5-c]pyrimidin-7-yl)benzonitrile;

3-(5-amino-2-((5-methyl-3-(trifluoromethyl)-1H-pyrazol-1-yl)methyl)-8-(pyrimidin-4-yl)-[1,2,4]triazolo[1,5-c]pyrimidin-7-yl)benzonitrile;

3-(5-amino-8-(4-ethyloxazol-5-yl)-2-(pyridin-2-ylmethyl)-[1,2,4]triazolo[1,5-c]pyrimidin-7-yl)benzonitrile;

3-(5-amino-8-(1-ethyl-1H-1,2,3-triazol-5-yl)-2-(pyridin-2-ylmethyl)-[1,2,4]triazolo[1,5-c]pyrimidin-7-yl)benzonitrile;

3-(5-amino-8-(4-methyloxazol-5-yl)-2-((3-methylpyridin-2-yl)methyl)-[1,2,4]triazolo[1,5-c]pyrimidin-7-yl)benzonitrile;

3-(5-amino-2-((3-fluoropyridin-2-yl)methyl)-8-(4-(hydroxymethyl)-2-methyloxazol-5-yl)-[1,2,4]triazolo[1,5-c]pyrimidin-7-yl)benzonitrile;

3-(5-amino-2-(2-((1,1-dioxidoisothiazolidin-2-yl)methyl)-6-fluorobenzyl)-8-(pyrimidin-4-yl)-[1,2,4]triazolo[1,5-c]pyrimidin-7-yl)benzonitrile;

3-(5-amino-2-(2-fluoro-6-((3-methyl-2,5-dioxoimidazolidin-1-yl)methyl)benzyl)-8-(pyrimidin-4-yl)-[1,2,4]triazolo[1,5-c]pyrimidin-7-yl)benzonitrile;

3-(5-amino-2-((3-fluoropyridin-2-yl)methyl)-8-(pyrimidin-4-yl)-[1,2,4]triazolo[1,5-c]pyrimidin-7-yl)benzonitrile;

3-(5-amino-8-(4-methyloxazol-5-yl)-2-((6-(trifluoromethyl)pyridin-2-yl)methyl)-[1,2,4]triazolo[1,5-c]pyrimidin-7-yl)benzonitrile;

3-(5-amino-2-((3-(hydroxymethyl)pyridin-2-yl)methyl)-8-(4-methyloxazol-5-yl)-[1,2,4]triazolo[1,5-c]pyrimidin-7-yl)benzonitrile;

3-(5-amino-2-((1-methyl-1H-pyrazol-3-yl)methyl)-8-(4-methyloxazol-5-yl)-[1,2,4]triazolo[1,5-c]pyrimidin-7-yl)benzonitrile;

3-(5-amino-2-((1-methyl-1H-pyrazol-3-yl)methyl)-8-(oxazol-5-yl)-[1,2,4]triazolo[1,5-c]pyrimidin-7-yl)benzonitrile;

2-((5-amino-7-(3-cyanophenyl)-8-(pyrimidin-4-yl)-[1,2,4]triazolo[1,5-c]pyrimidin-2-yl)methoxy)benzonitrile; and 3-(5-amino-2-(((3-methylpyridin-2-yl)methyl)amino)-8-(pyrimidin-4-yl)-[1,2,4]triazolo[1,5-c]pyrimidin-7-yl)benzonitrile;

or a pharmaceutically acceptable salt thereof.

21. A pharmaceutical composition comprising a compound of claim 1, or a pharmaceutically acceptable salt thereof, and a pharmaceutically acceptable excipient or carrier.

22. The compound of claim 1, which is 3-(5-amino-2-(pyridin-2-ylmethyl)-8-(pyrimidin-4-yl)-[1,2,4]triazolo[1,5-c]pyrimidin-7-yl)benzonitrile, or a pharmaceutically acceptable salt thereof.

23. The compound of claim 1, which is 3-(5-amino-2-((5-(pyridin-2-yl)-2H-tetrazol-2-yl)methyl)-8-(pyrimidin-4-yl)-[1,2,4]triazolo[1,5-c]pyrimidin-7-yl)benzonitrile, or a pharmaceutically acceptable salt thereof.

24. The compound of claim 1, which is 3-(2-((5-(1H-pyrazol-1-yl)-2H-tetrazol-2-yl)methyl)-5-amino-8-(pyrimidin-4-yl)-[1,2,4]triazolo[1,5-c]pyrimidin-7-yl)benzonitrile, or a pharmaceutically acceptable salt thereof.

25. The compound of claim 1, which is 3-(5-amino-8-(pyrimidin-4-yl)-2-((5-(thiazol-4-yl)-2H-tetrazol-2-yl)methyl)-[1,2,4]triazolo[1,5-a]pyridin-7-yl)benzonitrile, or a pharmaceutically acceptable salt thereof.

* * * * *

UNITED STATES PATENT AND TRADEMARK OFFICE
CERTIFICATE OF CORRECTION

PATENT NO. : 11,673,894 B2
APPLICATION NO. : 17/077713
DATED : June 13, 2023
INVENTOR(S) : Xiaozhao Wang et al.

It is certified that error appears in the above-identified patent and that said Letters Patent is hereby corrected as shown below:

In the Claims

Column 221, Line 41, Claim 1, delete "R" and insert -- $R^I$ --;

Column 221, Line 48, Claim 1, delete "R" and insert -- $R^I$ --;

Column 221, Line 61, Claim 1, delete "R" and insert -- $R^I$ --;

Column 222, Line 34, Claim 1, after "$NR^{c6}R^{d6}$" insert -- , --;

Column 222, Line 63, Claim 1, delete "R" and insert -- $R^J$ --;

Column 223, Line 3, Claim 1, delete "R" and insert -- $R^J$ --;

Column 223, Line 17, Claim 1, delete "R" and insert -- $R^J$ --;

Column 223, Line 54, Claim 1, after "$NR^{c7}R^{d7}$" insert -- , --;

Column 225, Line 19, Claim 2, after "$NR^{c7}R^{d7}$" insert -- , --;

Column 225, Lines 21-22, Claim 2, delete "$NR^7C(=NR^{e7})NR^{c7}R^{d7}$," and insert -- $NR^{c7}C(=NR^{e7})NR^{c7}R^{d7}$, --;

Column 225, Line 22, Claim 2, delete "$NR^7S(O)R^{b7}$," and insert -- $NR^{c7}S(O)R^{b7}$, --;

Column 225, Line 23, Claim 2, after "$NR^{c7}S(O)NR^{c7}R^{d7}$" insert -- , --;

Column 226, Line 24, Claim 6, after "compound" insert -- of --;

Column 226, Line 61, Claim 11, delete "for" and insert -- or --;

Signed and Sealed this
Twenty-second Day of August, 2023

Katherine Kelly Vidal
*Director of the United States Patent and Trademark Office*

CERTIFICATE OF CORRECTION (continued)
U.S. Pat. No. 11,673,894 B2

Column 227, Line 19, Claim 14, delete "claim/or" and insert -- claim 1, or --;

Column 227, Line 49, Claim 15, after "$NR^{c4}R^{d4}$" insert -- , --;

Column 228, Line 3, Claim 17, delete "$R^c$" and insert -- $R^C$ --;

Column 228, Line 36, Claim 17, delete "$NR^4S(O)_2R^{b4}$," and insert -- $NR^{c4}S(O)_2R^{b4}$, --;

Column 228, Line 36, Claim 17, after "$NR^{c4}S(O)_2NR^{c4}R^{d4}$" insert -- , --;

Column 228, Line 62, Claim 17, after "$NR^{c5}R^{d5}$" insert -- , --.